(12) United States Patent
Griebenow et al.

(10) Patent No.: US 11,485,733 B2
(45) Date of Patent: Nov. 1, 2022

(54) AZAQUINOLINE DERIVATIVES

(71) Applicant: BAYER ANIMAL HEALTH GMBH, Leverkusen (DE)

(72) Inventors: Nils Griebenow, Dormagen (DE); Wei Zhuang, Monheim (DE); Adeline Köhler, Langenfeld (DE); Daniel Kulke, Leverkusen (DE); Claudia Böhm, Hannover (DE); Kirsten Börngen, Cologne (DE); Thomas Ilg, Monheim (DE); Hans-Georg Schwarz, Dorsten (DE); Werner Hallenbach, Nordhorn (DE); Ulrich Görgens, Ratingen (DE); Walter Hübsch, Wuppertal (DE); Bernd Alig, Königswinter (DE); Iring Heisler, Düsseldorf (DE); Isa Jana Irina Janssen, Cologne (DE)

(73) Assignee: BAYER ANIMAL HEALTH GMBH, Leverkusen (DE)

( * ) Notice: Subject to any disclaimer, the term of this patent is extended or adjusted under 35 U.S.C. 154(b) by 0 days.

(21) Appl. No.: 16/624,117

(22) PCT Filed: Jun. 22, 2018

(86) PCT No.: PCT/EP2018/066776
§ 371 (c)(1),
(2) Date: Dec. 18, 2019

(87) PCT Pub. No.: WO2019/002132
PCT Pub. Date: Jan. 3, 2019

(65) Prior Publication Data
US 2020/0131175 A1 Apr. 30, 2020

(30) Foreign Application Priority Data
Jun. 30, 2017 (EP) ..................... 17179149

(51) Int. Cl.
*C07D 471/04* (2006.01)
*A61P 33/10* (2006.01)
*C07D 405/12* (2006.01)

(52) U.S. Cl.
CPC ............ *C07D 471/04* (2013.01); *A61P 33/10* (2018.01); *C07D 405/12* (2013.01)

(58) Field of Classification Search
CPC .................................................. C07D 471/04
(Continued)

(56) References Cited
U.S. PATENT DOCUMENTS

2003/0195212 A1* 10/2003 Lundstedt ................ A61P 1/14
514/237.8
2007/0142328 A1 6/2007 Chapdelaine
(Continued)

FOREIGN PATENT DOCUMENTS

RU   2008/122405 A   1/2010
WO   2007/073283 A1  6/2007
(Continued)

OTHER PUBLICATIONS

Venkatesh, J. Pharm. Sci. 89, 145-154 (2000) (p. 146, left column).*
(Continued)

*Primary Examiner* — Nizal S Chandrakumar
(74) *Attorney, Agent, or Firm* — McBee Moore & Vanik IP, LLC

(57) ABSTRACT

The present invention covers azaquinoline compounds of general formula (I), with A being (A1) or (A2), and in which T, $R^1$, $R^2$, $R^3$, $R^4$, $R^5$, $R^6$ and Q are as defined herein, methods of preparing said compounds, intermediate compounds useful for preparing said compounds, pharmaceutical compositions and combinations comprising said compounds and the use of said compounds for manufacturing pharmaceutical compositions for the treatment, control and/or prevention of diseases, in particular of helminth infections, as a sole agent or in combination with other active ingredients.

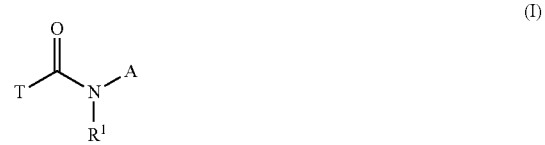

(I)

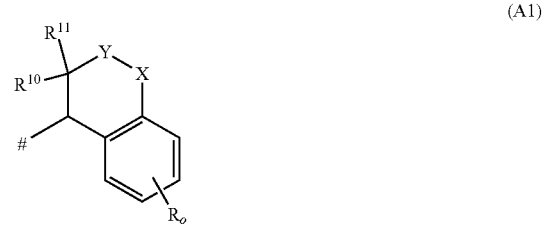

(A1)

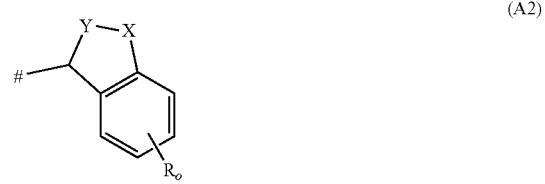

(A2)

20 Claims, No Drawings

(58) Field of Classification Search
USPC .......................................................... 544/36
See application file for complete search history.

(56) References Cited

U.S. PATENT DOCUMENTS

| | | |
|---|---|---|
| 2013/0150414 A1 | 6/2013 | Kagabu et al. |
| 2016/0137643 A1 | 5/2016 | Ceccarelli et al. |
| 2017/0217931 A1 | 8/2017 | Welz et al. |

FOREIGN PATENT DOCUMENTS

| | | |
|---|---|---|
| WO | WO2007073283 A1 | 6/2007 |
| WO | WO2013148603 A1 | 10/2013 |
| WO | 2016/012485 A1 | 1/2016 |
| WO | WO2016012485 A1 | 1/2016 |
| WO | WO2018087036 A1 | 5/2018 |

OTHER PUBLICATIONS

J. G. Cannon, Chapter Nineteen in Burger's Medicinal Chemistry and Drug Discovery, Fifth Edition, vol. I: Principles and Practice, Wiley-Interscience 1995, pp. 783-802.*

West, Solid State Chemistry and Its Applications, john Wiley & Sons, 1984.*

International Search Report dated Jul. 26, 2018 for International Application No. PCT/EP2018/066776, filed Jun. 22, 2018, 4 pages.

* cited by examiner

AZAQUINOLINE DERIVATIVES

CROSS REFERENCE TO RELATED APPLICATIONS

This application is a national stage application under 35 U.S.C. § 371 of International Application No. PCT/EP2018/066776, filed internationally on Jun. 22, 2018, which claims priority benefit to European Application No. 17179149.4, filed Jun. 30, 2017.

The present invention covers new azaquinoline derivatives of general formula (I) as described and defined herein, methods of preparing said compounds, intermediate compounds useful for preparing said compounds, pharmaceutical compositions and combinations comprising said compounds, and the use of said compounds for manufacturing pharmaceutical compositions for the control, treatment and/or prevention of diseases, in particular for the control, treatment and/or prevention of infections with helminths, more particularly of infections with gastro-intestinal and extra-intestinal nematodes, in animals and humans, formulations containing such compounds and methods for the control, treatment and/or prevention of infections with helminths, more particularly of infections with gastro-intestinal and extra-intestinal nematodes, in animals and humans as a sole agent or in combination with other active ingredients.

BACKGROUND

The occurrence of resistances against all commercial anthelmintics seems to be a growing problem in the area of veterinary medicine. The extensive utilisation of anthelmintics to manage the control of nematodes resulted in significant selection of highly resistant worm populations. Therefore, the spread of resistance against all anthelmintic drug classes threatens effective worm control in cattle, goats, sheep and horses. Furthermore, successful prevention of heartworm disease in dogs, which currently solely relies on the utilisation of macrocyclic lactones, is in danger as loss of efficacy for multiple macrocyclic lactones has been described for some regions of the United States of America—especially in those areas where the heartworm challenge for infection is high. Finally, experimental infection studies with *Dirofilaria immitis* larvae from suspected field loss of efficacy cases in the Lower Mississippi Delta provided in vivo confirmation of the existence of macrocyclic lactone resistance.

Although resistance of human helminths against anthelmintics seems currently to be rare, the spread of anthelmintic resistance in the veterinary field as mentioned before needs to be considered in the treatment of human helminthosis as well. Persistent underdosed treatments against filariosis may lead to highly resistant genotypes and resistances have already been described for certain anthelmintics (e.g. praziquantel, benzimidazole and niclosamide).

Therefore, resistance-breaking anthelmintics with new molecular modes of action are urgently required.

It is an object of the present invention to provide compounds which can be used as anthelmintics in the medical, especially veterinary, field with a satisfactory or improved anthelmintic activity against a broad spectrum of helminths, particularly at relatively low dosages, for the control, treatment and/or prevention of infections with helminths in animals and humans, preferably without any adverse toxic effects to the treated organism.

Certain cinnoline carboxamides are described in US 20070142328A1 as agents suitable for treatment and/or prophylaxis of anxiety disorders, cognitive disorders and/or mood disorders or the like.

Further, WO 2013148603 describes cinnolines and their activity as inhibitors of Bruton's tyrosine kinase (BTK) for treating diseases, disorders or conditions associated with BTK.

Recently published WO 2018/087036 discloses quinoline derivatives and their use in the control, treatment and/or prevention of diseases, such as infections with helminths.

However, the state of the art does not describe new azaquinoline derivatives of general formula (I) of the present invention as described and defined herein.

It has now been found, and this constitutes the basis of the present invention, that the compounds of the present invention have surprising and advantageous properties.

In particular, the compounds of the present invention have surprisingly been found to effectively interact with Slo-1 of nematodes. This interaction is characterized by achieving paralysis/inhibition in particular of gastro-intestinal nematodes, of free-living nematodes, and of filariae, for which data are given in the biological experimental section. Therefore the compounds of the present invention may be used as anthelmintics for the control, treatment and/or prevention of gastro-intestinal and extra-intestinal helminth infections, in particular gastro-intestinal and extra-intestinal infections with nematodes, including filariae.

DESCRIPTION OF THE INVENTION

In accordance with a first aspect, the present invention covers compounds of general formula (I):

in which:
A is A1 or A2,

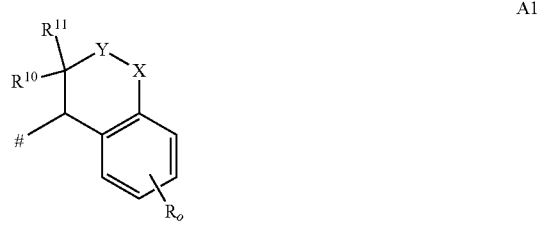

o is 0, 1, 2, 3 or 4,
R is selected from the group consisting of hydrogen, halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —$NH(C_1$-$C_4$-alkyl), —$N(C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl, —S(O)—$C_1$-$C_4$-halogenoalkyl and —$SO_2$—$C_1$-$C_4$-halogenoalkyl having 1 to 5 halogen atoms, X, Y are independently selected from the group consisting of $CR^7R^8$, O, S, and N—$R^9$, wherein at least one of X and Y is $CR^7R^8$, or X, Y form together a ring member selected from the group consisting of —C(O)—O—, —C(O)—$NR^9$—, —S(O)—$NR^9$—, —$SO_2$—$NR^9$— and —$SO_2$—O—

T is selected from $T^1$-$T^6$

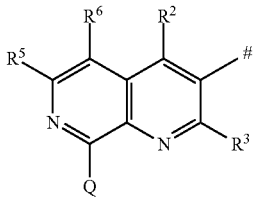
$T^1$

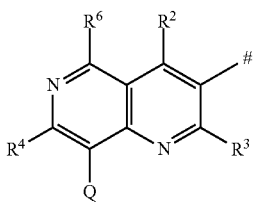
$T^2$

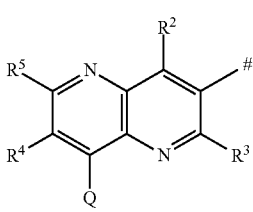
$T^3$

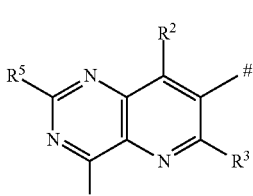
$T^4$

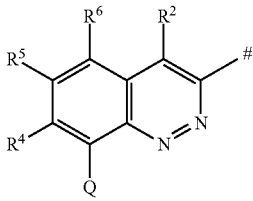
$T^5$

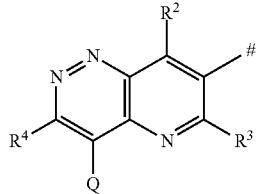
$T^6$ $R^1$ is selected from the group consisting of hydrogen, cyano, —CHO, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, $C_3$-$C_6$-halogenocycloalkyl having 1 to 5 halogen atoms, $C_3$-$C_4$-alkenyl, $C_3$-$C_4$-alkynyl, $C_1$-$C_4$-alkoxy-$C_1$-$C_4$-alkyl, $C_3$-$C_6$-cycloalkyl-$C_1$-$C_3$-alkyl, cyano-$C_1$-$C_4$-alkyl, —NH—$C_1$-$C_4$-alkyl, —$N(C_1$-$C_4$-alkyl)$_2$, $NH_2$—$C_1$-$C_4$-alkyl-, $C_1$-$C_4$-alkyl-NH—$C_1$-$C_4$-alkyl-, ($C_1$-$C_4$-alkyl)$_2$N—$C_1$-$C_4$-alkyl-, $C_1$-$C_4$-alkyl-C(O)—, $C_1$-$C_4$-halogenoalkyl-C(O)— having 1 to 5 halogen atoms, $C_1$-$C_4$-alkoxy-C(O)—, benzyloxy-C(O)—, $C_1$-$C_4$-alkoxy-$C_1$-$C_4$-alkyl-C(O)—, —$SO_2$—$C_1$-$C_4$-alkyl, and —$SO_2$—$C_1$-$C_4$-halogenoalkyl having 1 to 5 halogen atoms;

phenyl-$C_1$-$C_4$-alkyl, optionally substituted by 1, 2, 3, 4 or 5 substituents independently selected from the group consisting of halogen, —OH, —$NO_2$, cyano, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —$NH(C_1$-$C_4$-alkyl), —$N(C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, —OH, —$NO_2$, cyano, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —$NH(C_1$-$C_4$-alkyl), —$N(C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, $R^2$ is selected from the group consisting of
hydrogen, halogen, cyano, —COOH, $C_1$-$C_4$-alkoxy-C(O)—, —C(O)—$NH_2$, —C(O)—$NH(C_1$-$C_4$-alkyl), —C(O)—$N(C_1$-$C_4$-alkyl)$_2$;
—$NR^{12}R^{13}$;
—$OR^{14}$;
—$SR^{15}$, —S(O)$R^5$, —$SO_2R^{15}$;
$C_1$-$C_6$-alkyl, $C_3$-$C_6$-cycloalkyl, $C_2$-$C_4$-alkenyl, $C_3$-$C_6$-cycloalkenyl, $C_2$-$C_4$-alkynyl or phenyl-$C_1$-$C_4$-alkyl, each of which is optionally substituted by 1, 2, 3, 4 or 5 substituents independently selected from the group consisting of halogen, —OH, —$NO_2$, cyano, $C_1$-$C_4$-alkyl-C(O)—, $C_1$-$C_4$-alkoxy-C(O)—, —C(O)—$NH_2$, —C(O)—$NH(C_1$-$C_4$-alkyl), —C(O)—$N(C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, —$NH_2$, —$NH(C_1$-$C_4$- alkyl), —N($C_1$-$C_4$-alkyl)$_2$, —S—$C_1$-$C_4$-alkyl, —S(O)—$C_1$-$C_4$-alkyl, —SO$_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —SO$_2$—$C_1$-$C_4$-halogenoalkyl having 1 to 5 halogen atoms;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, —OH, —NO$_2$, cyano, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —NH$_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —SO$_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —SO$_2$—$C_1$-$C_4$-halogenoalkyl having 1 to 5 halogen atoms;

phenyl which is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —NH$_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —SO$_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —SO$_2$—$C_1$-$C_4$-halogenoalkyl having 1 to 5 halogen atoms; and a monocyclic or a bicyclic heterocycle selected from the group consisting of 4- to 10-membered heterocycloalkyl, heterospirocycloalkyl, 5-membered heteroaryl and 6-membered heteroaryl, each of which is optionally substituted by 1, 2, 3 or 4 substituents independently selected from the group consisting of halogen, cyano, nitro, —OH, oxo, thiono, —COOH, $C_1$-$C_4$-alkoxy-C(O)—, —C(O)—NH$_2$, —C(O)—NH($C_1$-$C_4$-alkyl), —C(O)—N($C_1$-$C_4$-alkyl)$_2$, $C_1$-$C_4$-alkyl, $C_1$-$C_4$-alkyl-C(O)—, $C_1$-$C_4$-halogenoalkyl having 1 to 5 halogen atoms, $C_1$-$C_4$-alkoxy, hydroxy-$C_1$-$C_4$-alkyl, $C_1$-$C_4$-alkoxy-$C_1$-$C_4$-alkyl-, $C_1$-$C_4$-halogenoalkoxy having 1 to 5 halogen atoms, $C_3$-$C_6$-cycloalkyl, —NH$_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —SO$_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, —SO$_2$—$C_1$-$C_4$-halogenoalkyl having 1 to 5 halogen atoms, and 4- to 10-membered heterocycloalkyl, $R^3$ is selected from the group consisting of hydrogen, halogen or $C_1$-$C_4$-alkyl, $R^4$ is selected from the group consisting of hydrogen, halogen, —OH, cyano, $C_1$-$C_4$-alkyl, $C_3$-$C_6$-cycloalkyl, $C_1$-$C_4$-halogenoalkyl having 1 to 5 halogen atoms, $C_1$-$C_4$-alkoxy-$C_1$-$C_4$-alkyl, $C_1$-$C_4$-alkoxy, $C_1$-$C_4$-alkyl-C(O)—, —NH$_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —SO$_2$—$C_1$-$C_4$-alkyl, $R^5$ is selected from the group consisting of hydrogen, halogen, —OH, cyano, $C_1$-$C_4$-alkyl, $C_3$-$C_6$-cycloalkyl, $C_1$-$C_4$-halogenoalkyl having 1 to 5 halogen atoms, $C_1$-$C_4$-alkoxy-$C_1$-$C_4$-alkyl, $C_1$-$C_4$-alkoxy, $C_1$-$C_4$-alkyl-C(O)—, —NH$_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —SO$_2$—$C_1$-$C_4$-alkyl, $R^6$ is selected from the group consisting of hydrogen, halogen, —OH, cyano, $C_1$-$C_4$-alkyl, $C_3$-$C_6$-cycloalkyl, $C_1$-$C_4$-halogenoalkyl having 1 to 5 halogen atoms, $C_1$-$C_4$-alkoxy-$C_1$-$C_4$-alkyl, $C_1$-$C_4$-alkoxy, $C_1$-$C_4$-alkyl-C(O)—, —NH$_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —SO$_2$—$C_1$-$C_4$-alkyl, $R^7$ is selected from the group consisting of hydrogen, —OH, halogen, $C_1$-$C_4$-alkyl and $C_1$-$C_4$-alkoxy, $R^8$ is selected from the group consisting of hydrogen, —OH, halogen, $C_1$-$C_4$-alkyl and $C_1$-$C_4$-alkoxy, or $R^7$ and $R^8$ form, together with the carbon atom to which they are attached, a 3- to 6-membered ring selected from the group consisting of $C_3$-$C_6$-cycloalkyl and 3- to 6-membered heterocycloalkyl, $R^9$ is selected from the group consisting of hydrogen, $C_1$-$C_4$-alkyl, $C_1$-$C_4$-halogenoalkyl having 1 to 5 halogen atoms and $C_1$-$C_4$-alkoxy, $R^{10}$ is selected from the group consisting of hydrogen, —OH, $C_1$-$C_4$-alkyl and $C_1$-$C_4$-alkoxy, $R^{11}$ is selected from the group consisting of hydrogen, $C_1$-$C_4$-alkyl and $C_1$-$C_4$-alkoxy, or $R^{10}$ and $R^{11}$ form, together with the carbon atom to which they are attached, a 3- to 6-membered ring selected from the group consisting of $C_3$-$C_6$-cycloalkyl and 3- to 6-membered heterocycloalkyl, $R^{12}$ and $R^{13}$ are independently selected from the group consisting of
hydrogen, —OH, —NH$_2$, —NH($C_1$-$C_4$-alkyl), —N($C_1$-$C_4$-alkyl)$_2$, —NH(—C(O)—$C_1$-$C_4$-alkyl), —N($C_1$-$C_4$-alkyl)(—C(O)—$C_1$-$C_4$-alkyl), $C_1$-$C_4$-alkoxy, $C_1$-$C_4$-alkoxy-C(O)—;

$C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, cyano, —COOH, $C_1$-$C_4$-alkoxy-C(O)—, —C(O)—NH$_2$, —C(O)—NH($C_1$-$C_4$-alkyl), —C(O)—N($C_1$-$C_4$-alkyl)$_2$, —NH—C(O)—$C_1$-$C_4$-alkyl, —N($C_1$-$C_4$-alkyl)(—C(O)—$C_1$-$C_4$-alkyl), $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —NH$_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —SO$_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, —SO$_2$—$C_1$-$C_4$-halogenoalkyl having 1 to 5 halogen atoms and ($C_1$-$C_4$-alkoxy)$_2$P(=O)—;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—NH$_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —NH$_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —SO$_2$—$C_1$-$C_4$-alkyl, —S—$C_1$-$C_4$-halogenoalkyl having 1 to 5 halogen atoms, —S(O)—C$_1$-C$_4$-halogenoalkyl having 1 to 5 halogen atoms and —SO$_2$—C$_1$-C$_4$-halogenoalkyl having 1 to 5 halogen atoms;

phenyl, benzo-C$_5$-C$_6$-cycloalkyl, each of which is optionally substituted by 1, 2 or 3 substituents independently selected from the group consisting of halogen, cyano, nitro, —OH, C$_1$-C$_4$-alkyl, C$_1$-C$_4$-halogenoalkyl having 1 to 5 halogen atoms, C$_1$-C$_4$-alkoxy, C$_1$-C$_4$-halogenoalkoxy having 1 to 5 halogen atoms, C$_3$-C$_6$-cycloalkyl, —NH$_2$, —NH(C$_1$-C$_4$-alkyl), —N(C$_1$-C$_4$-alkyl)$_2$, —S—C$_1$-C$_4$-alkyl, —S(O)—C$_1$-C$_4$-alkyl, —SO$_2$—C$_1$-C$_4$-alkyl, —S—C$_1$-C$_4$-halogenoalkyl having 1 to 5 halogen atoms, —S(O)—C$_1$-C$_4$-halogenoalkyl having 1 to 5 halogen atoms and —SO$_2$—C$_1$-C$_4$-halogenoalkyl having 1 to 5 halogen atoms;

a monocyclic or a bicyclic heterocycle selected from the group of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, C$_1$-C$_4$-alkoxy-C(O)—, —C(O)—NH$_2$, —C(O)—NH(C$_1$-C$_4$-alkyl), —C(O)—N(C$_1$-C$_4$-alkyl)$_2$, C$_1$-C$_4$-alkyl, C$_1$-C$_4$-halogenoalkyl having 1 to 5 halogen atoms, C$_1$-C$_4$-alkoxy, hydroxy-C$_1$-C$_4$-alkyl, C$_1$-C$_4$-halogenoalkoxy having 1 to 5 halogen atoms, C$_3$-C$_6$-cycloalkyl, —NH$_2$, —NH(C$_1$-C$_4$-alkyl), —N(C$_1$-C$_4$-alkyl)$_2$, —S—C$_1$-C$_4$-alkyl, —S(O)—C$_1$-C$_4$-alkyl, —SO$_2$—C$_1$-C$_4$-alkyl, —S—C$_1$-C$_4$-halogenoalkyl having 1 to 5 halogen atoms, —S(O)—C$_1$-C$_4$-halogenoalkyl having 1 to 5 halogen atoms and —SO$_2$—C$_1$-C$_4$-halogenoalkyl having 1 to 5 halogen atoms, $R^{14}$ is selected from the group consisting of —NH$_2$, —NH(C$_1$-C$_4$-alkyl), —N(C$_1$-C$_4$-alkyl)$_2$;

C$_1$-C$_4$-alkyl, C$_3$-C$_6$-cycloalkyl, phenyl-C$_1$-C$_4$-alkyl, each of which is optionally substituted by 1, 2 or 3 substituents independently selected from the group consisting of halogen, —OH, cyano, —COOH, C$_1$-C$_4$-alkoxy-C(O)—, —C(O)—NH$_2$, —C(O)—NH(C$_1$-C$_4$-alkyl), —C(O)—N(C$_1$-C$_4$-alkyl)$_2$, C$_1$-C$_4$-alkyl, C$_1$-C$_4$-halogenoalkyl having 1 to 5 halogen atoms, C$_1$-C$_4$-alkoxy, C$_1$-C$_4$-halogenoalkoxy having 1 to 5 halogen atoms, C$_3$-C$_6$-cycloalkyl, —NH$_2$, —NH(C$_1$-C$_4$-alkyl), —N(C$_1$-C$_4$-alkyl)$_2$, —S—C$_1$-C$_4$-alkyl, —S(O)—C$_1$-C$_4$-alkyl, —SO$_2$—C$_1$-C$_4$-alkyl, —S—C$_1$-C$_4$-halogenoalkyl having 1 to 5 halogen atoms, —S(O)—C$_1$-C$_4$-halogenoalkyl having 1 to 5 halogen atoms and —SO$_2$—C$_1$-C$_4$-halogenoalkyl having 1 to 5 halogen atoms;

heterocyclyl-C$_1$-C$_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, C$_1$-C$_4$-alkoxy-C(O)—, —C(O)—NH$_2$, —C(O)—NH(C$_1$-C$_4$-alkyl), —C(O)—N(C$_1$-C$_4$-alkyl)$_2$, C$_1$-C$_4$-alkyl, C$_1$-C$_4$-halogenoalkyl having 1 to 5 halogen atoms, C$_1$-C$_4$-alkoxy, hydroxy-C$_1$-C$_4$-alkyl, C$_1$-C$_4$-halogenoalkoxy having 1 to 5 halogen atoms, C$_3$-C$_6$-cycloalkyl, —NH$_2$, —NH(C$_1$-C$_4$-alkyl), —N(C$_1$-C$_4$-alkyl)$_2$, —S—C$_1$-C$_4$-alkyl, —S(O)—C$_1$-C$_4$-alkyl, —SO$_2$—C$_1$-C$_4$-alkyl, —S—C$_1$-C$_4$-halogenoalkyl having 1 to 5 halogen atoms, —S(O)—C$_1$-C$_4$-halogenoalkyl having 1 to 5 halogen atoms and —SO$_2$—C$_1$-C$_4$-halogenoalkyl having 1 to 5 halogen atoms;

phenyl, which is optionally substituted by 1, 2 or 3 substituents independently selected from the group consisting of halogen, cyano, nitro, —OH, C$_1$-C$_4$-alkyl, C$_1$-C$_4$-halogenoalkyl having 1 to 5 halogen atoms, C$_1$-C$_4$-alkoxy, C$_1$-C$_4$-halogenoalkoxy having 1 to 5 halogen atoms, C$_3$-C$_6$-cycloalkyl, —NH$_2$, —NH(C$_1$-C$_4$-alkyl), —N(C$_1$-C$_4$-alkyl)$_2$, —S—C$_1$-C$_4$-alkyl, —S(O)—C$_1$-C$_4$-alkyl, —SO$_2$—C$_1$-C$_4$-alkyl, —S—C$_1$-C$_4$-halogenoalkyl having 1 to 5 halogen atoms, —S(O)—C$_1$-C$_4$-halogenoalkyl having 1 to 5 halogen atoms and —SO$_2$—C$_1$-C$_4$-halogenoalkyl having 1 to 5 halogen atoms; and a monocyclic or a bicyclic heterocycle selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, C$_1$-C$_4$-alkoxy-C(O)—, —C(O)—NH$_2$, —C(O)—NH(C$_1$-C$_4$-alkyl), —C(O)—N(C$_1$-C$_4$-alkyl)$_2$, C$_1$-C$_4$-alkyl, C$_1$-C$_4$-halogenoalkyl having 1 to 5 halogen atoms, C$_1$-C$_4$-alkoxy, hydroxy-C$_1$-C$_4$-alkyl, C$_1$-C$_4$-halogenoalkoxy having 1 to 5 halogen atoms, C$_3$-C$_6$-cycloalkyl, —NH$_2$, —NH(C$_1$-C$_4$-alkyl), —N(C$_1$-C$_4$-alkyl)$_2$, —S—C$_1$-C$_4$-alkyl, —S(O)—C$_1$-C$_4$-alkyl, —SO$_2$—C$_1$-C$_4$-alkyl, —S—C$_1$-C$_4$-halogenoalkyl having 1 to 5 halogen atoms, —S(O)—C$_1$-C$_4$-halogenoalkyl having 1 to 5 halogen atoms and —SO$_2$—C$_1$-C$_4$-halogenoalkyl having 1 to 5 halogen atoms, $R^{15}$ is selected from the group consisting of C$_1$-C$_4$-alkyl, C$_3$-C$_6$-cycloalkyl, phenyl-C$_1$-C$_4$-alkyl, each of which is optionally substituted by 1, 2 or 3 substituents independently selected from the group consisting of halogen, —OH, cyano, —COOH, C$_1$-C$_4$-alkoxy-C(O)—, —C(O)—NH$_2$, —C(O)—NH(C$_1$-C$_4$-alkyl), —C(O)—N(C$_1$-C$_4$-alkyl)$_2$, C$_1$-C$_4$-alkyl, C$_1$-C$_4$-halogenoalkyl having 1 to 5 halogen atoms, C$_1$-C$_4$-alkoxy, C$_1$-C$_4$-halogenoalkoxy having 1 to 5 halogen atoms, C$_3$-C$_6$-cycloalkyl, —NH$_2$, —NH(C$_1$-C$_4$-alkyl), —N(C$_1$-C$_4$-alkyl)$_2$, —S—C$_1$-C$_4$-alkyl, —S(O)—C$_1$-C$_4$-alkyl, —SO$_2$—C$_1$-C$_4$-alkyl, —S—C$_1$-C$_4$-halogenoalkyl having 1 to 5 halogen atoms, —S(O)—C$_1$-C$_4$-halogenoalkyl having 1 to 5 halogen atoms and —SO$_2$—C$_1$-C$_4$-halogenoalkyl having 1 to 5 halogen atoms;

heterocyclyl-C$_1$-C$_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, C$_1$-C$_4$-alkoxy-C(O)—, —C(O)—NH$_2$, —C(O)—NH(C$_1$-C$_4$-alkyl), —C(O)—N(C$_1$-C$_4$-alkyl)$_2$, C$_1$-C$_4$-alkyl, C$_1$-C$_4$-halogenoalkyl having 1 to 5 halogen atoms, C$_1$-C$_4$-alkoxy, hydroxy-C$_1$-C$_4$-alkyl, C$_1$-C$_4$-halogenoalkoxy having 1 to 5 halogen atoms, C$_3$-C$_6$-cycloalkyl, —NH$_2$, —NH(C$_1$-C$_4$-alkyl), —N(C$_1$-C$_4$-alkyl)$_2$, —S—C$_1$-C$_4$-alkyl, —S(O)—C$_1$-C$_4$-alkyl, —SO$_2$—C$_1$-C$_4$-alkyl, —S—C$_1$-C$_4$-halogenoalkyl having 1 to 5 halogen atoms, —S(O)—C$_1$-C$_4$-halogenoalkyl having 1 to 5 halogen atoms and —SO$_2$—C$_1$-C$_4$-halogenoalkyl having 1 to 5 halogen atoms;

phenyl, which is optionally substituted by 1, 2 or 3 substituents independently selected from the group consisting of halogen, cyano, nitro, —OH, C$_1$-C$_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —$NH(C_1$-$C_4$-alkyl), —$N(C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms; and a monocyclic or a bicyclic heterocycle selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—$NH(C_1$-$C_4$-alkyl), —C(O)—$N(C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —$NH(C_1$-$C_4$-alkyl), —$N(C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, Q is selected from the group consisting of 6- or 10-membered aryl and 5- to 10-membered heteroaryl, each of which is optionally substituted by 1, 2, 3, 4 or 5 substituents selected from the group consisting of halogen, $SF_5$, cyano, —CHO, nitro, oxo, $C_1$-$C_4$-alkyl, $C_1$-$C_4$-hydroxyalkyl, $C_1$-$C_4$-halogenoalkyl having 1 to 5 halogen atoms, hydroxy, $C_1$-$C_4$-alkoxy, $C_3$-$C_6$-cycloalkyl-$C_1$-$C_4$-alkoxy, cyano-$C_1$-$C_4$-alkoxy, $C_1$-$C_4$-halogenoalkoxy having 1 to 5 halogen atoms, —$NH(C_1$-$C_4$-alkyl), —$N(C_1$-$C_4$-alkyl)$_2$, —NH—$SO_2$—($C_1$-$C_4$-alkyl), —$N(SO_2$—[$C_1$-$C_4$-alkyl])($C_1$-$C_4$-alkyl), ($C_1$-$C_4$-alkoxyimino)-$C_1$-$C_4$-alkyl, 4- to 6-membered heterocyclyl, which is optionally substituted with 1 or 2 substituents selected from the group consisting of fluorine, chlorine, bromine, methyl and cyano, —$CH_2$—O—($C_1$-$C_4$-alkyl), —$CH_2$—$NH(C_1$-$C_4$-alkyl), —$CH_2$—$N(C_1$-$C_4$-alkyl)$_2$, methyl substituted with a 4- to 6-membered heterocyclyl which itself is optionally substituted with 1 or 2 substituents selected from the group consisting of fluorine, chlorine, bromine, methyl and cyano, —$CH_2$—S—($C_1$-$C_4$-alkyl), —$CH_2$—S(O)—($C_1$-$C_4$-alkyl), —$CH_2$—$SO_2$—($C_1$-$C_4$-alkyl), —S—($C_1$-$C_4$-alkyl), —S(O)—($C_1$-$C_4$-alkyl), —$SO_2$—($C_1$-$C_4$-alkyl), —S—($C_1$-$C_4$-halogenoalkyl) having 1 to 5 halogen atoms, —S(O)—($C_1$-$C_4$-halogenoalkyl) having 1 to 5 halogen atoms, —$SO_2$—($C_1$-$C_4$-halogenoalkyl) having 1 to 5 halogen atoms, —$CONH(C_1$-$C_4$-alkyl), —$CONH(C_3$-$C_6$-cycloalkyl), —$NHCO(C_1$-$C_4$-alkyl), —$NHCO(C_3$-$C_6$-cycloalkyl), —$NHCO(C_1$-$C_4$-halogenoalkyl) having 1 to 5 halogen atoms, wherein when Y is O, S or N—$R^9$, none of $R^7$, $R^8$, $R^{10}$ and $R^{11}$ is —OH, and wherein when X is O, S or N—$R^9$, none of $R^7$ and $R^8$ is —OH, and stereoisomers, tautomers, N-oxides, hydrates, solvates, and salts thereof, and mixtures of same.

DEFINITIONS

The term "substituted" means that one or more hydrogen atoms on the designated atom or group are replaced with a selection from the indicated group, provided that the designated atom's normal valency under the existing circumstances is not exceeded. Combinations of substituents and/or variables are permissible.

The term "optionally substituted" means that the number of substituents can be equal to or different from zero. Unless otherwise indicated, it is possible that optionally substituted groups are substituted with as many optional substituents as can be accommodated by replacing a hydrogen atom with a non-hydrogen substituent on any available carbon or nitrogen atom. Commonly, it is possible for the number of optional substituents, when present, to be 1, 2, 3, 4 or 5, in particular 1, 2 or 3.

As used herein, the term "one or more", e.g. in the definition of the substituents of the compounds of general formula (I) of the present invention, means "1, 2, 3, 4 or 5, particularly 1, 2, 3 or 4, more particularly 1, 2 or 3, even more particularly 1 or 2".

As used herein, an oxo substituent represents an oxygen atom, which is bound to a carbon atom or to a sulfur atom via a double bond.

The term "ring substituent" means a substituent attached to an aromatic or nonaromatic ring which replaces an available hydrogen atom on the ring.

Should a composite substituent be composed of more than one parts, e.g. ($C_1$-$C_4$-alkoxy)-($C_1$-$C_4$-alkyl)-, it is possible for the position of a given part to be at any suitable position of said composite substituent, i.e. the $C_1$-$C_4$-alkoxy part can be attached to any carbon atom of the $C_1$-$C_4$-alkyl part of said ($C_1$-$C_4$-alkoxy)-($C_1$-$C_4$-alkyl)- group. A hyphen at the beginning or at the end of such a composite substituent indicates the point of attachment of said composite substituent to the rest of the molecule. Should a ring, comprising carbon atoms and optionally one or more heteroatoms, such as nitrogen, oxygen or sulfur atoms for example, be substituted with a substituent, it is possible for said substituent to be bound at any suitable position of said ring, be it bound to a suitable carbon atom and/or to a suitable heteroatom.

As used herein, the position via which a respective subsituent is connected to the rest of the molecule may in a drawn structure be depicted by a hash sign (#) or a dashed line in said substituent.

The term "comprising" when used in the specification includes "consisting of".

If within the present text any item is referred to as "as mentioned herein", it means that it may be mentioned anywhere in the present text.

The terms as mentioned in the present text have the following meanings:

The term "halogen atom" means a fluorine, chlorine, bromine or iodine atom, particularly a fluorine, chlorine or bromine atom.

The term "$C_1$-$C_6$-alkyl" means a linear or branched, saturated, monovalent hydrocarbon group having 1, 2, 3, 4, 5 or 6 carbon atoms. The term "$C_1$-$C_4$-alkyl" means a linear or branched, saturated, monovalent hydrocarbon group having 1, 2, 3, or 4 carbon atoms, e.g. a methyl, ethyl, n-propyl, isopropyl, n-butyl, sec-butyl, isobutyl or a tert-butyl group, or an isomer thereof. Particularly, said group has 1, 2 or 3 carbon atoms ("$C_1$-$C_3$-alkyl"), e.g. a methyl, ethyl, n-propyl or isopropyl group.

The term "$C_1$-$C_4$-hydroxyalkyl" means a linear or branched, saturated, monovalent hydrocarbon group in which the term "$C_1$-$C_4$-alkyl" is defined supra, and in which 1 or 2 hydrogen atoms are replaced with a hydroxy group, e.g. a hydroxymethyl, 1-hydroxyethyl, 2-hydroxyethyl, 1,2-dihydroxyethyl, 3-hydroxypropyl, 2-hydroxypropyl, 1-hydroxypropyl, 1-hydroxypropan-2-yl, 2-hydroxypropan-2-yl, 2,3-dihydroxypropyl, 1,3-dihydroxypropan-2-yl, 3-hydroxy-2-methyl-propyl, 2-hydroxy-2-methyl-propyl, 1-hydroxy-2-methyl-propyl group.

The term "—NH($C_1$-$C_4$-alkyl)" or "—N($C_1$-$C_4$-alkyl)$_2$" means a linear or branched, saturated, monovalent group in which the term "$C_1$-$C_4$-alkyl" is as defined supra, e.g. a methylamino, ethylamino, n-propylamino, isopropylamino, N,N-dimethylamino, N-methyl-N-ethylamino or N,N-diethylamino group.

The term "—S—$C_1$-$C_4$-alkyl", "—S(O)—$C_1$-$C_4$-alkyl" or "—SO$_2$—$C_1$-$C_4$-alkyl" means a linear or branched, saturated group in which the term "$C_1$-$C_4$-alkyl" is as defined supra, e.g. a methylsulfanyl, ethylsulfanyl, n-propylsulfanyl, isopropylsulfanyl, n-butylsulfanyl, sec-butylsulfanyl, isobutylsulfanyl or tert-butylsulfanyl group, a methylsulfinyl, ethylsulfinyl, n-propylsulfinyl, isopropylsulfinyl, n-butylsulfinyl, sec-butylsulfinyl, isobutylsulfinyl or tert-butylsulfinyl group, or a methylsulfonyl, ethylsulfonyl, n-propylsulfonyl, isopropylsulfonyl, n-butylsulfonyl, sec-butylsulfonyl, isobutylsulfonyl or tert-butylsulfonyl group.

The term "$C_1$-$C_4$-halogenoalkyl" means a linear or branched, saturated, monovalent hydrocarbon group in which the term "$C_1$-$C_4$-alkyl" is as defined supra, and in which one or more of the hydrogen atoms are replaced, identically or differently, with a halogen atom. Particularly, said halogen atom is a fluorine atom. More particularly, all said halogen atoms are fluorine atoms ("$C_1$-$C_4$-fluoroalkyl"). Said $C_1$-$C_4$-halogenoalkyl group is, for example, fluoromethyl, difluoromethyl, trifluoromethyl, 2-fluoroethyl, 2,2-difluoroethyl, 2,2,2-trifluoroethyl, pentafluoroethyl, 3,3,3-trifluoropropyl or 1,3-difluoropropan-2-yl.

The term "$C_1$-$C_4$-alkoxy" means a linear or branched, saturated, monovalent group of formula ($C_1$-$C_4$-alkyl)-O—, in which the term "$C_1$-$C_4$-alkyl" is as defined supra, e.g. a methoxy, ethoxy, n-propoxy, isopropoxy, n-butoxy, sec-butoxy, isobutoxy or tert-butoxy group, or an isomer thereof.

The term "$C_1$-$C_4$-halogenoalkoxy" means a linear or branched, saturated, monovalent $C_1$-$C_4$-alkoxy group, as defined supra, in which one or more of the hydrogen atoms is replaced, identically or differently, with a halogen atom. Particularly, said halogen atom is a fluorine atom. Said $C_1$-$C_4$-halogenoalkoxy group is, for example, fluoromethoxy, difluoromethoxy, trifluoromethoxy, 2,2,2-trifluoroethoxy or pentafluoroethoxy.

The term "$C_2$-$C_4$-alkenyl" means a linear or branched, monovalent hydrocarbon group, which contains one double bond, and which has 2, 3 or 4 carbon atoms. Said $C_2$-$C_4$-alkenyl group is, for example, an ethenyl (or "vinyl"), a prop-2-en-1-yl (or "allyl"), prop-1-en-1-yl, but-3-enyl, but-2-enyl, but-1-enyl, prop-1-en-2-yl (or "isopropenyl"), 2-methylprop-2-enyl, 1-methylprop-2-enyl, 2-methylprop-1-enyl or a 1-methylprop-1-enyl, group. Particularly, said group is allyl.

The term "$C_2$-$C_4$-alkynyl" means a linear monovalent hydrocarbon group which contains one triple bond, and which contains 2, 3 or 4 carbon atoms. Said $C_2$-$C_4$-alkynyl group is, for example, an ethynyl, a prop-1-ynyl, prop-2-ynyl (or "propargyl"), but-1-ynyl, but-2-ynyl, but-3-ynyl or 1-methylprop-2-ynyl, group. Particularly, said alkynyl group is prop-1-ynyl or prop-2-ynyl.

The term "$C_3$-$C_6$-cycloalkyl" means a saturated, monovalent, monocyclic hydrocarbon ring which contains 3, 4, 5 or 6 carbon atoms ("$C_3$-$C_6$-cycloalkyl"). Said $C_3$-$C_6$-cycloalkyl group is for example, a monocyclic hydrocarbon ring, e.g. a cyclopropyl, cyclobutyl, cyclopentyl or cyclohexyl group.

The term "$C_3$-$C_6$-halogenocycloalkyl" means a saturated, monovalent, monocyclic hydrocarbon ring in which the term "$C_3$-$C_6$-cycloalkyl" is as defined supra, and in which one or more of the hydrogen atoms are replaced, identically or differently, with a halogen atom. Particularly, said halogen atom is a fluorine or chlorine atom. Said $C_3$-$C_6$-halogenocycloalkyl group is for example, a monocyclic hydrocarbon ring substituted with one or two fluorine or chlorine atoms, e.g. a 1-fluoro-cyclopropyl, 2-fluorocyclopropyl, 2,2-difluorocyclopropyl, 2,3-difluorocyclopropyl, 1-chlorocyclopropyl, 2-chlorocyclopropyl, 2,2-dichlorocyclopropyl, 2,3-dichlorocyclopropyl, 2-fluoro-2-chlorocyclopropyl and 2-fluoro-3-chlorocyclopropyl group.

The term "—NH($C_3$-$C_6$-cycloalkyl)" or "—N($C_1$-$C_4$-alkyl)($C_3$-$C_6$-cycloalkyl)" means a linear or branched, saturated, monovalent group in which the term "$C_1$-$C_4$-alkyl" and the term "$C_3$-$C_6$-cycloalkyl" each is as defined supra, e.g. a cyclopropylamino, cyclobutylamino, cyclopentylamino, cyclohexylamino, N-methyl-N-cyclopropylamino, N-ethyl-N-cyclopropylamino, N-methyl-N-cyclobutylamino, N-ethyl-N-cyclobutylamino, N-methyl-N-cyclopentylamino, N-ethyl-N-cyclopentylamino, N-methyl-N-cyclohexylamino, or N-ethyl-N-cyclohexylamino group.

The term "benzo-$C_5$-$C_6$-cycloalkyl" means a monovalent, bicyclic hydrocarbon ring wherein a saturated, monovalent, monocyclic hydrocarbon ring which contains 5 or 6 carbon atoms ("$C_5$-$C_6$-cycloalkyl") is annelated to a phenyl ring. Said benzo-$C_5$-$C_6$-cycloalkyl group is for example, a bicyclic hydrocarbon ring, e.g. an indane (i.e. 2,3-dihydro-1H-indene) or tetraline (i.e. 1,2,3,4-tetrahydronaphthalene) group.

The term "spirocycloalkyl" means a saturated, monovalent bicyclic hydrocarbon group in which the two rings share one common ring carbon atom, and wherein said bicyclic hydrocarbon group contains 5, 6, 7, 8, 9, 10 or 11 carbon atoms, it being possible for said spirocycloalkyl group to be attached to the rest of the molecule via any one of the carbon atoms except the spiro carbon atom. Said spirocycloalkyl group is, for example, spiro[2.2]pentyl, spiro[2.3]hexyl, spiro[2.4]heptyl, spiro[2.5]octyl, spiro[2.6]nonyl, spiro[3.3]heptyl, spiro[3.4]octyl, spiro[3.5]nonyl, spiro[3.6]decyl, spiro[4.4]nonyl, spiro[4.5]decyl, spiro[4.6]undecyl or spiro[5.5]undecyl.

The term "heterocycloalkyl" means a monocyclic or bicyclic, saturated or partially saturated heterocycle with 4, 5, 6, 7, 8, 9 or 10 ring atoms in total (a "4- to 10-membered heterocloalkyl" group), particularly 4, 5 or 6 ring atoms (a "4- to 6-membered heterocycloalkyl" group), which contains one or two identical or different ring heteroatoms from the series N, O and S, it being possible for said heterocycloalkyl group to be attached to the rest of the molecule via any one of the carbon atoms or, if present, a nitrogen atom.

Said heterocycloalkyl group, without being limited thereto, can be a 4-membered ring, such as azetidinyl, oxetanyl or thietanyl, for example; or a 5-membered ring, such as tetrahydrofuranyl, 1,3-dioxolanyl, thiolanyl, pyrrolidinyl, imidazolidinyl, pyrazolidinyl, 1,1-dioxidothiolanyl, 1,2-oxazolidinyl, 1,3-oxazolidinyl, 1,3-thiazolidinyl or 1,2,4-triazolidinyl, for example; or a 6-membered ring, such as tetrahydropyranyl, tetrahydrothiopyranyl, piperidinyl, morpholinyl, dithianyl, thiomorpholinyl, piperazinyl, 1,3-dioxanyl, 1,4-dioxanyl or 1,2-oxazinanyl, for example; or a 7-membered ring, such as azepanyl, 1,4-diazepanyl or 1,4-oxazepanyl, for example; or a bicyclic 7-membered ring, such as 6-oxa-3-azabicyclo[3.1.1]heptan, for example; or a bicyclic 8-membered ring, such as 5,6-dihydro-4H-furo[2,3-c]pyrrole or 8-oxa-3-azabicyclo[3.2.1]octan, for example;

or a bicyclic 9-membered ring, such as octahydro-1H-pyrrolo[3,4-b]pyridine, 1,3-dihydro-isoindol, 2,3-dihydro-indol or 3,9-dioxa-7-azabicyclo[3.3.1]nonan, for example; or a bicyclic 10-membered ring, such as decahydroquinoline or 3,4-dihydroisoquinolin, for example.

The term "heterospirocycloalkyl" means a bicyclic, saturated heterocycle with 6, 7, 8, 9, 10 or 11 ring atoms in total, in which the two rings share one common ring carbon atom, which "heterospirocycloalkyl" contains one or two identical or different ring heteroatoms from the series: N, O, S; it being possible for said heterospirocycloalkyl group to be attached to the rest of the molecule via any one of the carbon atoms, except the spiro carbon atom, or, if present, a nitrogen atom.

Said heterospirocycloalkyl group is, for example, azaspiro[2.3]hexyl, azaspiro[3.3]heptyl, oxaazaspiro[3.3]heptyl, thiaazaspiro[3.3]heptyl, oxaspiro[3.3]heptyl, oxazaspiro[5.3]nonyl, oxaspiro[4.3]octyl, oxaazaspiro[2.5]octyl, azaspiro[4.5]decyl, oxazaspiro[5.5]undecyl, diazaspiro[3.3]heptyl, thiazaspiro[3.3]heptyl, thiazaspiro[4.3]octyl, azaspiro[5.5]undecyl, or one of the further homologous scaffolds such as spiro[3.4]-, spiro[4.4]-, spiro[2.4]-, spiro[2.5]-, spiro[2.6]-, spiro[3.5]-, spiro[3.6]-, spiro[4.5]- and spiro[4.6]-.

The term "6- or 10-membered aryl" means a monovalent, monocyclic or bicyclic aromatic ring having 6 or 10 carbon ring atoms, e.g. a phenyl or naphthyl group.

The term "heteroaryl" means a monovalent, monocyclic, bicyclic or tricyclic aromatic ring having 5, 6, 9 or 10 ring atoms (a "5- to 10-membered heteroaryl" group), particularly 5 or 6 ring atoms (a "5- to 6-membered heteroaryl" group), which contains at least one ring heteroatom and optionally one, two or three further ring heteroatoms from the series: N, O and/or S, and which is bound via a ring carbon atom or optionally via a ring nitrogen atom (if allowed by valency).

Said heteroaryl group can be a 5-membered heteroaryl group, such as, for example, thienyl, furanyl, pyrrolyl, oxazolyl, thiazolyl, imidazolyl, pyrazolyl, isoxazolyl, isothiazolyl, oxadiazolyl, triazolyl, thiadiazolyl or tetrazolyl; or a 6-membered heteroaryl group, such as, for example, pyridinyl, pyridazinyl, pyrimidinyl, pyrazinyl or triazinyl.

The term "heterocyclyl" means a heterocycle selected from the group consisting of heterocycloalkyl and heteroaryl. Particularly, the term "4- to 6-membered heterocyclyl" means a heterocycle selected from the group consisting of 4- to 6-membered heterocycloalkyl and 5- to 6-membered heteroaryl.

In general, and unless otherwise mentioned, the heteroaryl or heteroarylene groups include all possible isomeric forms thereof, e.g.: tautomers and positional isomers with respect to the point of linkage to the rest of the molecule. Thus, for some illustrative non-restricting examples, the term pyridinyl includes pyridin-2-yl, pyridin-3-yl and pyridin-4-yl; or the term thienyl includes thien-2-yl and thien-3-yl.

The term "$C_1$-$C_4$", as used in the present text, e.g. in the context of the definition of "$C_1$-$C_4$-alkyl", "$C_1$-$C_4$-halogenoalkyl", "$C_1$-$C_4$-hydroxyalkyl", "$C_1$-$C_4$-alkoxy" or "$C_1$-$C_4$-halogenoalkoxy" means an alkyl group having a finite number of carbon atoms of 1 to 4, i.e. 1, 2, 3 or 4 carbon atoms.

Further, as used herein, the term "$C_3$-$C_6$", as used in the present text, e.g. in the context of the definition of "$C_3$-$C_6$-cycloalkyl" or $C_3$-$C_6$-halogenocycloalkyl, means a cycloalkyl group having a finite number of carbon atoms of 3 to 6, i.e. 3, 4, 5 or 6 carbon atoms.

When a range of values is given, said range encompasses each value and sub-range within said range.

For example:
"$C_1$-$C_4$" encompasses $C_1$, $C_2$, $C_3$, $C_4$, $C_1$-$C_4$, $C_1$-$C_3$, $C_1$-$C_2$, $C_2$-$C_4$, $C_2$-$C_3$, and $C_3$-$C_4$;
"$C_2$-$C_6$" encompasses $C_2$, $C_3$, $C_4$, $C_5$, $C_6$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$;
"$C_3$-$C_4$" encompasses $C_3$, $C_4$, and $C_3$-$C_4$;
"$C_3$-$C_{10}$" encompasses $C_3$, $C_4$, $C_5$, $C_6$, $C_7$, $C_8$, $C_9$, $C_{10}$, $C_3$-$C_{10}$, $C_3$-$C_9$, $C_3$-$C_8$, $C_3$-$C_7$, $C_3$-$C_6$, $C_3$-$C_5$, $C_3$-$C_4$, $C_4$-$C_{10}$, $C_4$-$C_9$, $C_4$-$C_8$, $C_4$-$C_7$, $C_4$-$C_6$, $C_4$-$C_5$, $C_5$-$C_{10}$, $C_5$-$C_9$, $C_5$-$C_8$, $C_5$-$C_7$, $C_5$-$C_6$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_9$ and $C_9$-$C_{10}$;
"$C_3$-$C_8$" encompasses $C_3$, $C_4$, $C_5$, $C_6$, $C_7$, $C_8$, $C_3$-$C_8$, $C_3$-$C_7$, $C_3$-$C_6$, $C_3$-$C_5$, $C_3$-$C_4$, $C_4$-$C_8$, $C_4$-$C_7$, $C_4$-$C_6$, $C_4$-$C_5$, $C_5$-$C_8$, $C_5$-$C_7$, $C_5$-$C_6$, $C_6$-$C_8$, $C_6$-$C_7$ and $C_7$-$C_8$;
"$C_3$-$C_6$" encompasses $C_3$, $C_4$, $C_5$, $C_6$, $C_3$-$C_6$, $C_3$-$C_5$, $C_3$-$C_4$, $C_4$-$C_6$, $C_4$-$C_5$, and $C_5$-$C_6$;
"$C_4$-$C_8$" encompasses $C_4$, $C_5$, $C_6$, $C_7$, $C_8$, $C_4$-$C_8$, $C_4$-$C_7$, $C_4$-$C_6$, $C_4$-$C_5$, $C_5$-$C_8$, $C_5$-$C_7$, $C_5$-$C_6$, $C_6$-$C_8$, $C_6$-$C_7$ and $C_7$-$C_8$;
"$C_4$-$C_7$" encompasses $C_4$, $C_5$, $C_6$, $C_7$, $C_4$-$C_7$, $C_4$-$C_6$, $C_4$-$C_5$, $C_5$-$C_7$, $C_5$-$C_6$ and $C_6$-$C_7$;
"$C_4$-$C_6$" encompasses $C_4$, $C_5$, $C_6$, $C_4$-$C_6$, $C_4$-$C_5$ and $C_5$-$C_6$;
"$C_5$-$C_{10}$" encompasses $C_5$, $C_6$, $C_7$, $C_8$, $C_9$, $C_{10}$, $C_5$-$C_{10}$, $C_5$-$C_9$, $C_5$-$C_8$, $C_5$-$C_7$, $C_5$-$C_6$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_9$ and $C_9$-$C_{10}$;
"$C_6$-$C_{10}$" encompasses $C_6$, $C_7$, $C_8$, $C_9$, $C_{10}$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_9$ and $C_9$-$C_{10}$.

As used herein, the term "leaving group" means an atom or a group of atoms that is displaced in a chemical reaction as stable species taking with it the bonding electrons. In particular, such a leaving group is selected from the group comprising: halide, in particular fluoride, chloride, bromide or iodide, (methylsulfonyl)oxy, [(trifluoromethyl)sulfonyl]oxy, [(nonafluorobutyl)sulfonyl]oxy, (phenylsulfonyl)oxy, [(4-methylphenyl)sulfonyl]oxy, [(4-bromophenyl)sulfonyl]oxy, [(4-nitrophenyl)sulfonyl]oxy, [(2-nitrophenyl)sulfonyl]oxy, [(4-isopropylphenyl)sulfonyl]oxy, [(2,4,6-triisopropylphenyl)sulfonyl]oxy, [(2,4,6-trimethylphenyl)sulfonyl]oxy, [(4-tert-butyl-phenyl)sulfonyl]oxy and [(4-methoxyphenyl)sulfonyl]oxy.

An oxo substituent in the context of the invention means an oxygen atom, which is bound to a carbon atom via a double bond.

It is possible for the compounds of general formula (I) to exist as isotopic variants. The invention therefore includes one or more isotopic variant(s) of the compounds of general formula (I), particularly deuterium-containing compounds of general formula (I).

The term "Isotopic variant" of a compound or a reagent is defined as a compound exhibiting an unnatural proportion of one or more of the isotopes that constitute such a compound.

The term "Isotopic variant of the compound of general formula (I)" is defined as a compound of general formula (I) exhibiting an unnatural proportion of one or more of the isotopes that constitute such a compound.

The expression "unnatural proportion" means a proportion of such isotope which is higher than its natural abundance. The natural abundances of isotopes to be applied in this context are described in "Isotopic Compositions of the Elements 1997", Pure Appl. Chem., 70(1), 217-235, 1998.

Examples of such isotopes include stable and radioactive isotopes of hydrogen, carbon, nitrogen, oxygen, phosphorus, sulfur, fluorine, chlorine, bromine and iodine, such as $^2$H (deuterium), $^3$H (tritium), $^{11}$C, $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{125}$I, $^{129}$I and $^{131}$I, respectively.

With respect to the treatment and/or prevention of the disorders specified herein the isotopic variant(s) of the compounds of general formula (I) preferably contain deuterium ("deuterium-containing compounds of general formula (I)"). Isotopic variants of the compounds of general formula (I) in which one or more radioactive isotopes, such as $^3$H or $^{14}$C, are incorporated are useful e.g. in drug and/or substrate tissue distribution studies. These isotopes are particularly preferred for the ease of their incorporation and detectability. Positron emitting isotopes such as $^{18}$F or $^{11}$C may be incorporated into a compound of general formula (I). These isotopic variants of the compounds of general formula (I) are useful for in vivo imaging applications. Deuterium-containing and $^{13}$C-containing compounds of general formula (I) can be used in mass spectrometry analyses in the context of preclinical or clinical studies.

Isotopic variants of the compounds of general formula (I) can generally be prepared by methods known to a person skilled in the art, such as those described in the schemes and/or examples herein, by substituting a reagent for an isotopic variant of said reagent, preferably for a deuterium-containing reagent. Depending on the desired sites of deuteration, in some cases deuterium from D$_2$O can be incorporated either directly into the compounds or into reagents that are useful for synthesizing such compounds. Deuterium gas is also a useful reagent for incorporating deuterium into molecules. Catalytic deuteration of olefinic bonds and acetylenic bonds is a rapid route for incorporation of deuterium. Metal catalysts (i.e. Pd, Pt, and Rh) in the presence of deuterium gas can be used to directly exchange deuterium for hydrogen in functional groups containing hydrocarbons. A variety of deuterated reagents and synthetic building blocks are commercially available from companies such as for example C/D/N Isotopes, Quebec, Canada; Cambridge Isotope Laboratories Inc., Andover, Mass., USA; and CombiPhos Catalysts, Inc., Princeton, N.J., USA.

The term "deuterium-containing compound of general formula (I)" is defined as a compound of general formula (I), in which one or more hydrogen atom(s) is/are replaced by one or more deuterium atom(s) and in which the abundance of deuterium at each deuterated position of the compound of general formula (I) is higher than the natural abundance of deuterium, which is about 0.015%. Particularly, in a deuterium-containing compound of general formula (I) the abundance of deuterium at each deuterated position of the compound of general formula (I) is higher than 10%, 20%, 30%, 40%, 50%, 60%, 70% or 80%, preferably higher than 90%, 95%, 96% or 97%, even more preferably higher than 98% or 99% at said position(s). It is understood that the abundance of deuterium at each deuterated position is independent of the abundance of deuterium at other deuterated position(s).

The selective incorporation of one or more deuterium atom(s) into a compound of general formula (I) may alter the physicochemical properties (such as for example acidity [C. L. Perrin, et al., J. Am. Chem. Soc., 2007, 129, 4490], basicity [C. L. Perrin et al., J. Am. Chem. Soc., 2005, 127, 9641], lipophilicity [B. Testa et al., Int. J. Pharm., 1984, 19(3), 271]) and/or the metabolic profile of the molecule and may result in changes in the ratio of parent compound to metabolites or in the amounts of metabolites formed. Such changes may result in certain therapeutic advantages and hence may be preferred in some circumstances. Reduced rates of metabolism and metabolic switching, where the ratio of metabolites is changed, have been reported (A. E. Mutlib et al., Toxicol. Appl. Pharmacol., 2000, 169, 102). These changes in the exposure to parent drug and metabolites can have important consequences with respect to the pharmacodynamics, tolerability and efficacy of a deuterium-containing compound of general formula (I). In some cases deuterium substitution reduces or eliminates the formation of an undesired or toxic metabolite and enhances the formation of a desired metabolite (e.g. Nevirapine: A. M. Sharma et al., Chem. Res. Toxicol., 2013, 26, 410; Efavirenz: A. E. Mutlib et al., Toxicol. Appl. Pharmacol., 2000, 169, 102). In other cases the major effect of deuteration is to reduce the rate of systemic clearance. As a result, the biological half-life of the compound is increased. The potential clinical benefits would include the ability to maintain similar systemic exposure with decreased peak levels and increased trough levels.

This could result in lower side effects and enhanced efficacy, depending on the particular compound's pharmacokinetic/pharmacodynamic relationship. ML-337 (C. J. Wenthur et al., J. Med. Chem., 2013, 56, 5208) and Odanacatib (K. Kassahun et al., WO2012/112363) are examples for this deuterium effect. Still other cases have been reported in which reduced rates of metabolism result in an increase in exposure of the drug without changing the rate of systemic clearance (e.g. Rofecoxib: F. Schneider et al., Arzneim. Forsch./Drug. Res., 2006, 56, 295; Telaprevir: F. Maltais et al., J. Med. Chem., 2009, 52, 7993). Deuterated drugs showing this effect may have reduced dosing requirements (e.g. lower number of doses or lower dosage to achieve the desired effect) and/or may produce lower metabolite loads.

A compound of general formula (I) may have multiple potential sites of attack for metabolism. To optimize the above-described effects on physicochemical properties and metabolic profile, deuterium-containing compounds of general formula (I) having a certain pattern of one or more deuterium-hydrogen exchange(s) can be selected. Particularly, the deuterium atom(s) of deuterium-containing compound(s) of general formula (I) is/are attached to a carbon atom and/or is/are located at those positions of the compound of general formula (I), which are sites of attack for metabolizing enzymes such as e.g. cytochrome P$_{450}$.

Where the plural form of the word compounds, salts, polymorphs, hydrates, solvates and the like, is used herein, this is taken to mean also a single compound, salt, polymorph, isomer, hydrate, solvate or the like.

By "stable compound" or "stable structure" is meant a compound that is sufficiently robust to survive isolation to a useful degree of purity from a reaction mixture, and formulation into an efficacious therapeutic agent.

The compounds of the present invention optionally contain one or more asymmetric centres, depending upon the location and nature of the various substituents desired. It is possible that one or more asymmetric carbon atoms are present in the (R) or (S) configuration, which can result in racemic mixtures in the case of a single asymmetric centre, and in diastereomeric mixtures in the case of multiple asymmetric centres. In certain instances, it is possible that asymmetry also be present due to restricted rotation about a given bond, for example, the central bond adjoining two substituted aromatic rings of the specified compounds.

Preferred compounds are those which produce the more desirable biological activity. Separated, pure or partially purified isomers and stereoisomers or racemic or diastereomeric mixtures of the compounds of the present invention are also included within the scope of the present invention.

The purification and the separation of such materials can be accomplished by standard techniques known in the art.

Preferred isomers are those which produce the more desirable biological activity. These separated, pure or partially purified isomers or racemic mixtures of the compounds of this invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., HPLC columns using a chiral phase), with or without conventional derivatisation, optimally chosen to maximise the separation of the enantiomers. Suitable HPLC columns using a chiral phase are commercially available, such as those manufactured by Daicel, e.g., Chiracel OD and Chiracel OJ, for example, among many others, which are all routinely selectable. Enzymatic separations, with or without derivatisation, are also useful. The optically active compounds of the present invention can likewise be obtained by chiral syntheses utilizing optically active starting materials.

In order to distinguish different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, e.g. (R)- or (S)-isomers, in any ratio. Isolation of a single stereoisomer, e.g. a single enantiomer or a single diastereomer, of a compound of the present invention is achieved by any suitable state of the art method, such as chromatography, especially chiral chromatography, for example.

Further, it is possible for the compounds of the present invention to exist as tautomers. For example, any compound of the present invention which contains a substitution pattern resulting in α-CH-moiety at the azaquinoline that has an increased C—H-acidity can exist as a tautomer, or even a mixture in any amount of the two tautomers.

The present invention includes all possible tautomers of the compounds of the present invention as single tautomers, or as any mixture of said tautomers, in any ratio.

Further, the compounds of the present invention can exist as N-oxides, which are defined in that at least one nitrogen of the compounds of the present invention is oxidised. The present invention includes all such possible N-oxides.

The present invention also covers useful forms of the compounds of the present invention, such as metabolites, hydrates, solvates, prodrugs, salts, in particular pharmaceutically acceptable salts, and/or co-precipitates.

The compounds of the present invention can exist as a hydrate, or as a solvate, wherein the compounds of the present invention contain polar solvents, in particular water, methanol or ethanol for example, as structural element of the crystal lattice of the compounds. It is possible for the amount of polar solvents, in particular water, to exist in a stoichiometric or non-stoichiometric ratio. In the case of stoichiometric solvates, e.g. a hydrate, hemi-, (semi-), mono-, sesqui-, di-, tri-, tetra-, penta- etc. solvates or hydrates, respectively, are possible. The present invention includes all such hydrates or solvates.

Further, it is possible for the compounds of the present invention to exist in free form, e.g. as a free base, or as a free acid, or as a zwitterion, or to exist in the form of a salt. Said salt may be any salt, either an organic or inorganic addition salt, particularly any pharmaceutically acceptable organic or inorganic addition salt, which is customarily used in pharmacy, or which is used, for example, for isolating or purifying the compounds of the present invention.

The term "pharmaceutically acceptable salt" refers to an inorganic or organic acid addition salt of a compound of the present invention. For example, see S. M. Berge, et al. "Pharmaceutical Salts," J. Pharm. Sci. 1977, 66, 1-19.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, or "mineral acid", such as hydrochloric, hydrobromic, hydroiodic, sulfuric, sulfamic, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, 3-phenylpropionic, pivalic, 2-hydroxyethanesulfonic, itaconic, trifluoromethanesulfonic, dodecylsulfuric, ethanesulfonic, benzenesulfonic, para-toluenesulfonic, methanesulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, or thiocyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium, magnesium or strontium salt, or an aluminium or a zinc salt, or an ammonium salt derived from ammonia or from an organic primary, secondary or tertiary amine having 1 to 20 carbon atoms, such as ethylamine, diethylamine, triethylamine, ethyldiisopropylamine, monoethanolamine, diethanolamine, triethanolamine, dicyclohexylamine, dimethylaminoethanol, diethylaminoethanol, tris(hydroxymethyl)aminomethane, procaine, dibenzylamine, N-methylmorpholine, arginine, lysine, 1,2-ethylenediamine, N-methylpiperidine, N-methyl-glucamine, N,N-dimethyl-glucamine, N-ethyl-glucamine, 1,6-hexanediamine, glucosamine, sarcosine, serinol, 2-amino-1,3-propanediol, 3-amino-1,2-propanediol, 4-amino-1,2,3-butanetriol, or a salt with a quarternary ammonium ion having 1 to 20 carbon atoms, such as tetramethylammonium, tetraethylammonium, tetra(n-propyl)ammonium, tetra(n-butyl)ammonium, N-benzyl-N,N,N-trimethylammonium, choline or benzalkonium.

Those skilled in the art will further recognise that it is possible for acid addition salts of the claimed compounds to be prepared by reaction of the compounds with the appropriate inorganic or organic acid via any of a number of known methods. Alternatively, alkali and alkaline earth metal salts of acidic compounds of the present invention are prepared by reacting the compounds of the present invention with the appropriate base via a variety of known methods.

The present invention includes all possible salts of the compounds of the present invention as single salts, or as any mixture of said salts, in any ratio.

In the present text, in particular in the Experimental Section, for the synthesis of intermediates and of examples of the present invention, when a compound is mentioned as a salt form with the corresponding base or acid, the exact stoichiometric composition of said salt form, as obtained by the respective preparation and/or purification process, is, in most cases, unknown.

Unless specified otherwise, suffixes to chemical names or structural formulae relating to salts, such as "hydrochloride", "trifluoroacetate", "sodium salt", or "x HCl", "x CF$_3$COOH", "x Na$^+$", for example, mean a salt form, the stoichiometry of which salt form not being specified.

This applies analogously to cases in which synthesis intermediates or example compounds or salts thereof have been obtained, by the preparation and/or purification processes described, as solvates, such as hydrates, with (if defined) unknown stoichiometric composition.

Furthermore, the present invention includes all possible crystalline forms, or polymorphs, of the compounds of the present invention, either as single polymorph, or as a mixture of more than one polymorph, in any ratio.

Moreover, the present invention also includes prodrugs of the compounds according to the invention. The term "prodrugs" here designates compounds which themselves can be biologically active or inactive, but are converted (for example metabolically or hydrolytically) into compounds according to the invention during their residence time in the body.

In accordance with a second embodiment of the first aspect, the present invention covers compounds of general formula (I), supra, in which:

A is A1 or A2,

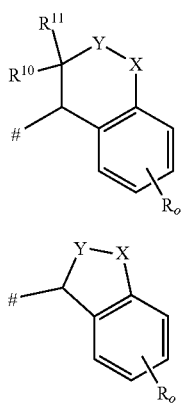

o is 0, 1, 2, 3 or 4,

R is selected from the group consisting of hydrogen, halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —NH$_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —SO$_2$—$C_1$-$C_4$-alkyl, —S—$C_1$-$C_4$-halogenoalkyl, —S(O)—$C_1$-$C_4$-halogenoalkyl and —SO$_2$—$C_1$-$C_4$-halogenoalkyl having 1 to 5 halogen atoms, X, Y are independently selected from the group consisting of CR$^7$R$^8$, O, S, and N—R$^9$, wherein at least one of X and Y is CR$^7$R$^8$, or X, Y form together a ring member selected from the group consisting of —C(O)—O—, —C(O)—NR$^9$—, —S(O)—NR$^9$—, —SO$_2$—NR$^9$— and —SO$_2$—O—, T is selected from T$^1$-T$^6$ as defined supra R$^1$ is selected from the group consisting of hydrogen, cyano, —CHO, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, $C_3$-$C_6$-halogenocycloalkyl having 1 to 5 halogen atoms, $C_3$-$C_4$-alkenyl, $C_3$-$C_4$-alkynyl, $C_1$-$C_4$-alkoxy-$C_1$-$C_4$-alkyl, $C_3$-$C_6$-cycloalkyl-$C_1$-$C_3$-alkyl, cyano-$C_1$-$C_4$-alkyl, —NH—$C_1$-$C_4$-alkyl, —N($C_1$-$C_4$-alkyl)$_2$, NH$_2$—$C_1$-$C_4$-alkyl-, $C_1$-$C_4$-alkyl-NH—$C_1$-$C_4$-alkyl-, ($C_1$-$C_4$-alkyl)$_2$N—$C_1$-$C_4$-alkyl-, $C_1$-$C_4$-alkyl-C(O)—, $C_1$-$C_4$-halogenoalkyl-C(O)— having 1 to 5 halogen atoms, $C_1$-$C_4$-alkoxy-C(O)—, benzyloxy-C(O)—, $C_1$-$C_4$-alkoxy-$C_1$-$C_4$-alkyl-C(O)—, —SO$_2$—$C_1$-$C_4$-alkyl, and —SO$_2$—$C_1$-$C_4$-halogenoalkyl having 1 to 5 halogen atoms;

phenyl-$C_1$-$C_4$-alkyl, optionally substituted by 1, 2, 3, 4 or 5 substituents independently selected from the group consisting of halogen, —OH, —NO$_2$, cyano, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —NH$_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —SO$_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —SO$_2$—$C_1$-$C_4$-halogenoalkyl having 1 to 5 halogen atoms;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, —OH, —NO$_2$, cyano, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —NH$_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —SO$_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —SO$_2$—$C_1$-$C_4$-halogenoalkyl having 1 to 5 halogen atoms, R$^2$ is selected from the group consisting of
hydrogen, halogen, cyano, —COOH, $C_1$-$C_4$-alkoxy-C(O)—, —C(O)—NH$_2$, —C(O)—NH($C_1$-$C_4$-alkyl), —C(O)—N($C_1$-$C_4$-alkyl)$_2$;
—NR$^{12}$R$^{13}$;
—OR$^{14}$;
—SR$^{15}$, —S(O)R$^{15}$, —SO$_2$R$^{15}$;
$C_1$-$C_6$-alkyl, $C_3$-$C_6$-cycloalkyl, $C_2$-$C_4$-alkenyl, $C_3$-$C_6$-cycloalkenyl, $C_2$-$C_4$-alkynyl or phenyl-$C_1$-$C_4$-alkyl, each of which is optionally substituted by 1, 2, 3, 4 or 5 substituents independently selected from the group consisting of halogen, —OH, —NO$_2$, cyano, $C_1$-$C_4$-alkyl-C(O)—, $C_1$-$C_4$-alkoxy-C(O)—, —C(O)—NH$_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, —NH$_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —SO$_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, —OH, —$NO_2$, cyano, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

phenyl which is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms; and a monocyclic or a bicyclic heterocycle selected from the group consisting of 4- to 10-membered heterocycloalkyl, heterospirocycloalkyl, 5-membered heteroaryl and 6-membered heteroaryl, each of which is optionally substituted by 1, 2, 3 or 4 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-alkyl-C(O)—, $C_1$-$C_4$-halogenoalkyl having 1 to 5 halogen atoms, $C_1$-$C_4$-alkoxy, hydroxy-$C_1$-$C_4$-alkyl, $C_1$-$C_4$-alkoxy-$C_1$-$C_4$-alkyl-, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, —$SO_2$—$C_1$-$C_4$-halogenoalkyl having 1 to 5 halogen atoms and 4- to 10-membered heterocycloalkyl, $R^3$ is selected from the group consisting of hydrogen, halogen or $C_1$-$C_4$-alkyl, $R^4$ is selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $R^5$ is selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $R^6$ is selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $R^7$ is selected from the group consisting of hydrogen, —OH, fluorine, $C_1$-$C_4$-alkyl and $C_1$-$C_4$-alkoxy, $R^8$ is selected from the group consisting of hydrogen, —OH, fluorine, $C_1$-$C_4$-alkyl and $C_1$-$C_4$-alkoxy, $R^9$ is selected from the group consisting of hydrogen, $C_1$-$C_4$-alkyl, $C_1$-$C_4$-halogenoalkyl having 1 to 5 halogen atoms and $C_1$-$C_4$-alkoxy, $R^{10}$ is selected from the group consisting of hydrogen, —OH, $C_1$-$C_4$-alkyl and $C_1$-$C_4$-alkoxy, $R^{11}$ is selected from the group consisting of hydrogen, $C_1$-$C_4$-alkyl and $C_1$-$C_4$-alkoxy, $R^{12}$ and $R^{13}$ are independently selected from the group consisting of hydrogen, —OH, —$NH_2$, —NH($C_1$-$C_4$-alkyl), —N($C_1$-$C_4$-alkyl)$_2$, —NH(—C(O)—$C_1$-$C_4$-alkyl), $C_1$-$C_4$-alkoxy;

$C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, —NH—C(O)—$C_1$-$C_4$-alkyl, —N($C_1$-$C_4$-alkyl)-(—C(O)—$C_1$-$C_4$-alkyl), $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, —$SO_2$—$C_1$-$C_4$-halogenoalkyl having 1 to 5 halogen atoms and ($C_1$-$C_4$-alkoxy)$_2$P(=O)—;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

phenyl, benzo-$C_5$-$C_6$-cycloalkyl, each of which is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms; and a monocyclic or a bicyclic heterocycle selected from the group of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —$NH(C_1$-$C_4$-alkyl), —$N(C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, $R^{14}$ is selected from the group consisting of
- —$NH_2$, —$NH(C_1$-$C_4$-alkyl), —$N(C_1$-$C_4$-alkyl)$_2$;
- $C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, cyano, —COOH, $C_1$-$C_4$-alkoxy-C(O)—, —C(O)—$NH_2$, —C(O)—$NH(C_1$-$C_4$-alkyl), —C(O)—$N(C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —$NH(C_1$-$C_4$-alkyl), —$N(C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;
- heterocyclyl-$C_1$-$C_4$-alkyl, wherein the heterocyclyl substitutent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—$NH(C_1$-$C_4$-alkyl), —C(O)—$N(C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —$NH(C_1$-$C_4$-alkyl), —$N(C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;
- phenyl, which is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —$NH(C_1$-$C_4$-alkyl), —$N(C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms; and
- a monocyclic or a bicyclic heterocycle selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—$NH(C_1$-$C_4$-alkyl), —C(O)—$N(C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —$NH(C_1$-$C_4$-alkyl), —$N(C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, $R^{15}$ is selected from the group consisting of
- $C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, cyano, —COOH, $C_1$-$C_4$-alkoxy-C(O)—, —C(O)—$NH_2$, —C(O)—$NH(C_1$-$C_4$-alkyl), —C(O)—$N(C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —$NH(C_1$-$C_4$-alkyl), —$N(C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;
- heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—$NH(C_1$-$C_4$-alkyl), —C(O)—$N(C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —$NH(C_1$-$C_4$-alkyl), —$N(C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;
- phenyl, which is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —$NH(C_1$-$C_4$-alkyl), —$N(C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms; and
- a monocyclic or a bicyclic heterocycle selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—$NH(C_1$-$C_4$-alkyl), —C(O)—$N(C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —$NH(C_1$-$C_4$-alkyl), —$N(C_1$-$C_4$-alkyl)$_2$, —S—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-

$C_4$-halogenoalkyl having 1 to 5 halogen atoms and —$SO_2$—$C_1$-$C_4$-halogenoalkyl having 1 to 5 halogen atoms, Q is a substituted phenyl ring of the formula (Q1)

(Q1)

in which:

$Z^1$, $Z^2$, $Z^3$, $Z^4$, and $Z^5$ are independently selected from the group consisting of hydrogen, halogen, $SF_5$, cyano, —CHO, nitro, $C_1$-$C_4$-alkyl, $C_1$-$C_4$-halogenoalkyl having 1 to 5 halogen atoms, hydroxy, $C_1$-$C_4$-alkoxy, $C_3$-$C_6$-cycloalkyl-$C_1$-$C_4$-alkoxy, cyano-$C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, —NH—$SO_2$—($C_1$-$C_4$-alkyl), —N($SO_2$—[$C_1$-$C_4$-alkyl])($C_1$-$C_4$-alkyl), ($C_1$-$C_4$-alkoxyimino)-$C_1$-$C_4$-alkyl, 4- to 6-membered heterocyclyl, which is optionally substituted with 1 or 2 substituents selected from the group consisting of fluorine, chlorine, bromine, methyl and cyano, —$CH_2$—O—($C_1$-$C_4$-alkyl), —$CH_2$—NH($C_1$-$C_4$-alkyl), —$CH_2$—N($C_1$-$C_4$-alkyl)$_2$, methyl substituted with a 4- to 6-membered heterocyclyl which itself is optionally substituted with 1 or 2 substituents selected from the group consisting of fluorine, chlorine, bromine, methyl and cyano, —$CH_2$—S—($C_1$-$C_4$-alkyl), —$CH_2$—S(O)—($C_1$-$C_4$-alkyl), —$CH_2$—$SO_2$—($C_1$-$C_4$-alkyl), —S—($C_1$-$C_4$-alkyl), —S(O)—($C_1$-$C_4$-alkyl), —$SO_2$—($C_1$-$C_4$-alkyl), —S—($C_1$-$C_4$-halogenoalkyl) having 1 to 5 halogen atoms, —S(O)—($C_1$-$C_4$-halogenoalkyl) having 1 to 5 halogen atoms, —$SO_2$—($C_1$-$C_4$-halogenoalkyl) having 1 to 5 halogen atoms, —CONH($C_1$-$C_4$-alkyl), —CONH($C_3$-$C_6$-cycloalkyl), —NHCO($C_1$-$C_4$-alkyl), —NHCO($C_3$-$C_6$-cycloalkyl), —NHCO($C_1$-$C_4$-halogenoalkyl) having 1 to 5 halogen atoms, or $Z^1$ and $Z^2$ form, together with the carbon atoms that they are connected to, a 5- or 6-membered saturated or partially saturated heterocyclic ring, a 5-membered heteroaryl, or a 6-membered heteroaryl, each of which may be optionally substituted with one or two substituents selected from the group consisting of methyl, fluorine and oxo, and $Z^3$, $Z^4$, and $Z^5$ are independently selected from the group consisting of hydrogen, halogen, $SF_5$, cyano, CHO, nitro, $C_1$-$C_4$-alkyl, $C_1$-$C_4$-halogenoalkyl having 1 to 5 halogen atoms, hydroxy, $C_1$-$C_4$-alkoxy, $C_3$-$C_6$-cycloalkyl-$C_1$-$C_4$-alkoxy, cyano-$C_1$-$C_4$-alkoxy, $C_1$-$C_4$-alkoxy-C(O)—, $C_1$-$C_4$-halogenoalkoxy having 1 to 5 halogen atoms, —NH($C_1$-$C_4$-alkyl), —N($C_1$-$C_4$-alkyl)$_2$, —NH—$SO_2$—($C_1$-$C_4$-alkyl), —N($SO_2$—[$C_1$-$C_4$-alkyl])($C_1$-$C_4$-alkyl), ($C_1$-$C_4$-alkoxyimino)-$C_1$-$C_4$-alkyl, 4- to 6-membered heterocycloalkyl which is optionally substituted with 1 or 2 substituents selected from the group consisting of fluorine, methyl or cyano, —$CH_2$—O—($C_1$-$C_4$-alkyl), —$CH_2$—NH($C_1$-$C_4$-alkyl), —$CH_2$—N($C_1$-$C_4$-alkyl)$_2$, methyl substituted with a 4- to 6-membered heterocycloalkyl which itself is optionally substituted with 1 or 2 substituents selected from the group consisting of fluorine, methyl or cyano, —$CH_2$—S—($C_1$-$C_4$-alkyl), —$CH_2$—S(O)—($C_1$-$C_4$-alkyl), —$CH_2$—$SO_2$—($C_1$-$C_4$-alkyl), —S—($C_1$-$C_4$-alkyl), —S(O)—($C_1$-$C_4$-alkyl), —$SO_2$—($C_1$-$C_4$-alkyl), —S—($C_1$-$C_4$-halogenoalkyl) having 1 to 5 halogen atoms, —S(O)—($C_1$-$C_4$-halogenoalkyl) having 1 to 5 halogen atoms, —$SO_2$—($C_1$-$C_4$-halogenoalkyl) having 1 to 5 halogen atoms, —CONH($C_1$-$C_4$-alkyl), —CONH($C_3$-$C_6$-cycloalkyl), —NHCO($C_1$-$C_4$-alkyl), —NHCO($C_3$-$C_6$-cycloalkyl), —NHCO($C_1$-$C_4$-halogenoalkyl) having 1 to 5 halogen atoms, or $Z^2$ and $Z^3$ form, together with the carbon atoms that they are connected to, a 5- or 6-membered saturated or partially saturated heterocyclic ring, a 5-membered heteroaryl, or a 6-membered heteroaryl, each of which may be optionally substituted with one or two substituents selected from the group consisting of methyl, fluorine and oxo, and $Z^1$, $Z^4$, and $Z^5$ are independently selected from the group consisting of hydrogen, halogen, $SF_5$, cyano, CHO, nitro, $C_1$-$C_4$-alkyl, $C_1$-$C_4$-halogenoalkyl having 1 to 5 halogen atoms, hydroxy, $C_1$-$C_4$-alkoxy, $C_3$-$C_6$-cycloalkyl-$C_1$-$C_4$-alkoxy, cyano-$C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, —NH—$SO_2$—($C_1$-$C_4$-alkyl), —N($SO_2$—[$C_1$-$C_4$-alkyl])($C_1$-$C_4$-alkyl), ($C_1$-$C_4$-alkoxyimino)-$C_1$-$C_4$-alkyl, 4- to 6-membered heterocycloalkyl which is optionally substituted with 1 or 2 substituents selected from the group consisting of fluorine, methyl or cyano, —$CH_2$—O—($C_1$-$C_4$-alkyl), —$CH_2$—NH($C_1$-$C_4$-alkyl), —$CH_2$—N($C_1$-$C_4$-alkyl)$_2$, methyl substituted with a 4- to 6-membered heterocycloalkyl which itself is optionally substituted with 1 or 2 substituents selected from the group consisting of fluorine, methyl or cyano, —$CH_2$—S—($C_1$-$C_4$-alkyl), —$CH_2$—S(O)—($C_1$-$C_4$-alkyl), —$CH_2$—$SO_2$—($C_1$-$C_4$-alkyl), —S—($C_1$-$C_4$-alkyl), —S(O)—($C_1$-$C_4$-alkyl), —$SO_2$—($C_1$-$C_4$-alkyl), —S—($C_1$-$C_4$-halogenoalkyl) having 1 to 5 halogen atoms, —S(O)—($C_1$-$C_4$-halogenoalkyl) having 1 to 5 halogen atoms, —$SO_2$—($C_1$-$C_4$-halogenoalkyl) having 1 to 5 halogen atoms, —CONH($C_1$-$C_4$-alkyl), —CONH($C_3$-$C_6$-cycloalkyl), —NHCO($C_1$-$C_4$-alkyl), —NHCO($C_3$-$C_6$-cycloalkyl), —NHCO($C_1$-$C_4$-halogenoalkyl) having 1 to 5 halogen atoms, or Q is a pyridine ring of the formula (Q2)

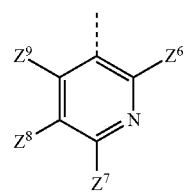

(Q2)

in which:

$Z^6$, $Z^7$, $Z^8$ and $Z^9$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, or Q is a pyrimidine ring of the formula (Q3)

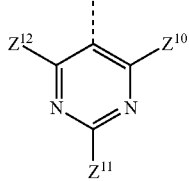

(Q3)

in which:
$Z^{10}$, $Z^{11}$ and $Z^{12}$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, or Q is a pyridine ring of the formula (Q4)

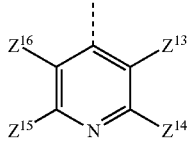

(Q4)

in which:
$Z^{13}$, $Z^{14}$, $Z^{15}$ and $Z^{16}$ are independently selected from the group consisting of hydrogen halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_1$-$C_4$-hydroxyalkyl, $NH_2$, —NH($C_1$-$C_4$-alkyl), —N($C_1$-$C_4$-alkyl)$_2$, —NH—CO—$C_1$-$C_4$-alkyl, and monocyclic heterocycles selected from the group of 4- to 7-membered heterocycloalkyl or 5-membered heteroaryls having at least one nitrogen atom via which the heteroaryl ring is connected to the pyridine ring, each of which is optionally substituted with 1, 2 or 3 substituents independently selected from the group consisting of halogen, cyano, nitro, —OH, oxo, thiono, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—($C_1$-$C_4$-halogenoalkyl) having 1 to 5 halogen atoms, —S(O)—($C_1$-$C_4$-halogenoalkyl) having 1 to 5 halogen atoms, —$SO_2$—($C_1$-$C_4$-halogenoalkyl) having 1 to 5 halogen atoms, or Q is a pyridine ring of the formula (Q5)

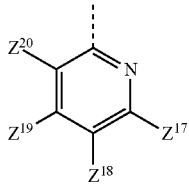

(Q5)

in which:
$Z^{17}$, $Z^{18}$, $Z^{19}$ and $Z^{20}$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, or Q is a 5-membered aromatic heterocycle of the formula (Q6)

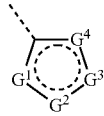

(Q6)

in which:
$G^1$-$G^4$ are independently selected from the group consisting of N, O, S, C—$Z^{21}$ and N—$Z^{22}$ wherein not more than one of $G^1$-$G^4$ is O, not more than one of $G^1$-$G^4$ is S, not more than one of $G^1$-$G^4$ is N—$Z^{22}$, and wherein each $Z^{21}$ is independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, and each $Z^{22}$ is independently selected from the group consisting of hydrogen, $C_1$-$C_4$-alkyl, $C_1$-$C_4$-halogenoalkyl having 1 to 5 halogen atoms, $C_1$-$C_4$-alkyl-$C_3$-$C_6$-cycloalkyl, $C_1$-$C_4$-alkoxy-$C_1$-$C_4$-alkyl, or Q is a 5-membered aromatic heterocycle of the formula (Q7)

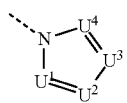

(Q7)

in which:
$U^1$-$U^4$ are independently selected from the group consisting of N and C—$Z^{23}$, wherein not more than three of $U^1$-$U^4$ are N, and wherein each $Z^{23}$ is independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, wherein when Y is O, S or N—$R^9$, none of $R^7$, $R^8$, $R^{10}$ and $R^{11}$ is —OH, and wherein when X is O, S or N—$R^9$, none of $R^7$ and $R^8$ is —OH, and stereoisomers, tautomers, N-oxides, hydrates, solvates, and salts thereof, and mixtures of same.

In accordance with a third embodiment of the first aspect, the present invention covers compounds of general formula (I), supra, in which:

A is A1 or A2,

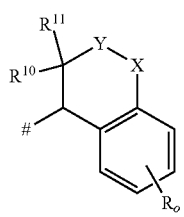

A1

-continued

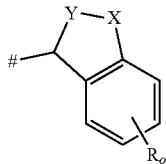

A2 o is 0, 1 or 2,

R is selected from the group consisting of hydrogen, halogen, $C_1$-$C_4$-alkyl and $C_1$-$C_4$-alkoxy, cyano, $C_1$-$C_4$-halogenoalkyl having 1 to 5 halogen atoms, X, Y are independently selected from the group consisting of $CR^7R^8$, O, S, and N—$R^9$, wherein at least one of X and Y is $CR^7R^8$, T is selected from $T^1$-$T^6$ as defined supra $R^1$ is selected from the group consisting of hydrogen, $C_1$-$C_4$-alkyl, $C_3$-$C_6$-cycloalkyl, $C_3$-$C_4$-alkenyl, $C_3$-$C_4$-alkynyl, $C_1$-$C_4$-alkoxy-$C_1$-$C_4$-alkyl, $C_3$-$C_6$-cycloalkyl-$C_1$-$C_3$-alkyl, cyano-$C_1$-$C_4$-alkyl, $R^2$ is selected from the group consisting of
hydrogen, halogen, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$;
—$NR^{12}R^{13}$;
—$OR^{14}$;
—$SR^{15}$, —S(O)$R^5$, —$SO_2R^{15}$;
$C_1$-$C_4$-alkyl, $C_3$-$C_6$-cycloalkyl, $C_2$-$C_4$-alkenyl, $C_3$-$C_6$-cycloalkenyl, $C_2$-$C_4$-alkynyl or phenyl-$C_1$-$C_4$-alkyl, each of which is optionally substituted by 1, 2, 3, 4 or 5 substituents independently selected from the group consisting of halogen, —OH, cyano, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms; and
a monocyclic or a bicyclic heterocycle selected from the group consisting of 4- to 10-membered heterocycloalkyl, heterospirocycloalkyl, 5-membered heteroaryl and 6-membered heteroaryl, each of which is optionally substituted by 1, 2, 3 or 4 substituents independently selected from the group consisting of halogen, cyano, —OH, oxo, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-alkyl-C(O)—, $C_1$-$C_4$-halogenoalkyl having 1 to 5 halogen atoms, $C_1$-$C_4$-alkoxy, hydroxy-$C_1$-$C_4$-alkyl, $C_1$-$C_4$-alkoxy-$C_1$-$C_4$-alkyl-, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, and 4- to 10-membered heterocycloalkyl, $R^3$ is selected from the group consisting of hydrogen, halogen or $C_1$-$C_4$-alkyl, $R^4$ is selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $R^5$ is selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $R^6$ is selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $R^7$ is selected from the group consisting of hydrogen and $C_1$-$C_4$-alkyl, $R^8$ is selected from the group consisting of hydrogen and $C_1$-$C_4$-alkyl, $R^9$ is $C_1$-$C_4$-alkyl, $R^{10}$ is selected from the group consisting of hydrogen, —OH, $C_1$-$C_4$-alkyl and $C_1$-$C_4$-alkoxy, $R^{11}$ is hydrogen, $R^{12}$ and $R^{13}$ are independently selected from the group consisting of
hydrogen, —NH(—C(O)—$C_1$-$C_4$-alkyl), $C_1$-$C_4$-alkoxy;
$C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, —NH—C(O)—$C_1$-$C_4$-alkyl, —N($C_1$-$C_4$-alkyl)-(—C(O)—$C_1$-$C_4$-alkyl), $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, —$SO_2$—$C_1$-$C_4$-halogenoalkyl having 1 to 5 halogen atoms and ($C_1$-$C_4$-alkoxy)$_2$P(=O)—;
heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, —OH, oxo, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;
phenyl, benzo-$C_5$-$C_6$-cycloalkyl, each of which is optionally substituted by 1, 2 or 3 substituents independently selected from the group consisting of halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms; and
a monocyclic or a bicyclic heterocycle selected from the group of 4- to 10-membered heterocycloalkyl, 5-membered heteroaryl and 6-membered heteroaryl, each of which is optionally substituted by 1, 2 or 3 substituents independently selected from the group consisting of halogen, cyano, —OH, oxo, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $R^{14}$ is selected from the group consisting of
$C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl; and
heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, —OH, oxo, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;

$R^{15}$ is selected from the group consisting of
  $C_1$-$C_4$-alkyl, phenyl-$C_1$-$C_4$-alkyl, each of which is optionally substituted by 1, 2 or 3 substituents independently selected from the group consisting of halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;
  heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;

Q is a substituted phenyl ring of the formula (Q1)

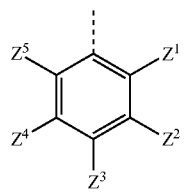

(Q1)

in which:
$Z^1$, $Z^2$, $Z^3$, $Z^4$, and $Z^5$ are independently selected from the group consisting of hydrogen, halogen, cyano, $C_1$-$C_4$-alkyl, $C_1$-$C_4$-halogenoalkyl having 1 to 5 halogen atoms, hydroxy, $C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, 4- to 6-membered heterocyclyl, which is optionally substituted with 1 or 2 substituents selected from the group consisting of fluorine, chlorine, bromine, methyl and cyano, —S—($C_1$-$C_4$-alkyl), —S(O)—($C_1$-$C_4$-alkyl), —SO$_2$—($C_1$-$C_4$-alkyl), or
$Z^1$ and $Z^2$ form, together with the carbon atoms that they are connected to, a 5- or 6-membered heterocycloalkyl, a 5-membered heteroaryl, or a 6-membered heteroaryl, each of which may be optionally substituted with one or two substitutents selected from the group consisting of methyl, fluorine and oxo, and
$Z^3$, $Z^4$, and $Z^5$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-alkoxy-C(O)—, $C_1$-$C_4$-halogenoalkoxy having 1 to 5 halogen atoms, or
$Z^2$ and $Z^3$ form, together with the carbon atoms that they are connected to, a 5- or 6-membered saturated or partially saturated heterocyclic ring, a 5-membered heteroaryl, or a 6-membered heteroaryl, each of which may be optionally substituted with one or two substitutents selected from the group consisting of methyl, fluorine and oxo, and
$Z^1$, $Z^4$, and $Z^5$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, or Q is a pyridine ring of the formula (Q2)

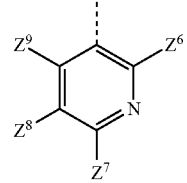

(Q2)

in which:
$Z^6$, $Z^7$, $Z^8$ and $Z^9$ are independently selected from the group consisting of hydrogen halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, or Q is a pyrimidine ring of the formula (Q3)

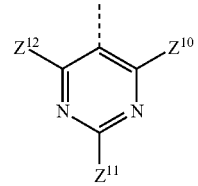

(Q3)

in which:
$Z^{10}$, $Z^{11}$ and $Z^{12}$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, or Q is a pyridine ring of the formula (Q4)

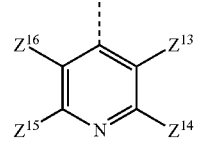

(Q4)

in which:
$Z^{13}$, $Z^{14}$, $Z^{15}$ and $Z^{16}$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_1$-$C_4$-hydroxyalkyl, NH$_2$, —NH($C_1$-$C_4$-alkyl), —N($C_1$-$C_4$-alkyl)$_2$, —NH—CO—$C_1$-$C_4$-alkyl, and monocyclic heterocycles selected from the group of 4- to 7-membered heterocycloalkyl or 5-membered heteroaryls having at least one nitrogen atom via which the heteroaryl ring is connected to the pyridine ring, each of which is optionally substituted with 1, 2 or 3 substituents independently selected from the group consisting of halogen, cyano, nitro, —OH, oxo, thiono, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —NH$_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —SO$_2$—$C_1$-$C_4$-alkyl, —S—($C_1$-$C_4$-halogenoalkyl) having 1 to 5 halogen atoms, —S(O)—($C_1$-$C_4$-halogenoalkyl) having 1 to 5 halogen atoms, —$SO_2$—($C_1$-$C_4$-halogenoalkyl) having 1 to 5 halogen atoms, or Q is a pyridine ring of the formula (Q5)

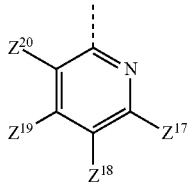

(Q5)

in which:

$Z^{17}$, $Z^{18}$, $Z^{19}$ and $Z^{20}$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, or Q is a 5-membered aromatic heterocycle of the formula (Q6)

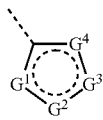

(Q6)

in which:

$G^1$-$G^4$ are independently selected from the group consisting of N, O, S, C—$Z^2$ and N—$Z^{22}$, wherein not more than one of $G^1$-$G^4$ is O, not more than one of $G^1$-$G^4$ is S, not more than one of $G^1$-$G^4$ is N—$Z^{22}$, and wherein each $Z^{21}$ is independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, and each $Z^{22}$ is independently selected from the group consisting of hydrogen, $C_1$-$C_4$-alkyl, $C_1$-$C_4$-halogenoalkyl having 1 to 5 halogen atoms, $C_1$-$C_4$-alkyl-$C_3$-$C_6$-cycloalkyl, $C_1$-$C_4$-alkoxy-$C_1$-$C_4$-alkyl, or Q is a 5-membered aromatic heterocycle of the formula (Q7)

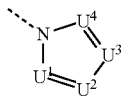

(Q7)

in which:

$U^1$-$U^4$ are independently selected from the group consisting of N and C—$Z^{23}$, wherein not more than three of $U^1$-$U^4$ are N, and wherein each $Z^{23}$ is independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, wherein when Y is O, S or N—$R^9$, $R^{10}$ is not —OH, and stereoisomers, tautomers, N-oxides, hydrates, solvates, and salts thereof, and mixtures of same.

In accordance with a fourth embodiment of the first aspect, the present invention covers compounds of general formula (I), supra, in which:

A is A1 or A2,

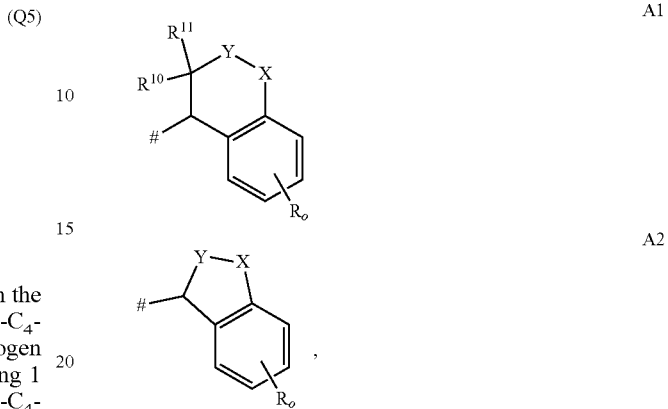

o is 0 or 1,

R is selected from the group consisting of hydrogen, halogen, $C_1$-$C_4$-alkyl and $C_1$-$C_4$-alkoxy, X is selected from the group consisting of $CR^7R^8$, O, S, and N—$R^9$, Y is $CR^7R^8$, T is selected from $T^1$-$T^6$ as defined supra $R^1$ is hydrogen or $C_1$-$C_4$-alkyl, $R^2$ is selected from the group consisting of hydrogen, halogen,
—$NR^{12}R^{13}$;
—$OR^{14}$;
—$SR^{15}$, —S(O)$R^{15}$, —$SO_2R^{15}$;

$C_1$-$C_4$-alkyl, $C_3$-$C_6$-cycloalkyl, $C_2$-$C_4$-alkenyl or $C_3$-$C_6$-cycloalkenyl, each of which is optionally substituted by 1, 2, 3, 4 or 5 substituents independently selected from the group consisting of halogen, cyano, $C_1$-$C_4$-alkoxy-C(O)— and —C(O)—$NH_2$; and a monocyclic or a bicyclic heterocycle selected from the group consisting of 4- to 10-membered heterocycloalkyl, heterospirocycloalkyl, 5-membered heteroaryl, and 6-membered heteroaryl, each of which is optionally substituted by 1, 2, 3 or 4 substituents independently selected from the group consisting of halogen, —OH, oxo, —COOH, $C_1$-$C_4$-alkoxy-C(O)—, —C(O)—$NH_2$, $C_1$-$C_4$-alkyl, $C_1$-$C_4$-alkyl-C(O)—, $C_1$-$C_4$-halogenoalkyl having 1 to 5 halogen atoms, hydroxy-$C_1$-$C_4$-alkyl-, $C_1$-$C_4$-alkoxy-$C_1$-$C_4$-alkyl-, —$NH_2$, —N($C_1$-$C_4$-alkyl)$_2$, and 4- to 10-membered heterocycloalkyl, $R^3$ is selected from the group consisting of hydrogen, halogen or $C_1$-$C_4$-alkyl, $R^4$ is selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $R^5$ is selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $R^6$ is selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $R^7$ is selected from the group consisting of hydrogen and $C_1$-$C_4$-alkyl, $R^8$ is selected from the group consisting of hydrogen and $C_1$-$C_4$-alkyl, $R^9$ is $C_1$-$C_4$-alkyl, $R^{10}$ is selected from the group consisting of hydrogen, —OH and $C_1$-$C_4$-alkyl, $R^{11}$ is hydrogen, $R^{12}$ and $R^{13}$ are independently selected from the group consisting of hydrogen, —NH(—C(O)—$C_1$-$C_4$-alkyl), $C_1$-$C_4$-alkoxy;

$C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, —COOH, $C_1$-$C_4$-alkoxy-C(O)—, —C(O)—$NH_2$, —C(O)—N($C_1$-$C_4$-alkyl)$_2$, —NH—C(O)—$C_1$-$C_4$-alkyl, $C_1$-$C_4$-alkyl, $C_1$-$C_4$-alkoxy, $C_3$-$C_6$-cycloalkyl, —$NH_2$, —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, and ($C_1$-$C_4$-alkoxy)$_2$P(=O)—;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, —OH, oxo, $C_1$-$C_4$-alkyl, $C_1$-$C_4$-halogenoalkyl having 1 to 5 halogen atoms and $C_1$-$C_4$-alkoxy;

phenyl and benzo-$C_5$-$C_6$-cycloalkyl, each of which is optionally substituted by 1, 2 or 3 substituents independently selected from the group consisting of halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms; and a monocyclic or a bicyclic heterocycle selected from the group of 4- to 10-membered heterocycloalkyl, 5-membered heteroaryl and 6-membered heteroaryl each of which is optionally substituted by 1, 2 or 3 substituents independently selected from the group consisting of halogen, —OH, oxo, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $R^{14}$ is selected from the group consisting of $C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, $C_1$-$C_4$-alkyl, $C_1$-$C_4$-alkoxy and $C_3$-$C_6$-cycloalkyl; and 4- to 10-membered heterocycloalkyl, $R^{15}$ is selected from the group consisting of $C_1$-$C_4$-alkyl, which is optionally substituted by 1, 2 or 3 substituents independently selected from the group consisting of —OH and —COOH; and a 6-membered heteroaryl, Q is a substituted phenyl ring of the formula (Q1)

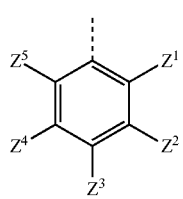

(Q1)

in which:

$Z^1$ is selected from the group consisting of hydrogen, halogen, $C_1$-$C_4$-alkyl and $C_1$-$C_4$-alkoxy, $Z^2$ is selected from the group consisting of hydrogen, halogen, —OH, $C_1$-$C_4$-alkyl, $C_1$-$C_4$-alkoxy, —NH($C_1$-$C_4$-alkyl), —N($C_1$-$C_4$-alkyl)$_2$, —NH($C_3$-$C_6$-cycloalkyl), —N($C_1$-$C_4$-alkyl)($C_3$-$C_6$-cycloalkyl), $C_1$-$C_4$-halogenoalkyl having 1 to 5 halogen atoms, $C_1$-$C_4$-halogenoalkoxy having 1 to 5 halogen atoms, —S—($C_1$-$C_4$-alkyl) and a 4- to 6-membered heterocycloalkyl, and $Z^3$ is selected from the group consisting of hydrogen, halogen, $C_1$-$C_4$-alkyl, $C_1$-$C_4$-alkoxy, —NH($C_1$-$C_4$-alkyl) and —N($C_1$-$C_4$-alkyl)$_2$, $Z^4$ is selected from the group consisting of hydrogen, halogen, —OH, $C_1$-$C_4$-alkyl, $C_1$-$C_4$-alkoxy, —NH($C_1$-$C_4$-alkyl), —N($C_1$-$C_4$-alkyl)$_2$, —NH($C_3$-$C_6$-cycloalkyl), —N($C_1$-$C_4$-alkyl)($C_3$-$C_6$-cycloalkyl), $C_1$-$C_4$-halogenoalkyl having 1 to 5 halogen atoms, $C_1$-$C_4$-halogenoalkoxy having 1 to 5 halogen atoms, —S—($C_1$-$C_4$-alkyl) and a 4- to 6-membered heterocycloalkyl, $Z^5$ is selected from the group consisting of hydrogen, halogen, $C_1$-$C_4$-alkyl, and $C_1$-$C_4$-alkoxy, Q is a pyridine ring of the formula (Q4)

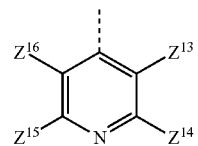

(Q4)

in which:

$Z^{13}$, $Z^{14}$, $Z^{15}$ and $Z^{16}$ are independently selected from the group consisting of hydrogen, halogen, cyano, $C_1$-$C_4$-alkyl, $C_1$-$C_4$-alkoxy, $C_1$-$C_4$-hydroxyalkyl, $NH_2$, —NH($C_1$-$C_4$-alkyl), —N($C_1$-$C_4$-alkyl)$_2$, —NH—CO—$C_1$-$C_4$-alkyl, and monocyclic heterocycles selected from the group of 4- to 7-membered heterocycloalkyl or 5-membered heteroaryls having at least one nitrogen atom via which the heteroaryl ring is connected to the pyridine ring, each of which is optionally substituted with 1, 2 or 3 substituents independently selected from the group consisting of halogen, cyano, nitro, —OH, oxo, thiono, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—($C_1$-$C_4$-halogenoalkyl) having 1 to 5 halogen atoms, —S(O)—($C_1$-$C_4$-halogenoalkyl) having 1 to 5 halogen atoms, —$SO_2$—($C_1$-$C_4$-halogenoalkyl) having 1 to 5 halogen atoms, or Q is a pyridine ring of the formula (Q5)

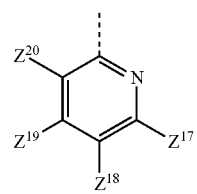

(Q5)

in which:

$Z^{17}$, $Z^{18}$, $Z^{19}$ and $Z^{20}$ are independently selected from the group consisting of hydrogen, halogen, $C_1$-$C_4$-alkyl and $C_1$-$C_4$-alkoxy, or Q is a 5-membered aromatic heterocycle of the formula (Q6)

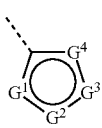

(Q6)

in which:
$G^1$-$G^4$ are independently selected from the group consisting of N, O, S, C—$Z^{21}$ and N—$Z^{22}$ wherein not more than one of $G^1$-$G^4$ is O, not more than one of $G^1$-$G^4$ is S, not more than one of $G^1$-$G^4$ is N—$Z^{22}$, and wherein
each $Z^{21}$ is independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, and
each $Z^{22}$ is independently selected from the group consisting of hydrogen, $C_1$-$C_4$-alkyl, $C_1$-$C_4$-halogenoalkyl having 1 to 5 halogen atoms, $C_1$-$C_4$-alkyl-$C_3$-$C_6$-cycloalkyl, $C_1$-$C_4$-alkoxy-$C_1$-$C_4$-alkyl, or
Q is a 5-membered aromatic heterocycle of the formula (Q7)

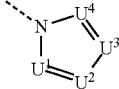

(Q7)

in which:
$U^1$-$U^4$ are independently selected from the group consisting of N and C—$Z^{23}$, wherein not more than three of $U^1$-$U^4$ are N, and wherein
each $Z^{23}$ is independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy,
and stereoisomers, tautomers, N-oxides, hydrates, solvates, and salts thereof, and mixtures of same.

A particular embodiment of the first aspect, the present invention covers compounds of general formula (I) according to the second, third or fourth embodiment supra, in which:
Q is a substituted phenyl ring of the formula (Q1)

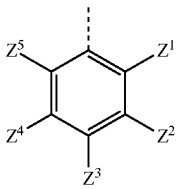

(Q1)

in which:
$Z^1$, $Z^2$, $Z^3$, $Z^4$, and $Z^5$ are independently selected from the group consisting of hydrogen, halogen, SF$_5$, cyano, —CHO, nitro, $C_1$-$C_4$-alkyl, $C_1$-$C_4$-halogenoalkyl having 1 to 5 halogen atoms, hydroxy, $C_1$-$C_4$-alkoxy, $C_3$-$C_6$-cycloalkyl-$C_1$-$C_4$-alkoxy, cyano-$C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, —NH—SO$_2$—($C_1$-$C_4$-alkyl), —N(SO$_2$—[$C_1$-$C_4$-alkyl])($C_1$-$C_4$-alkyl), ($C_1$-$C_4$-alkoxyimino)-$C_1$-$C_4$-alkyl, 4- to 6-membered heterocyclyl, which is optionally substituted with 1 or 2 substituents selected from the group consisting of fluorine, chlorine, bromine, methyl and cyano, —CH$_2$—O—($C_1$-$C_4$-alkyl), —CH$_2$—NH($C_1$-$C_4$-alkyl), —CH$_2$—N($C_1$-$C_4$-alkyl)$_2$, methyl substituted with a 4- to 6-membered heterocyclyl which itself is optionally substituted with 1 or 2 substituents selected from the group consisting of fluorine, chlorine, bromine, methyl and cyano, —CH$_2$—S—($C_1$-$C_4$-alkyl), —CH$_2$—S(O)—($C_1$-$C_4$-alkyl), —CH$_2$—SO$_2$—($C_1$-$C_4$-alkyl), —S—($C_1$-$C_4$-alkyl), —S(O)—($C_1$-$C_4$-alkyl), —SO$_2$—($C_1$-$C_4$-alkyl), —S—($C_1$-$C_4$-halogenoalkyl) having 1 to 5 halogen atoms, —S(O)—($C_1$-$C_4$-halogenoalkyl) having 1 to 5 halogen atoms, —SO$_2$—($C_1$-$C_4$-halogenoalkyl) having 1 to 5 halogen atoms, —CONH($C_1$-$C_4$-alkyl), —CONH($C_3$-$C_6$-cycloalkyl), —NHCO($C_1$-$C_4$-alkyl), —NHCO($C_3$-$C_6$-cycloalkyl), —NHCO($C_1$-$C_4$-halogenoalkyl) having 1 to 5 halogen atoms, or
$Z^1$ and $Z^2$ form, together with the carbon atoms that they are connected to, a 5- or 6-membered saturated or partially saturated heterocyclic ring, a 5-membered heteroaryl, or a 6-membered heteroaryl, each of which may be optionally substituted with one or two substitutents selected from the group consisting of methyl, fluorine and oxo, and
$Z^3$, $Z^4$, and $Z^5$ are independently selected from the group consisting of hydrogen, halogen, SF$_5$, cyano, CHO, nitro, $C_1$-$C_4$-alkyl, $C_1$-$C_4$-halogenoalkyl having 1 to 5 halogen atoms, hydroxy, $C_1$-$C_4$-alkoxy, $C_3$-$C_6$-cycloalkyl-$C_1$-$C_4$-alkoxy, cyano-$C_1$-$C_4$-alkoxy, $C_1$-$C_4$-alkoxy-C(O)—, $C_1$-$C_4$-halogenoalkoxy having 1 to 5 halogen atoms, —NH($C_1$-$C_4$-alkyl), —N($C_1$-$C_4$-alkyl)$_2$, —NH—SO$_2$—($C_1$-$C_4$-alkyl), —N(SO$_2$—[$C_1$-$C_4$-alkyl])($C_1$-$C_4$-alkyl), ($C_1$-$C_4$-alkoxyimino)-$C_1$-$C_4$-alkyl, 4- to 6-membered heterocycloalkyl which is optionally substituted with 1 or 2 substituents selected from the group consisting of fluorine, methyl or cyano, —CH$_2$—O—($C_1$-$C_4$-alkyl), —CH$_2$—NH($C_1$-$C_4$-alkyl), —CH$_2$—N($C_1$-$C_4$-alkyl)$_2$, methyl substituted with a 4- to 6-membered heterocycloalkyl which itself is optionally substituted with 1 or 2 substituents selected from the group consisting of fluorine, methyl or cyano, —CH$_2$—S—($C_1$-$C_4$-alkyl), —CH$_2$—S(O)—($C_1$-$C_4$-alkyl), —CH$_2$—SO$_2$—($C_1$-$C_4$-alkyl), —S—($C_1$-$C_4$-alkyl), —S(O)—($C_1$-$C_4$-alkyl), —SO$_2$—($C_1$-$C_4$-alkyl), —S—($C_1$-$C_4$-halogenoalkyl) having 1 to 5 halogen atoms, —S(O)—($C_1$-$C_4$-halogenoalkyl) having 1 to 5 halogen atoms, —SO$_2$—($C_1$-$C_4$-halogenoalkyl) having 1 to 5 halogen atoms, —CONH($C_1$-$C_4$-alkyl), —CONH($C_3$-$C_6$-cycloalkyl), —NHCO($C_1$-$C_4$-alkyl), —NHCO($C_3$-$C_6$-cycloalkyl), —NHCO($C_1$-$C_4$-halogenoalkyl) having 1 to 5 halogen atoms, or
$Z^2$ and $Z^3$ form, together with the carbon atoms that they are connected to, a 5- or 6-membered saturated or partially saturated heterocyclic ring, a 5-membered heteroaryl, or a 6-membered heteroaryl, each of which may be optionally substituted with one or two substitutents selected from the group consisting of methyl, fluorine and oxo, and
$Z^1$, $Z^4$, and $Z^5$ are independently selected from the group consisting of hydrogen, halogen, SF$_5$, cyano, CHO, nitro, $C_1$-$C_4$-alkyl, $C_1$-$C_4$-halogenoalkyl having 1 to 5 halogen atoms, hydroxy, $C_1$-$C_4$-alkoxy, $C_3$-$C_6$-cycloalkyl-$C_1$-$C_4$-alkoxy, cyano-$C_1$-$C_4$-alkoxy, $C_1$-$C_4$-halogenoalkoxy having 1 to 5 halogen atoms, —NH($C_1$-$C_4$- alkyl), —N(C$_1$-C$_4$-alkyl)$_2$, —NH—SO$_2$—(C$_1$-C$_4$-alkyl), —N(SO$_2$—[C$_1$-C$_4$-alkyl])(C$_1$-C$_4$-alkyl), (C$_1$-C$_4$-alkoxyimino)-C$_1$-C$_4$-alkyl, 4- to 6-membered heterocycloalkyl which is optionally substituted with 1 or 2 substituents selected from the group consisting of fluorine, methyl or cyano, —CH$_2$—O—(C$_1$-C$_4$-alkyl), —CH$_2$—NH(C$_1$-C$_4$-alkyl), —CH$_2$—N(C$_1$-C$_4$-alkyl)$_2$, methyl substituted with a 4- to 6-membered heterocycloalkyl which itself is optionally substituted with 1 or 2 substituents selected from the group consisting of fluorine, methyl or cyano, —CH$_2$—S—(C$_1$-C$_4$-alkyl), —CH$_2$—S(O)—(C$_1$-C$_4$-alkyl), —CH$_2$—SO$_2$—(C$_1$-C$_4$-alkyl), —S—(C$_1$-C$_4$-alkyl), —S(O)—(C$_1$-C$_4$-alkyl), —SO$_2$—(C$_1$-C$_4$-alkyl), —S—(C$_1$-C$_4$-halogenoalkyl) having 1 to 5 halogen atoms, —S(O)—(C$_1$-C$_4$-halogenoalkyl) having 1 to 5 halogen atoms, —SO$_2$—(C$_1$-C$_4$-halogenoalkyl) having 1 to 5 halogen atoms, —CONH(C$_1$-C$_4$-alkyl), —CONH(C$_3$-C$_6$-cycloalkyl), —NHCO(C$_1$-C$_4$-alkyl), —NHCO(C$_3$-C$_6$-cycloalkyl), —NHCO(C$_1$-C$_4$-halogenoalkyl) having 1 to 5 halogen atoms, and stereoisomers, tautomers, N-oxides, hydrates, solvates, and salts thereof, and mixtures of same.

A particular embodiment of the first aspect, the present invention covers compounds of general formula (I) according to the second, third or fourth embodiment supra, in which:

Q is a substituted phenyl ring of the formula (Q1)

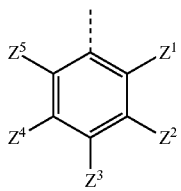

(Q1)

in which:

$Z^1$, $Z^2$, $Z^3$, $Z^4$, and $Z^5$ are independently selected from the group consisting of hydrogen, halogen, cyano, C$_1$-C$_4$-alkyl, C$_1$-C$_4$-halogenoalkyl having 1 to 5 halogen atoms, hydroxy, C$_1$-C$_4$-alkoxy, C$_1$-C$_4$-halogenoalkoxy having 1 to 5 halogen atoms, —NH(C$_1$-C$_4$-alkyl), —N(C$_1$-C$_4$-alkyl)$_2$, —NH(C$_3$-C$_6$-cycloalkyl), —N(C$_1$-C$_4$-alkyl)(C$_3$-C$_6$-cycloalkyl), 4- to 6-membered heterocyclyl, which is optionally substituted with 1 or 2 substituents selected from the group consisting of fluorine, chlorine, bromine, methyl and cyano, —S—(C$_1$-C$_4$-alkyl), —S(O)—(C$_1$-C$_4$-alkyl), —SO$_2$—(C$_1$-C$_4$-alkyl), or $Z^1$ and $Z^2$ form, together with the carbon atoms that they are connected to, a 5- or 6-membered heterocycloalkyl, a 5-membered heteroaryl, or a 6-membered heteroaryl, each of which may be optionally substituted with one or two substituents selected from the group consisting of methyl, fluorine and oxo, and $Z^3$, $Z^4$, and $Z^5$ are independently selected from the group consisting of hydrogen, halogen, cyano, C$_1$-C$_4$-alkyl, C$_1$-C$_4$-halogenoalkyl having 1 to 5 halogen atoms, C$_1$-C$_4$-alkoxy, C$_1$-C$_4$-alkoxy-C(O)—, C$_1$-C$_4$-halogenoalkoxy having 1 to 5 halogen atoms, or $Z^2$ and $Z^3$ form, together with the carbon atoms that they are connected to, a 5- or 6-membered saturated or partially saturated heterocyclic ring, a 5-membered heteroaryl, or a 6-membered heteroaryl, each of which may be optionally substituted with one or two substitutents selected from the group consisting of methyl, fluorine and oxo, and $Z^1$, $Z^4$, and $Z^5$ are independently selected from the group consisting of hydrogen, halogen, cyano, C$_1$-C$_4$-alkyl, C$_1$-C$_4$-halogenoalkyl having 1 to 5 halogen atoms, C$_1$-C$_4$-alkoxy, C$_1$-C$_4$-halogenoalkoxy having 1 to 5 halogen atoms, and stereoisomers, tautomers, N-oxides, hydrates, solvates, and salts thereof, and mixtures of same.

A particular embodiment of the first aspect, the present invention covers compounds of general formula (I) according to the second, third or fourth embodiment supra, in which:

Q is a substituted phenyl ring of the formula (Q1)

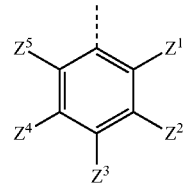

(Q1)

in which:

$Z^1$ is selected from the group consisting of hydrogen, halogen, C$_1$-C$_4$-alkyl and C$_1$-C$_4$-alkoxy, $Z^2$ is selected from the group consisting of hydrogen, halogen, —OH, C$_1$-C$_4$-alkyl, C$_1$-C$_4$-alkoxy, —NH(C$_1$-C$_4$-alkyl), —N(C$_1$-C$_4$-alkyl)$_2$, —NH(C$_3$-C$_6$-cycloalkyl), —N(C$_1$-C$_4$-alkyl)(C$_3$-C$_6$-cycloalkyl), C$_1$-C$_4$-halogenoalkyl having 1 to 5 halogen atoms, C$_1$-C$_4$-halogenoalkoxy having 1 to 5 halogen atoms, —S—(C$_1$-C$_4$-alkyl) and a 4- to 6-membered heterocycloalkyl, and $Z^3$ is selected from the group consisting of hydrogen, halogen, C$_1$-C$_4$-alkyl, C$_1$-C$_4$-alkoxy, —NH(C$_1$-C$_4$-alkyl) and —N(C$_1$-C$_4$-alkyl)$_2$, $Z^4$ is selected from the group consisting of hydrogen, halogen, —OH, C$_1$-C$_4$-alkyl, C$_1$-C$_4$-alkoxy, —NH(C$_1$-C$_4$-alkyl), —N(C$_1$-C$_4$-alkyl)$_2$, —NH(C$_3$-C$_6$-cycloalkyl), —N(C$_1$-C$_4$-alkyl)(C$_3$-C$_6$-cycloalkyl), C$_1$-C$_4$-halogenoalkyl having 1 to 5 halogen atoms, C$_1$-C$_4$-halogenoalkoxy having 1 to 5 halogen atoms, —S—(C$_1$-C$_4$-alkyl) and a 4- to 6-membered heterocycloalkyl, $Z^5$ is selected from the group consisting of hydrogen, halogen, C$_1$-C$_4$-alkyl, and C$_1$-C$_4$-alkoxy In accordance with a fifth embodiment of the first aspect, the present invention covers compounds of general formula (I), supra, in which:

A is selected from the group consisting of

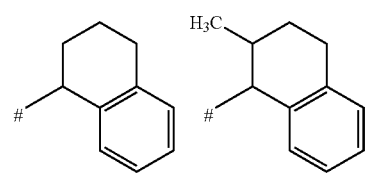

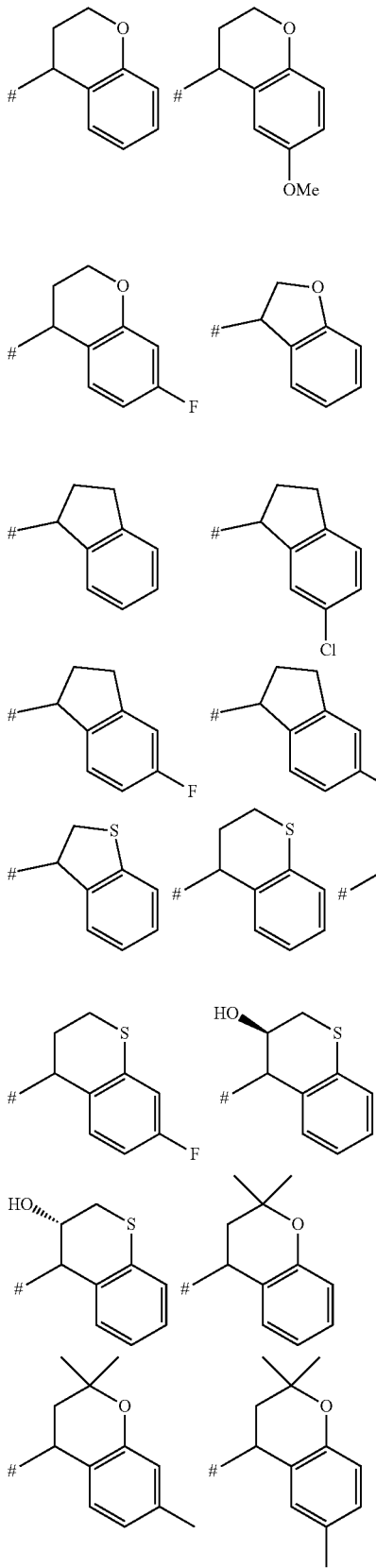
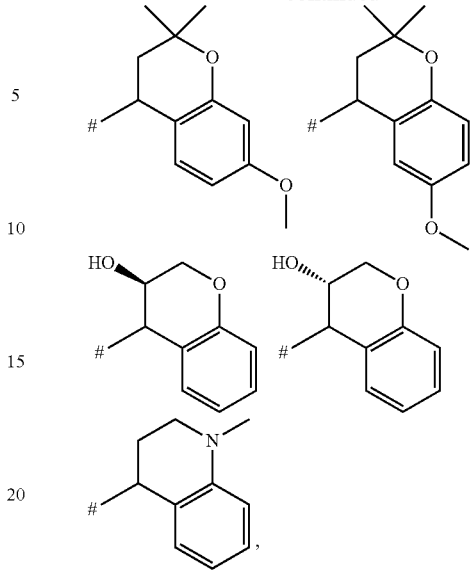

T is selected from T¹-T⁶ as defined supra

R¹ is hydrogen or methyl,

R² is selected from the group consisting of hydrogen, chlorine, fluorine, bromine, —NR$^{12}$R$^{13}$;

—OR$^{14}$;

—SR$^5$, —S(O)R$^5$, —SO$_2$R$^{15}$;

methyl, ethyl, propyl, isopropyl, cyclopropyl, cyclohexyl, propenyl, cyclopentenyl, cyclohexenyl, each of which is optionally substituted by 1 or 2 substituents independently selected from the group consisting of cyano, ethoxy-C(O)—, and —C(O)—NH$_2$; and a monocyclic or a bicyclic heterocycle selected from the group consisting of azetidine, pyrrolidine, pyrazolidine, imidazolidine, 1,2,4-triazolidine, piperidine, piperazine, tetrahydropyridine, dihydro-2H-pyrane, tetrahydropyrane, 1,2-oxazolidine, 1,2-oxazine, morpholine, thiomorpholine, 3,4-dihydroisoquinoline, 2,3-dihydro-indole, 1,3-dihydro-isoindole, 3,9-dioxa-7-azabicyclo[3.3.1]nonane, 6-oxa-3-azabicyclo[3.1.1]heptane, 8-oxa-3-azabicyclo[3.2.1]octane, imidazole, pyrazole, 1,2,4-triazole, 1,2,3-triazole, 4-oxa-7-azaspiro[2.5]octane, each of which is optionally substituted by 1, 2, 3 or 4 substituents independently selected from the group consisting of fluorine, chlorine, cyano, —OH, oxo, —COOH, methoxy-C(O)—, ethoxy-C(O)—, tert-butoxy-C(O)—, —C(O)—NH$_2$, methyl, methyl-C(O)—, trifluoromethyl, hydroxymethyl-, methoxymethyl-, —NH$_2$, —NMe$_2$, pyrrolidine, R³ is hydrogen, chlorine or methyl, R⁴ is selected from the group consisting of hydrogen, fluorine, chlorine, cyano, methyl, methoxy and trifluoromethyl, R⁵ is selected from the group consisting of hydrogen, fluorine, chlorine and methyl, R⁶ is selected from the group consisting of hydrogen, fluorine, chlorine, methyl and methoxy, R$^{12}$ and R$^{13}$ are independently selected from the group consisting of hydrogen, —NH(—C(O)-methyl), methoxy;

methyl, ethyl, propyl, isopropyl, butyl, isobutyl, cyclopropyl, cyclobutyl, benzyl, 1-phenylethyl, each of which is optionally substituted by 1, 2 or 3 substituents independently selected from the group consisting of fluorine, —OH, —COOH, methoxy-C(O)—, ethoxy-C(O)—, tert-butoxy-C(O)—, —C(O)—NH$_2$, —C(O)—NMe$_2$, —NH—C(O)-methyl, methyl, methoxy, cyclopropyl, —NH$_2$, NMe$_2$, S-methyl, S(O)-methyl, SO$_2$-methyl, and (EtO)$_2$P(=O)—;

heterocyclyl-methyl, heterocyclyl-ethyl, wherein the heterocyclyl substituent is selected from the group consisting of pyrrolidine, morpholine, pyrazole, 1,2,4-oxadiazole, pyridine, each of which is optionally substituted by 1 substituent independently selected from the group consisting of fluorine, chlorine, —OH, oxo and methyl;

phenyl; and a monocyclic or a bicyclic heterocycle selected from the group of oxetane, thietane, pyrrolidine, morpholine, tetrahydropyrane, pyridine and pyrazole, each of which is optionally substituted by 1 or 2 substituents independently selected from the group consisting of fluorine, chlorine, —OH, oxo, methyl;

$R^{14}$ is selected from the group consisting of methyl, ethyl, isopropyl, butyl, cyclopentyl, benzyl, each of which is optionally substituted by 1 or 2 substituents independently selected from the group consisting of fluorine, —OH, methyl, methoxy and cyclopentyl; and a monocyclic or a bicyclic heterocycle selected from the group consisting of pyrrolidine and tetrahydropyrane, $R^{15}$ is selected from the group consisting of methyl and ethyl, each of which is optionally substituted by 1 substituent independently selected from the group consisting of —OH and —COOH; and pyridine, Q is a substituted phenyl ring of the formula (Q1)

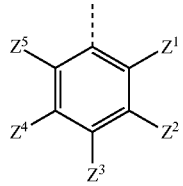

(Q1)

in which:

$Z^1$ and $Z^5$ are independently selected from the group consisting of hydrogen, fluorine, chlorine, methyl and methoxy, $Z^2$ and $Z^4$ are independently selected from the group consisting of hydrogen, fluorine, chlorine, —OH, methyl, ethyl, —NHMe, —NMe$_2$, trifluoromethyl, methoxy, trifluoromethoxy, —SMe and morpholinyl, and $Z^3$ is independently selected from the group consisting of hydrogen, fluorine, chlorine, methyl, methoxy and —NMe$_2$, and stereoisomers, tautomers, N-oxides, hydrates, solvates, and salts thereof, and mixtures of same.

In accordance with a sixth embodiment of the first aspect, the present invention covers compounds of general formula (I), supra, in which:

T, A and $R^1$ to $R^{15}$ have the meaning as defined for the fifth embodiment of the first aspect supra, and wherein Q is a pyridine ring of the formula (Q4)

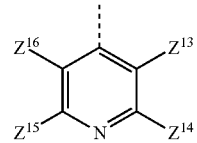

(Q4)

in which:

$Z^{13}$, $Z^{14}$, $Z^{15}$ and $Z^{16}$ are independently selected from the group consisting of hydrogen, fluorine, chlorine, cyano, methyl, methoxy, ethoxy, isopropoxy, hydroxymethyl, NH$_2$, —NHMe-NMe$_2$, —NH—C(O)-Me, morpholinyl, or Q is a pyridine ring of the formula (Q5)

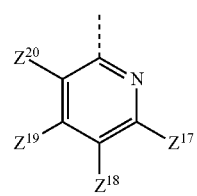

(Q5)

in which:

$Z^{17}$, $Z^{18}$, $Z^{19}$ and $Z^{20}$ are independently selected from the group consisting of hydrogen, fluorine, chlorine, methyl, ethyl, methoxy and ethoxy, or Q is selected from the group consisting of

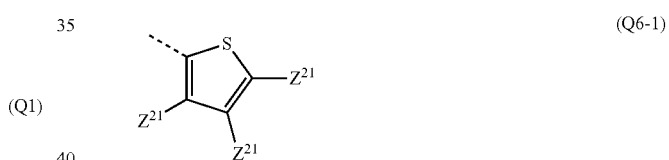

(Q6-1)

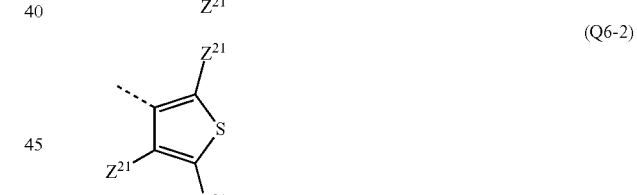

(Q6-2)

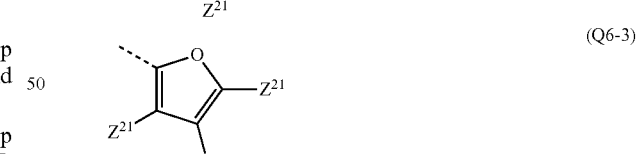

(Q6-3)

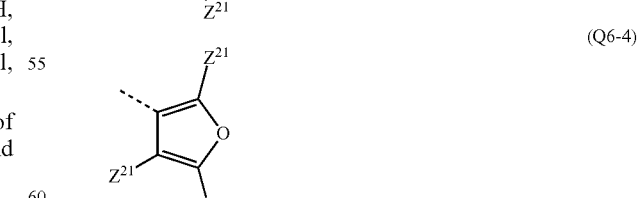

(Q6-4)

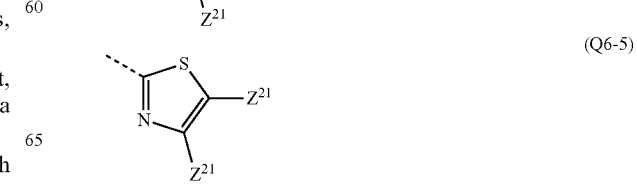

(Q6-5)

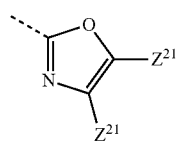 (Q6-6)
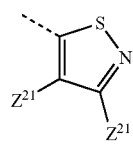 (Q6-7)
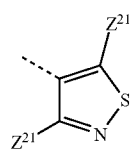 (Q6-8)
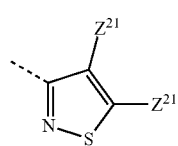 (Q6-9)
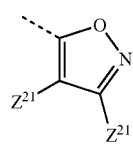 (Q6-10)
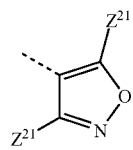 (Q6-11)
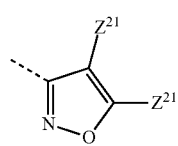 (Q6-12)
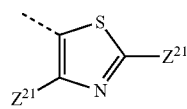 (Q6-13)
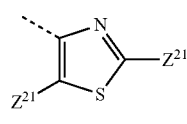 (Q6-14)
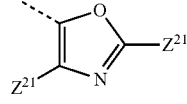 (Q6-15)
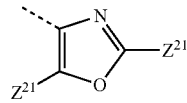 (Q6-16)
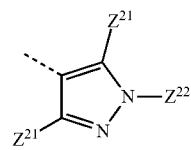 (Q6-17)
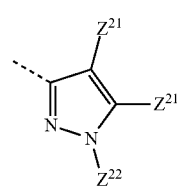 (Q6-18)
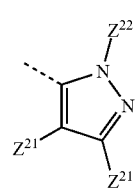 (Q6-19)
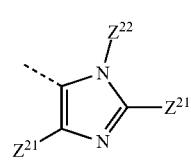 (Q6-20)
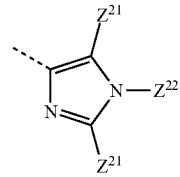 (Q6-21)
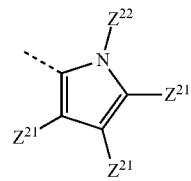 (Q6-22)
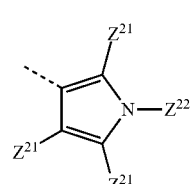 (Q6-23)
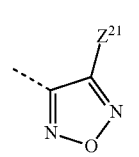 (Q6-24)
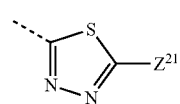 (Q6-25)
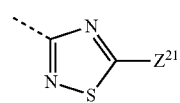 (Q6-26)

-continued
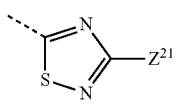 (Q6-27)
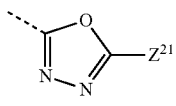 (Q6-28)
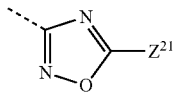 (Q6-29)
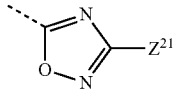 (Q6-30)
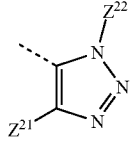 (Q6-31)
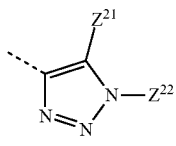 (Q6-32)
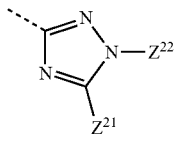 (Q6-33)
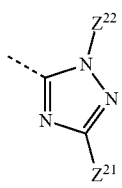 (Q6-34)
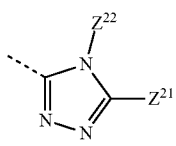 (Q6-35)
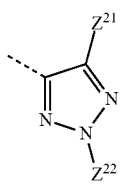 (Q6-36)
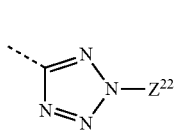 (Q6-37)
-continued
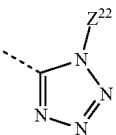 (Q6-38)
in which:
each $Z^{21}$ is independently selected from the group consisting of hydrogen, fluorine, chlorine, cyano, methyl, trifluoromethyl, methoxy and
$Z^{22}$ is hydrogen, methyl, or
Q is selected from the group consisting of
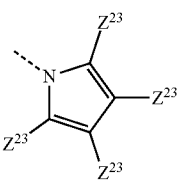 (Q7-1)
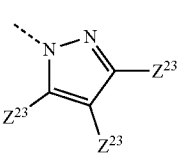 (Q7-2)
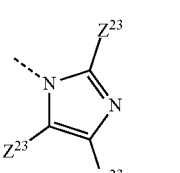 (Q7-3)
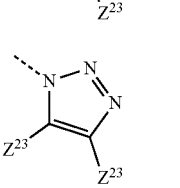 (Q7-4)
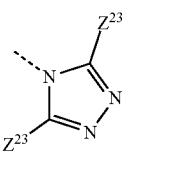 (Q7-5)
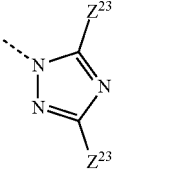 (Q7-6)
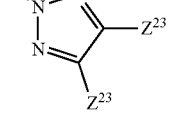 (Q7-7)

-continued

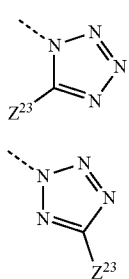

(Q7-8)

(Q7-9)

in which:
each $Z^{23}$ is independently selected from the group consisting of hydrogen, fluorine, chlorine, cyano, methyl, trifluoromethyl, methoxy, or
Q is selected from the group consisting of

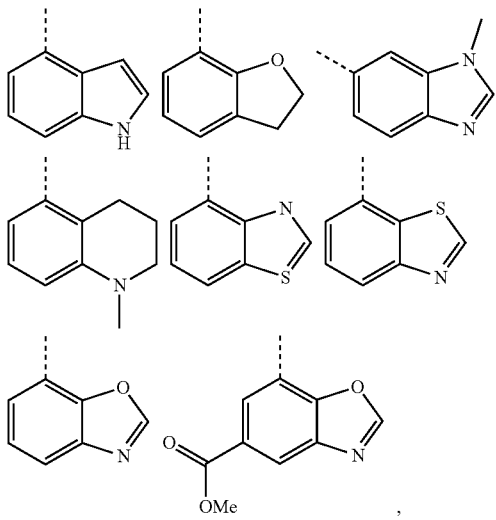

and stereoisomers, tautomers, N-oxides, hydrates, solvates, and salts thereof, and mixtures of same.

In an alternative embodiment of the fifth and sixth embodiment of the first aspect of the present invention supra, A is selected from the group consisting of:

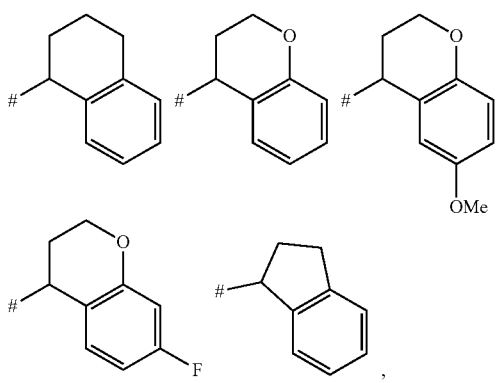

In a further alternative embodiment of the fifth and sixth embodiment of the first aspect of the present invention supra, A is selected from the group consisting of:

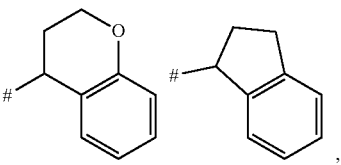

preferably A is

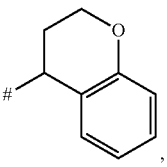

,

In accordance with a seventh embodiment of the first aspect, the present invention covers compounds of general formula (I), supra, in which:
A is selected from the group consisting of:

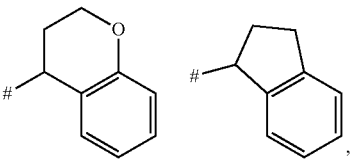

, preferably A is

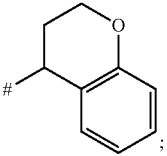

;

T is selected from $T^1$-$T^6$ as defined supra
$R^1$ is hydrogen or methyl,
$R^2$ is selected from the group consisting of
  hydrogen, chlorine, fluorine, bromine,
  —$NH_2$, —$NH(CH_3)$, —$N(CH_3)_2$,
  methoxy, ethoxy,
  methyl, ethyl, propyl, isopropyl, cyclopropyl; and
  a monocyclic heterocycle selected from the group consisting of azetidine, pyrrolidine, pyrazolidine, imidazolidine, 1,2,4-triazolidine, piperazine, 1,2-oxazolidine, morpholine, thiomorpholine, tetrahydropyrane, imidazole, pyrazole, 1,2,3-triazole, each of which is optionally substituted by 1, 2, 3 or 4 substituents independently selected from the group consisting of fluorine, —OH, oxo, —COOH, methoxy-C(O)—, ethoxy-C(O)—, tert-butoxy-C(O)—, —C(O)—$NH_2$, methyl, methyl-C(O)—, trifluoromethyl, hydroxymethyl-, methoxymethyl-, —$NH_2$, —$NMe_2$, pyrrolidine,
$R^3$ is hydrogen,
$R^4$ is selected from the group consisting of hydrogen, chlorine, fluorine, methyl, methoxy and trifluoromethyl,
$R^5$ is selected from the group consisting of hydrogen, chlorine, fluorine and methyl, $R^6$ is selected from the group consisting of hydrogen, fluorine, methyl and methoxy, Q is a substituted phenyl ring of the formula (Q1)

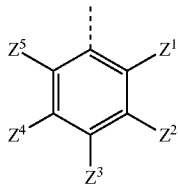
(Q1)

in which:
$Z^1$ and $Z^5$ are independently selected from the group consisting of hydrogen, fluorine, chlorine, methyl and methoxy, $Z^2$ and $Z^4$ are independently selected from the group consisting of hydrogen, fluorine, chlorine, —OH, methyl, ethyl, —NHMe, —NMe$_2$, trifluoromethyl, methoxy, trifluoromethoxy, —SMe and morpholinyl, and $Z^3$ is independently selected from the group consisting of hydrogen, fluorine, chlorine, methyl, methoxy and —NMe$_2$ and stereoisomers, tautomers, N-oxides, hydrates, solvates, and salts thereof, and mixtures of same.

In accordance with an eighth embodiment of the first aspect, the present invention covers compounds of general formula (I), supra, in which:

A is

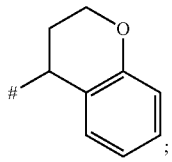;

T is selected from $T^1$-$T^6$ as defined supra
$R^1$ is hydrogen or methyl,
$R^2$ is selected from the group consisting of
hydrogen, chlorine, fluorine, bromine,
—NH$_2$, —NH(CH$_3$), —N(CH$_3$)$_2$,
methoxy, ethoxy,
methyl, ethyl, propyl, isopropyl, cyclopropyl; and
a monocyclic heterocycle selected from the group consisting of tetrahydropyrane, morpholine, and 2-fluoro azetidine,
$R^3$ is hydrogen,
$R^4$ is selected from the group consisting of hydrogen, chlorine, fluorine, methyl, methoxy and trifluoromethyl,
$R^5$ is selected from the group consisting of hydrogen, chlorine, fluorine and methyl,
$R^6$ is selected from the group consisting of hydrogen, fluorine, methyl and methoxy,
Q is selected from the group consisting of phenyl, 1,3-benzothiazol-4-yl, 1,3-benzothiazol-7-yl, 1,3-benzoxazol-7-yl, 1H-indol-4-yl, 1-methyl-1H-benzimidazol-6-yl, 2,3,4-trifluorophenyl, 2,3,4-trichlorophenyl, 2,3,5-trifluorophenyl, 2,3,5-trichlorophenyl, 2,3,6-trifluorophenyl, 2,3,6-trichlorophenyl, 2,3-difluorophenyl, 2,3-dichlorophenyl, 2,4,5-trifluorophenyl, 2,4,5-trichlorophenyl, 2,4,6-trifluorophenyl, 2,4,6-trichlorophenyl, 2,4,6-trifluoro-3-methoxyphenyl, 2,4,6-trichloro-3-methoxyphenyl, 2,4-difluoro-3-hydroxyphenyl, 2,4-dichloro-3-hydroxyphenyl, 2,4-difluoro-3-methoxyphenyl, 2,4-dichloro-3-methoxyphenyl, 2,4-difluoro-3-(dimethylamino)phenyl, 2,4-dichloro-3-(dimethylamino)phenyl, 2,5-difluoro-4-methoxyphenyl, 2,5-dichloro-4-methoxyphenyl, 2,6-difluorophenyl, 2,6-dichlorophenyl, 2-fluoro-3-chlorophenyl, 2-chloro-3-fluorophenyl, 2-fluoro-3-(dimethylamino)phenyl, 2-chloro-3-(dimethylamino)phenyl, 2-chloro-4-fluorophenyl, 2-fluoro-4-chlorophenyl, 2-chloro-5-fluorophenyl, 2-fluoro-4-(dimethylamino)phenyl, 2-chloro-4-(dimethylamino)phenyl, 2-chloro-6-fluorophenyl, 2-fluorophenyl, 2-chlorophenyl, 2-fluoro-3-(trifluoromethoxy)phenyl, 2-chloro-3-(trifluoromethoxy)phenyl, 2-fluoro-3-(trifluoromethyl)phenyl, 2-chloro-3-(trifluoromethyl)phenyl, 3-(dimethylamino)phenyl, 3-(methylamino)phenyl, 3-(trifluoromethoxy)phenyl, 3,4,5-trifluorophenyl, 3,4,5-trichlorophenyl, 3,4-difluoro-5-(dimethylamino)phenyl, 3,4-dichloro-5-(dimethylamino)phenyl, 3,4-difluorophenyl, 3,4-dichlorophenyl, 3,4-difluoro-2-methoxyphenyl, 3,4-dichloro-2-methoxyphenyl, 3,5-difluoro-4-(dimethylamino)phenyl, 3,5-dichloro-4-(dimethylamino)phenyl, 3,5-difluoro-4-chlorophenyl, 3,5-dichloro-4-fluorophenyl, 3,5-difluorophenyl, 3,5-dichlorophenyl, 3,5-dimethylphenyl, 3-fluoro-2-chloro-5-methylphenyl, 3-chloro-2-fluoro-5-methylphenyl, 3-chloro-2-methylphenyl, 3-fluoro-4-(dimethylamino)-5-chlorophenyl, 3-fluoro-4-(dimethylamino)phenyl, 3-chloro-4-(dimethylamino)phenyl, 3-fluoro-4-fluorophenyl, 3-fluoro-4-methylphenyl, 3-chloro-4-methylphenyl, 3-fluoro-5-(dimethylamino)phenyl, 3-chloro-5-(dimethylamino)phenyl, 3-fluoro-5-(methylsulfanyl)phenyl, 3-chloro-5-(methylsulfanyl)phenyl, 3-fluoro-5-(morpholin-4-yl)phenyl, 3-chloro-5-(morpholin-4-yl)phenyl, 3-fluoro-5-(trifluoromethyl)phenyl, 3-chloro-5-(trifluoromethyl)phenyl, 3-fluoro-5-ethylphenyl, 3-chloro-5-ethylphenyl, 3-chloro-5-fluorophenyl, 3-fluoro-5-methoxyphenyl, 3-chloro-5-methoxyphenyl, 3-fluoro-5-methylphenyl, 3-fluorophenyl, 3-chlorophenyl, 3-fluoro-4-methoxyphenyl, 3-chloro-4-methoxyphenyl, 3-fluoro-5-methylphenyl, 3-chloro-5-methylphenyl, 4-fluoro-3-(dimethylamino)phenyl, 4-chloro-3-(dimethylamino)phenyl, 4-fluoro-3-methoxyphenyl, 4-chloro-3-methoxyphenyl, 5-chloro-2,4-difluorophenyl, 5-fluoro-2,4-dichlorophenyl, 5-fluoro-2-chloro-3-methylphenyl, 5-chloro-2-fluoro-3-methylphenyl, 5-fluoro-2-chloro-4-methylphenyl, 5-chloro-2-fluoro-4-methylphenyl, 5-chloro-2-fluorophenyl, 5-chloro-2-methoxyphenyl, and 5-fluoro-2-methoxyphenyl, and stereoisomers, tautomers, N-oxides, hydrates, solvates, and salts thereof, and mixtures of same.

In accordance with a ninth embodiment of the first aspect, the present invention covers compounds of general formula (I), supra, in which:

A is

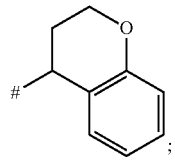;

T is selected from $T^1$-$T^6$ as defined supra $R^1$ is hydrogen or methyl, $R^2$ is selected from the group consisting of hydrogen, chlorine, fluorine, bromine

—$NH_2$, —$NH(CH_3)$, —$N(CH_3)_2$, methoxy, ethoxy, methyl, ethyl, propyl, isopropyl, cyclopropyl; and a monocyclic heterocycle selected from the group consisting of tetrahydropyrane, morpholine, and 2-fluoro azetidine, $R^3$ is hydrogen, $R^4$ is selected from the group consisting of hydrogen, chlorine, fluorine, methyl, methoxy and trifluoromethyl, $R^5$ is selected from the group consisting of hydrogen, chlorine, fluorine and methyl, $R^6$ is selected from the group consisting of hydrogen, fluorine, methyl and methoxy, Q is selected from the group consisting of phenyl, 2,3,4-trifluorophenyl, 2,3,4-trichlorophenyl, 2,3,5-trifluorophenyl, 2,3,5-trichlorophenyl, 2,3,6-trifluorophenyl, 2,3,6-trichlorophenyl, 2,3-difluorophenyl, 2,3-dichlorophenyl, 2,4,5-trifluorophenyl, 2,4,5-trichlorophenyl, 2,4,6-trifluorophenyl, 2,4,6-trichlorophenyl, 2,6-difluorophenyl, 2,6-dichlorophenyl, 2-fluoro-3-chlorophenyl, 2-chloro-3-fluorophenyl, 2-chloro-4-fluorophenyl, 2-fluoro-4-chlorophenyl, 2-chloro-5-fluorophenyl, 2-chloro-6-fluorophenyl, 2-fluorophenyl, 2-chlorophenyl, 3,4,5-trifluorophenyl, 3,4,5-trichlorophenyl, 3,4-difluorophenyl, 3,4-dichlorophenyl, 3,5-difluoro-4-chlorophenyl, 3,5-dichloro-4-fluorophenyl, 3,5-difluorophenyl, 3,5-dichlorophenyl, 3-chloro-4-fluorophenyl, 3-chloro-5-fluorophenyl, 3-fluorophenyl, 3-chlorophenyl, 5-chloro-2,4-difluorophenyl, 5-fluoro-2,4-dichlorophenyl, 5-chloro-2-fluorophenyl, and stereoisomers, tautomers, N-oxides, hydrates, solvates, and salts thereof, and mixtures of same.

In accordance with a tenth embodiment of the first aspect, the present invention covers compounds of general formula (II):

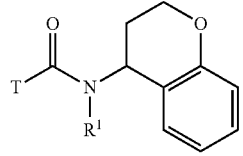

(II)

in which:

T is selected from $T^1$-$T^6$ as defined supra preferably T is selected from $T^1$, $T^2$ or $T^3$ as defined supra, and $R^1$ to $R^6$ and $R^{12}$ to $R^{15}$ have the meaning as defined for any of the embodiments of the first aspect supra, and stereoisomers, tautomers, N-oxides, hydrates, solvates, and salts thereof, and mixtures of same.

In accordance with a further particular embodiment of the first aspect, the present invention covers compounds of general formula (I) or (II) supra, in which:

T is $T^1$ as defined supra:

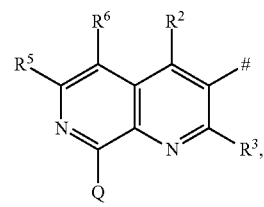

and

A and $R^1$ to $R^{15}$ have the meaning as defined for any of embodiments of the first aspect supra, and stereoisomers, tautomers, N-oxides, hydrates, solvates, and salts thereof, and mixtures of same.

In accordance with a further particular embodiment of the first aspect, the present invention covers compounds of general formula (I) or (II) supra, in which:

T is $T^2$ as defined supra:

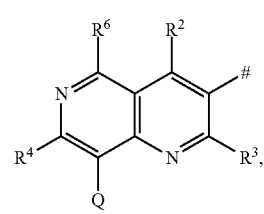

and

A and $R^1$ to $R^{15}$ have the meaning as defined for any of embodiments of the first aspect supra, and stereoisomers, tautomers, N-oxides, hydrates, solvates, and salts thereof, and mixtures of same.

In accordance with a further particular embodiment of the first aspect, the present invention covers compounds of general formula (I) or (II) supra, in which:

T is $T^3$ as defined supra:

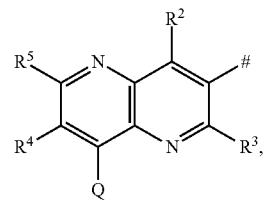

and

A and $R^1$ to $R^{15}$ have the meaning as defined for any of embodiments of the first aspect supra, and stereoisomers, tautomers, N-oxides, hydrates, solvates, and salts thereof, and mixtures of same.

In accordance with a further particular embodiment of the first aspect, the present invention covers compounds of general formula (I) or (II) supra, in which:

T is T⁴ as defined supra:

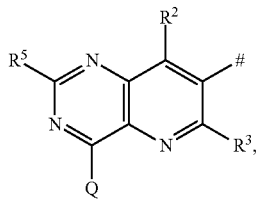

T⁴ and

A and R¹ to R¹⁵ have the meaning as defined for any of embodiments of the first aspect supra, and stereoisomers, tautomers, N-oxides, hydrates, solvates, and salts thereof, and mixtures of same.

In accordance with a further particular embodiment of the first aspect, the present invention covers compounds of general formula (I) or (II) supra, in which:

T is T⁵ as defined supra:

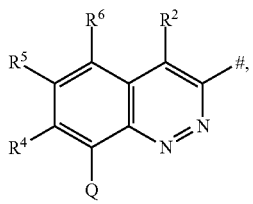

T⁵ and

A and R¹ to R¹⁵ have the meaning as defined for any of embodiments of the first aspect supra, and stereoisomers, tautomers, N-oxides, hydrates, solvates, and salts thereof, and mixtures of same.

In accordance with a further particular embodiment of the first aspect, the present invention covers compounds of general formula (I) or (II), supra, in which:

T is T⁶ as defined supra:

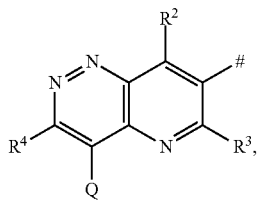

T⁶ and

A and R¹ to R¹⁵ have the meaning as defined for any of embodiments of the first aspect supra, and stereoisomers, tautomers, N-oxides, hydrates, solvates, and salts thereof, and mixtures of same.

Further embodiments of the first aspect of the present invention:

In a further embodiment of the first aspect, the present invention covers compounds of formula (I), supra, in which:
A is A1 or A2,

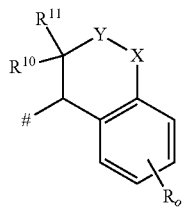

A1

A2 o is 0, 1 or 2,
R is selected from the group consisting of hydrogen, halogen, $C_1$-$C_4$-alkyl and $C_1$-$C_4$-alkoxy, cyano, $C_1$-$C_4$-halogenoalkyl having 1 to 5 halogen atoms,
T is selected from $T^1$-$T^6$ as defined supra
X, Y are independently selected from the group consisting of $CR^7R^8$, O, S, and N—$R^9$, wherein at least one of X and Y is $CR^7R^8$,
$R^7$ is selected from the group consisting of hydrogen and $C_1$-$C_4$-alkyl,
$R^8$ is selected from the group consisting of hydrogen and $C_1$-$C_4$-alkyl,
$R^9$ is $C_1$-$C_4$-alkyl,
$R^{10}$ is selected from the group consisting of hydrogen, —OH, $C_1$-$C_4$-alkyl and $C_1$-$C_4$-alkoxy, and
$R^{11}$ is hydrogen,
wherein when Y is O, S or N—$R^9$, $R^{10}$ is not —OH,
and stereoisomers, tautomers, N-oxides, hydrates, solvates, and salts thereof, and mixtures of same.

In a further embodiment of the first aspect, the present invention covers compounds of formula (I), supra, in which:
T is selected from $T^1$-$T^6$ as defined supra
A is A1 or A2,

A1

A2 o is 0 or 1,
R is selected from the group consisting of halogen, $C_1$-$C_4$-alkyl and $C_1$-$C_4$-alkoxy,
X is selected from the group consisting of $CR^7R^8$, O, S, and N—$R^9$,
Y is $CR^7R^8$,
$R^7$ is selected from the group consisting of hydrogen and $C_1$-$C_4$-alkyl,
$R^8$ is selected from the group consisting of hydrogen and $C_1$-$C_4$-alkyl,
$R^9$ is $C_1$-$C_4$-alkyl,
$R^{10}$ is selected from the group consisting of hydrogen, —OH and $C_1$-$C_4$-alkyl, and
$R^{11}$ is hydrogen,
and stereoisomers, tautomers, N-oxides, hydrates, solvates, and salts thereof, and mixtures of same.

In a further embodiment of the first aspect, the present invention covers compounds of formula (I), supra, in which:
T is selected from $T^1$ supra and
A is selected from the group consisting of

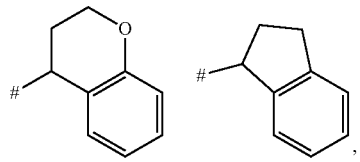

preferably A is

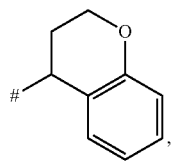

and $R^1$ to $R^9$ and $R^{12}$ to $R^{15}$ have the meaning as defined for any of embodiments of the first aspect supra;
and stereoisomers, tautomers, N-oxides, hydrates, solvates, and salts thereof, and mixtures of same.

In a further embodiment of the first aspect, the present invention covers compounds of formula (I), supra, in which:
T is selected from $T^2$ supra and
A is selected from the group consisting of

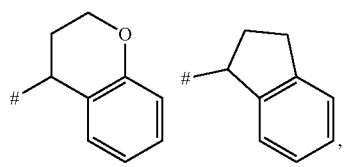

preferably A is

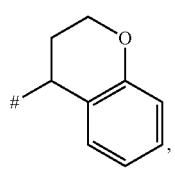

and $R^1$ to $R^9$ and $R^{12}$ to $R^{15}$ have the meaning as defined for any of embodiments of the first aspect supra;
and stereoisomers, tautomers, N-oxides, hydrates, solvates, and salts thereof, and mixtures of same.

In a further embodiment of the first aspect, the present invention covers compounds of formula (I), supra, in which:
T is selected from $T^3$ supra and
A is selected from the group consisting of

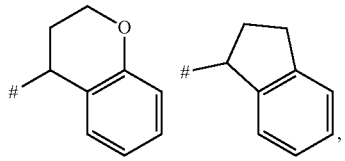

preferably A is

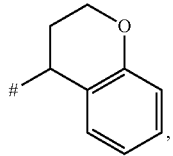

and $R^1$ to $R^9$ and $R^{12}$ to $R^{15}$ have the meaning as defined for any of embodiments of the first aspect supra;
and stereoisomers, tautomers, N-oxides, hydrates, solvates, and salts thereof, and mixtures of same.

In a further embodiment of the first aspect, the present invention covers compounds of formula (I), supra, in which:
T is selected from $T^4$ supra and
A is selected from the group consisting of

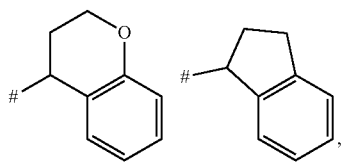

preferably A is

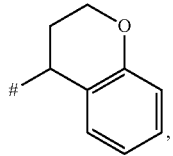

and $R^1$ to $R^9$ and $R^{12}$ to $R^{15}$ have the meaning as defined for any of embodiments of the first aspect supra;
and stereoisomers, tautomers, N-oxides, hydrates, solvates, and salts thereof, and mixtures of same.

In a further embodiment of the first aspect, the present invention covers compounds of formula (I), supra, in which:
T is selected from T⁵ supra and
A is selected from the group consisting of

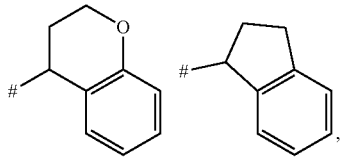

preferably A is

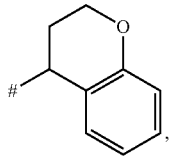

and R¹ to R⁹ and R¹² to R¹⁵ have the meaning as defined for any of embodiments of the first aspect supra;
and stereoisomers, tautomers, N-oxides, hydrates, solvates, and salts thereof, and mixtures of same.

In a further embodiment of the first aspect, the present invention covers compounds of formula (I), supra, in which:
T is selected from T⁶ supra and
A is selected from the group consisting of

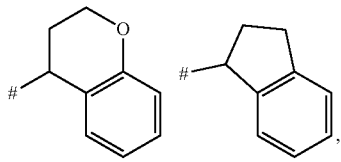

preferably A is

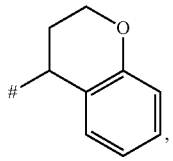

and R¹ to R⁹ and R¹² to R¹⁵ have the meaning as defined for any of embodiments of the first aspect supra;
and stereoisomers, tautomers, N-oxides, hydrates, solvates, and salts thereof, and mixtures of same.

In a further embodiment of the first aspect, the present invention covers compounds of formula (I) or (II), supra, in which:
R² is selected from the group consisting of
hydrogen, halogen, cyano, —COOH, $C_1$-$C_4$-alkoxy-C(O)—, —C(O)—NH$_2$, —C(O)—NH($C_1$-$C_4$-alkyl), —C(O)—N($C_1$-$C_4$-alkyl)$_2$;
—NR¹²R¹³;
—OR¹⁴;
—SR¹⁵, —S(O)R¹⁵, —SO$_2$R¹⁵;
$C_1$-$C_4$-alkyl, $C_3$-$C_6$-cycloalkyl, $C_2$-$C_4$-alkenyl, $C_3$-$C_6$-cycloalkenyl, $C_2$-$C_4$-alkynyl or phenyl-$C_1$-$C_4$-alkyl, each of which is optionally substituted by 1, 2, 3, 4 or 5 substituents independently selected from the group consisting of halogen, —OH, cyano, $C_1$-$C_4$-alkoxy-C(O)—, —C(O)—NH$_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, —NH$_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —SO$_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —SO$_2$—$C_1$-$C_4$-halogenoalkyl having 1 to 5 halogen atoms; and a monocyclic or a bicyclic heterocycle selected from the group consisting of 4- to 10-membered heterocycloalkyl, heterospirocycloalkyl, 5-membered heteroaryl and 6-membered heteroaryl, each of which is optionally substituted by 1, 2, 3 or 4 substituents independently selected from the group consisting of halogen, cyano, —OH, oxo, —COOH, $C_1$-$C_4$-alkoxy-C(O)—, —C(O)—NH$_2$, —C(O)—NH($C_1$-$C_4$-alkyl), —C(O)—N($C_1$-$C_4$-alkyl)$_2$, $C_1$-$C_4$-alkyl, $C_1$-$C_4$-alkyl-C(O)—, $C_1$-$C_4$-halogenoalkyl having 1 to 5 halogen atoms, $C_1$-$C_4$-alkoxy, hydroxy-$C_1$-$C_4$-alkyl, $C_1$-$C_4$-alkoxy-$C_1$-$C_4$-alkyl-, $C_1$-$C_4$-halogenoalkoxy having 1 to 5 halogen atoms, $C_3$-$C_6$-cycloalkyl, —NH$_2$, —NH($C_1$-$C_4$-alkyl), —N($C_1$-$C_4$-alkyl)$_2$, and 4- to 10-membered heterocycloalkyl, R¹² and R¹³ are independently selected from the group consisting of
hydrogen, —NH(—C(O)—$C_1$-$C_4$-alkyl), $C_1$-$C_4$-alkoxy;
$C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, cyano, —COOH, $C_1$-$C_4$-alkoxy-C(O)—, —C(O)—NH$_2$, —C(O)—NH($C_1$-$C_4$-alkyl), —C(O)—N($C_1$-$C_4$-alkyl)$_2$, —NH—C(O)—$C_1$-$C_4$-alkyl, —N($C_1$-$C_4$-alkyl)-(—C(O)—$C_1$-$C_4$-alkyl), $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —NH$_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —SO$_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, —SO$_2$—$C_1$-$C_4$-halogenoalkyl having 1 to 5 halogen atoms and ($C_1$-$C_4$-alkoxy)$_2$P(=O)—;
heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, —OH, oxo, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;
Phenyl, benzo-$C_5$-$C_6$-cycloalkyl, each of which is optionally substituted by 1, 2 or 3 substituents independently selected from the group consisting of halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms; and a monocyclic or a bicyclic heterocycle selected from the group of 4- to 10-membered heterocycloalkyl, 5-membered heteroaryl and 6-membered heteroaryl, each of which is optionally substituted by 1, 2 or 3 substituents independently selected from the group consisting of halogen, cyano, —OH, oxo, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $R^{14}$ is selected from the group consisting of $C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl; and heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, —OH, oxo, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;

$R^{15}$ is selected from the group consisting of $C_1$-$C_4$-alkyl, phenyl-$C_1$-$C_4$-alkyl, each of which is optionally substituted by 1, 2 or 3 substituents independently selected from the group consisting of halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;

and stereoisomers, tautomers, N-oxides, hydrates, solvates, and salts thereof, and mixtures of same.

In a further embodiment of the first aspect, the present invention covers compounds of formula (I) or (II), supra, in which:

$R^1$ is hydrogen or methyl;

and stereoisomers, tautomers, N-oxides, hydrates, solvates, and salts thereof, and mixtures of same.

In a further embodiment of the first aspect, the present invention covers compounds of formula (I) or (II), supra, in which:

$R^2$ is selected from the group consisting of
hydrogen, chlorine,
—NH(CH$_3$), —N(CH$_3$)$_2$,
methoxy, ethoxy,
methyl, ethyl, propyl, isopropyl, cyclopropyl; and
a monocyclic heterocycle selected from the group consisting of tetrahydropyrane, morpholine, and thiomorpholine;

and stereoisomers, tautomers, N-oxides, hydrates, solvates, and salts thereof, and mixtures of same.

In a further embodiment of the first aspect, the present invention covers compounds of formula (I) or (II), supra, in which:

$R^3$ is selected from the group consisting of hydrogen, chlorine or methyl;

and stereoisomers, tautomers, N-oxides, hydrates, solvates, and salts thereof, and mixtures of same.

In a further embodiment of the first aspect, the present invention covers compounds of formula (I) or (II), supra, in which:

$R^4$ is selected from the group consisting of hydrogen, fluorine, chlorine, methyl, methoxy and trifluoromethyl;

and stereoisomers, tautomers, N-oxides, hydrates, solvates, and salts thereof, and mixtures of same.

In a further embodiment of the first aspect, the present invention covers compounds of formula (I) or (II), supra, in which:

$R^5$ is selected from the group consisting of hydrogen, fluorine, chlorine, and methyl;

and stereoisomers, tautomers, N-oxides, hydrates, solvates, and salts thereof, and mixtures of same.

In a further embodiment of the first aspect, the present invention covers compounds of formula (I) or (II), supra, in which:

$R^6$ is selected from the group consisting of hydrogen, fluorine, chlorine, methyl and methoxy;

and stereoisomers, tautomers, N-oxides, hydrates, solvates, and salts thereof, and mixtures of same.

In a further embodiment of the first aspect, the present invention covers compounds of formula (I) or (II), supra, in which:

Q is a substituted phenyl ring of the formula (Q1)

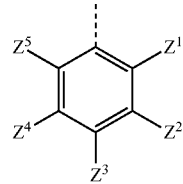

(Q1)

in which:

$Z^1$, $Z^2$, $Z^3$, $Z^4$, and $Z^5$ are independently selected from the group consisting of hydrogen, halogen, cyano, $C_1$-$C_4$-alkyl, $C_1$-$C_4$-halogenoalkyl having 1 to 5 halogen atoms, hydroxy, $C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, 4- to 6-membered heterocyclyl, which is optionally substituted with 1 or 2 substituents selected from the group consisting of fluorine, chlorine, bromine, methyl and cyano, —S—($C_1$-$C_4$-alkyl), —S(O)—($C_1$-$C_4$-alkyl), —SO$_2$—($C_1$-$C_4$-alkyl), or $Z^1$ and $Z^2$ form, together with the carbon atoms that they are connected to, a 5- or 6-membered heterocycloalkyl, a 5-membered heteroaryl, or a 6-membered heteroaryl, each of which may be optionally substituted with one or two substitutents selected from the group consisting of methyl, fluorine and oxo, and $Z^3$, $Z^4$, and $Z^5$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-alkoxy-C(O)—, $C_1$-$C_4$-halogenoalkoxy having 1 to 5 halogen atoms, or $Z^2$ and $Z^3$ form, together with the carbon atoms that they are connected to, a 5- or 6-membered saturated or partially saturated heterocyclic ring, a 5-membered heteroaryl, or a 6-membered heteroaryl, each of which may be optionally substituted with one or two substitutents selected from the group consisting of methyl, fluorine and oxo, and $Z^1$, $Z^4$, and $Z^5$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, preferably Z¹ and Z⁵ are independently selected from the group consisting of hydrogen, halogen, $C_1$-$C_4$-alkyl and $C_1$-$C_4$-alkoxy, Z² and Z⁴ are independently selected from the group consisting of hydrogen, halogen, —OH, $C_1$-$C_4$-alkyl, $C_1$-$C_4$-alkoxy, —NH($C_1$-$C_4$-alkyl), —N($C_1$-$C_4$-alkyl)$_2$, $C_1$-$C_4$-halogenoalkyl having 1 to 5 halogen atoms, $C_1$-$C_4$-halogenoalkoxy having 1 to 5 halogen atoms, —S—($C_1$-$C_4$-alkyl) and a 4- to 6-membered heterocycloalkyl, and Z³ is selected from the group consisting of hydrogen, halogen, $C_1$-$C_4$-alkyl, $C_1$-$C_4$-alkoxy and —N($C_1$-$C_4$-alkyl)$_2$, or Z¹ and Z² form, together with the carbon atoms that they are connected to, a 5-membered heterocycloalkyl or a 5-membered heteroaryl, each of which may be optionally substituted with one or two substituents selected from the group consisting of methyl, fluorine and oxo, Z³ and Z⁵ are hydrogen, and Z⁴ is selected from the group consisting of hydrogen and $C_1$-$C_4$-alkoxy-C(O)—, more preferably Z¹ and Z⁵ are independently selected from the group consisting of hydrogen, fluorine, chlorine, methyl and methoxy, Z² and Z⁴ are independently selected from the group consisting of hydrogen, fluorine, chlorine, —OH, methyl, ethyl, —NHMe, —NMe$_2$, trifluoromethyl, methoxy, trifluoromethoxy, —SMe and morpholinyl, and Z³ is independently selected from the group consisting of hydrogen, fluorine, chlorine, methyl, methoxy and —NMe$_2$, even more preferably Q is selected from the group consisting of phenyl, 2,3-difluorophenyl, 2,3-dichlorophenyl, 2,6-difluorophenyl, 2,6-dichlorophenyl, 2-fluoro-3-chlorophenyl, 2-chloro-3-fluorophenyl, 2-chloro-4-fluorophenyl, 2-fluoro-4-chlorophenyl, 2-chloro-5-fluorophenyl, 2-chloro-6-fluorophenyl, 2-fluorophenyl, 2-chlorophenyl, 3,4-difluorophenyl, 3,4-dichlorophenyl, 3,5-difluorophenyl, 3,5-dichlorophenyl, 3-chloro-4-fluorophenyl, 3-chloro-5-fluorophenyl, 3-fluorophenyl, 3-chlorophenyl, 5-chloro-2-fluorophenyl, 2,3,5-trifluorophenyl and 2,3,5-trichlorophenyl and stereoisomers, tautomers, N-oxides, hydrates, solvates, and salts thereof, and mixtures of same.

In a further embodiment of the first aspect, the present invention covers compounds of formula (I), supra, in which A is A3 or A4

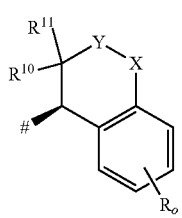

A3

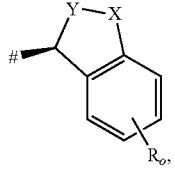

A4 and stereoisomers, tautomers, N-oxides, hydrates, solvates, and salts thereof, and mixtures of same.

In a particular further embodiment of the first aspect, the present invention covers combinations of two or more of the above mentioned embodiments under the heading "further embodiments of the first aspect of the present invention".

The present invention covers any sub-combination within any embodiment or aspect of the present invention of compounds of general formula (I) or (II), supra.

The present invention covers the compounds of general formula (I) which are disclosed in the Example Section of this text, infra.

The compounds according to the invention of general formula (I) and (II) can be prepared according to the schemes 1 to 6 as shown in the Experimental Section to the present invention (General Procedures).

The schemes and procedures described illustrate synthetic routes to the compounds of general formula (I) and (II) of the invention and are not intended to be limiting. It is clear to the person skilled in the art that the order of transformations as exemplified in schemes 1 to 6 can be modified in various ways. The order of transformations exemplified in these schemes is therefore not intended to be limiting. In addition, interconversion of any of the substituents, T, Q, A, R¹, R², R³, R⁴, R⁵ or R⁶ can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in *Protective Groups in Organic Synthesis*, 3$^{rd}$ edition, Wiley 1999). Specific examples are described in the subsequent paragraphs.

In the following, several routes for the preparation of compounds of general formula (I) and (II) are described in schemes 1 to 6.

In accordance with a second aspect, the present invention covers methods of preparing compounds of general formula (I) as defined supra, said methods comprising the step of allowing an intermediate compound of general formula 1N-T1, 1N-T2, 1N-T3, 1N-T4, 1N-T5, or 1N-T6:

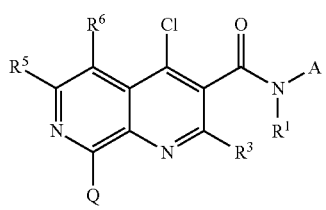

1N-T1

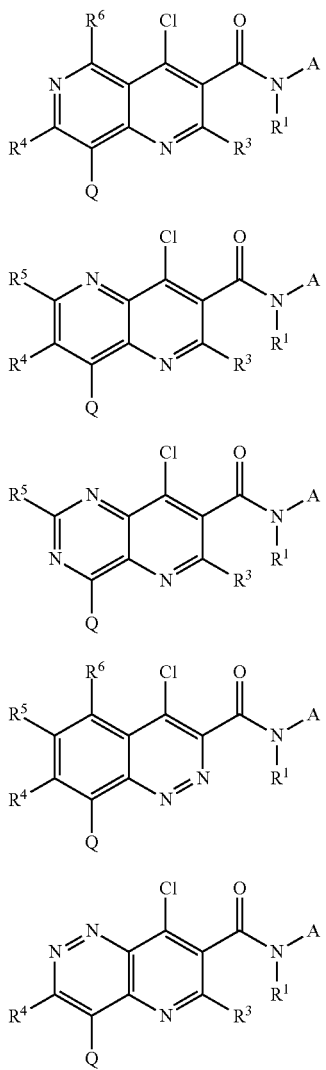

in which A, R¹, R³, R⁴, R⁵, R⁶, and Q are as defined for the compound of general formula (I) as defined supra,
to react with a compound of general formula 1F:

R²H    1F, in which R² is NR¹²R¹³, OR¹⁴, or SR¹⁵, each as defined for the compound of general formula (I) as defined supra,
thereby giving a compound of general formula (I):

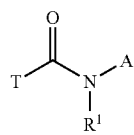
(I)

in which T, A, R¹, R², R³, R⁴, R⁵, R⁶, and Q are as defined supra.

In accordance with an alternative embodiment of the second aspect, the present invention covers methods of preparing compounds of general formula (I) as defined supra, said methods comprising the step of allowing an intermediate compound of general formula 1M-T1, 1M-T2, 1M-T3, 1M-T4, 1M-T5, or 1M-T6:

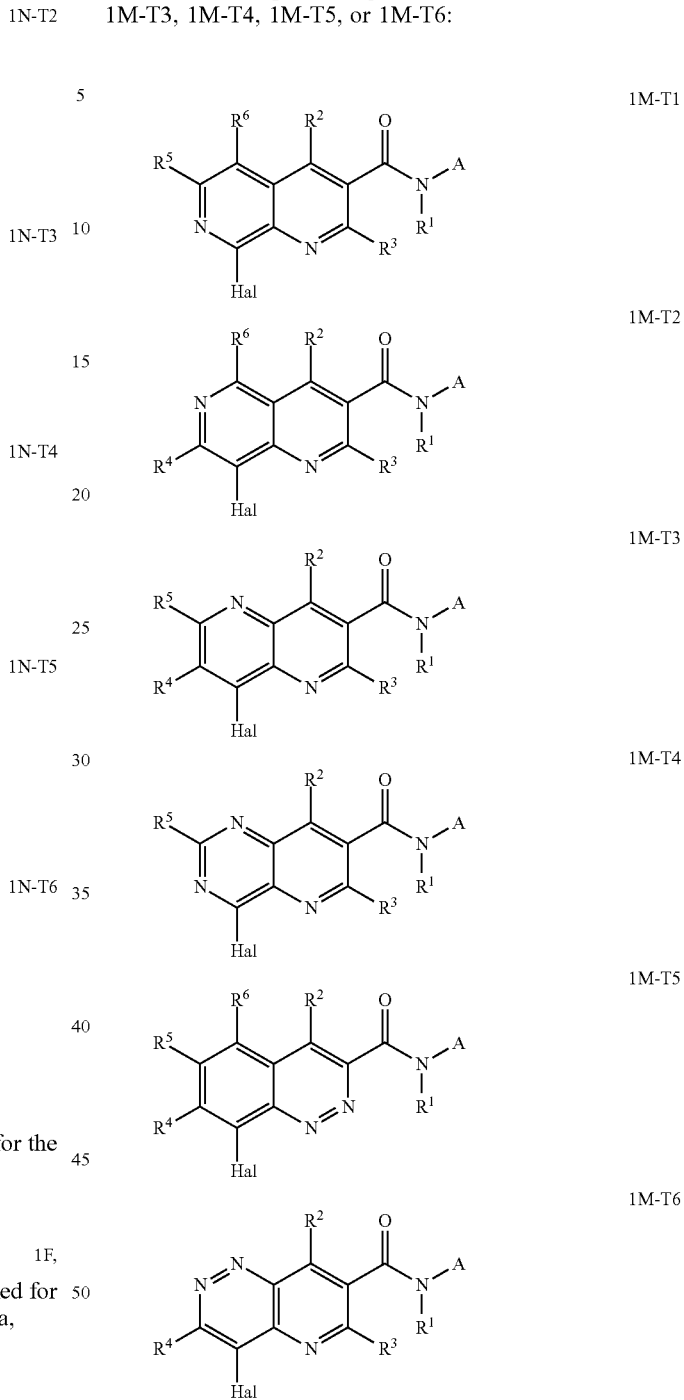

in which A, R¹, R², R³, R⁴, R⁵ and R⁶ are as defined for the compound of general formula (I) as defined supra, and in which Hal is halogen, particularly chlorine, bromine or iodine,
to react with a compound of general formula 1H:

Q-B(OR)₂    1H, in which Q is as defined for the compound of general formula (I) as defined supra, and each R may be individually H or Me or both R are pinacolate, thereby giving a compound of general formula (I):

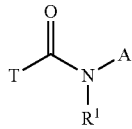
(I)

in which T, A, $R^1$, $R^2$, $R^3$, $R^4$, $R^5$, $R^6$, and Q are as defined supra.

In accordance with an alternative embodiment of the second aspect, the present invention covers methods of preparing compounds of general formula (I) as defined supra, said methods comprising the step of allowing an intermediate compound of general formula 1W-T1, 1W-T2, 1W-T3, 1W-T4, 1W-T5, or 1W-T6:

1W-T1
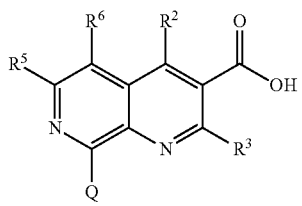

1W-T2
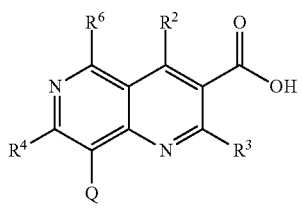

1W-T3
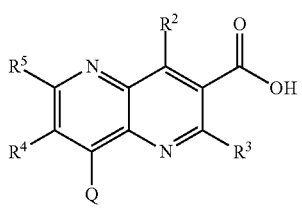

1W-T4
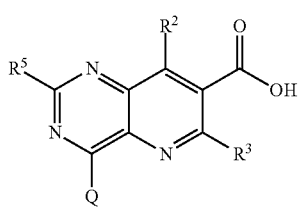

1W-T5
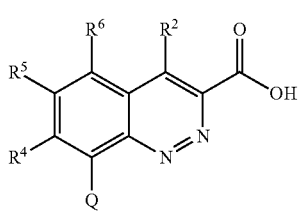

1W-T6
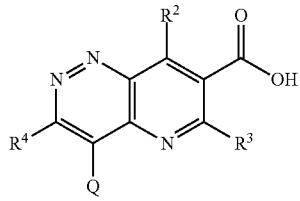

in which Q, $R^2$, $R^3$, $R^4$, $R^5$ and $R^6$ are as defined for the compound of general formula (I) as defined supra, to react with a compound of general formula 1V:

1V

in which $R^1$ and A are as defined for the compound of general formula (I) as defined supra, thereby giving a compound of general formula (I):

(I)
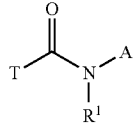

in which T, A, $R^1$, $R^2$, $R^3$, $R^4$, $R^5$, $R^6$, and Q are as defined supra.

In accordance with an alternative embodiment of the second aspect, the present invention covers methods of preparing compounds of general formula (I) as defined supra, said methods comprising the step of allowing an intermediate compound of general formula 1X-T1, 1X-T2, 1X-T3, 1X-T4, 1X-T5, or 1X-T6:

1X-T1
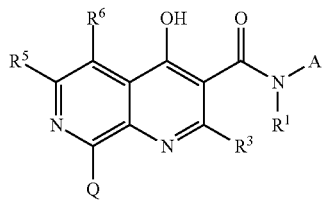

1X-T2
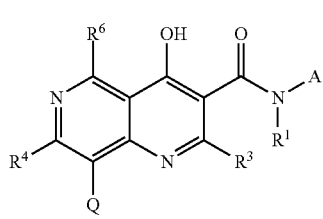

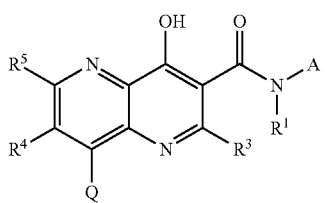
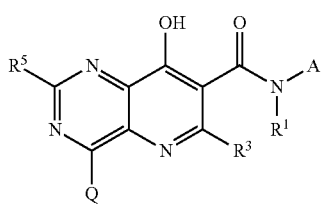
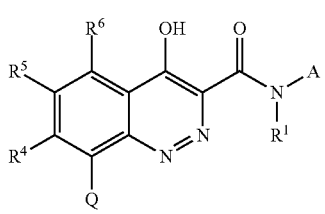
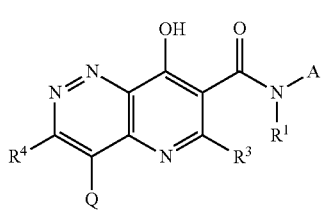

in which Q, A, R¹, R³, R⁴, R⁵ and R⁶ are as defined for the compound of general formula (I) as defined supra, to react with a compound of general formula 1Y:

R²H         1Y, in which R² is C¹—C⁴-alkoxy which is optionally substituted as defined for the compound of general formula (I) as defined supra, thereby giving a compound of general formula (I):

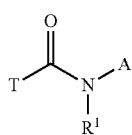

(I)

in which T, A, R¹, R³, R⁴, R⁵, R⁶, and Q are as defined supra and R² is C¹—C⁴-alkoxy which is optionally substituted as defined supra.

In accordance with an alternative embodiment of the second aspect, the present invention covers methods of preparing compounds of general formula (I) as defined supra, said methods comprising the step of allowing an intermediate compound of general formula 1N-T1, 1N-T2, 1N-T3, 1N-T4, 1N-T5, or 1N-T6:

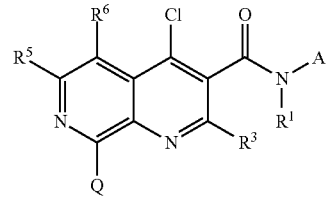
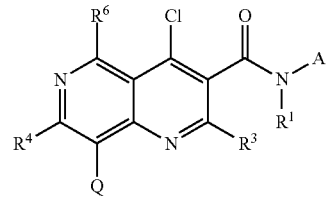
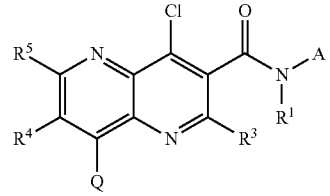
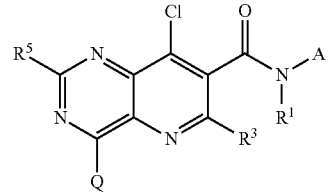
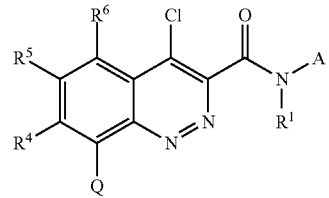
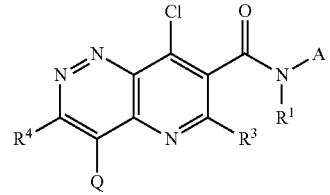

in which A, R¹, R³, R⁴, R⁵, R⁶, and Q are as defined for the compound of general formula (I) as defined supra, to react with a compound of general formula 2A:

R²Met-X         2A, in which R² is C₁-C₄-alkyl, C₃-C₆-cycloalkyl, C₂-C₄-alkenyl, C₃-C₆-cycloalkenyl, C₂-C₄-alkynyl, phenyl-C₁-C₄-alkyl, heterocyclyl-C₁-C₄-alkyl, phenyl or a monocyclic or bicyclic heterocycle, each of which as defined for the compound of general formula (I) as defined supra, Met is magnesium, or zinc, and X is chlorine, bromine or iodine, thereby giving a compound of general formula (I):

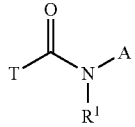
(I)

in which T, A, $R^1$, $R^3$, $R^4$, $R^5$, $R^6$, and Q are as defined supra and $R^2$ is $C_1$-$C_4$-alkyl, $C_3$-$C_6$-cycloalkyl, $C_2$-$C_4$-alkenyl, $C_3$-$C_6$-cycloalkenyl, $C_2$-$C_4$-alkynyl or phenyl-$C_1$-$C_4$-alkyl, each of which is optionally substituted as defined supra.

In accordance with a third aspect, the present invention covers methods of preparing compounds of general formula (I) as defined supra, said methods comprising the step of allowing an intermediate compound of general formula 1N-T1, 1N-T2, 1N-T3, 1N-T4, 1N-T5, or 1N-T6:

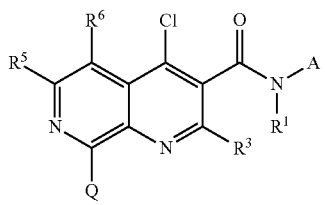
1N-T1

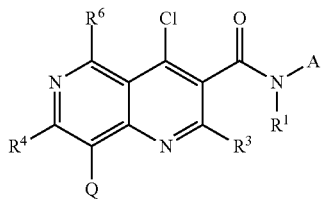
1N-T2

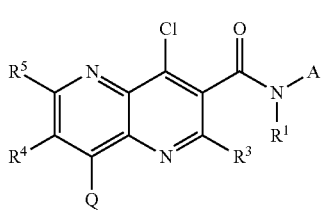
1N-T3

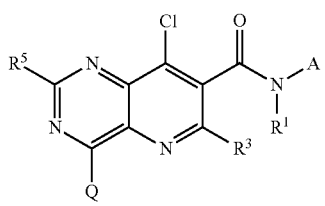
1N-T4

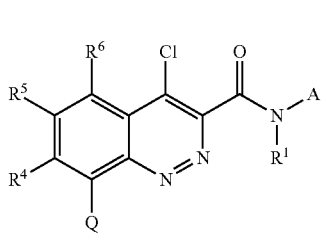
1N-T5

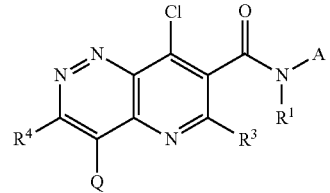
1N-T6 in which A, $R^1$, $R^3$, $R^4$, $R^5$, $R^6$, and Q are as defined for the compound of general formula (I) as defined supra, to react with a compound of general formula 1F:

$R^2H$      1F, in which $R^2$ is $NR^{12}R^{13}$, $OR^{14}$, $SR^{15}$ as defined for the compound of general formula (I) as defined supra, thereby giving a compound of general formula (I):

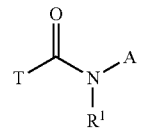
(I)

in which T, A, $R^1$, $R^2$, $R^3$, $R^4$, $R^5$, $R^6$, and Q are as defined supra.

then optionally converting said compound into solvates, salts and/or solvates of such salts using the corresponding (i) solvents and/or (ii) bases or acids.

In accordance with an alternative embodiment of the third aspect, the present invention covers methods of preparing compounds of general formula (I) as defined supra, said methods comprising the step of allowing an intermediate compound of general formula 1M-T1, 1M-T2, 1M-T3, 1M-T4, 1M-T5, or 1M-T6:

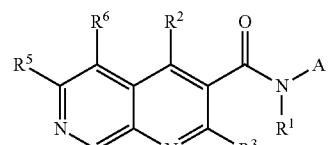
1M-T1

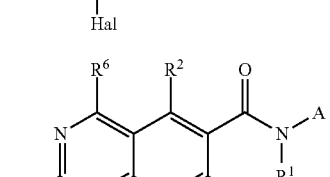
1M-T2

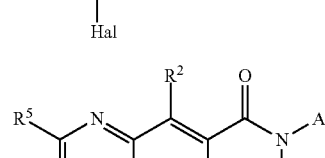
1M-T3

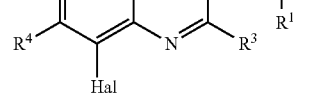

-continued

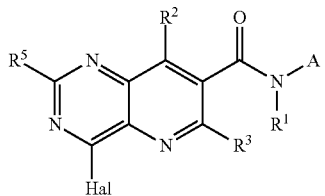
1M-T4

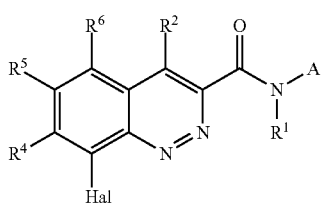
1M-T5

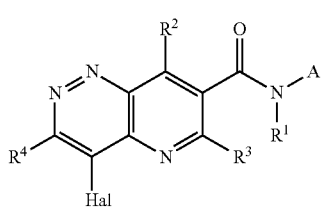
1M-T6

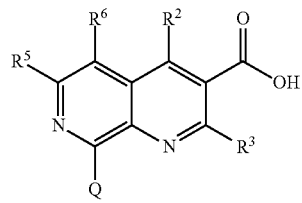
1W-T1

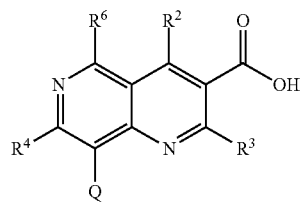
1W-T2

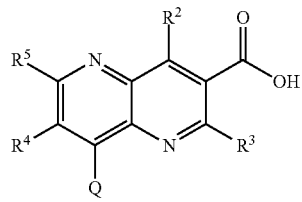
1W-T3

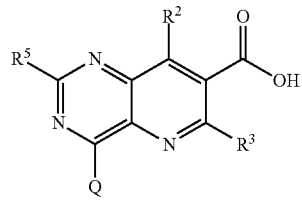
1W-T4

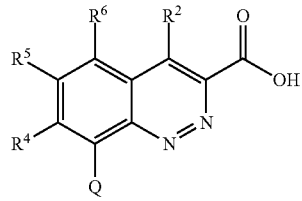
1W-T5

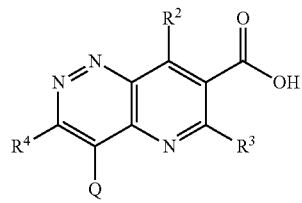
1W-T6 in which A, $R^1$, $R^2$, $R^3$, $R^4$, $R^5$ and $R^6$ are as defined for the compound of general formula (I) as defined supra, and in which Hal is halogen, particularly chlorine, bromine or iodine, to react with a compound of general formula 1H:

Q-B(OR)$_2$   1H, in which Q is as defined for the compound of general formula (I) as defined supra, and each R may be individually H or Me or both R are pinacolate, thereby giving a compound of general formula (I):

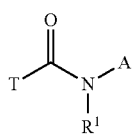
(I)

in which T, A, $R^1$, $R^2$, $R^3$, $R^4$, $R^5$, $R^6$, and Q are as defined supra.

then optionally converting said compound into solvates, salts and/or solvates of such salts using the corresponding (i) solvents and/or (ii) bases or acids.

In accordance with an alternative embodiment of the third aspect, the present invention covers methods of preparing compounds of general formula (I) as defined supra, said methods comprising the step of allowing an intermediate compound of general formula 1W-T1, 1W-T2, 1W-T3, 1W-T4, 1W-T5, or 1W-T6:

in which Q, $R^2$, $R^3$, $R^4$, $R^5$ and $R^6$ are as defined for the compound of general formula (I) as defined supra, to react with a compound of general formula 1V:

1V in which $R^1$ and A are as defined for the compound of general formula (I) as defined supra, thereby giving a compound of general formula (I):

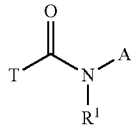

(I)

in which T, A, $R^1$, $R^2$, $R^3$, $R^4$, $R^5$, $R^6$, and Q are as defined supra,
then optionally converting said compound into solvates, salts and/or solvates of such salts using the corresponding (i) solvents and/or (ii) bases or acids.

In accordance with an alternative embodiment of the third aspect, the present invention covers methods of preparing compounds of general formula (I) as defined 1X-T1, 1X-T2, 1X-T3, 1X-T4, 1X-T5, or 1X-T6:

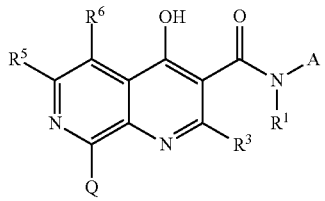

1X-T1

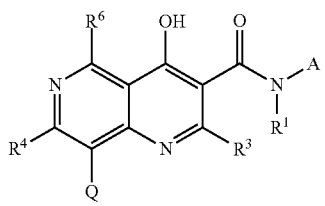

1X-T2

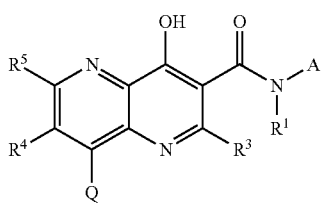

1X-T3

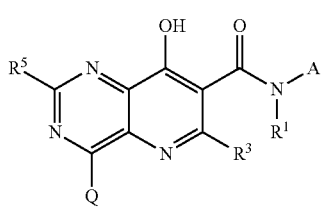

1X-T4

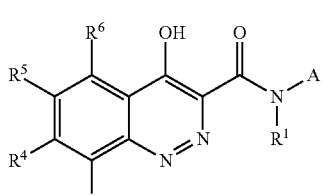

1X-T5

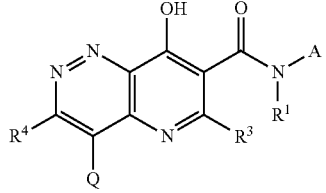

1X-T6 in which Q, A, $R^1$, $R^3$, $R^4$, $R^5$ and $R^6$ are as defined for the compound of general formula (I) as defined supra,
to react with a compound of general formula 1Y:

$R^2H$      1Y, in which $R^2$ is $C_1$-$C_4$-alkoxy which is optionally substituted as defined for the compound of general formula (I) as defined supra,
thereby giving a compound of general formula (I):

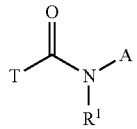

(I)

in which T, A, $R^1$, $R^2$, $R^3$, $R^4$, $R^5$, $R^6$, and Q are as defined supra and $R^2$ is $C_1$-$C_4$-alkoxy which is optionally substituted as defined supra,
then optionally converting said compound into solvates, salts and/or solvates of such salts using the corresponding (i) solvents and/or (ii) bases or acids.

In accordance with an alternative embodiment of the third aspect, the present invention covers methods of preparing compounds of general formula (I) as defined supra, said methods comprising the step of allowing an intermediate compound of general formula 1N-T1, 1N-T2, 1N-T3, 1N-T4, 1N-T5, or 1N-T6:

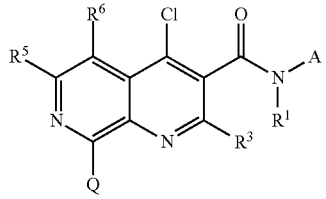

1N-T1

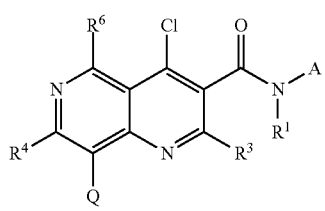

1N-T2

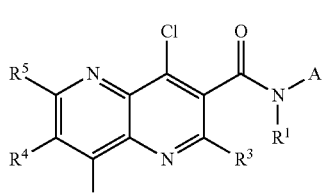

1N-T3

-continued

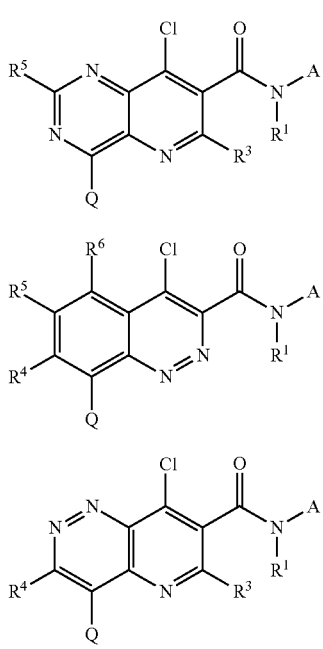

in which Q, A, $R^1$, $R^3$, $R^4$, $R^5$ and $R^6$ are as defined for the compound of general formula (I) as defined supra, to react with a compound of general formula 2A:

$R^2$Met-X     2A, in which $R^2$ is $C_1$-$C_4$-alkyl, $C_3$-$C_6$-cycloalkyl, $C_2$-$C_4$-alkenyl, $C_3$-$C_6$-cycloalkenyl, $C_2$-$C_4$-alkynyl, phenyl-$C_1$-$C_4$-alkyl, heterocyclyl-$C_1$-$C_4$-alkenyl, phenyl or a monocyclic or bicyclic heterocycle, each of which as defined for the compound of general formula (I) as defined supra, Met is magnesium or zinc, and X is chlorine, bromine or iodine, thereby giving a compound of general formula (I):

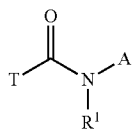

in which T, A, $R^1$, $R^3$, $R^4$, $R^5$, $R^6$, and Q are as defined supra and $R^2$ is $C_1$-$C_4$-alkyl, $C_3$-$C_6$-cycloalkyl, $C_2$-$C_4$-alkenyl, $C_3$-$C_6$-cycloalkenyl, $C_2$-$C_4$-alkynyl or phenyl-$C_1$-$C_4$-alkyl, each of which is optionally substituted as defined supra, then optionally converting said compound into solvates, salts and/or solvates of such salts using the corresponding (i) solvents and/or (ii) bases or acids.

The present invention covers methods of preparing compounds of the present invention of general formula (I) and (II), said methods comprising the steps as described in the Experimental Section herein.

In accordance with a fourth aspect, the present invention covers intermediate compounds which are useful for the preparation of the compounds of general formula (I) and (II), supra.

Particularly, the inventions covers the intermediate compounds of general formula (I-INT-T1), (I-INT-T2), (I-INT-T3), (I-INT-T4), (I-INT-T5) and (I-INT-T6):

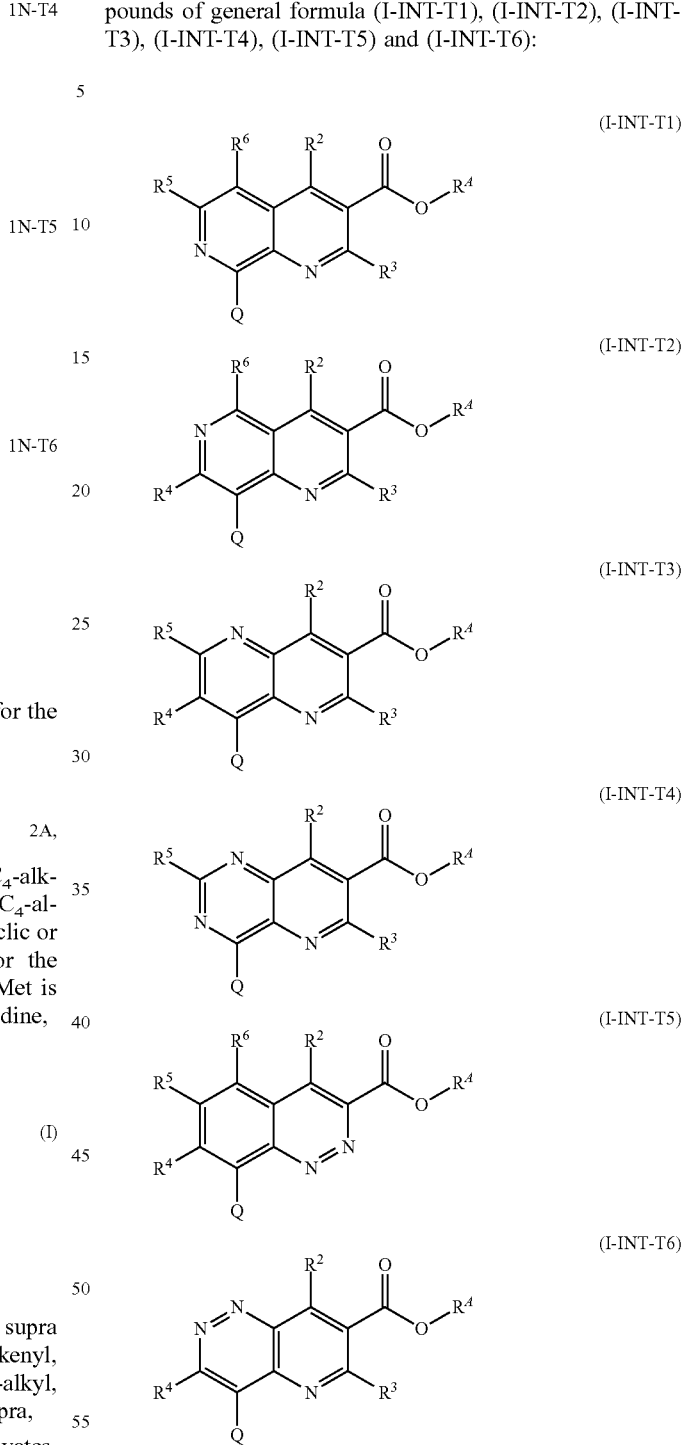

in which $R^2$ is —OH or as defined for the compound of general formula (I) supra, $R^3$, $R^4$, $R^5$, $R^6$, and Q are as defined for the compound of general formula (I) supra, and $R^A$ is H or $C_1$-$C_4$-alkyl, and stereoisomers, tautomers, N-oxides, hydrates, solvates, and salts thereof, and mixtures of same.

Particularly, the inventions covers also the intermediate compounds of general formula (II-INT-T1), (II-INT-T2), (II-INT-T3), (II-INT-T4), (II-INT-T5) and (II-INT-T6):

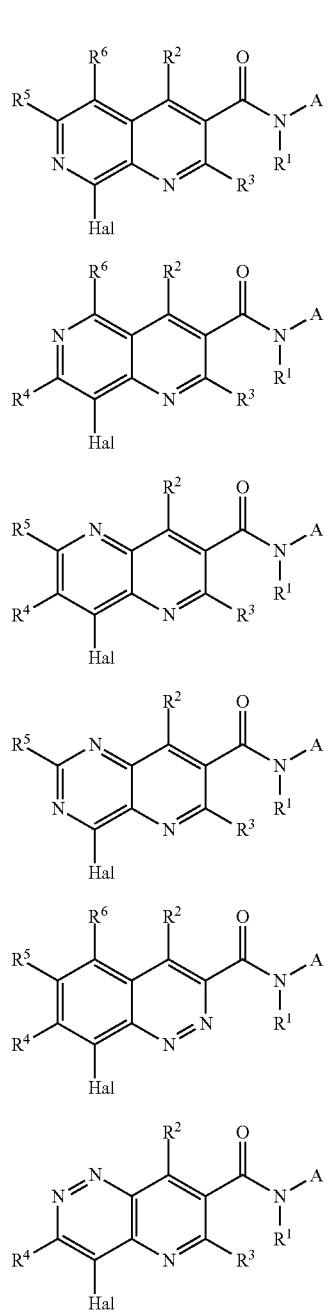

Particularly, the inventions covers the use of intermediate compounds of general formula (I-INT-T1), (I-INT-T2), (I-INT-T3), (I-INT-T4), (I-INT-T5) and (I-INT-T6):

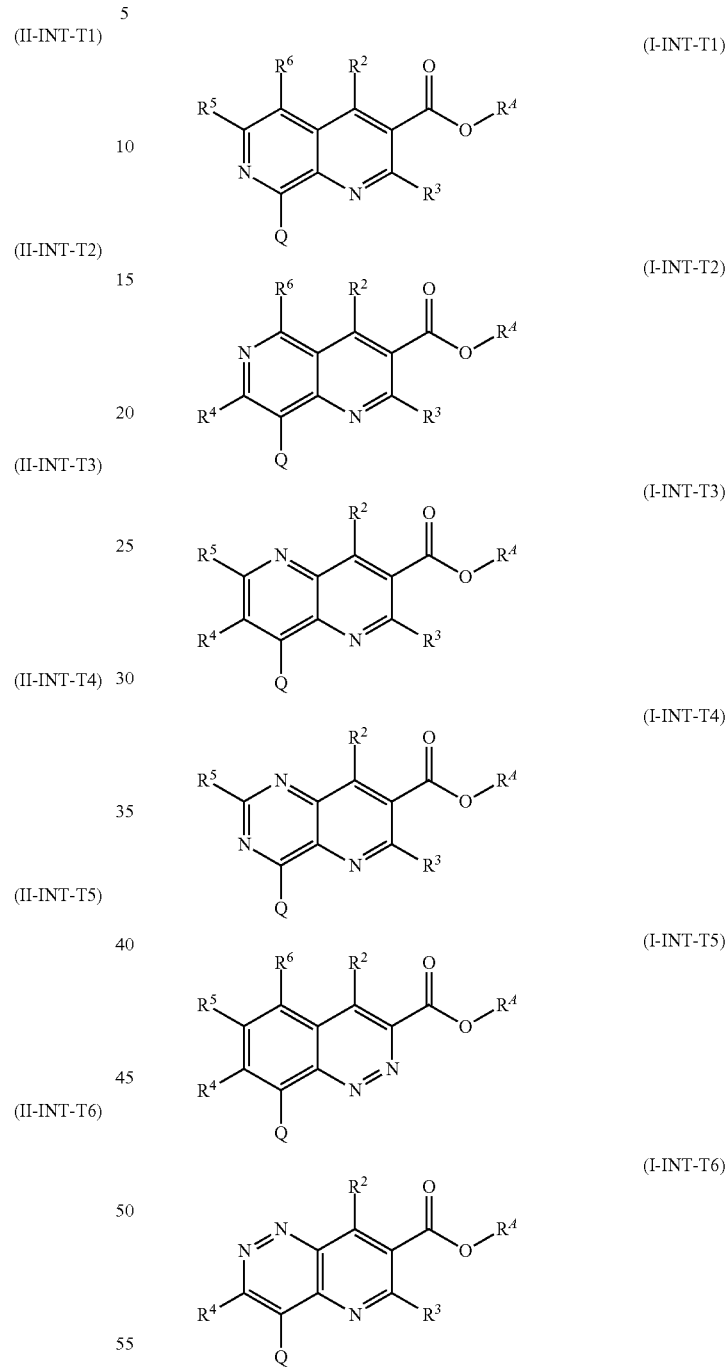

in which
$R^2$ is —OH or as defined for the compound of general formula (I) supra,
A, $R^1$, $R^3$, $R^4$, $R^5$, and $R^6$ are as defined for the compound of general formula (I) supra, and
Hal is halogen,
and stereoisomers, tautomers, N-oxides, hydrates, solvates, and salts thereof, and mixtures of same.

In accordance with a fifth aspect, the present invention covers the use of said intermediate compounds for the preparation of a compound of general formula (I) as defined supra.

in which $R^2$ is —OH or as defined for the compound of general formula (I) supra, $R^3$, $R^4$, $R^5$, $R^6$, and Q are as defined for the compound of general formula (I) supra, and $R^A$ is H or $C_1$-$C_4$-alkyl, for the preparation of a compound of general formula (I) as defined supra.

Particularly, the inventions covers also the use of intermediate compounds of general formula (II-INT-T1), (II-INT-T2), (II-INT-T3), (II-INT-T4), (II-INT-T5) and (II-INT-T6):

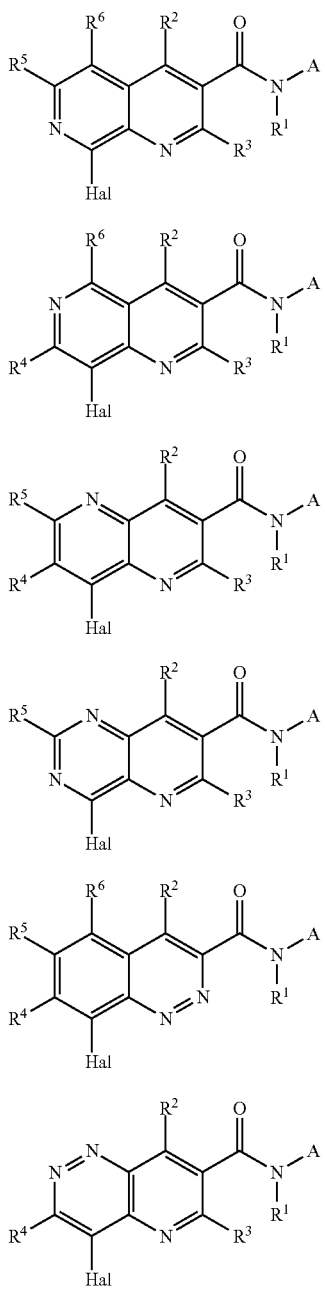

(II-INT-T1)
(II-INT-T2)
(II-INT-T3)
(II-INT-T4)
(II-INT-T5)
(II-INT-T6)

in which
$R^2$ is —OH as defined for the compound of general formula (I) supra,
A, $R^1$, $R^3$, $R^4$, $R^5$, and $R^6$ are as defined for the compound of general formula (I) supra, and
Hal is halogen,
for the preparation of a compound of general formula (I) as defined supra.

The present invention covers the intermediate compounds which are disclosed in the Example Section of this text, infra.

The compounds of general formula (I) and (II) of the present invention can be converted to any salt, preferably pharmaceutically acceptable salts, as described herein, by any method which is known to the person skilled in the art. Similarly, any salt of a compound of general formula (I) and (II) of the present invention can be converted into the free compound, by any method which is known to the person skilled in the art.

Compounds of general formula (I) and (II) of the present invention demonstrate a valuable pharmacological spectrum of action, which could not have been predicted. Compounds of the present invention have surprisingly been found to effectively interact with Slo-1 and it is possible therefore that said compounds be used for the treatment or prevention of diseases, preferably helminthic infections, particulary of gastro-intestinal and extra-intestinal helminth infections, more particulary of gastro-intestinal and extra-intestinal infections with nematodes in humans and animals.

Compounds of the present invention can be utilized to control, treat and/or prevent helminth infections, in particular gastro-intestinal and extra-intestinal helminth infections. This method comprises administering to a mammal in need thereof an amount of a compound of this invention, or a pharmaceutically acceptable salt, isomer, polymorph, metabolite, hydrate, solvate or ester thereof; which is effective to treat the disorder.

In an alternative aspect, this method comprises administering to birds, namely cage birds or in particular poultry, in need thereof an amount of a compound of this invention, or a pharmaceutically acceptable salt, isomer, polymorph, metabolite, hydrate, solvate or ester thereof; which is effective to treat the disorder.

Specifically in the field of veterinary medicine, compounds of the present invention are suitable, with favourable toxicity in warm blooded animals, for controlling parasites, in particular helminths, which occur in animal breeding and animal husbandry in livestock, breeding, zoo, laboratory, experimental and domestic animals. They are active against all or specific stages of development of the parasites, in particular of the helminths.

Agricultural livestock include, for example, mammals, such as, sheep, goats, horses, donkeys, camels, buffaloes, rabbits, reindeers, fallow deers, and in particular cattle and pigs; or poultry, such as turkeys, ducks, geese, and in particular chickens; or fish or crustaceans, e.g. in aquaculture.

Domestic animals include, for example, mammals, such as hamsters, guinea pigs, rats, mice, chinchillas, ferrets or in particular dogs, cats; cage birds; reptiles; amphibians or aquarium fish.

The present invention also provides methods of treating helminth infections, particularly gastro-intestinal and extra-intestinal helminth infections, more particularly gastro-intestinal and extra-intestinal infections with nematodes.

These disorders have been well characterized in animals, and can be treated by administering pharmaceutical compositions of the present invention.

The term "treating" or "treatment" as used in the present text is used conventionally, e.g., the management or care of a subject for the purpose of combating, alleviating, reducing, relieving, improving the condition of a disease or disorder, such as a nematode infection. In particular, and particularly in the animal health or veterinary field, the term "treating" or "treatment" includes prophylactic, metaphylactic or therapeutical treatment Helminths pathogenic for humans or animals include, for example, acanthocephala, nematodes, pentastoma and platyhelmintha (e.g. monogenea, cestodes and trematodes).

Exemplary helminths include, without any limitation:

Monogenea: e.g.: *Dactylogyrus* spp., *Gyrodactylus* spp., *Microbothrium* spp., *Polystoma* spp., *Troglocephalus* spp.

Cestodes: from the order of the Pseudophyllidea, for example: *Bothridium* spp., *Diphyllobothrium* spp., *Diplogonoporus* spp., *Ichthyobothrium* spp., *Ligula* spp., *Schistocephalus* spp., *Spirometra* spp. from the order of the Cyclophyllida, for example: *Andyra* spp., *Anoplocephala* spp., *Avitellina* spp., *Bertiella* spp., *Cittotaenia* spp., *Davainea* spp., *Diorchis* spp., *Diplopylidium* spp., *Dipylidium* spp., *Echinococcus* spp., *Echinocotyle* spp., *Echinolepis* spp., *Hydatigera* spp., *Hymenolepis* spp., *Joyeuxiella* spp., *Mesocestoides* spp., *Moniezia* spp., *Paranoplocephala* spp., *Raillietina* spp., *Stilesia* spp., *Taenia* spp., *Thysaniezia* spp., *Thysanosoma* spp.

Trematodes: from the class of the Digenea, for example: *Austrobilharzia* spp., *Brachylaima* spp., *Calicophoron* spp., *Catatropis* spp., *Clonorchis* spp. *Collyriclum* spp., *Cotylophoron* spp., *Cyclocoelum* spp., *Dicrocoelium* spp., *Diplostomum* spp., *Echinochasmus* spp., *Echinoparyphium* spp., *Echinostoma* spp., *Eurytrema* spp., *Fasciola* spp., *Fasciolides* spp., *Fasciolopsis* spp., *Fischoederius* spp., *Gastrothylacus* spp., *Gigantobilharzia* spp., *Gigantocotyle* spp., *Heterophyes* spp., *Hypoderaeum* spp., *Leucochloridium* spp., *Metagonimus* spp., *Metorchis* spp., *Nanophyetus* spp., *Notocotylus* spp., *Opisthorchis* spp., *Ornithobilharzia* spp., *Paragonimus* spp., *Paramphistomum* spp., *Plagiorchis* spp., *Posthodiplostomum* spp., *Prosthogonimus* spp., *Schistosoma* spp., *Trichobilharzia* spp., *Troglotrema* spp., *Typhlocoelum* spp.

Nematodes: from the order of the Trichinellida, for example: *Capillaria* spp., *Eucoleus* spp., *Paracapillaria* spp., *Trichinella* spp., *Trichomosoides* spp., *Trichuris* spp.

from the order of the Tylenchida, for example: *Micronema* spp., *Parastrongyloides* spp., *Strongyloides* spp.

from the order of the Rhabditina, for example: *Aelurostrongylus* spp., *Amidostomum* spp., *Ancylostoma* spp., *Angiostrongylus* spp., *Bronchonema* spp., *Bunostomum* spp., *Chabertia* spp., *Cooperia* spp., *Cooperioides* spp., *Crenosoma* spp., *Cyathostomum* spp., *Cyclococercus* spp., *Cyclodontostomum* spp., *Cylicocyclus* spp., *Cylicostephanus* spp., *Cylindropharynx* spp., *Cystocaulus* spp., *Dictyocaulus* spp., *Elaphostrongylus* spp., *Filaroides* spp., *Globocephalus* spp., *Graphidium* spp., *Gyalocephalus* spp., *Haemonchus* spp., *Heligmosomoides* spp., *Hyostrongylus* spp., *Marshallagia* spp., *Metastrongylus* spp., *Muellerius* spp., *Necator* spp., *Nematodirus* spp., *Neostrongylus* spp., *Nippostrongylus* spp., *Obeliscoides* spp., *Oesophagodontus* spp., *Oesophagostomum* spp., *Ollulanus* spp.; *Ornithostrongylus* spp., *Oslerus* spp., *Ostertagia* spp., *Paracooperia* spp., *Paracrenosoma* spp., *Parafilaroides* spp., *Parelaphostrongylus* spp., *Pneumocaulus* spp., *Pneumostrongylus* spp., *Poteriostomum* spp., *Protostrongylus* spp., *Spicocaulus* spp., *Stephanurus* spp., *Strongylus* spp., *Syngamus* spp., *Teladorsagia* spp., *Trichonema* spp., *Trichostrongylus* spp., *Triodontophorus* spp., *Troglostrongylus* spp., *Uncinaria* spp.

from the order of the Spirurida, for example: *Acanthocheilonema* spp., *Anisakis* spp., *Ascaridia* spp.; *Ascaris* spp., *Ascarops* spp., *Aspiculuris* spp., *Baylisascaris* spp., *Brugia* spp., *Cercopithifilaria* spp., *Crassicauda* spp., *Dipetalonema* spp., *Dirofilaria* spp., *Dracunculus* spp.; *Draschia* spp., *Enterobius* spp., *Filaria* spp., *Gnathostoma* spp., *Gongylonema* spp., *Habronema* spp., *Heterakis* spp.; *Litomosoides* spp., *Loa* spp., *Onchocerca* spp., *Oxyuris* spp., *Parabronema* spp., *Parafilaria* spp., *Parascaris* spp., *Passalurus* spp., *Physaloptera* spp., *Probstmayria* spp., *Pseudofilaria* spp., *Setaria* spp., *Skjrabinema* spp., *Spirocerca* spp., *Stephanofilaria* spp., *Strongyluris* spp., *Syphacia* spp., *Thelazia* spp., *Toxascaris* spp., *Toxocara* spp., *Wuchereria* spp.

Acantocephala: from the order of the Oligacanthorhynchida, for example: *Macracanthorhynchus* spp., *Prosthenorchis* spp.; from the order of the Moniliformida, for example: *Moniliformis* spp.

from the order of the Polymorphida, for example: *Filicollis* spp.; from the order of the Echinorhynchida, for example: *Acanthocephalus* spp., *Echinorhynchus* spp., *Leptorhynchoides* spp.

Pentastoma: from the order of the Porocephalida, for example: *Linguatula* spp.

The compounds of the present invention can be used in particular in therapy and prevention, i.e. prophylaxis, of helminth infections, particularly gastro-intestinal and extra-intestinal helminth infections, more particularly gastro-intestinal and extra-intestinal infections with nematodes.

By using the compounds of the present invention to control animal parasites, in particular helminths, it is intended to reduce or prevent illness, cases of deaths and performance reductions (in the case of meat, milk, wool, hides, eggs, honey and the like), so that more economical and simpler animal keeping is made possible and better animal well-being is achievable.

The term "control" or "controlling", as used herein with regard to the animal health field, means that the compounds of the present invention are effective in reducing the incidence of the respective parasite in an animal infected with such parasites to innocuous levels. More specifically, "controlling", as used herein, means that the compounds of the present invention are effective in killing the respective parasite, inhibiting its growth, or inhibiting its proliferation.

In accordance with a further aspect, the present invention covers compounds of general formula (I), as described supra, or stereoisomers, tautomers, N-oxides, hydrates, solvates, and salts thereof, particularly pharmaceutically acceptable salts thereof, or mixtures of same, for use in the treatment or prevention of diseases, in particular of helminth infections, particulary of gastro-intestinal and extra-intestinal helminth infections, more particulary of gastro-intestinal and extra-intestinal infections with nematodes.

The pharmaceutical activity of the compounds according to the invention can be explained by their interaction with the Slo-1 ion channel.

In accordance with a further aspect, the present invention covers the use of compounds of general formula (I), as described supra, or stereoisomers, tautomers, N-oxides, hydrates, solvates, and salts thereof, particularly pharmaceutically acceptable salts thereof, or mixtures of same, for the treatment or prevention of diseases, in particular of helminth infections, particulary of gastro-intestinal and extra-intestinal helminth infections, more particulary of gastro-intestinal and extra-intestinal infections with nematodes.

In accordance with a further aspect, the present invention covers the use of compounds of general formula (I), as described supra, or stereoisomers, tautomers, N-oxides, hydrates, solvates, and salts thereof, particularly pharmaceutically acceptable salts thereof, or mixtures of same, in a method of treatment or prevention of diseases, in particular of helminth infections, particulary of gastro-intestinal and extra-intestinal helminth infections, more particulary of gastro-intestinal and extra-intestinal infections with nematodes.

In accordance with a further aspect, the present invention covers use of a compound of general formula (I), as described supra, or stereoisomers, tautomers, N-oxides, hydrates, solvates, and salts thereof, particularly pharmaceutically acceptable salts thereof, or mixtures of same, for the preparation of a pharmaceutical composition, preferably a medicament, for the prevention or treatment of diseases, in particular of helminth infections, particulary of gastro-intestinal and extra-intestinal helminth infections, more particulary of gastro-intestinal and extra-intestinal infections with nematodes.

In accordance with a further aspect, the present invention covers a method of treatment or prevention of diseases, in particular of helminth infections, particularly of gastro-intestinal and extra-intestinal helminth infections, more particulary of gastro-intestinal and extra-intestinal infections with nematodes, using an effective amount of a compound of general formula (I), as described supra, or stereoisomers, tautomers, N-oxides, hydrates, solvates, and salts thereof, particularly pharmaceutically acceptable salts thereof, or mixtures of same.

In accordance with a further aspect, the present invention covers compounds of general formula (I), as described supra, or stereoisomers, tautomers, N-oxides, hydrates, solvates, and salts thereof, particularly pharmaceutically acceptable salts thereof, or mixtures of same, for use as an antiendoparasitical agent.

In accordance with a further aspect, the present invention covers compounds of general formula (I), as described supra, or stereoisomers, tautomers, N-oxides, hydrates, solvates, and salts thereof, particularly pharmaceutically acceptable salts thereof, or mixtures of same, for use as a anthelmintic agent, in particular for use as a nematicidal agent, a platyhelminthicidal agent, an acanthocephalicidal agent, or a pentastomicidal agent.

In accordance with a further aspect, the present invention covers pharmaceutical compositions, in particular a veterinary formulation, comprising a compound of general formula (I), as described supra, or a stereoisomer, a tautomer, an N-oxide, a hydrate, a solvate, a salt thereof, particularly a pharmaceutically acceptable salt, or a mixture of same, and one or more excipients), in particular one or more pharmaceutically acceptable excipient(s). Conventional procedures for preparing such pharmaceutical compositions in appropriate dosage forms can be utilized.

In accordance with a further aspect, the present invention covers a method for preparing a pharmaceutical composition, in particular a veterinary formulation, comprising the step of mixing a compound of general formula (I), as described supra, or a stereoisomer, a tautomer, an N-oxide, a hydrate, a solvate, a salt thereof, particularly a pharmaceutically acceptable salt, or a mixture of same, with one or more excipients), in particular one or more pharmaceutically acceptable excipient(s).

In accordance with a further aspect, the present invention covers a method of treatment or prevention of diseases, in particular of helminth infections, particularly of gastro-intestinal and extra-intestinal helminth infections, more particulary of gastro-intestinal and extra-intestinal infections with nematodes, using a pharmaceutical composition, in particular a veterinary formulation, comprising an effective amount of a compound of general formula (I), as described supra, or stereoisomers, tautomers, N-oxides, hydrates, solvates, and salts thereof, particularly pharmaceutically acceptable salts thereof, or mixtures of same.

Accordingly, the present invention covers a method for controlling helminth infections in humans and/or animals by administering an anthelminthically effective amount of at least one compound of general formula (I) or (II) supra to a human or an animal in need thereof.

The present invention furthermore covers pharmaceutical compositions, in particular veterinary formulations, which comprise at least one compound according to the invention, conventionally together with one or more pharmaceutically suitable excipients, and to their use for the above mentioned purposes.

It is possible for the compounds according to the invention to have systemic and/or local activity. For this purpose, they can be administered in a suitable manner, such as, for example, via the oral, parenteral, pulmonary, nasal, sublingual, lingual, buccal, rectal, vaginal, dermal, transdermal, conjunctival, otic route or as an implant or stent. Such administration can be carried out prophylactically, methaphylactically or therapeutically.

For these administration routes, it is possible for the compounds according to the invention to be administered in suitable administration forms.

For oral administration, it is possible to formulate the compounds according to the invention to dosage forms known in the art that deliver the compounds of the invention rapidly and/or in a modified manner, such as, for example, tablets (uncoated or coated tablets, for example with enteric or controlled release coatings that dissolve with a delay or are insoluble), orally-disintegrating tablets, films/wafers, films/lyophylisates, capsules (for example hard or soft gelatine capsules), sugar-coated tablets, granules, pellets, chewables (for example soft chewables), powders, emulsions, suspensions, aerosols or solutions. It is possible to incorporate the compounds according to the invention in crystalline and/or amorphised and/or dissolved form into said dosage forms.

Parenteral administration can be effected with avoidance of an absorption step (for example intravenous, intraarterial, intracardial, intraspinal or intralumbal) or with inclusion of absorption (for example intramuscular, subcutaneous, intracutaneous, percutaneous or intraperitoneal). Administration forms which are suitable for parenteral administration are, inter alia, preparations for injection and infusion in the form of solutions, suspensions, emulsions, lyophylisates or sterile powders.

Examples which are suitable for other administration routes are pharmaceutical forms for inhalation [inter alia powder inhalers, nebulizers], nasal drops, nasal solutions, nasal sprays; tablets/films/wafers/capsules for lingual, sublingual or buccal administration; suppositories; eye drops, eye ointments, eye baths, ocular inserts, ear drops, ear sprays, ear powders, ear-rinses, ear tampons; vaginal capsules, aqueous suspensions (lotions, mixturae agitandae), lipophilic suspensions, emulsions, ointments, creams, transdermal therapeutic systems (such as, for example, patches), milk, pastes, foams, spot-ons, dusting powders, implants or stents.

The compounds according to the invention can be incorporated into the stated administration forms. This can be effected in a manner known per se by mixing with pharmaceutically suitable excipients. Pharmaceutically suitable excipients include, inter alia, fillers and carriers (for example cellulose, microcrystalline cellulose (such as, for example, Avicel®), lactose, mannitol, starch, calcium phosphate (such as, for example, Di-Cafos®)), ointment bases (for example petroleum jelly, paraffins, triglycerides, waxes, wool wax, wool wax alcohols, lanolin, hydrophilic ointment, polyethylene glycols), bases for suppositories (for example polyethylene glycols, cacao butter, hard fat), solvents (for example water, ethanol, isopropanol, glycerol, propylene glycol, medium chain-length triglycerides fatty oils, liquid polyethylene glycols, paraffins), surfactants, emulsifiers, dispersants or wetters (for example sodium dodecyl sulfate), lecithin, phospholipids, fatty alcohols (such as, for example, Lanette®), sorbitan fatty acid esters (such as, for example, Span®), polyoxyethylene sorbitan fatty acid esters (such as, for example, Tween®), polyoxyethylene fatty acid glycerides (such as, for example, Cremophor®), polyoxethylene fatty acid esters, polyoxyethylene fatty alcohol ethers, glycerol fatty acid esters, poloxamers (such as, for example, Pluronic®), buffers, acids and bases (for example phosphates, carbonates, citric acid, acetic acid, hydrochloric acid, sodium hydroxide solution, ammonium carbonate, trometamol, triethanolamine), isotonicity agents (for example glucose, sodium chloride), adsorbents (for example highly-disperse silicas), viscosity-increasing agents, gel formers, thickeners and/or binders (for example polyvinylpyrrolidone, methylcellulose, hydroxypropylmethylcellulose, hydroxypropylcellulose, carboxymethylcellulose-sodium, starch, carbomers, polyacrylic acids (such as, for example, Carbopol®); alginates, gelatine), disintegrants (for example modified starch, carboxymethylcellulose-sodium, sodium starch glycolate (such as, for example, Explotab®), cross-linked polyvinylpyrrolidone, croscarmellose-sodium (such as, for example, AcDiSol®)), flow regulators, lubricants, glidants and mould release agents (for example magnesium stearate, stearic acid, talc, highly-disperse silicas (such as, for example, Aerosil®)), coating materials (for example sugar, shellac) and film formers for films or diffusion membranes which dissolve rapidly or in a modified manner (for example polyvinylpyrrolidones (such as, for example, Kollidon®), polyvinyl alcohol, hydroxypropylmethylcellulose, hydroxypropylcellulose, ethylcellulose, hydroxypropylmethylcellulose phthalate, cellulose acetate, cellulose acetate phthalate, polyacrylates, polymethacrylates (such as, for example, Eudragit®)), capsule materials (for example gelatine, hydroxypropylmethylcellulose), synthetic polymers (for example polylactides, polyglycolides, polyacrylates, polymethacrylates (such as, for example, Eudragit®), polyvinylpyrrolidones (such as, for example, Kollidon®), polyvinyl alcohols, polyvinyl acetates, polyethylene oxides, polyethylene glycols and their copolymers and blockcopolymers), plasticizers (for example polyethylene glycols, propylene glycol, glycerol, triacetine, triacetyl citrate, dibutyl phthalate), penetration enhancers, stabilisers (for example antioxidants such as, for example, ascorbic acid, ascorbyl palmitate, sodium ascorbate, butylhydroxyanisole, butylhydroxytoluene, propyl gallate), preservatives (for example parabens, sorbic acid, thiomersal, benzalkonium chloride, chlorhexidine acetate, sodium benzoate), colourants (for example inorganic pigments such as, for example, iron oxides, titanium dioxide), flavourings, sweeteners, flavour- and/or odour-masking agents.

The present invention furthermore relates to a pharmaceutical composition which comprise at least one compound according to the invention, conventionally together with one or more pharmaceutically suitable excipient(s), and to their use according to the present invention.

In accordance with another aspect, the present invention covers pharmaceutical combinations, in particular medicaments, comprising at least one compound of general formula (I) of the present invention and at least one or more further active ingredients, in particular for the treatment and/or prevention of an endo- and/or ectoparasiticidal infection.

The term "endoparasite" in the present invention is used as known to persons skilled in the art, and refers in particular to helminths. The term "ectoparasite" in the present invention is used as known to persons skilled in the art, and refers in particular to arthropods, particularly insects or acarids.

Particularly, the present invention covers a pharmaceutical combination, in particular a veterinary combination, which comprises:
 one or more first active ingredients, in particular compounds of general formula (I) as defined supra, and
 one or more further active ingredients, in particular one or more endo- and/or ectoparasiticides.

The term "combination" in the present invention is used as known to persons skilled in the art, it being possible for said combination to be a fixed combination, a non-fixed combination or a kit-of-parts.

A "fixed combination" in the present invention is used as known to persons skilled in the art and is defined as a combination wherein, for example, a first active ingredient, such as one or more compounds of general formula (I) of the present invention, and a further active ingredient are present together in one unit dosage or in one single entity. One example of a "fixed combination" is a pharmaceutical composition wherein a first active ingredient and a further active ingredient are present in admixture for simultaneous administration, such as in a formulation. Another example of a "fixed combination" is a pharmaceutical combination wherein a first active ingredient and a further active ingredient are present in one unit without being in admixture.

A non-fixed combination or "kit-of-parts" in the present invention is used as known to persons skilled in the art and is defined as a combination wherein a first active ingredient and a further active ingredient are present in more than one unit. One example of a non-fixed combination or kit-of-parts is a combination wherein the first active ingredient and the further active ingredient are present separately. It is possible for the components of the non-fixed combination or kit-of-parts to be administered separately, sequentially, simultaneously, concurrently or chronologically staggered.

The compounds of the present invention can be administered as the sole pharmaceutical agent or in combination with one or more other pharmaceutically active ingredients where the combination causes no unacceptable adverse effects. The present invention also covers such pharmaceutical combinations. For example, the compounds of the present invention can be combined with known ectoparasiticides and/or endoparasiticides.

The other or further active ingredients specified herein by their common names are known and described, for example, in the Pesticide Manual ("The Pesticide Manual" 16th Ed., British Crop Protection Council 2012) or can be searched in the internet (e.g. http://www.alanwood.net/pesticides). The classification is based on the current IRAC Mode of Action Classification Scheme at the time of filing of this patent application.

Examples of ectoparasiticides and/or endoparasiticides are insecticides, acaricides and nematicides, and include in particular:

(1) Acetylcholinesterase (AChE) inhibitors, such as, for example, carbamates, for example alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, for example acephate, azamethiphos, azinphos-ethyl, azinphos-methyl, cadusafos, chlorethoxyfos, chlorfenvinphos, chlormephos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel blockers, such as, for example, cyclodiene-organochlorines, for example chlordane and endosulfan or phenylpyrazoles (fiproles), for example ethiprole and fipronil.

(3) Sodium channel modulators, such as, for example, pyrethroids, e.g. acrinathrin, allethrin, d-cis-trans allethrin, d-trans allethrin, bifenthrin, bioallethrin, bioallethrin s-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans-isomer], deltamethrin, empenthrin [(EZ)-(1R)-isomer], esfenvalerate, etofenprox, fenpropathrin, fenvalerate, flucythrinate, flumethrin, tau-fluvalinate, halfenprox, imiprothrin, kadethrin, momfluorothrin, permethrin, phenothrin [(1R)-trans-isomer], prallethrin, pyrethrins (pyrethrum), resmethrin, silafluofen, tefluthrin, tetramethrin, tetramethrin [(1R)-isomer)], tralomethrin and transfluthrin or DDT or methoxychlor.

(4) Nicotinic acetylcholine receptor (nAChR) competitive modulators, such as, for example, neonicotinoids, e.g. acetamiprid, clothianidin, dinotefuran, imidacloprid, nitenpyram, thiacloprid and thiamethoxam or nicotine or sulfoxaflor or flupyradifurone.

(5) Nicotinic acetylcholine receptor (nAChR) allosteric modulators, such as, for example, spinosyns, e.g. spinetoram and spinosad.

(6) Glutamate-gated chloride channel (GluCl) allosteric modulators, such as, for example, avermectins/milbemycins, for example abamectin, emamectin benzoate, lepimectin and milbemectin.

(7) Juvenile hormone mimics, such as, for example, juvenile hormone analogues, e.g. hydroprene, kinoprene and methoprene or fenoxycarb or pyriproxyfen.

(9) Modulators of Chordotonal Organs, such as, for example pymetrozine or flonicamid.

(10) Mite growth inhibitors, such as, for example clofentezine, hexythiazox and diflovidazin or etoxazole.

(12) Inhibitors of mitochondrial ATP synthase, such as, ATP disruptors such as, for example, diafenthiuron or organotin compounds, for example azocyclotin, cyhexatin and fenbutatin oxide or propargite or tetradifon.

(13) Uncouplers of oxidative phosphorylation via disruption of the proton gradient, such as, for example, chlorfenapyr, DNOC and sulfluramid.

(14) Nicotinic acetylcholine receptor channel blockers, such as, for example, bensultap, cartap hydrochloride, thiocylam, and thiosultap-sodium.

(15) Inhibitors of chitin biosynthesis, type 0, such as, for example, bistrifluron, chlorfluazuron, diflubenzuron, flucycloxuron, flufenoxuron, hexaflumuron, lufenuron, novaluron, noviflumuron, teflubenzuron and triflumuron.

(16) Inhibitors of chitin biosynthesis, type 1, for example buprofezin.

(17) Moulting disruptor (in particular for Diptera, i.e. dipterans), such as, for example, cyromazine.

(18) Ecdysone receptor agonists, such as, for example, chromafenozide, halofenozide, methoxyfenozide and tebufenozide.

(19) Octopamine receptor agonists, such as, for example, amitraz.

(20) Mitochondrial complex III electron transport inhibitors, such as, for example, hydramethylnone or acequinocyl or fluacrypyrim.

(21) Mitochondrial complex I electron transport inhibitors, such as, for example from the group of the METI acaricides, e.g. fenazaquin, fenpyroximate, pyrimidifen, pyridaben, tebufenpyrad and tolfenpyrad or rotenone (Derris).

(22) Voltage-dependent sodium channel blockers, such as, for example indoxacarb or metaflumizone.

(23) Inhibitors of acetyl CoA carboxylase, such as, for example, tetronic and tetramic acid derivatives, e.g. spirodiclofen, spiromesifen and spirotetramat.

(25) Mitochondrial complex II electron transport inhibitors, such as, for example, beta-ketonitrile derivatives, e.g. cyenopyrafen and cyflumetofen and carboxanilides, such as, for example, pyflubumide.

(28) Ryanodine receptor modulators, such as, for example, diamides, e.g. chlorantraniliprole, cyantraniliprole and flubendiamide, further active ingredients such as, for example, Afidopyropen, Afoxolaner, Azadirachtin, Benclothiaz, Benzoximate, Bifenazate, Broflanilide, Bromopropylate, Chinomethionat, Chloroprallethrin, Cryolite, Cyclaniliprole, Cycloxaprid, Cyhalodiamide, Dicloromezotiaz, Dicofol, epsilon-Metofluthrin, epsilon-Momfluthrin, Flometoquin, Fluazaindolizine, Fluensulfone, Flufenerim, Flufenoxystrobin, Flufiprole, Fluhexafon, Fluopyram, Fluralaner, Fluxametamide, Fufenozide, Guadipyr, Heptafluthrin, Imidaclothiz, Iprodione, kappa-Bifenthrin, kappa-Tefluthrin, Lotilaner, Meperfluthrin, Paichongding, Pyridalyl, Pyrifluquinazon, Pyriminostrobin, Spirobudiclofen, Tetramethylfluthrin, Tetraniliprole, Tetrachlorantraniliprole, Tioxazafen, Thiofluoximate, Triflumezopyrim and iodomethane; furthermore preparations based on *Bacillus firmus* (1-1582, BioNeem, Votivo), and also the following compounds: 1-{2-fluoro-4-methyl-5-[(2,2,2-trifluoroethyl)sulphinyl]phenyl}-3-(trifluoromethyl)-1H-1,2,4-triazole-5-amine (known from WO2006/043635) (CAS 885026-50-6), {1'-[(2E)-3-(4-chlorophenyl)prop-2-en-1-yl]-5-fluorospiro[indol-3,4'-piperidin]-1 (2H)-yl}(2-chloropyridin-4-yl)methanone (known from WO2003/106457) (CAS 637360-23-7), 2-chloro-N-[2-{1-[(2E)-3-(4-chlorophenyl)prop-2-en-1-yl]piperidin-4-yl}-4-(trifluoromethyl)phenyl]

isonicotinamide (known from WO2006/003494) (CAS 872999-66-1), 3-(4-chloro-2,6-dimethylphenyl)-4-hydroxy-8-methoxy-1,8-diazaspiro[4.5]dec-3-en-2-one (known from WO 2010052161) (CAS 1225292-17-0), 3-(4-chloro-2,6-dimethylphenyl)-8-methoxy-2-oxo-1,8-diazaspiro[4.5]dec-3-en-4-yl ethyl carbonate (known from EP2647626) (CAS 1440516-42-6) 4-(but-2-yn-1-yloxy)-6-(3,5-dimethylpiperidin-1-yl)-5-fluoropyrimidine (known from WO2004/099160) (CAS 792914-58-0), PF1364 (known from JP2010/018586) (CAS 1204776-60-2), N-[(2E)-1-[(6-chloropyridin-3-yl)methyl]pyridin-2(1H)-ylidene]-2,2,2-trifluoroacetamide (known from WO2012/029672) (CAS 1363400-41-2), (3E)-3-[1-[(6-chloro-3-pyridyl)methyl]-2-pyridylidene]-1,1,1-trifluoro-propan-2-one (known from WO2013/144213) (CAS 1461743-15-6), N-[3-(benzylcarbamoyl)-4-chlorophenyl]-1-methyl-3-(pentafluoroethyl)-4-(trifluoromethyl)-1H-pyrazole-5-carboxamide (known from WO2010/051926) (CAS 1226889-14-0), 5-bromo-4-chloro-N-[4-chloro-2-methyl-6-(methylcarbamoyl)phenyl]-2-(3-chloro-2-pyridyl)pyrazole-3-carboxamide (known from CN103232431) (CAS 1449220-44-3), 4-[5-(3,5-dichlorophenyl)-4,5-dihydro-5-(trifluoromethyl)-3-isoxazolyl]-2-methyl-N-(cis-1-oxido-3-thietanyl)-benzamide, 4-[5-(3,5-dichlorophenyl)-4,5-dihydro-5-(trifluoromethyl)-3-isoxazolyl]-2-methyl-N-(trans-1-oxido-3-thietanyl)-benzamide and 4-[(5S)-5-(3,5-dichlorophenyl)-4,5-dihydro-5-(trifluoromethyl)-3-isoxazolyl]-2-methyl-N-(cis-1-oxido-3-thietanyl)benzamide (known from WO 2013/050317 A1) (CAS 1332628-83-7), N-[3-chloro-1-(3-pyridinyl)-1H-pyrazol-4-yl]-N-ethyl-3-[(3,3,3-trifluoropropyl)sulfinyl]-propanamide, (+)-N-[3-chloro-1-(3-pyridinyl)-1H-pyrazol-4-yl]-N-ethyl-3-[(3,3,3-trifluoropropyl)sulfinyl]-propanamide and (−)-N-[3-chloro-1-(3-pyridinyl)-1H-pyrazol-4-yl]-N-ethyl-3-[(3,3,3-trifluoropropyl)sulfinyl]-propanamide (known from WO 2013/162715 A2, WO 2013/162716 A2, US 2014/0213448 A1) (CAS 1477923-37-7), 5-[[(2E)-3-chloro-2-propen-1-yl]amino]-1-[2,6-dichloro-4-(trifluoromethyl)phenyl]-4-[(trifluoromethyl)sulfinyl]-1H-pyrazole-3-carbonitrile (known from CN 101337937 A) (CAS 1105672-77-2), 3-bromo-N-[4-chloro-2-methyl-6-[(methylamino)thioxomethyl]phenyl]-1-(3-chloro-2-pyridinyl)-1H-pyrazole-5-carboxamide, (Liudaibenjiaxuanan, known from CN 103109816 A) (CAS 1232543-85-9); N-[4-chloro-2-[[(1,1-dimethylethyl)amino]carbonyl]-6-methylphenyl]-1-(3-chloro-2-pyridinyl)-3-(fluoromethoxy)-1H-Pyrazole-5-carboxamide (known from WO 2012/034403 A1) (CAS 1268277-22-0), N-[2-(5-amino-1,3,4-thiadiazol-2-yl)-4-chloro-6-methylphenyl]-3-bromo-1-(3-chloro-2-pyridinyl)-1H-pyrazole-5-carboxamide (known from WO 2011/085575 A1) (CAS 1233882-22-8), 4-[3-[2,6-dichloro-4-[(3,3-dichloro-2-propen-1-yl)oxy]phenoxy]propoxy]-2-methoxy-6-(trifluoromethyl)-pyrimidine (known from CN 101337940 A) (CAS 1108184-52-6); (2E)- and 2(Z)-2-[2-(4-cyanophenyl)-1-[3-(trifluoromethyl)phenyl]ethylidene]-N-[4-(difluoromethoxy)phenyl]-hydrazinecarboxamide (known from CN 101715774 A) (CAS 1232543-85-9); 3-(2,2-dichloroethenyl)-2,2-dimethyl-4-(1H-benzimidazol-2-yl)phenyl-cyclopropanecarboxylic acid ester (known from CN 103524422 A) (CAS 1542271-46-4); (4aS)-7-chloro-2,5-dihydro-2-[[(methoxycarbonyl)[4-[(trifluoromethyl)thio]phenyl]amino]carbonyl-indeno[1,2-e][1,3,4]oxadiazine-4a (3H)-carboxylic acid methyl ester (known from CN 102391261 A) (CAS 1370358-69-2); 6-deoxy-3-O-ethyl-2,4-di-O-methyl-, 1-[N-[4-[1-[4-(1,1,2,2,2-pentafluoroethoxy)phenyl]-1H-1,2,4-triazol-3-yl]phenyl]carbamate)-α-L-mannopyranose (known from US 2014/0275503 A1) (CAS 1181213-14-8); 8-(2-cyclopropylmethoxy-4-trifluoromethyl-phenoxy)-3-(6-trifluoromethyl-pyridazin-3-yl)-3-azabicyclo[3.2.1]octane (CAS 1253850-56-4), (8-anti)-8-(2-cyclopropylmethoxy-4-trifluoromethyl-phenoxy)-3-(6-trifluoromethyl-pyridazin-3-yl)-3-aza-bicyclo[3.2.1]octane (CAS 933798-27-7), (8-syn)-8-(2-cyclopropylmethoxy-4-trifluoromethyl-phenoxy)-3-(6-trifluoromethyl-pyridazin-3-yl)-3-aza-bicyclo[3.2.1]octane (known from WO 2007040280 A1, WO 2007040282 A1) (CAS 934001-66-8) and N-[3-chloro-1-(3-pyridinyl)-1H-pyrazol-4-yl]-N-ethyl-3-[(3,3,3-trifluoropropyl)thio]-propanamide (known from WO 2015/058021 A1, WO 2015/058028 A1) (CAS 1477919-27-9) and N-[4-(aminothioxomethyl)-2-methyl-6-[(methylamino)carbonyl]phenyl]-3-bromo-1-(3-chloro-2-pyridinyl)-1H-pyrazole-5-carboxamide (known from CN 103265527 A) (CAS 1452877-50-7), 5-(1,3-dioxan-2-yl)-4-[[4-(trifluoromethyl)phenyl]methoxy]-pyrimidine (known from WO 2013/115391 A1) (CAS 1449021-97-9), 3-(4-chloro-2,6-dimethylphenyl)-4-hydroxy-8-methoxy-1-methyl-1,8-diazaspiro[4.5]dec-3-en-2-one (known from WO 2010/066780 A1, WO 2011/151146 A1) (CAS 1229023-34-0), 3-(4-chloro-2,6-dimethylphenyl)-8-methoxy-1-methyl-1,8-diazaspiro[4.5]decane-2,4-dione (known from WO 2014/187846 A1) (CAS 1638765-58-8), 3-(4-chloro-2,6-dimethylphenyl)-8-methoxy-1-methyl-2-oxo-1,8-diazaspiro[4.5]dec-3-en-4-yl-carbonic acid ethyl ester (known from WO 2010/066780 A1, WO 2011151146 A1) (CAS 1229023-00-0), N-[1-[(6-chloro-3-pyridinyl)methyl]-2(1H)-pyridinylidene]-2,2,2-trifluoro-acetamide (known from DE 3639877 A1, WO 2012029672 A1) (CAS 1363400-41-2), [N(E)]-N-[1-[(6-chloro-3-pyridinyl)methyl]-2(1H)-pyridinylidene]-2,2,2-trifluoro-acetamide, (known from WO 2016005276 A1) (CAS 1689566-03-7), [N(Z)]—N-[1-[(6-chloro-3-pyridinyl)methyl]-2(1H)-pyridinylidene]-2,2,2-trifluoro-acetamide, (CAS 1702305-40-5), 3-endo-3-[2-propoxy-4-(trifluoromethyl)phenoxy]-9-[[5-(trifluoromethyl)-2-pyridinyl]oxy]-9-azabicyclo[3.3.1]nonane (known from WO 2011/105506 A1, WO 2016/133011 A1) (CAS 1332838-17-1).

Active ingredients with unknown or non-specific mode of action, e.g., fentrifanil, fenoxacrim, cycloprene, chlorobenzilate, chlordimeform, flubenzimine, dicyclanil, amidoflumet, quinomethionate, triarathene, clothiazoben, tetrasul, potassium oleate, petroleum, metoxadiazone, gossyplure, flutenzin, bromopropylate, cryolite;

Active ingredients from other classes, e.g. butacarb, dimetilan, cloethocarb, phosphocarb, pirimiphos (-ethyl), parathion (-ethyl), methacrifos, isopropyl o-salicylate, trichlorfon, sulprofos, propaphos, sebufos, pyridathion, prothoate, dichlofenthion, demeton-S-methylsulphone, isazofos, cyanofenphos, dialifos, carbophenothion, autathiofos, aromfenvinfos (-methyl), azinphos (-ethyl), chlorpyrifos (-ethyl), fosmethilan, iodofenphos, dioxabenzofos, formothion, fonofos, flupyrazofos, fensulfothion, etrimfos;

organochlorines, e.g. camphechlor, lindane, heptachlor; or phenylpyrazoles, e.g. acetoprole, pyrafluprole, pyriprole, vaniliprole, sisapronil; or isoxazolines, e.g. sarolaner, afoxolaner, lotilaner, fluralaner;

pyrethroids, e.g. (cis-, trans-), metofluthrin, profluthrin, flufenprox, flubrocythrinate, fubfenprox, fenfluthrin, protrifenbute, pyresmethrin, RU15525, terallethrin, cis-resmethrin, heptafluthrin, bioethanomethrin, biopermethrin, fenpyrithrin, cis-cypermethrin, cis-permethrin, clocythrin, cyhalothrin (lambda-), chlovaporthrin, or halogenated carbonhydrogen compounds (HCHs);

neonicotinoids, e.g. nithiazine;

dicloromezotiaz, triflumezopyrim;

macrocyclic lactones, e.g. nemadectin, ivermectin, latidectin, moxidectin, selamectin, eprinomectin, doramectin, emamectin benzoate; milbemycin oxime;

triprene, epofenonane, diofenolan;

Biologicals, hormones or pheromones, for example natural products, e.g. thuringiensin, codlemone or neem components;

dinitrophenols, e.g. dinocap, dinobuton, binapacryl;

benzoylureas, e.g. fluazuron, penfluron;

amidine derivatives, e.g. chlormebuform, cymiazole, demiditraz;

Bee hive varroa acaricides, for example organic acids, e.g. formic acid, oxalic acid.

Non-limiting examples of insecticides and acaricides of particular interest for use in animal health are and include in particular [i.e. Mehlhorn et al Encyclpaedic Reference of Parasitology $4^{th}$ edition (ISBN 978-3-662-43978-4)]:

Effectors at arthropod ligand gated chloride channels: chlordane, heptachlor, endoculfan. Dieldrin, bromocyclen, toxaphene, lindane, fipronil, pyriprole, sisapronil, afoxolaner, fluralaner, sarolaner, lotilaner, fluxametamide, broflanilide, avermectin, doramectin, eprinomectin, ivermectin, milbemycin, moxidectin, selamectin;

Modulators of arthropod octopaminergic receptors: amitraz, BTS27271, cymiazole, demiditraz;

Effectors at arthropod voltage-gated sodium channels: DDT, methoxychlor, metaflumizone, indoxacarb, cinerin I, cinerin II, jasmolin I, jasmolin II, pyrethrin I, pyrethrin II, allethrin, alphacypermethrin, bioallethrin, betacyfluthrin, cyfluthrin, cyhalothrin, cypermethrin, deltamethrin, etofenprox, fenvalerate, flucythrinate, flumethrin, halfenprox, permethrin, phenothrin, resmethrin, tau-fluvalinate, tetramethrin;

Effectors at arthropod nicotinic cholinergic synapses (acetylcholine esterase, acetylcholine receptors): bromoprypylate, bendiocarb, carbaryl, methomyl, promacyl, propoxur, azamethiphos, chlorfenvinphos, chlorpyrifos, coumaphos, cythioate, diazinon, diclorvos, dicrotophos, dimethoate, ethion, famphur, fenitrothion, fenthion, heptenophos, malathion, naled, phosmet, phoxim, phtalofos, propetamphos, temephos, tetrachlorvinphos, trichlorfon, imidacloprid, nitenpyram, dinotefuran, spinosad, spinetoram;

Effectors on arthropod development processes: cyromazine, dicyclanil, diflubenzuron, fluazuron, lufenuron, triflumuron, fenoxycarb, hydroprene, methoprene, pyriproxyfen, fenoxycarb, hydroprene, S-methoprene, pyriproxyfen.

Exemplary active ingredients from the group of endoparasiticides, as a further or other active ingredient in the present invention, include, without limitation, anthelmintically active compounds and antiprotozoal active compounds.

Anthelmintically active compounds, including, without limitation, the following nematicidally, trematicidally and/or cestocidally active compounds:

from the class of macrocyclic lactones, for example: eprinomectin, abamectin, nemadectin, moxidectin, doramectin, selamectin, lepimectin, latidectin, milbemectin, ivermectin, emamectin, milbemycin;

from the class of benzimidazoles and probenzimidazoles, for example: oxibendazole, mebendazole, triclabendazole, thiophanate, parbendazole, oxfendazole, netobimin, fenbendazole, febantel, thiabendazole, cyclobendazole, cambendazole, albendazole-sulphoxide, albendazole, flubendazole;

from the class of depsipeptides, preferably cyclic depsipetides, in particular 24-membered cyclic depsipeptides, for example: emodepside, PF1022A;

from the class of tetrahydropyrimidines, for example: morantel, pyrantel, oxantel;

from the class of imidazothiazoles, for example: butamisole, levamisole, tetramisole;

from the class of aminophenylamidines, for example: amidantel, deacylated amidantel (dAMD), tribendimidine;

from the class of aminoacetonitriles, for example: monepantel;

from the class of paraherquamides, for example: paraherquamide, derquantel;

from the class of salicylanilides, for example: tribromsalan, bromoxanide, brotianide, clioxanide, closantel, niclosamide, oxyclozanide, rafoxanide;

from the class of substituted phenols, for example: nitroxynil, bithionol, disophenol, hexachlorophene, niclofolan, meniclopholan;

from the class of organophosphates, for example: trichlorfon, naphthalofos, dichlorvos/DDVP, crufomate, coumaphos, haloxon;

from the class of piperazinones/quinolines, for example: praziquantel, epsiprantel;

from the class of piperazines, for example: piperazine, hydroxyzine;

from the class of tetracyclines, for example: tetracyclin, chlorotetracycline, doxycyclin, oxytetracyclin, rolitetracyclin;

from diverse other classes, for example: bunamidine, niridazole, resorantel, omphalotin, oltipraz, nitroscanate, nitroxynile, oxamniquine, mirasan, miracil, lucanthone, hycanthone, hetolin, emetine, diethylcarbamazine, dichlorophen, diamfenetide, clonazepam, bephenium, amoscanate, clorsulon.

Antiprotozoal active ingredients in the present invention, including, without limitation, the following active ingredients:

from the class of triazines, for example: diclazuril, ponazuril, letrazuril, toltrazuril;

from the class of polyether ionophore, for example: monensin, salinomycin, maduramicin, narasin;

from the class of macrocyclic lactones, for example: milbemycin, erythromycin;

from the class of quinolones, for example: enrofloxacin, pradofloxacin;

from the class of quinines, for example: chloroquine;

from the class of pyrimidines, for example: pyrimethamine;

from the class of sulfonamides, for example: sulfaquinoxaline, trimethoprim, sulfaclozin;

from the class of thiamines, for example: amprolium;

from the class of lincosamides, for example: clindamycin;

from the class of carbanilides, for example: imidocarb;

from the class of nitrofuranes, for example: nifurtimox;

from the class of quinazolinone alkaloids, for example: halofuginon;

from diverse other classes, for example: oxamniquin, paromomycin;

from the class of vaccines or antigenes from microorganisms, for example: *Babesia canis rossi, Eimeria tenella, Eimeria praecox, Eimeria necatrix, Eimeria mitis, Eimeria maxima, Eimeria brunetti, Eimeria acervulina, Babesia canis vogeli, Leishmania infantum, Babesia canis canis, Dictyocaulus viviparus.*

All named other or further active ingredients in the present invention can, if their functional groups enable this, optionally form salts with suitable bases or acids.

Based upon standard laboratory techniques known to evaluate compounds useful for the treatment of helminth infections, by standard toxicity tests and by standard pharmacological assays for the determination of treatment of the conditions identified above in animals, and by comparison of these results with the results of known active ingredients or medicaments that are used to treat these conditions, the effective dosage of the compounds of the present invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the subject treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, it is possible for "drug holidays", in which a subject is not dosed with a drug for a certain period of time, to be beneficial to the overall balance between pharmacological effect and tolerability. Furthermore, it is possible to have long-acting treatments, wherein the subject gets treated once for more than four weeks. It is possible for a unit dosage to contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each subject will vary according to the nature and severity of the condition as determined by the attending diagnostician, the activity of the specific compound employed, the age and general condition of the subject, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

EXPERIMENTAL SECTION

Abbreviations:
atm standard atmosphere
DAD diode array detector
DMSO dimethyl sulfoxide
ELSD evaporative light scattering detector
ESI electrospray ionization
h hour(s)
LC-MS liquid chromatography-coupled mass spectrometry
min minute(s)
NMR nuclear magnetic resonance spectrometry
$R_t$ retention time
TLC thin layer chromatography The various aspects of the invention described in this application are illustrated by the following examples which are not meant to limit the invention in any way.

The example testing experiments described herein serve to illustrate the present invention and the invention is not limited to the examples given.

EXPERIMENTAL SECTION—GENERAL PART

All reagents, for which the synthesis is not described in the experimental part, are either commercially available, or are known compounds or may be formed from known compounds by known methods by a person skilled in the art.

The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallization. In some cases, impurities may be stirred out using a suitable solvent. In some cases, the compounds may be purified by chromatography, particularly flash column chromatography, using for example prepacked silica gel cartridges, e.g. Biotage SNAP cartidges KP-Sil® or KP-NH® in combination with a Biotage autopurifier system (SP4® or Isolera Four®) and eluents such as gradients of hexane/ethyl acetate or dichloromethane/methanol. In some cases, the compounds may be purified by preparative HPLC using for example a Waters autopurifier equipped with a diode array detector and/or on-line electrospray ionization mass spectrometer in combination with a suitable prepacked reverse phase column and eluents such as gradients of water and acetonitrile which may contain additives such as trifluoroacetic acid, formic acid or aqueous ammonia.

In some cases, purification methods as described above can provide those compounds of the present invention which possess a sufficiently basic or acidic functionality in the form of a salt, such as, in the case of a compound of the present invention which is sufficiently basic, a trifluoroacetate or formate salt for example, or, in the case of a compound of the present invention which is sufficiently acidic, an ammonium salt for example. A salt of this type can either be transformed into its free base or free acid form, respectively, by various methods known to the person skilled in the art, or be used as salts in subsequent biological assays. It is to be understood that the specific form (e.g. salt, free base etc.) of a compound of the present invention as isolated and as described herein is not necessarily the only form in which said compound can be applied to a biological assay in order to quantify the specific biological activity.

ANALYTICAL METHODS

Analytical Liquid Chromatography

Analytical (UP)LC-MS was performed by means of different equipments as described below. The masses (m/z) are reported from the positive mode electrospray ionisation unless the negative mode is indicated (ESI-).

Method L1:

Instrument type: Waters UPLC system; column: Zorbax Eclipse Plus C18, 50 mm×2.1 mm, 1.8 µm; eluent A: acetonitrile+1 ml formic acid/L, eluent B: millipore water+ 0.9 ml formic acid/L; gradient: 0.0 min 10% A→1.7 min 95% A→2.40 min 95% A→2.41 min 10% A→2.50 min 10% A; oven: 55° C.; flow: 0.85 ml/min; UV-detection: 210 nm. Waters SQD2 MS detector: 100-1000 Amu, ES-ionization, positive or negative.

Method L2:

Instrument type: Agilent 1290; column: Zorbax Eclipse Plus C18, 50 mm×2.1 mm, 1.8 μm; eluent A: acetonitrile+1 ml formic acid/L, eluent B: millipore water+0.9 ml formic acid/L; gradient: 0.0 min 10% A→1.8 min 95% A→2.50 min 95% A→2.52 min 10% A→2.60 min 10% A; oven: 55° C.; flow: 1 ml/min; UV-detection: 210 nm. Agilent MS detector: 100-1000 Amu, ES-ionization, positive or negative.

Method L3:

MS instrument type: Agilent Technologies 6130 Quadrupole LC-MS; HPLC instrument type: Agilent Technologies 1260 Infinity; column: Waters XSelect (C18, 30×2.1 mm, 3.5 g); flow: 1 mL/min; column temp: 35° C.; eluent A: 0.1% formic acid in acetonitrile; eluent B: 0.1% formic acid in water; lin. gradient: t=0 min 5% A, t=1.6 min 98% A, t=3 min 98% A; detection: DAD (220-320 nm); detection: MSD (ESI pos/neg) mass range: 100-800; detection: ELSD (PL-ELS 2100): gas flow 1.2 mL/min, gas temp: 70° C., neb: 50° C.

Method L4:

MS instrument type: Agilent Technologies 6130 Quadrupole LC-MS; HPLC instrument type: Agilent Technologies 1260 Infinity; column: Waters XSelect (C18, 50×2.1 mm, 3.5 g); flow: 0.8 mL/min; column temp: 35° C.; eluent A: 0.1% formic acid in acetonitrile; eluent B: 0.1% formic acid in water; lin. gradient: t=0 min 5% A, t=3.5 min 98% A, t=6 min 98% A; detection: DAD (220-320 nm); detection: MSD (ESI pos/neg) mass range: 100-800; detection: ELSD (PL-ELS 2100): gas flow 1.2 mL/min, gas temp: 70° C., neb: 50° C.

Method L5:

MS instrument type: Agilent Technologies LC/MSD SL; HPLC instrument type: Agilent Technologies 1100 Series; column: Waters XSelect (C18, 30×2.1 mm, 3.5 g); flow: 1 mL/min; column temp: 25° C., eluent A: 95% acetonitrile+5% 10 mM ammoniumbicarbonate in water, eluent B: 10 mM ammoniumbicarbonate in water pH=9.0; lin. gradient: t=0 min 5% A, t=1.6 min 98% A, t=3 min 98% A; detection: DAD (220-320 nm); detection: MSD (ESI pos/neg) mass range: 100-800.

Method L6:

MS instrument type: Agilent Technologies LC/MSD SL; HPLC instrument type: Agilent Technologies 1100 Series; column: Waters XSelect (C18, 50×2.1 mm, 3.5 g; flow: 0.8 mL/min; column temp: 25° C.; eluent A: 95% acetonitrile+5% 10 mM ammoniumbicarbonate in water, eluent B: 10 mM ammoniumbicarbonate in water pH=9.0; lin. gradient: t=0 min 5% A, t=3.5 min 98% A, t=6 min 98% A; detection: DAD (220-320 nm); detection: MSD (ESI pos/neg) mass range: 100-800.

For the Following Methods of Liquid Chromatography:

LCMS analyses were performed on a SHIMADZU LCMS consisting of an UFLC 20-AD and LCMS 2020 MS detector. The Diode Array Detector was scanned from 190-400 nm. The mass spectrometer was equipped with an electrospray ion source (ESI) operated in a positive or negative mode. The mass spectrometer was scanned between m/z 90-900 with a scan time from 0.5 to 1.0 s.

Liquid Chromatography-Mass Spectrometry Method M1:

The column used was a Shim-pack XR-ODS, 2.2 μm, 3.0×50 mm. A linear gradient was applied, starting at 95% A (A: 0.05% TFA in water) and ending at 100% B (B: 0.05% TFA in MeCN) over 1.80 min with a total run time of 2.10 min. The column temperature was at 45° C. with the flow rate of 1.20 mL/min.

Liquid Chromatography-Mass Spectrometry Method M2:

The column used was an EVO, 2.6 μm, 3.0×50 mm. A linear gradient was applied, starting at 90% A (A: 0.1% FA in water) and ending at 95% B (B: 0.1% FA in MeCN) over 4.20 min with a total run time of 4.50 min. The column temperature was at 40° C. with the flow rate of 1.00 mL/min.

Liquid Chromatography-Mass Spectrometry Method M3:

The column used was a CORTECS C18, 2.7 μm, 2.1×50 mm. A linear gradient was applied, starting at 95% A (A: 0.09% FA in water) and ending at 100% B (B: 0.1% FA in MeCN) over 1.70 min with a total run time of 2.00 min. The column temperature was at 40° C. with the flow rate of 1.00 mL/min.

Liquid Chromatography-Mass Spectrometry Method M4:

The column used was a CORTECS C18+, 2.7 μm, 2.1×50 mm. A linear gradient was applied, starting at 90% A (A: 0.1% FA in water) and ending at 100% B (B: 0.1% FA in MeCN) over 1.70 min with a total run time of 2.00 min. The column temperature was at 45° C. with the flow rate of 1.00 mL/min.

Liquid Chromatography-Mass Spectrometry Method M5:

The column used was a Kinetex EVO C18, 2.6 μm, 3.0×50 mm. A linear gradient was applied, starting at 90% A (A: 0.1% FA in water) and ending at 100% B (B: 0.1% FA in MeCN) over 1.70 min with a total run time of 2.00 min. The column temperature was at 40° C. with the flow rate of 1.00 mL/min.

Liquid Chromatography-Mass Spectrometry Method M6:

The column used was a CORTECS C18, 2.7 μm, 2.1×50 mm. A linear gradient was applied, starting at 95% A (A: 0.09% FA in water) and ending at 100% B (B: 0.1% FA in MeCN) over 2.60 min with a total run time of 3.00 min. The column temperature was at 40° C. with the flow rate of 1.00 mL/min.

Liquid Chromatography-Mass Spectrometry Method M7:

The column used was a Shim-pack XR-ODS, 2.2 μm, 3.0×50 mm. A linear gradient was applied, starting at 95% A (A: 0.05% TFA in water) and ending at 100% B (B: 0.05% TFA in MeCN) over 2.80 min with a total run time of 3.30 min. The column temperature was at 45° C. with the flow rate of 1.20 mL/min.

Liquid Chromatography-Mass Spectrometry Method M8:

The column used was a CORTECS C18+, 2.7 μm, 2.1×50 mm. A linear gradient was applied, starting at 90% A (A: 0.1% FA in water) and ending at 100% B (B: 0.1% FA in MeCN) over 1.70 min with a total run time of 2.00 min. The column temperature was at 40° C. with the flow rate of 1.00 mL/min.

Liquid Chromatography-Mass Spectrometry Method M9:

The column used was a Kinetex EVO C18, 2.6 μm, 3.0×50 mm. A linear gradient was applied, starting at 90% A (A: 0.1% FA in water) and ending at 95% B (B: 0.1% FA in MeCN) over 4.20 min with a total run time of 4.50 min. The column temperature was at 40° C. with the flow rate of 1.00 mL/min.

Liquid Chromatography-Mass Spectrometry Method M10:

The column used was a Kinetex EVO C18, 2.6 μm, 3.0×50 mm. A linear gradient was applied, starting at 90% A (A: 0.1% FA in water) and ending at 100% B (B: 0.1% FA in MeCN) over 1.70 min with a total run time of 2.00 min. The column temperature was at 40° C. with the flow rate of 1.00 mL/min.

Liquid Chromatography-Mass Spectrometry Method M11:

The column used was a CORTECS C18+, 2.7 μm, 2.1×50 mm. A linear gradient was applied, starting at 90% A (A: 0.1% FA in water) and ending at 95% B (B: 0.1% FA in MeCN) over 2.70 min with a total run time of 3.00 min. The column temperature was at 40° C. with the flow rate of 1.00 mL/min.

Liquid Chromatography-Mass Spectrometry Method M12:

The column used was an Ascentis Express C18, 2.7 μm, 3.0×50 mm. A linear gradient was applied, starting at 90% A (A: 0.09% FA in water) and ending at 100% B (B: 0.1% FA in MeCN) over 1.70 min with a total run time of 2.00 min. The column temperature was at 40° C. with the flow rate of 1.50 mL/min.

Liquid Chromatography-Mass Spectrometry Method M13:

The column used was an Ascentis Express C18, 2.7 μm, 2.1×50 mm. A linear gradient was applied, starting at 95% A (A: 0.05% TFA in water) and ending at 100% B (B: 0.05% TFA in MeCN) over 1.70 min with a total run time of 2.00 min. The column temperature was at 40° C. with the flow rate of 1.00 mL/min.

Liquid Chromatography-Mass Spectrometry Method M14:

The column used was an Ascentis Express C18, 2.7 μm, 2.1×50 mm. A linear gradient was applied, starting at 95% A (A: 0.05% TFA in water) and ending at 95% B (B: 0.05% TFA in MeCN) over 2.70 min with a total run time of 3.00 min. The column temperature was at 40° C. with the flow rate of 1.00 mL/min.

Liquid Chromatography-Mass Spectrometry Method M15:

The column used was an Ascentis Express C18, 2.7 μm, 2.1×50 mm. A linear gradient was applied, starting at 70% A (A: 0.05% TFA in water) and ending at 95% B (B: 0.05% TFA in MeCN) over 2.70 min with a total run time of 3.00 min. The column temperature was at 40° C. with the flow rate of 1.00 mL/min.

Liquid Chromatography-Mass Spectrometry Method M16:

The column used was a CORTECS C18, 2.7 μm, 2.1×50 mm. A linear gradient was applied, starting at 95% A (A: 0.09% FA in water) and ending at 100% B (B: 0.1% FA in MeCN) over 1.70 min with a total run time of 2.00 min. The column temperature was at 40° C. with the flow rate of 1.00 mL/min.

Liquid Chromatography-Mass Spectrometry Method M17:

The column used was a CORTECS C18+100 A, 2.7 μm, 2.1×50 mm. A linear gradient was applied, starting at 90% A (A: 0.1% FA in water) and ending at 100% B (B: 0.1% FA in MeCN) over 1.60 min with a total run time of 2.00 min. The column temperature was at 40° C. with the flow rate of 1.00 mL/min.

Liquid Chromatography-Mass Spectrometry Method M18:

The column used was a Kinetex EVO C18, 2.6 μm, 3.0×50 mm. A linear gradient was applied, starting at 90% A (A: 0.09% FA in water) and ending at 100% B (B: 0.1% FA in MeCN) over 1.70 min with a total run time of 2.00 min. The column temperature was at 40° C. with the flow rate of 1.00 mL/min.

Liquid Chromatography-Mass Spectrometry Method M19:

The column used was a Kinetex EVO C18 100 A, 2.6 μm, 3.0×50 mm. A linear gradient was applied, starting at 90% A (A: 0.1% FA in water) and ending at 100% B (B: 0.1% FA in MeCN) over 1.60 min with a total run time of 2.00 min. The column temperature was at 40° C. with the flow rate of 1.00 mL/min.

Liquid Chromatography-Mass Spectrometry Method M20:

The column used was an Ascentis Express C18, 2.7 μm, 3.0×50 mm. A linear gradient was applied, starting at 95% A (A: 0.05% TFA in water) and ending at 95% B (B: 0.05% TFA in MeCN) over 1.70 min with a total run time of 2.00 min. The column temperature was at 40° C. with the flow rate of 1.50 mL/min.

Liquid Chromatography-Mass Spectrometry Method M21:

The column used was a Kinetex EVO C18, 2.6 μm, 3.0×50 mm. A linear gradient was applied, starting at 90% A (A: 0.09% FA in water) and ending at 100% B (B: 0.1% FA in MeCN) over 1.70 min with a total run time of 2.00 min. The column temperature was at 40° C. with the flow rate of 1.50 mL/min.

Liquid Chromatography-Mass Spectrometry Method M22:

The column used was a Kinetex EVO C18, 2.6 μm, 3.0×50 mm. A linear gradient was applied, starting at 90% A (A: 0.09% FA in water) and ending at 95% B (B: 0.1% FA in MeCN) over 2.70 min with a total run time of 3.00 min. The column temperature was at 40° C. with the flow rate of 1.50 mL/min.

Liquid Chromatography-Mass Spectrometry Method M23:

The column used was an Ascentis Express C18, 2.7 μm, 3.0×50 mm. A linear gradient was applied, starting at 90% A (A: 0.09% FA in water) and ending at 95% B (B: 0.1% FA in MeCN) over 2.70 min with a total run time of 3.00 min. The column temperature was at 40° C. with the flow rate of 1.50 mL/min.

Liquid Chromatography-Mass Spectrometry Method M24:

The column used was an Ascentis Express C18, 2.7 μm, 3.0×50 mm. A linear gradient was applied, starting at 95% A (A: 0.05% TFA in water) and ending at 95% B (B: 0.05% TFA in MeCN) over 2.70 min with a total run time of 3.00 min. The column temperature was at 40° C. with the flow rate of 1.50 mL/min.

Liquid Chromatography-Mass Spectrometry Method M25:

The column used was a Kinetex EVO C18, 2.6 μm, 4.6×50 mm. A linear gradient was applied, starting at 90% A (A: 5 mM $NH_4HCO_3$ in water) and ending at 95% B (B: MeCN) over 1.75 min with a total run time of 2.00 min. The column temperature was at 40° C. with the flow rate of 1.80 mL/min.

Liquid Chromatography-Mass Spectrometry Method M26:

The column used was an Ascentis Express C18, 2.7 μm, 3.0×50 mm. A linear gradient was applied, starting at 95% A (A: 0.05% TFA in water) and ending at 95% B (B: 0.05% TFA in MeCN) over 4.90 min with a total run time of 5.30 min. The column temperature was at 45° C. with the flow rate of 1.50 mL/min.

Liquid Chromatography-Mass Spectrometry Method M27:

The column used was an Poroshell HPH-C18, 2.7 μm, 3.0×50 mm. A linear gradient was applied, starting at 95% A (A: 0.1% FA in water) and ending at 100% B (B: 0.1% FA in MeCN) over 1.70 min with a total run time of 2.00 min. The column temperature was at 40° C. with the flow rate of 1.00 mL/min.

Liquid Chromatography-Mass Spectrometry Method M28:

The column used was a CORTECS C18+, 2.7 μm, 2.1×50 mm. A linear gradient was applied, starting at 90% A (A: 0.1% FA in water) and ending at 95% B (B: 0.1% FA in MeCN) over 2.70 min with a total run time of 3.00 min. The column temperature was at 45° C. with the flow rate of 1.00 mL/min.

Liquid Chromatography-Mass Spectrometry Method M29:

The column used was a Shim-pack XR-ODS, 2.2 μm, 3.0×50 mm. A linear gradient was applied, starting at 95% A (A: 0.05% TFA in water) and ending at 100% B (B: 0.05% TFA in MeCN) over 4.60 min with a total run time of 5.30 min. The column temperature was at 40° C. with the flow rate of 1.20 mL/min.

Liquid Chromatography-Mass Spectrometry Method M30:

The column used was a Shim-pack XR-ODS, 2.2 µm, 3.0×50 mm. A linear gradient was applied, starting at 95% A (A: 0.05% TFA in water) and ending at 100% B (B: 0.05% TFA in MeCN) over 2.80 min with a total run time of 3.30 min. The column temperature was at 45° C. with the flow rate of 1.20 mL/min.

Liquid Chromatography-Mass Spectrometry Method M31:

The column used was a Shim-pack XR-ODS, 2.2 µm, 3.0×50 mm. A linear gradient was applied, starting at 95% A (A: 0.05% TFA in water) and ending at 100% B (B: 0.05% TFA in MeCN) over 4.70 min with a total run time of 5.00 min. The column temperature was at 45° C. with the flow rate of 1.20 mL/min.

Liquid Chromatography-Mass Spectrometry Method M32:

The column used was a CORTECS C18+, 2.7 µm, 2.1×50 mm. A linear gradient was applied, starting at 90% A (A: 0.1% FA in water) and ending at 95% B (B: 0.1% FA in MeCN) over 5.20 min with a total run time of 5.70 min. The column temperature was at 45° C. with the flow rate of 1.00 mL/min.

Liquid Chromatography-Mass Spectrometry Method M33:

The column used was a Shim-pack XR-ODS, 2.2 µm, 3.0×50 mm. A linear gradient was applied, starting at 95% A (A: 0.05% TFA in water) and ending at 100% B (B: 0.05% TFA in MeCN) over 2.20 min with a total run time of 2.60 min. The column temperature was at 40° C. with the flow rate of 1.00 mL/min.

Liquid Chromatography-Mass Spectrometry Method M34:

The column used was a Shim-pack XR-ODS, 2.2 µm, 3.0×50 mm. A linear gradient was applied, starting at 95% A (A: 0.05% TFA in water) and ending at 100% B (B: 0.05% TFA in MeCN) over 1.70 min with a total run time of 2.00 min. The column temperature was at 40° C. with the flow rate of 1.20 mL/min.

Liquid Chromatography-Mass Spectrometry Method M35:

The column used was a CORTECS C18+, 2.7 µm, 2.1×50 mm. A linear gradient was applied, starting at 95% A (A: 0.09% FA in water) and ending at 95% B (B: 0.1% FA in MeCN) over 2.70 min with a total run time of 3.00 min. The column temperature was at 40° C. with the flow rate of 1.00 mL/min.

Liquid Chromatography-Mass Spectrometry Method M36:

The column used was a CORTECS C18+100 A, 2.7 µm, 2.1×50 mm. A linear gradient was applied, starting at 90% A (A: 0.1% FA in water) and ending at 100% B (B: 0.1% FA in MeCN) over 2.60 min with a total run time of 3.00 min. The column temperature was at 40° C. with the flow rate of 1.00 mL/min.

Liquid Chromatography-Mass Spectrometry Method M37:

The column used was a CORTECS C18, 2.7 µm, 2.1×50 mm. A linear gradient was applied, starting at 95% A (A: 0.09% FA in water) and ending at 95% B (B: 0.1% FA in MeCN) over 2.60 min with a total run time of 3.00 min. The column temperature was at 40° C. with the flow rate of 1.00 mL/min.

Liquid Chromatography-Mass Spectrometry Method M38:

The column used was a CORTECS C18, 2.7 µm, 2.1×50 mm. A linear gradient was applied, starting at 95% A (A: 0.05% TFA in water) and ending at 100% B (B: 0.05% TFA in MeCN) over 1.80 min with a total run time of 2.00 min. The column temperature was at 45° C. with the flow rate of 1.00 mL/min.

Liquid Chromatography-Mass Spectrometry Method M39:

The column used was an Ascentis Express C18, 2.7 µm, 2.1×50 mm. A linear gradient was applied, starting at 70% A (A: 0.05% TFA in water) and ending at 95% B (B: 0.05% TFA in MeCN) over 5.70 min with a total run time of 6.50 min. The column temperature was at 40° C. with the flow rate of 1.00 mL/min.

Liquid Chromatography-Mass Spectrometry Method M40:

The column used was an Ascentis Express C18, 2.7 µm, 2.1×50 mm. A linear gradient was applied, starting at 60% A (A: 0.05% TFA in water) and ending at 95% B (B: 0.05% TFA in MeCN) over 2.70 min with a total run time of 3.00 min. The column temperature was at 40° C. with the flow rate of 1.00 mL/min.

Liquid Chromatography-Mass Spectrometry Method M41:

The column used was a Kinetex EVO C18, 2.6 µm, 3.0×50 mm. A linear gradient was applied, starting at 90% A (A: 5 mM NH4HCO3 in water) and ending at 95% B (B: MeCN) over 1.80 min with a total run time of 2.00 min. The column temperature was at 45° C. with the flow rate of 1.50 mL/min.

Liquid Chromatography-Mass Spectrometry Method M42:

The column used was a Shim-pack XR-ODS, 2.2 µm, 3.0×50 mm. A linear gradient was applied, starting at 95% A (A: 0.05% TFA in water) and ending at 100% B (B: 0.05% TFA in MeCN) over 1.70 min with a total run time of 2.00 min. The column temperature was at 40° C. with the flow rate of 1.20 mL/min.

Liquid Chromatography-Mass Spectrometry Method M43:

The column used was a Kinetex EVO C18 100 A, 2.6 µm, 2.1×50 mm. A linear gradient was applied, starting at 90% A (A: 5 mM NH4HCO3 in water) and ending at 95% B (B: MeCN) over 2.60 min with a total run time of 3.00 min. The column temperature was at 40° C. with the flow rate of 1.00 mL/min.

Liquid Chromatography-Mass Spectrometry Method M44:

The column used was a HPH-C18, 2.7 µm, 3.0×50 mm. A linear gradient was applied, starting at 90% A (A: 5 mM NH4HCO3 in water) and ending at 100% B (B: MeCN) over 2.60 min with a total run time of 3.00 min. The column temperature was at 40° C. with the flow rate of 1.50 mL/min.

Liquid Chromatography-Mass Spectrometry Method M45:

The column used was an Ascentis Express C18, 2.7 µm, 2.1×50 mm. A linear gradient was applied, starting at 95% A (A: 0.05% TFA in water) and ending at 95% B (B: 0.05% TFA in MeCN) over 3.10 min with a total run time of 3.60 min. The column temperature was at 40° C. with the flow rate of 1.00 mL/min.

Liquid Chromatography-Mass Spectrometry Method M46:

The column used was an Ascentis Express C18, 2.7 µm, 2.1×50 mm. A linear gradient was applied, starting at 95% A (A: 0.05% TFA in water) and ending at 100% B (B: 0.05% TFA in MeCN) over 2.10 min with a total run time of 2.60 min. The column temperature was at 40° C. with the flow rate of 1.00 mL/min.

Liquid Chromatography-Mass Spectrometry Method M47:

The column used was an Ascentis Express C18, 2.7 µm, 3.0×50 mm. A linear gradient was applied, starting at 95% A (A: 0.05% TFA in water) and ending at 95% B (B: 0.05% TFA in MeCN) over 4.20 min with a total run time of 4.50 min. The column temperature was at 40° C. with the flow rate of 1.50 mL/min.

Liquid Chromatography-Mass Spectrometry Method M48:

The column used was a Shim-pack XR-ODS, 2.2 µm, 3.0×50 mm. A linear gradient was applied, starting at 80% A (A: 0.05% TFA in water) and ending at 95% B (B: 0.05% TFA in MeCN) over 5.00 min with a total run time of 5.60 min. The column temperature was at 45° C. with the flow rate of 1.20 mL/min.

Liquid Chromatography-Mass Spectrometry Method M49:

The column used was an Poroshell HPH-C18, 2.7 μm, 3.0×50 mm. A linear gradient was applied, starting at 90% A (A: 6.5 mM $NH_4HCO_3$+$NH_3H_2O$ in water) and ending at 95% B (B: MeCN) over 1.10 min with a total run time of 2.00 min. The column temperature was at 40° C. with the flow rate of 1.20 mL/min.

Liquid Chromatography-Mass Spectrometry Method M50:

The column used was a CORTECS C18+, 2.7 μm, 2.1×50 mm. A linear gradient was applied, starting at 90% A (A: 0.1% FA in water) and ending at 95% B (B: 0.1% FA in MeCN) over 2.00 min with a total run time of 3.00 min. The column temperature was at 40° C. with the flow rate of 0.80 mL/min.

Liquid Chromatography-Mass Spectrometry Method M51:

The column used was a Kinetex EVO C18 100 A, 2.6 μm, 3.0×50 mm. A linear gradient was applied, starting at 90% A (A: 0.03% $NH_3H_2O$ in water) and ending at 95% B (B: MeCN) over 1.70 min with a total run time of 2.00 min. The column temperature was at 40° C. with the flow rate of 1.20 mL/min.

Liquid Chromatography-Mass Spectrometry Method M52:

The column used was an Ascentis Express C18, 2.7 μm, 2.1×50 mm. A linear gradient was applied, starting at 90% A (A: 0.1% FA in water) and ending at 95% B (B: 0.1% FA in MeCN) over 2.70 min with a total run time of 3.00 min. The column temperature was at 40° C. with the flow rate of 1.00 mL/min.

Liquid Chromatography-Mass Spectrometry Method M53:

The column used was an Ascentis Express C18, 2.7 μm, 2.1×50 mm. A linear gradient was applied, starting at 90% A (A: 0.1% FA in water) and ending at 100% B (B: 0.1% FA in MeCN) over 1.70 min with a total run time of 2.00 min. The column temperature was at 40° C. with the flow rate of 1.00 mL/min.

Liquid Chromatography-Mass Spectrometry Method M54:

The column used was an Omega, 3.0 μm, 2.1×30 mm. A linear gradient was applied, starting at 95% A (A: 0.09% FA in water) and ending at 95% B (B: 0.1% FA in MeCN) over 2.60 min with a total run time of 2.00 min. The column temperature was at 40° C. with the flow rate of 1.20 mL/min.

Liquid Chromatography-Mass Spectrometry Method M55:

The column used was a Poroshell HPH-C18, 2.7 μm, 3.0×50 mm. A linear gradient was applied, starting at 90% A (A: 6.5 mM NH4HCO3+$NH_3H_2O$ in water) and ending at 95% B (B: MeCN) over 1.80 min with a total run time of 2.00 min. The column temperature was at 40° C. with the flow rate of 1.20 mL/min.

Liquid Chromatography-Mass Spectrometry Method M56:

The column used was a Kinetex EVO C18, 2.6 μm, 3.0×50 mm. A linear gradient was applied, starting at 90% A (A: 5 mM $NH_4HCO_3$ in water) and ending at 95% B (B: MeCN) over 2.70 min with a total run time of 3.00 min. The column temperature was at 40° C. with the flow rate of 1.20 mL/min.

Liquid Chromatography-Mass Spectrometry Method M57:

The column used was a Kinetex EVO, 2.6 μm, 4.6×50 mm. A linear gradient was applied, starting at 90% A (A: 5 mM $NH_4HCO_3$ in water) and ending at 95% B (B: MeCN) over 2.70 min with a total run time of 3.00 min. The column temperature was at 40° C. with the flow rate of 1.80 mL/min.

Liquid Chromatography-Mass Spectrometry Method M58:

The column used was a Poroshell HPH-C18, 2.7 μm, 3.0×50 mm. A linear gradient was applied, starting at 90% A (A: 6.5 mM $NH_4HCO_3$+$NH_3H_2O$ in water) and ending at 95% B (B: MeCN) over 2.70 min with a total run time of 3.00 min. The column temperature was at 40° C. with the flow rate of 1.20 mL/min.

Liquid Chromatography-Mass Spectrometry Method M59:

The column used was a CORTECS C18, 2.7 μm, 2.1×50 mm. A linear gradient was applied, starting at 95% A (A: 0.05% TFA in water) and ending at 100% B (B: 0.05% TFA in MeCN) over 2.80 min with a total run time of 3.00 min. The column temperature was at 45° C. with the flow rate of 1.00 mL/min.

Liquid Chromatography-Mass Spectrometry Method M60:

The column used was a Kinetex 2.6 μm EVO C18 100 A, 2.6 μm, 3.0×50 mm. A linear gradient was applied, starting at 90% A (A: 5 mM NH4HCO3 in water) and ending at 95% B (B: MeCN) over 1.80 min with a total run time of 2.00 min. The column temperature was at 40° C. with the flow rate of 1.20 mL/min.

Liquid Chromatography-Mass Spectrometry Method M61:

The column used was a Kinetex EVO, 2.6 μm, 3.0×50 mm. A linear gradient was applied, starting at 95% A (A: 0.03% $NH_3H_2O$ in water) and ending at 95% B (B: MeCN) over 1.60 min with a total run time of 1.80 min. The column temperature was at 40° C. with the flow rate of 1.20 mL/min.

Liquid Chromatography-Mass Spectrometry Method M62:

The column used was an Poroshell HPH-C18, 2.7 μm, 3.0×50 mm. A linear gradient was applied, starting at 90% A (A: 6.5 mM NH4HCO3+$NH_3H_2O$ in water) and ending at 95% B (B: MeCN) over 1.80 min with a total run time of 2.00 min. The column temperature was at 40° C. with the flow rate of 1.20 mL/min.

Liquid Chromatography-Mass Spectrometry Method M63:

The column used was a Kinetex 2.6 μm EVO C18 100 A, 2.6 μm, 3.0×50 mm. A linear gradient was applied, starting at 90% A (A: 5 mM NH4HCO3 in water) and ending at 95% B (B: MeCN) over 2.70 min with a total run time of 2.90 min. The column temperature was at 40° C. with the flow rate of 1.20 mL/min.

Liquid Chromatography-Mass Spectrometry Method M64:

The column used was a XBridge C18, 2.5 μm, 3.0×50 mm. A linear gradient was applied, starting at 90% A (A: 5 mM $NH_4HCO_3$ in water) and ending at 95% B (B: MeCN) over 2.70 min with a total run time of 3.00 min. The column temperature was at 40° C. with the flow rate of 1.20 mL/min.

Liquid Chromatography-Mass Spectrometry Method M65:

The column used was a Kinelex 2.6 u XB-C18, 2.6 μm, 3.0×50 mm. A linear gradient was applied, starting at 95% A (A: 0.05% TFA in water) and ending at 100% B (B: 0.05% TFA in MeCN) over 2.80 min with a total run time of 3.00 min. The column temperature was at 45° C. with the flow rate of 1.50 mL/min.

Liquid Chromatography-Mass Spectrometry Method M66:

The column used was a Shim-pack XR-ODS, 2.2 μm, 3.0×50 mm. A linear gradient was applied, starting at 95% A (A: 0.05% TFA in water) and ending at 95% B (B: 0.05% TFA in MeCN) over 1.60 min with a total run time of 1.80 min. The column temperature was at 40° C. with the flow rate of 1.50 mL/min.

Liquid Chromatography-Mass Spectrometry Method M67:

The column used was a Shim-pack XR-ODS, 2.2 μm, 3.0×50 mm. A linear gradient was applied, starting at 95% A (A: 0.05% TFA in water) and ending at 95% B (B: 0.05% TFA in MeCN) over 2.70 min with a total run time of 3.00 min. The column temperature was at 40° C. with the flow rate of 1.50 mL/min.

Liquid Chromatography-Mass Spectrometry Method M68:

The column used was a Kinetex EVO, 2.6 μm, 3.0×50 mm. A linear gradient was applied, starting at 90% A (A: 5 mM NH$_4$HCO$_3$ in water) and ending at 95% B (B: MeCN) over 2.60 min with a total run time of 3.00 min. The column temperature was at 40° C. with the flow rate of 1.20 mL/min.

Liquid Chromatography-Mass Spectrometry Method M69:
The column used was a Kinetex EVO C18, 2.6 μm, 3.0×50 mm. A linear gradient was applied, starting at 95% A (A: 0.03% NH3H$_2$O in water) and ending at 95% B (B: Acetonitrile) over 1.60 min with a total run time of 1.80 min. The column temperature was at 40° C. with the flow rate of 1.20 mL/min.

Liquid Chromatography-Mass Spectrometry Method M70:
The column used was a Kinetex 2.6 um EVO C18 100 A, 2.6 μm, 3.0×50 mm. A linear gradient was applied, starting at 90% A (A: 5 mM NH$_4$HCO$_3$ in water) and ending at 95% B (B: MeCN) over 5.00 min with a total run time of 5.60 min. The column temperature was at 40° C. with the flow rate of 1.20 mL/min.

Liquid Chromatography-Mass Spectrometry Method M71:
The column used was a Kinetex EVO, 2.6 μm, 3.0×50 mm. A linear gradient was applied, starting at 90% A (A: 0.03% NH3H$_2$O in water) and ending at 95% B (B: MeCN) over 2.60 min with a total run time of 3.00 min. The column temperature was at 40° C. with the flow rate of 1.20 mL/min.

Liquid Chromatography-Mass Spectrometry Method M72:
The column used was a Kinetex EVO, 2.6 μm, 3.0×50 mm. A linear gradient was applied, starting at 90% A (A: 0.03% NH3H$_2$O in water) and ending at 95% B (B: MeCN) over 4.20 min with a total run time of 4.50 min. The column temperature was at 40° C. with the flow rate of 1.20 mL/min.

Liquid Chromatography-Mass Spectrometry Method M73:
The column used was a Kinetex 2.6 um EVO C18 100 A, 2.6 μm, 3.0×50 mm. A linear gradient was applied, starting at 90% A (A: 5 mM NH4HCO3 in water) and ending at 95% B (B: MeCN) over 1.80 min with a total run time of 2.00 min. The column temperature was at 40° C. with the flow rate of 1.20 mL/min.

Liquid Chromatography-Mass Spectrometry Method M74:
The column used was a Kinetex 2.6 um EVO C18 100 A, 2.6 μm, 3.0×50 mm. A linear gradient was applied, starting at 95% A (A: 5 mM NH$_4$HCO$_3$ in water) and ending at 95% B (B: MeCN) over 1.80 min with a total run time of 2.00 min. The column temperature was at 40° C. with the flow rate of 1.20 mL/min.

Liquid Chromatography-Mass Spectrometry Method M75:
The column used was an XBridge C18, 2.5 μm, 3.0×50 mm. A linear gradient was applied, starting at 90% A (A: 0.04% NH$_3$H$_2$O in water) and ending at 95% B (B: MeCN) over 1.80 min with a total run time of 2.00 min. The column temperature was at 40° C. with the flow rate of 1.20 mL/min.

Liquid Chromatography-Mass Spectrometry Method M76:
The column used was an XBridge C18, 2.5 μm, 3.0×50 mm. A linear gradient was applied, starting at 90% A (A: 5 mM NH$_4$HCO$_3$ in water) and ending at 95% B (B: MeCN) over 1.80 min with a total run time of 2.00 min. The column temperature was at 40° C. with the flow rate of 1.20 mL/min.

Liquid Chromatography-Mass Spectrometry Method M77:
The column used was an XBridge C18, 2.5 μm, 3.0×50 mm. A linear gradient was applied, starting at 90% A (A: 5 mM NH$_4$HCO$_3$ in water) and ending at 95% B (B: MeCN) over 2.70 min with a total run time of 3.00 min. The column temperature was at 40° C. with the flow rate of 1.20 mL/min.

Liquid Chromatography-Mass Spectrometry Method M78:
The column used was an XBridge C18, 2.5 μm, 3.0×50 mm. A linear gradient was applied, starting at 70% A (A: 5 mM NH$_4$HCO$_3$ in water) and ending at 95% B (B: MeCN) over 2.70 min with a total run time of 3.00 min. The column temperature was at 40° C. with the flow rate of 1.20 mL/min.

Liquid Chromatography-Mass Spectrometry Method M79:
The column used was a Kinetex EVO C18, 2.6 μm, 3.0×50 mm. A linear gradient was applied, starting at 60% A (A: 0.1% FA in water) and ending at 100% B (B: 0.1% FA in MeCN) over 5.00 min with a total run time of 5.30 min. The column temperature was at 40° C. with the flow rate of 1.00 mL/min.

Liquid Chromatography-Mass Spectrometry Method M80:
The column used was a Kinetex EVO C18, 2.6 μm, 3.0×50 mm. A linear gradient was applied, starting at 60% A (A: 0.1% FA in water) and ending at 100% B (B: 0.1% FA in MeCN) over 5.00 min with a total run time of 5.30 min. The column temperature was at 40° C. with the flow rate of 1.00 mL/min.

Liquid Chromatography-Mass Spectrometry Method M81:
The column used was a Kinetex EVO, 2.6 μm, 3.0×50 mm. A linear gradient was applied, starting at 40% A (A: 0.03% NH$_3$H$_2$O in water) and ending at 95% B (B: MeCN) over 2.60 min with a total run time of 3.00 min. The column temperature was at 40° C. with the flow rate of 1.20 mL/min.

Liquid Chromatography-Mass Spectrometry Method M82:
The column used was a Kinelex 2.6 u XB-C18, 2.6 μm, 3.0×50 mm. A linear gradient was applied, starting at 95% A (A: 0.05% TFA in water) and ending at 100% B (B: 0.05% TFA in MeCN) over 1.80 min with a total run time of 2.00 min. The column temperature was at 40° C. with the flow rate of 1.50 mL/min.

Liquid Chromatography-Mass Spectrometry Method M83:
The column used was an Ascentis Express C18, 2.7 μm, 3.0×50 mm. A linear gradient was applied, starting at 90% A (A: 0.1% FA in water) and ending at 95% B (B: 0.1% FA in MeCN) over 5.20 min with a total run time of 5.70 min. The column temperature was at 40° C. with the flow rate of 1.00 mL/min.

Liquid Chromatography-Mass Spectrometry Method M84:
The column used was an Ascentis Express C18, 2.7 μm, 2.1×50 mm. A linear gradient was applied, starting at 90% A (A: 0.1% FA in water) and ending at 95% B (B: 0.1% FA in MeCN) over 5.20 min with a total run time of 5.70 min. The column temperature was at 45° C. with the flow rate of 1.00 mL/min.

Liquid Chromatography-Mass Spectrometry Method M85:
The column used was a CORTECS C18, 2.7 μm, 2.1×50 mm. A linear gradient was applied, starting at 95% A (A: 0.09% FA in water) and ending at 95% B (B: 0.1% FA in MeCN) over 2.60 min with a total run time of 3.00 min. The column temperature was at 40° C. with the flow rate of 1.20 mL/min.

Liquid Chromatography-Mass Spectrometry Method M86:
The column used was an Ascentis Express C18, 2.7 μm, 2.1×50 mm. A linear gradient was applied, starting at 70% A (A: 0.1% FA in water) and ending at 95% B (B: 0.1% FA in MeCN) over 4.80 min with a total run time of 5.20 min. The column temperature was at 45° C. with the flow rate of 1.00 mL/min.

Liquid Chromatography-Mass Spectrometry Method M87:
The column used was a Shim-pack XR-ODS, 2.2 μm, 3.0×50 mm. A linear gradient was applied, starting at 95% A (A: 0.05% TFA in water) and ending at 95% B (B: 0.05% TFA in MeCN) over 1.70 min with a total run time of 2.00 min. The column temperature was at 40° C. with the flow rate of 1.50 mL/min.

Liquid Chromatography-Mass Spectrometry Method M88:
The column used was an Ascentis Express C18, 2.7 μm, 3.0×50 mm. A linear gradient was applied, starting at 95% A (A: 0.05% TFA in water) and ending at 95% B (B: 0.05%

TFA in MeCN) over 1.80 min with a total run time of 2.00 min. The column temperature was at 40° C. with the flow rate of 1.50 mL/min.

Liquid Chromatography-Mass Spectrometry Method M89:
The column used was an Ascentis Express C18, 2.7 µm, 3.0×50 mm. A linear gradient was applied, starting at 100% A (A: 0.05% TFA in water) and ending at 95% B (B: 0.05% TFA in MeCN) over 2.70 min with a total run time of 3.00 min. The column temperature was at 40° C. with the flow rate of 1.50 mL/min.

Liquid Chromatography-Mass Spectrometry Method M90:
The column used was a Kinetex EVO C18, 2.6 µm, 3.0×50 mm. A linear gradient was applied, starting at 90% A (A: 0.1% FA in water) and ending at 95% B (B: 0.1% FA in MeCN) over 2.70 min with a total run time of 3.00 min. The column temperature was at 40° C. with the flow rate of 1.00 mL/min.

Liquid Chromatography-Mass Spectrometry Method M91:
The column used was a Shim-pack XR-ODS, 2.2 µm, 3.0×50 mm. A linear gradient was applied, starting at 95% A (A: 0.05% TFA in water) and ending at 95% B (B: 0.05% TFA in MeCN) over 4.20 min with a total run time of 4.50 min. The column temperature was at 40° C. with the flow rate of 1.50 mL/min.

Liquid Chromatography-Mass Spectrometry Method M92:
The column used was a Kinetex EVO C18 100 A, 2.6 µm, 3.0×50 mm. A linear gradient was applied, starting at 90% A (A: 5 mM $NH_4HCO_3$) and ending at 95% B (B: MeCN) over 4.0 min with a total run time of 5.6 min. The column temperature was at 40° C. with the flow rate of 1.20 mL/min.

Liquid Chromatography-Mass Spectrometry Method M93:
The column used was a Kinetex EVO C18, 2.6 µm, 3.0×50 mm. A linear gradient was applied, starting at 90% A (A: 0.03% $NH_3H_2O$ in water) and ending at 95% B (B: MeCN) over 3.50 min with a total run time of 4.50 min. The column temperature was at 40° C. with the flow rate of 1.20 mL/min.

Liquid Chromatography-Mass Spectrometry Method M94:
The column used was a Kinetex EVO C18 100 A, 2.6 µm, 3.0×50 mm. A linear gradient was applied, starting at 90% A (A: 5 mM $NH_4HCO_3$) and ending at 95% B (B: MeCN) over 1.8 min with a total run time of 2.0 min. The column temperature was at 40° C. with the flow rate of 1.20 mL/min.

Liquid Chromatography-Mass Spectrometry Method M95:
The column used was an Ascentis Express C18, 2.7 µm, 3.0×50 mm. A linear gradient was applied, starting at 95% A (A: 0.05% TFA in water) and ending at 95% B (B: 0.05% TFA in MeCN) over 1.60 min with a total run time of 1.80 min. The column temperature was at 40° C. with the flow rate of 1.50 mL/min.

Liquid Chromatography-Mass Spectrometry Method M96:
The column used was a Kinetex EVO C18 100 A, 2.6 µm, 3.0×50 mm. A linear gradient was applied, starting at 90% A (A: 5 mM $NH_4HCO_3$ in water) and ending at 95% B (B: MeCN) over 2.7 min with a total run time of 3.00 min. The column temperature was at 40° C. with the flow rate of 1.20 mL/min.

Liquid Chromatography-Mass Spectrometry Method M97:
The column used was a Shim-pack XR-ODS, 3.0 µm, 3.0×50 mm. A linear gradient was applied, starting at 95% A (A: 0.05% TFA in water) and ending at 100% B (B: 0.05% TFA in MeCN) over 1.65 min with a total run time of 1.90 min. The column temperature was at 45° C. with the flow rate of 1.20 mL/min.

Liquid Chromatography-Mass Spectrometry Method M98:
The column used was an Ascentis Express C18, 2.7 µm, 2.1×50 mm. A linear gradient was applied, starting at 90% A (A: 0.1% FA in water) and ending at 95% B (B: 0.1% FA in MeCN) over 1.7 min with a total run time of 2.00 min. The column temperature was at 40° C. with the flow rate of 1.00 mL/min.

Liquid Chromatography-Mass Spectrometry Method M99:
The column used was a Kinetex EVO C18, 2.6 µm, 3.0×50 mm. A linear gradient was applied, starting at 90% A (A: 0.04% $NH_4OH$ in water) and ending at 95% B (B: MeCN) over 1.70 min with a total run time of 2.00 min. The column temperature was at 40° C. with the flow rate of 1.20 mL/min.

Liquid Chromatography-Mass Spectrometry Method M100:
The column used was a Kinetex EVO C18 100 A, 2.6 µm, 3.0×50 mm. A linear gradient was applied, starting at 90% A (A: 5 mM NH4HCO3 in water) and ending at 95% B (B: MeCN) over 5.20 min with a total run time of 5.60 min. The column temperature was at 40° C. with the flow rate of 1.20 mL/min.

Liquid Chromatography-Mass Spectrometry Method M101:
The column used was a Kinetex XB-C18 100 A, 2.6 µm, 3.0×50 mm. A linear gradient was applied, starting at 90% A (A: 0.1% FA in water) and ending at 100% B (B: 0.1% FA in MeCN) over 1.60 min with a total run time of 1.90 min. The column temperature was at 40° C. with the flow rate of 1.20 mL/min.

Liquid Chromatography-Mass Spectrometry Method M102:
The column used was a Shim-pack XR-ODS, 2.2 µm, 3.0×50 mm. A linear gradient was applied, starting at 95% A (A: 0.05% TFA in water) and ending at 100% B (B: 0.05% TFA in MeCN) over 1.65 min with a total run time of 1.90 min. The column temperature was at 45° C. with the flow rate of 1.20 mL/min.

Liquid Chromatography-Mass Spectrometry Method M103:
The column used was a Poroshell HPH-C18, 2.7 µm, 3.0×50 mm. A linear gradient was applied, starting at 95% A (A: 6.5 mM $NH_4HCO_3+NH_3H_2O$ in water) and ending at 100% B (B: MeCN) over 1.80 min with a total run time of 2.00 min. The column temperature was at 45° C. with the flow rate of 1.50 mL/min.

Liquid Chromatography-Mass Spectrometry Method M104:
The column used was an InertSustain AQ-C18, 3.0 Gm, 2.1×50 mm. A linear gradient was applied, starting at 90% A (A: 0.03% $NH_3H_2O$ in water) and ending at 95% B (B: 0.05% TFA in MeCN) over 1.70 min with a total run time of 2.00 min. The column temperature was at 40° C. with the flow rate of 1.20 mL/min.

Liquid Chromatography-Mass Spectrometry Method M105:
The column used was a Kinetex EVO C18, 2.6 µm, 3.0×50 mm. A linear gradient was applied, starting at 90% A (A: 0.03% $NH_3H_2O$ in water) and ending at 95% B (B: MeCN) over 1.70 min with a total run time of 2.00 min. The column temperature was at 40° C. with the flow rate of 1.20 mL/min.

Liquid Chromatography-Mass Spectrometry Method M106:
The column used was a Kinelex 2.6 u XB-C18, 2.6 µm, 3.0×50 mm. A linear gradient was applied, starting at 95% A (A: 0.05% TFA in water) and ending at 100% B (B: 0.05% TFA in MeCN) over 2.50 min with a total run time of 6.00 min. The column temperature was at 45° C. with the flow rate of 1.50 mL/min.

Liquid Chromatography-Mass Spectrometry Method M107:
The column used was a Kinetex EVO C18, 2.6 µm, 3.0×50 mm. A linear gradient was applied, starting at 90% A (A: 0.03% $NH_3H_2O$ in water) and ending at 95% B (B: MeCN) over 2.70 min with a total run time of 3.00 min. The column temperature was at 40° C. with the flow rate of 1.20 mL/min.

Liquid Chromatography-Mass Spectrometry Method M108:
The column used was a Kinetex EVO C18 100 A, 2.6 µm, 3.0×50 mm. A linear gradient was applied, starting at 90% A (A: 5 mM NH4HCO3 in water) and ending at 95% B (B: MeCN) over 4.60 min with a total run time of 5.00 min. The column temperature was at 40° C. with the flow rate of 1.20 mL/min.

Liquid Chromatography-Mass Spectrometry Method M109:
The column used was a Poroshell HPH-C18, 2.7 µm, 3.0×50 mm. A linear gradient was applied, starting at 75% A (A: 6.5 mM $NH_4HCO_3+NH_3H_2O$ in water) and ending at 100% B (B: MeCN) over 6.00 min with a total run time of 6.60 min. The column temperature was at 45° C. with the flow rate of 1.20 mL/min.

Liquid Chromatography-Mass Spectrometry Method M110:
The column used was a Shim-pack XR-ODS, 2.2 µm, 3.0×50 mm. A linear gradient was applied, starting at 95% A (A: 0.05% TFA in water) and ending at 95% B (B: 0.05% TFA in MeCN) over 1.80 min with a total run time of 2.00 min. The column temperature was at 40° C. with the flow rate of 1.20 mL/min.

Liquid Chromatography-Mass Spectrometry Method M111:
The column used was a Kinetex EVO C18, 2.6 µm, 3.0×50 mm. A linear gradient was applied, starting at 70% A (A: 0.1% FA in water) and ending at 80% B (B: 0.1% FA in MeCN) over 4.8 min with a total run time of 5.2 min. The column temperature was at 45° C. with the flow rate of 1.00 mL/min.

Liquid Chromatography-Mass Spectrometry Method M112:
The column used was a Shim-pack XR-ODS, 2.2 µm, 3.0×50 mm. A linear gradient was applied, starting at 65% A (A: 0.05% TFA in water) and ending at 95% B (B: 0.05% TFA in MeCN) over 5.00 min with a total run time of 5.60 min. The column temperature was at 45° C. with the flow rate of 1.20 mL/min.

Liquid Chromatography-Mass Spectrometry Method M113:
The column used was a Poroshell HPH-C18, 2.7 µm, 3.0×50 mm. A linear gradient was applied, starting at 90% A (A: 5 mM $NH_4HCO_3$ in water) and ending at 95% B (B: MeCN) over 2.70 min with a total run time of 2.95 min. The column temperature was at 40° C. with the flow rate of 1.00 mL/min.

Liquid Chromatography-Mass Spectrometry Method M114:
The column used was a Shim-pack XR-ODS, 2.2 µm, 3.0×50 mm. A linear gradient was applied, starting at 90% A (A: 0.05% TFA in water) and ending at 60% B (B: 0.05% TFA in MeCN) over 5.00 min with a total run time of 5.60 min. The column temperature was at 40° C. with the flow rate of 1.20 mL/min.

Liquid Chromatography-Mass Spectrometry Method M115:
The column used was a CORTECS C18, 2.7 µm, 2.1×50 mm. A linear gradient was applied, starting at 95% A (A: 0.09% FA in water) and ending at 95% B (B: 0.1% FA in MeCN) over 1.6 min with a total run time of 1.8 min. The column temperature was at 40° C. with the flow rate of 1.20 mL/min Liquid Chromatography-Mass Spectrometry Method M116:
The column used was an Ascentis Express C18, 2.7 µm, 2.1×50 mm. A linear gradient was applied, starting at 90% A (A: 0.1% FA in water) and ending at 95% B (B: 0.1% FA in MeCN) over 4.7 min with a total run time of 5.00 min. The column temperature was at 40° C. with the flow rate of 1.00 mL/min.

Liquid Chromatography-Mass Spectrometry Method M117:
The column used was a CORTECS C18+, 2.7 µm, 2.1×50 mm. A linear gradient was applied, starting at 90% A (A: 0.1% FA in water) and ending at 100% B (B: 0.1% FA in MeCN) over 1.60 min with a total run time of 1.90 min. The column temperature was at 40° C. with the flow rate of 1.00 mL/min.

Liquid Chromatography-Mass Spectrometry Method M118:
The column used was a Kinetex EVO C18, 2.6 µm, 3.0×50 mm. A linear gradient was applied, starting at 95% A (A: 0.03% $NH_3H_2O$ in water) and ending at 95% B (B: MeCN) over 1.60 min with a total run time of 1.80 min. The column temperature was at 40° C. with the flow rate of 1.20 mL/min.

Liquid Chromatography-Mass Spectrometry Method M119:
The column used was a Kinetex EVO C18 100 A, 2.6 µm, 3.0×50 mm. A linear gradient was applied, starting at 70% A (A: 5 mM NH4HCO3 in water) and ending at 95% B (B: MeCN) over 2.70 min with a total run time of 3.00 min. The column temperature was at 40° C. with the flow rate of 1.20 mL/min.

Liquid Chromatography-Mass Spectrometry Method M120:
The column used was a Kinetex EVO, 2.6 µm, 3.0×50 mm. A linear gradient was applied, starting at 95% A (A: 5 mM NH4HCO3) and ending at 95% B (B: MeCN) over 1.6 min with a total run time of 1.8 min. The column temperature was at 40° C. with the flow rate of 1.20 mL/min.

Liquid Chromatography-Mass Spectrometry Method M121:
The column used was an XSelect CSH C18, 2.5 µm, 3.0×50 mm. A linear gradient was applied, starting at 95% A (A: 0.1% FA in water) and ending at 100% B (B: 0.1% FA in MeCN) over 1.75 min with a total run time of 2.00 min. The column temperature was at 45° C. with the flow rate of 1.20 mL/min.

Liquid Chromatography-Mass Spectrometry Method M122:
The column used was a Kinetex EVO C18 100 A, 2.6 µm, 3.0×50 mm. A linear gradient was applied, starting at 75% A (A: 5 mM NH4HCO3 in water) and ending at 95% B (B: MeCN) over 5.00 min with a total run time of 5.60 min. The column temperature was at 40° C. with the flow rate of 1.20 mL/min.

Liquid Chromatography-Mass Spectrometry Method M123:
The column used was an Xselect CSH C18, 2.5 µm, 3.0×50 mm. A linear gradient was applied, starting at 95% A (A: 0.1% FA in water) and ending at 100% B (B: 0.1% FA in MeCN) over 1.7 min with a total run time of 2 min. The column temperature was at 40° C. with the flow rate of 1.20 mL/min.

Liquid Chromatography-Mass Spectrometry Method M124:
The column used was a Poroshell HPH-C18, 2.7 µm, 3.0×50 mm. A linear gradient was applied, starting at 90% A (A: 0.1% FA in water) and ending at 100% B (B: 0.1% FA in MeCN) over 1.70 min with a total run time of 2.00 min. The column temperature was at 40° C. with the flow rate of 1.00 mL/min.

Liquid Chromatography-Mass Spectrometry Method M125:
The column used was a Poroshell HPH-C18, 2.7 µm, 3.0×50 mm. A linear gradient was applied, starting at 90% A (A: 6.5 mM $NH_4HCO_3+NH_3H_2O$ in water) and ending at 95% B (B: MeCN) over 4.7 min with a total run time of 5.0 min. The column temperature was at 45° C. with the flow rate of 1.20 mL/min.

Liquid Chromatography-Mass Spectrometry Method M126:
The column used was an Omega, 3.0 µm, 2.1×30 mm. A linear gradient was applied, starting at 95% A (A: 0.09% FA in water) and ending at 95% B (B: 0.1% FA in MeCN) over 1.37 min with a total run time of 1.50 min. The column temperature was at 40° C. with the flow rate of 1.20 mL/min.

Liquid Chromatography-Mass Spectrometry Method M127:
The column used was a Kinetex EVO C18 100 A, 2.6 µm, 3.0×50 mm. A linear gradient was applied, starting at 70%

A (A: 5 mM NH4HCO3 in water) and ending at 95% B (B: MeCN) over 5.2 min with a total run time of 5.60 min. The column temperature was at 40° C. with the flow rate of 1.20 mL/min.

Liquid Chromatography-Mass Spectrometry Method M128:

The column used was a CORTECS C18, 2.7 µm, 2.1×50 mm. A linear gradient was applied, starting at 95% A (A: 0.05% TFA in water) and ending at 100% B (B: 0.05% TFA in MeCN) over 4.4 min with a total run time of 5.0 min. The column temperature was at 45° C. with the flow rate of 1.00 mL/min.

Liquid Chromatography-Mass Spectrometry Method M129:

The column used was a Poroshell HPH-C18, 2.7 µm, 3.0×50 mm. A linear gradient was applied, starting at 90% A (A: 6.5 mM $NH_4HCO_3+NH_3H_2O$ in water) and ending at 95% B (B: MeCN) over 4.8 min with a total run time of 5.1 min. The column temperature was at 45° C. with the flow rate of 1.20 mL/min.

Liquid Chromatography-Mass Spectrometry Method M130:

The column used was a Kinetex EVO, 2.6 µm, 3.0×50 mm. A linear gradient was applied, starting at 70% A (A: 5 mM NH4HCO3 in water) and ending at 95% B (B: MeCN) over 2.7 min with a total run time of 3.0 min. The column temperature was at 40° C. with the flow rate of 1.20 mL/min.

Liquid Chromatography-Mass Spectrometry Method M131:

The column used was an Ascentis Express C18, 2.7 µm, 2.1×50 mm. A linear gradient was applied, starting at 90% A (A: 0.05% TFA in water) and ending at 100% B (B: 0.05% TFA in MeCN) over 2.70 min with a total run time of 3.00 min. The column temperature was at 40° C. with the flow rate of 1.00 mL/min.

Liquid Chromatography-Mass Spectrometry Method M132:

The column used was a Shim-pack XR-ODS, 2.2 µm, 3.0×50 mm. A linear gradient was applied, starting at 90% A (A: 0.1% FA in water) and ending at 100% B (B: 0.05% FA in MeCN) over 1.60 min with a total run time of 1.80 min. The column temperature was at 40° C. with the flow rate of 1.20 mL/min.

$^1$H-NMR Data $^1$H-NMR data were determined with a Bruker Avance 400 (equipped with a flow cell (60 µl volume), or with a Bruker AVIII 400 equipped with 1.7 mm cryo CPTCI probe head, or with a Bruker AVIII 400 (400.13 MHz) equipped with a 5 mm probe head, or with a Bruker AVII 600 (600.13 MHz) equipped with a 5 mm cryo TCI probe head, or with a Bruker AVIII 600 (601.6 MHz) equipped with a 5 mm cryo CPMNP probe head, or with a Bruker AVIII 500 (500.13 MHz) equipped with a 5 mm broadband head or a 5 mm Prodigy™ probe head, with tetramethylsilane as reference (0.0) and the solvents $CD_3CN$, $CDCl_3$ or $D_6$-DMSO. Alternative $^1$H- and $^{13}$C-NMR instrument types: Bruker DMX300 ($^1$H NMR: 300 MHz; $^{13}$C NMR: 75 MHz), Bruker Avance III 400 ($^1$H NMR: 400 MHz; $^{13}$C NMR: 100 MHz), Bruker 400 Ultrashield ($^1$H NMR: 400 MHz; $^{13}$C NMR: 100 MHz) or Bruker Mercury Plus 300/400 NMR Spectrometer.

Chemical shifts (δ) are displayed in parts per million [ppm]; the following abbreviations are used: s=singlet, d=doublet, t=triplet, q=quartet, m=multiplet, br.=broad; coupling constants are displayed in Hertz [Hz].

NMR-Peak Lists $^1$H-NMR data of selected examples are written in form of $^1$H-NMR-peak lists. To each signal peak are listed the δ-value in ppm and the signal intensity in round brackets. Between the δ-value—signal intensity pairs are semicolons as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

Microwave

Biotage™ Initiator, Microwave Synthesizer; temperature range: 40° C.-250° C.; pressure range: 0-20 bar; power range: 0-400 W.

EXPERIMENTAL SECTION—GENERAL PROCEDURES

The synthesis of the compounds of the formula (I) can be performed according to or in analogy to the following schemes (Scheme 1-6). Therein and in the overall context of the present invention crossed bonds indicate cis/trans mixtures.

Scheme 1 for preparing a compound (I) with T=T¹ (I-T1)

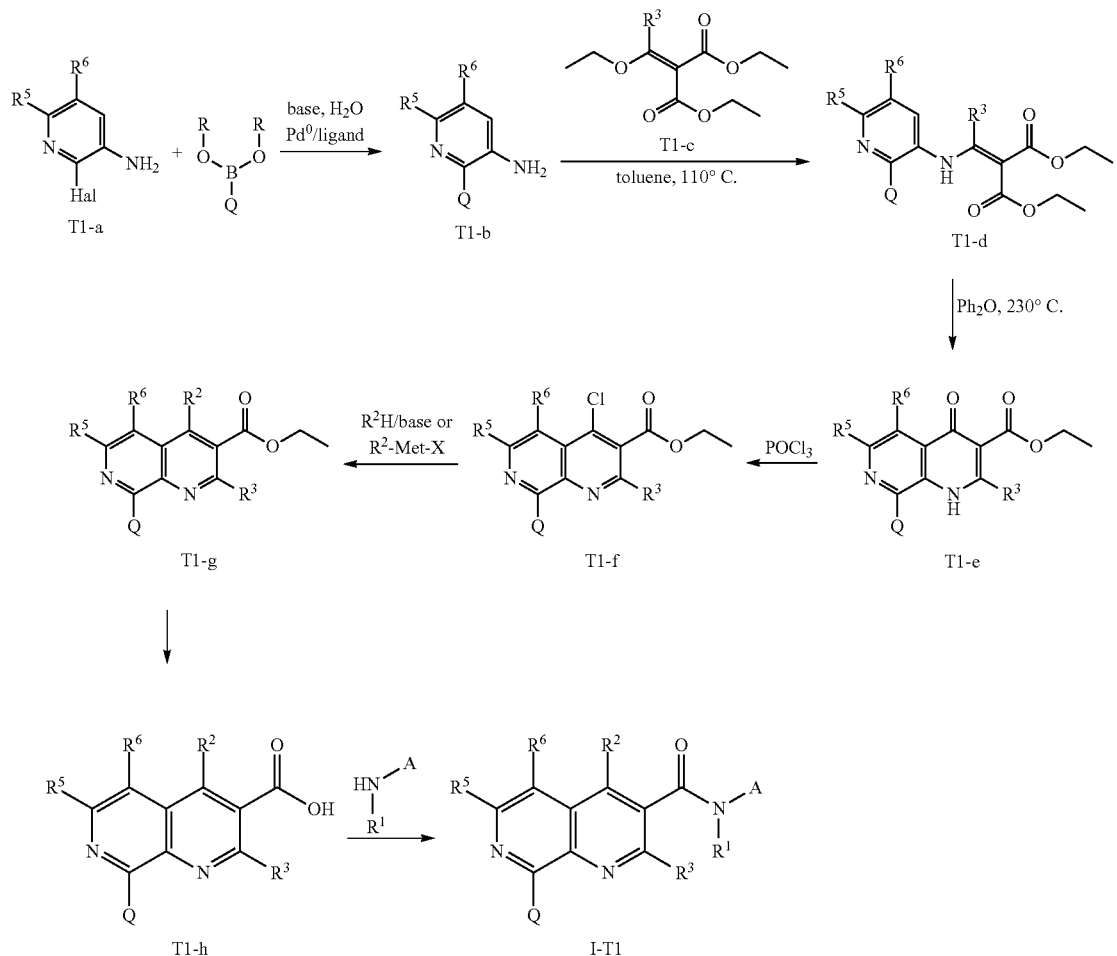

Aminopyridines T1-a can be converted via a Suzuki cross coupling reaction with boronic acids or boronic esters Q-B(OR)$_2$ (R=H; R=Me or R,R=pinacolate) as described in European Journal of Organic Chemistry, 2012 (31), 6248-6259, into aryl- or hetaryl-substituted aminopyridines T1-b. Such substituted aminopyridines can be readily converted with (alkoxymethylen)malonates T1-c dissolved in the corresponding alcohol solvent or toluene, preferably under boiling conditions, into (pyrid-3-ylaminomethylene)-malonates T1-d or without any solvent as described in WO 20060135551. The ring closure is performed in high boiling solvents, preferably in diphenylether or xylol, to achieve aza-quinolone carboxylic esters T1-e as described in WO 2002004444. The aza-quinolone carboxylic esters T1-e can be converted into the corresponding chloro aza-quinolines T1-f in the presence of chlorination agents like phosphorus oxychloride as described in WO 2008154447 with similar aza-quinolines. Dependending on the nature of the nucleophile R²H, the chloro aza-quinolines T1-f react with R²H in the presence of a base, e.g. sodium ethylate, sodium methylate, potassium t-butylate, triethylamine N,N-diisopropyl ethylamine, diazabicycloundecan, sodium hydride, lithium hydroxide, sodium hydroxide, potassium hydroxide, potassium carbonate, cesium carbonate, or the like to obtain the aza-quinoline carboxylic esters T1-g as described in WO 199703074. Alternatively, T1-f can be converted with certain Grignard- or metal organic compounds R²Met-X, e.g. $C_1$-$C_4$-alkyl-Met-X, $C_3$-$C_6$-cycloalkyl-Met-X, $C_2$-$C_4$-alkenyl-Met-X, $C_3$-$C_6$-cycloalkenyl-Met-X, $C_2$-$C_4$-alkynyl-Met-X or phenyl-$C_1$-$C_4$-alkyl-Met-X (Met=Mg, Zn; X=I, Br, Cl) introducing $C_1$-$C_4$-alkyl, $C_3$-$C_6$-cycloalkyl, $C_2$-$C_4$-alkenyl, $C_3$-$C_6$-cycloalkenyl, $C_2$-$C_4$-alkynyl or phenyl-$C_1$-$C_4$-alkyl, each of which is optionally substituted as defined supra for the R² group, as described in Tetrahedron Letters, 2000, 41(33), 6387-6391 for example, into aza-quinoline carboxylic esters T1-g. Intermediate esters T1-g react under hydrolytic conditions to yield aza-quinoline carboxylic acids T1-h as described with similar syntheses in CN 102199152. Final products I-T1 are obtained by amide coupling conditions, e.g. via carboxylic acid chlorides formed from T1-h which are combined with amines R¹—NH-A under basic conditions, e.g. pyridine, triethylamine or N,N-diisopropyl ethylamine or via amide formation from the carboxylic acids T1-h which are combined with amines R¹—NH-A and dehydration reagents, e.g. N-(3-dimethylaminoisopropyl)-N'-ethylcarbo-diimide-hydrochloride (EDC). Similar syntheses are described in WO 2015014768 for example.

Scheme 2a for Preparing a Compound (I) with T=T2 (I-T2)

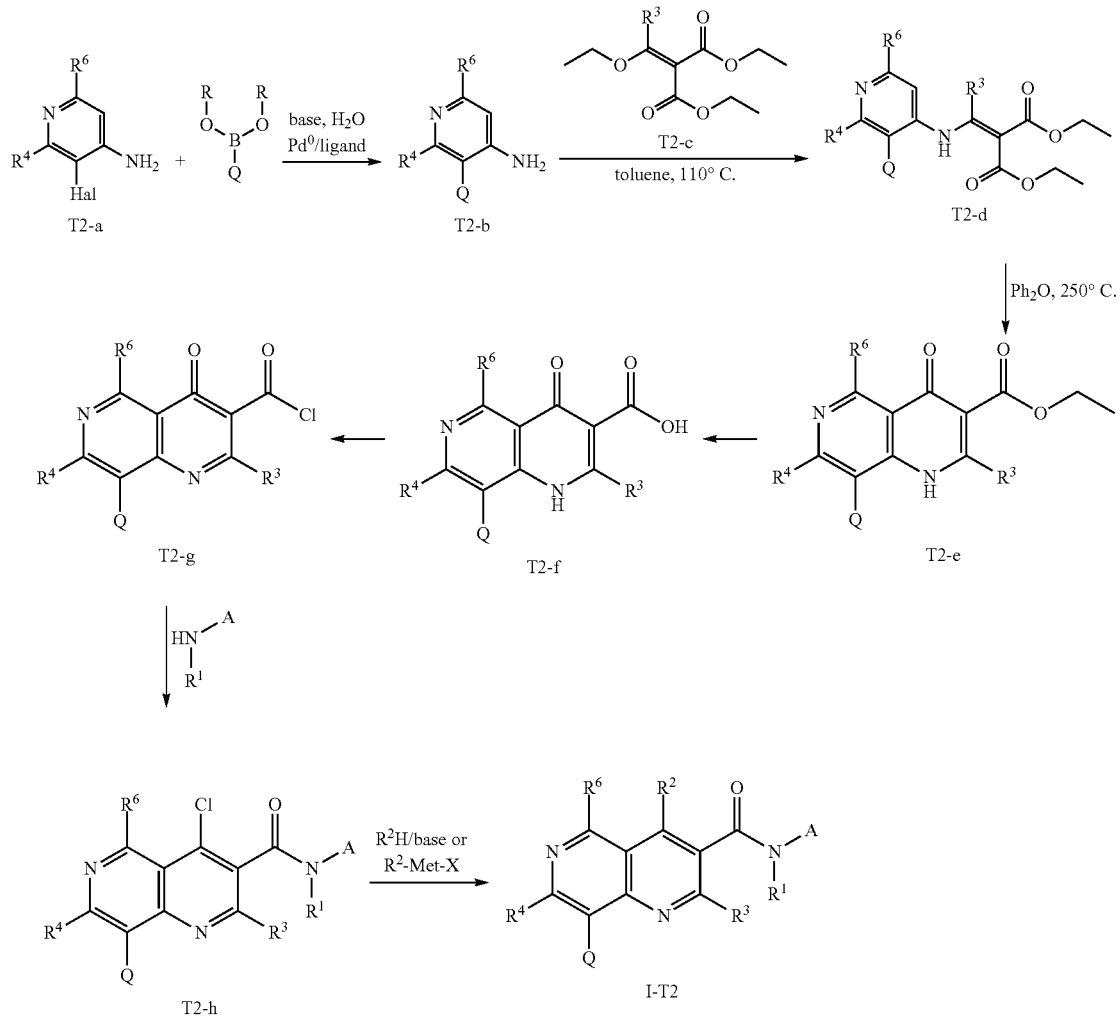

Aminopyridines T2-a can be converted via a Suzuki cross coupling reaction with boronic acids or boronic esters Q-B(OR)$_2$ (R=H; R=Me or R,R=pinacolate) as described in Journal of Organic Chemistry, 1999, 64 (26), 9430-9443, into aryl- or hetaryl-substituted aminopyridines T2-b. Such aminopyridines can be readily converted with (alkoxymethylen)malonates T2-c dissolved in the corresponding alcohol solvent or toluene, preferably under boiling conditions, into (pyrid-4-ylaminomethylene)-malonates T2-d as described in Journal of Medicinal Chemistry, 2007, 50 (22), 5471-5484, or without any solvent as described in Medicinal Chemistry Letters, 2012, 3 (1), 74-78. The ring closure is performed in high boiling solvents, preferably in diphenylether or xylol, to achieve aza-quinolone carboxylic esters T2-e as described in WO 2016196961. Intermediate esters T2-e react under hydrolytic conditions to yield aza-quinolone carboxylic acids T2-f as described with similar syntheses in WO 2009036412. The aza-quinolone carboxylic acids T2-f can be converted into the corresponding chloro aza-quinoline T2-g in the presence of chlorination agents like phosphorus oxychloride as described in WO 2016196961 with similar aza-quinolines. The acid chloride is formed simultaneously and can easily be converted with amines $R^1$—NH-A into amides T2-h in the presence of bases like triethylamine. Dependendent on the nature of the nucleophile $R^2H$, the chloro aza-quinolines T2-h react with $R^2H$ in the presence of a base, e.g. sodium ethylate, sodium methylate, potassium t-butylate, triethylamine N,N-diisopropyl ethylamine, diazabicycloundecan, sodium hydride, lithium hydroxide, sodium hydroxide, potassium hydroxide, potassium carbonate, cesium carbonate, or the like to obtain the final compounds I-T2. Alternatively, T2-h can be converted with certain Grignard- or metal organic compounds $R^2$Met-X, e.g. $C_1$-$C_4$-alkyl-Met-X, $C_3$-$C_6$-cycloalkyl-Met-X, $C_2$-$C_4$-alkenyl-Met-X, $C_3$-$C_6$-cycloalkenyl-Met-X, $C_2$-$C_4$-alkynyl-Met-X or phenyl-$C_1$-$C_4$-alkyl-Met-X (Met=Mg, Zn; X=I, Br, Cl) introducing $C_1$-$C_4$-alkyl, $C_3$-$C_6$-cycloalkyl, $C_2$-$C_4$-alkenyl, $C_3$-$C_6$-cycloalkenyl, $C_2$-$C_4$-alkynyl or phenyl-$C_1$-$C_4$-alkyl, each of which is optionally substituted as defined supra for the $R^2$ group, as described in Tetrahedron Letters, 2000, 41(33), 6387-6391 for example, into final compounds I-T2.

Scheme 2b for Preparing a Compound (I) with T=T2 (I-T2)

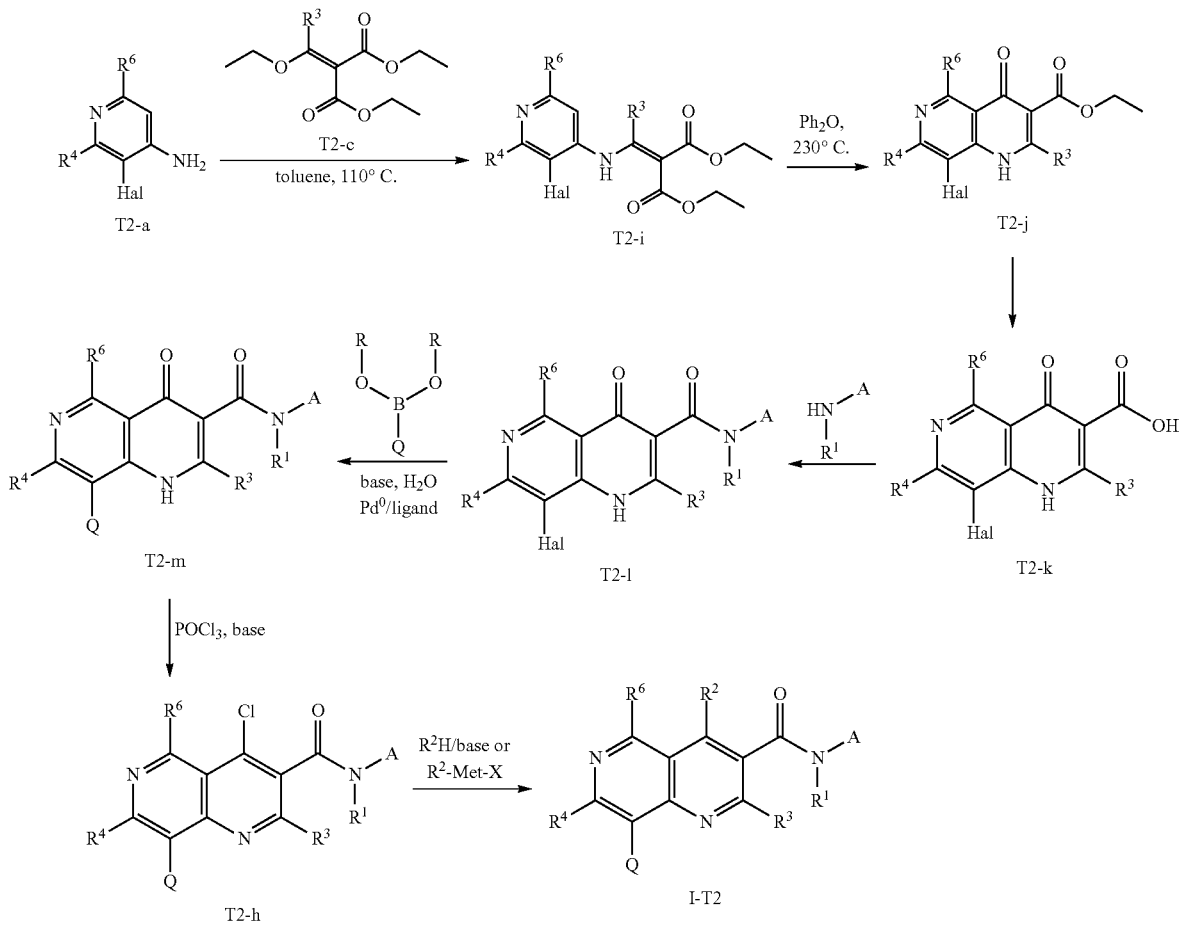

Aminopyridines T2-a can be readily converted with (alkoxymethylen)malonates T2-c dissolved in the corresponding alcohol solvent or toluene, preferably under boiling conditions, into (pyrid-4-ylaminomethylene)-malonates T2-i as described in Journal of Medicinal Chemistry, 2007, 50 (22), 5471-5484, or without any solvent as described in Medicinal Chemistry Letters, 2012, 3 (1), 74-78. The ring closure is performed in high boiling solvents, preferably in diphenylether or xylol, to achieve aza-quinolone carboxylic esters T2-j as described in WO 2016196961. Intermediate esters T2-j react under hydrolytic conditions to yield aza-quinolone carboxylic acids T2-k as described with similar syntheses in WO 2009036412. The aza-quinolone carboxylic acids T2-k can be converted into the corresponding amides T2-l by amide coupling conditions, e.g. via carboxylic acid chlorides formed from T2-k which are combined with amines $R^1$—NH-A under basic conditions, e.g. pyridine, triethylamine or N,N-diisopropyl ethylamine or via amide formation from the carboxylic acids T2-k which are combined with amines $R^1$—NH-A and dehydration reagents, e.g. N-(3-dimethylaminoisopropyl)-N'-ethylcarbodiimide-hydrochloride (EDC). Similar syntheses are described in WO 2009036412 for example.

Aza-quinolone amides T2-l can be converted via a Suzuki cross coupling reaction with boronic acids or boronic esters Q-B(OR)$_2$ (R=H; R=Me or R,R=pinacolate) as described with similar reactions in WO 2015144001, into aryl- or hetaryl-substituted Aza-quinolone amides T2-m.

The aza-quinolone amides T2-m can be converted into the corresponding chloro aza-quinoline T2-h in the presence of chlorination agents like phosphorus oxychloride or oxalyl chloride as described in WO 2008154447 with similar aza-quinolines. Depending on the nature of the nucleophile $R^2H$, the chloro aza-quinolines T2-h react with $R^2H$ in the presence of a base, e.g. sodium ethylate, sodium methylate, potassium t-butylate, triethylamine N,N-diisopropyl ethylamine, diazabicycloundecan, sodium hydride, lithium hydroxide, sodium hydroxide, potassium hydroxide, potassium carbonate, cesium carbonate, or the like to obtain the final compounds I-T2. Alternatively, T2-h can be converted with certain Grignard- or metal organic compounds $R^2$Met-X, e.g. $C_1$-$C_4$-alkyl-Met-X, $C_3$-$C_6$-cycloalkyl-Met-X, $C_2$-$C_4$-alkenyl-Met-X, $C_3$-$C_6$-cycloalkenyl-Met-X, $C_2$-$C_4$-alkynyl-Met-X or phenyl-$C_1$-$C_4$-alkyl-Met-X (Met=Mg, Zn; X=I, Br, Cl) introducing $C_1$-$C_4$-alkyl, $C_3$-$C_6$-cycloalkyl, $C_2$-$C_4$-alkenyl, $C_3$-$C_6$-cycloalkenyl, $C_2$-$C_4$-alkynyl or phenyl-$C_1$-$C_4$-alkyl, each of which is optionally substituted as defined supra for the $R^2$ group, as described in Tetrahedron Letters, 2000, 41(33), 6387-6391 for example, into final compounds I-T2.

Scheme 3 for Preparing a Compound (I) with T=T (I-T3)

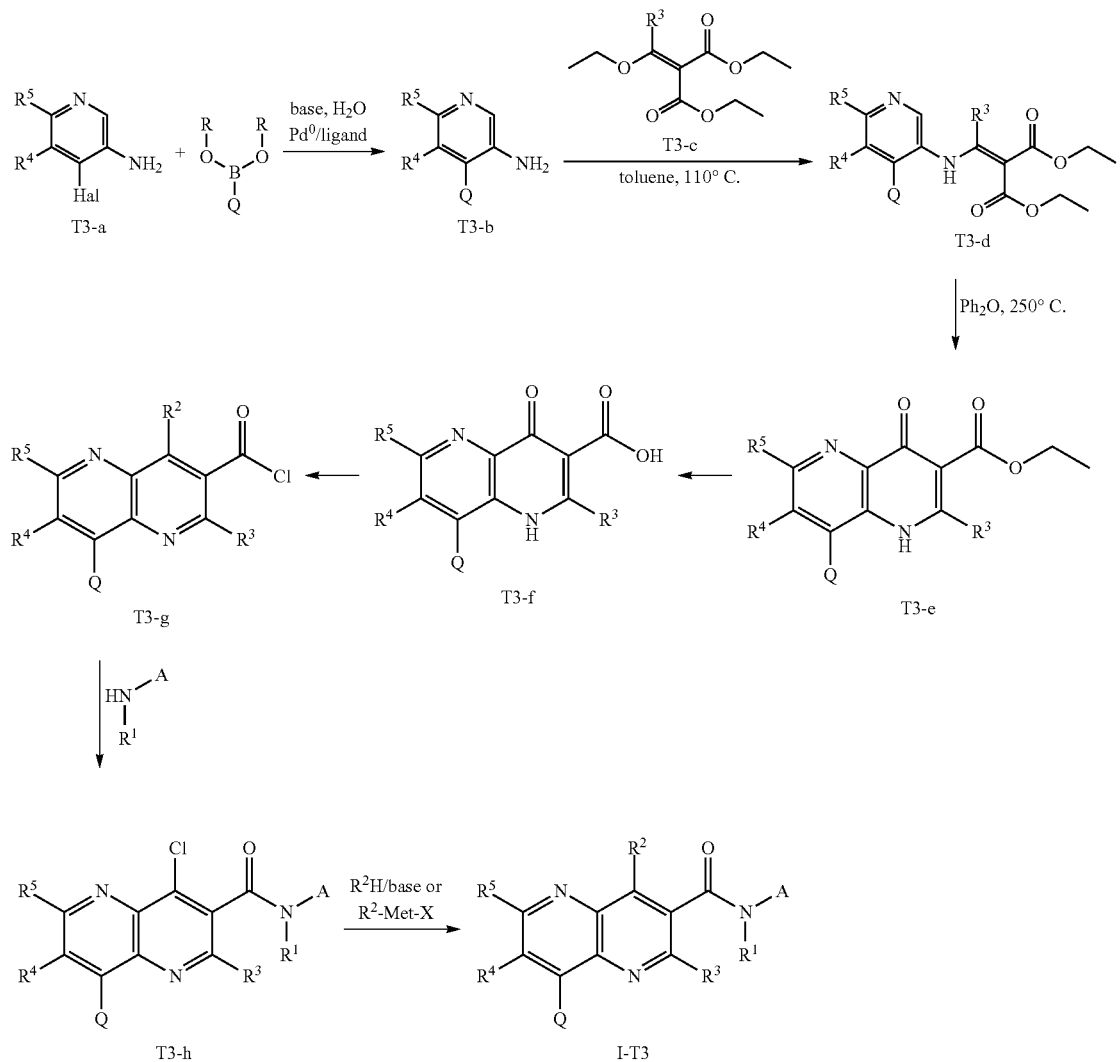

Aminopyridines T3-a can be converted via a Suzuki cross coupling reaction with boronic acids or boronic esters Q-B(OR)$_2$ (R=H; R=Me or R,R=pinacolate) as described in WO 2015170693 into aryl- or hetaryl-substituted aminopyridines T3-b. Such aminopyridines can be readily converted with (alkoxymethylen)malonates T3-c dissolved in the corresponding alcohol solvent or toluene, preferably under boiling conditions, into (pyrid-3-ylaminomethylene)-malonates T3-d as described in US 20140336182, or without any solvent as described in Journal of the American Chemical Society, 1946, 68, 1204-1208. The ring closure is performed in high boiling solvents, preferably in diphenylether or xylol, to achieve aza-quinolone carboxylic esters T3-e as described in WO 2013132376. Intermediate esters T3-e react under hydrolytic conditions to yield aza-quinolone carboxylic acids T3-f as described with similar syntheses in WO 20060223843. The carboxylic acids T3-f can be converted into the corresponding acid chlorides T3-g in the presence of chlorination agents like phosphorus oxychloride as described in WO 2006125974 with similar aza-quinolines. The acid chloride can easily be converted with amines R$^1$—NH-A into amides T3-h in the presence of bases like triethylamine. Dependend on the nature of the nucleophile R$^2$H, the chloro aza-quinolines T3-h react with R$^2$H in the presence of a base, e.g. sodium ethylate, sodium methylate, potassium t-butylate, triethylamine N,N-diisopropyl ethylamine, diazabicycloundecan, sodium hydride, lithium hydroxide, sodium hydroxide, potassium hydroxide, potassium carbonate, cesium carbonate, or the like to obtain the final compounds I-T3. Alternatively, T3-h can be converted with certain Grignard- or metal organic compounds R$^2$Met-X, e.g. $C_1$-$C_4$-alkyl-Met-X, $C_3$-$C_6$-cycloalkyl-Met-X, $C_2$-$C_4$-alkenyl-Met-X, $C_3$-$C_6$-cycloalkenyl-Met-X, $C_2$-$C_4$-alkynyl-Met-X or phenyl-$C_1$-$C_4$-alkyl-Met-X (Met=Mg, Zn; X=I, Br, Cl) introducing $C_1$-$C_4$-alkyl, $C_3$-$C_6$-cycloalkyl, $C_2$-$C_4$-alkenyl, $C_3$-$C_6$-cycloalkenyl, $C_2$-$C_4$-alkynyl or phenyl-$C_1$-$C_4$-alkyl, each of which is optionally substituted as defined supra for the R$^2$ group, as described in Tetrahedron Letters, 2000, 41(33), 6387-6391 for example, into final compounds I-T3.

Scheme 4 for Preparing a Compound (I) with T=T⁴ (I-T4)

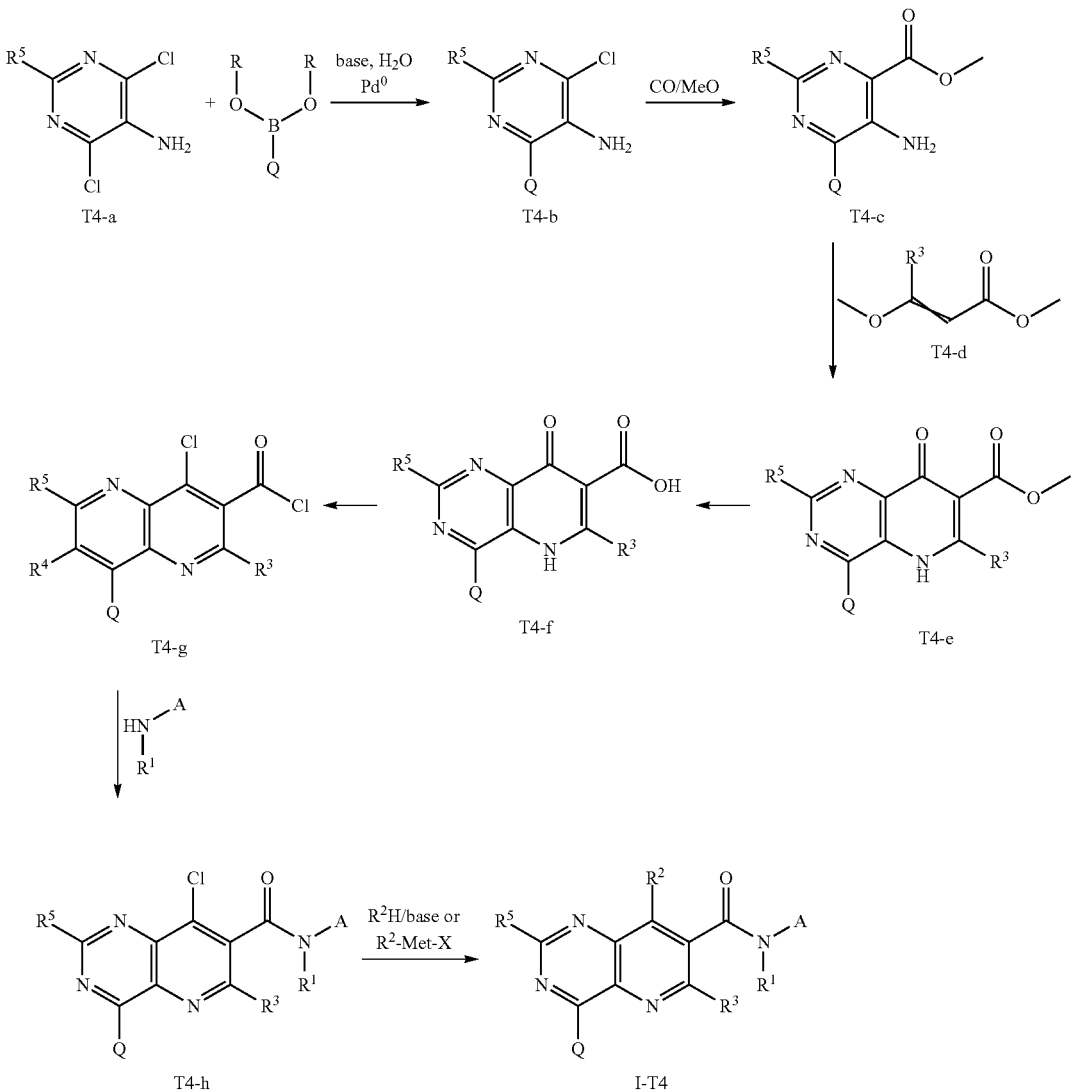

Aminopyrimidines T4-a can be converted via a Suzuki cross coupling reaction with boronic acids or boronic esters Q-B(OR)₂ (R=H; R=Me or R,R=pinacolate) as described in WO 2008134679 or WO 2009112461 into aryl- or hetaryl-substituted pyrimidines T4-b. Subsequently, T4-b can easily be converted into pyrimidinyl ester T4-c under autoclave conditions and carbon monoxide atmosphere in the presence of methanol as described in WO 199835967. The next step involves acrylester T4-d which can be condensed with T4-c to provide aza-quinolones like T4-e as described in Journal of the Chemical Society [Section C: Organic] (1967), (18), 1745-1750. Intermediates T4-e react under hydrolytic conditions to yield aza-quinolone carboxylic acids T4-f as described with similar syntheses in WO 2009089263. The carboxylic acids T4-f can be converted into the corresponding acid chlorides T4-g in the presence of chlorination agents like phosphorus oxychloride as described in EP 115469 with similar naphthyridines. The acid chloride can easily be converted with amines $R^1$—NH-A into amides T4-h in the presence of bases like triethylamine. Dependend on the nature of the nucleophile $R^2H$, the chloro aza-quinolines T4-h react with $R^2H$ in the presence of a base, e.g. sodium ethylate, sodium methylate, potassium t-butylate, triethylamine N,N-diisopropyl ethylamine, diazabicycloundecan, sodium hydride, lithium hydroxide, sodium hydroxide, potassium hydroxide, potassium carbonate, cesium carbonate, or the like to obtain the final compounds I-T4. Alternatively, T4-h can be converted with certain Grignard- or metal organic compounds $R^2$Met-X, e.g. $C_1$-$C_4$-alkyl-Met-X, $C_3$-$C_6$-cycloalkyl-Met-X, $C_2$-$C_4$-alkenyl-Met-X, $C_3$-$C_6$-cycloalkenyl-Met-X, $C_2$-$C_4$-alkynyl-Met-X or phenyl-$C_1$-$C_4$-alkyl-Met-X (Met=Mg, Zn; X=I, Br, Cl) introducing $C_1$-$C_4$-alkyl, $C_3$-$C_6$-cycloalkyl, $C_2$-$C_4$-alkenyl, $C_3$-$C_6$-cycloalkenyl, $C_2$-$C_4$-alkynyl or phenyl-$C_1$-$C_4$-alkyl, each of which is optionally substituted as defined supra for the $R^2$ group, as described in Tetrahedron Letters, 2000, 41(33), 6387-6391 for example, into final compounds I-T4.

Scheme 5 for Preparing a Compound (I) with T=T⁵ (I-T5)

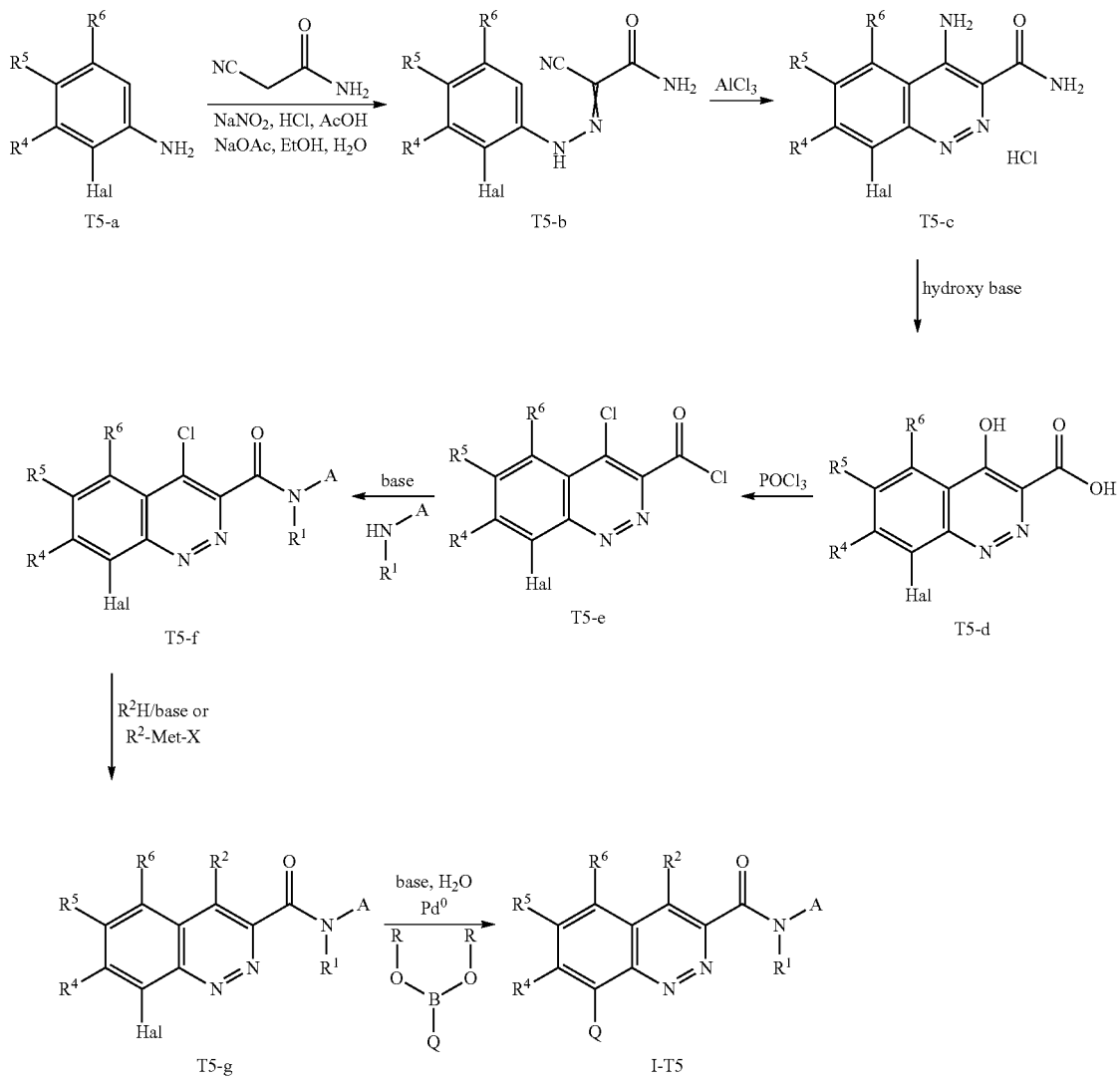

2-Halogenanilines T5-a can easily converted into oxoacetohydrazonoyl cyanides T5-b in a two-step diazotation-condensation reaction with 2-cyanoacetamide as described in Journal of Medicinal Chemistry, 2015, 58(14), 5437-5444. The cyclisation of T5-b into cinnoline carboxamides T5-c occurs in the presence of Lewis acids, e.g. aluminium trichloride, as described in WO 2013148603. The amino functions of T5-c can be saponified in the presence of hydroxyl bases, e.g. potassium hydroxide, to obtain cinnoline carboxylic acid T5-d as described in WO 2004016615. T5-d can be easily chlorinated, e.g. with phosphorus oxychloride, into cinnoline caroboxylic acid chloride T5-e as described in WO 2012162254. The acid chlorid can be converted with amines R¹—NH-A into amides T5-f in the presence of bases like triethylamine as described in WO 2012162254. Dependend on the nature of the nucleophile R²H, the chloro cinnolines T5-f react with R²H in the presence of a base, e.g. sodium ethylate, sodium methylate, potassium t-butylate, triethylamine N,N-diisopropyl ethylamine, diazabicycloundecan, sodium hydride, lithium hydroxide, sodium hydroxide, potassium hydroxide, potassium carbonate, cesium carbonate, or the like to obtain the cinnoline carboxamides T5-g as described in Bioorganic & Medicinal Chemistry Letters, 2013, 23(1), 71-74. Alternatively, T5-f can be converted with certain Grignard- or metal organic compounds R²Met-X, e.g. $C_1$-$C_4$-alkyl-Met-X, $C_3$-$C_6$-cycloalkyl-Met-X, $C_2$-$C_4$-alkenyl-Met-X, $C_3$-$C_6$-cycloalkenyl-Met-X, $C_2$-$C_4$-alkynyl-Met-X or phenyl-$C_1$-$C_4$-alkyl-Met-X (Met=Mg, Zn; X=I, Br, Cl) introducing $C_1$-$C_4$-alkyl, $C_3$-$C_6$-cycloalkyl, $C_2$-$C_4$-alkenyl, $C_3$-$C_6$-cycloalkenyl, $C_2$-$C_4$-alkynyl or phenyl-$C_1$-$C_4$-alkyl, each of which is optionally substituted as defined supra for the $R^2$ group, as described in Journal of Medicinal Chemistry, 2013, 56(3), 1023-1040. Finally, T5-g can be converted via a Suzuki cross coupling reaction with boronic acids or boronic esters Q-B(OR)₂ (R=H; R=Me or R,R=pinacolate) as described in WO 2013148603 to provide the final compounds I-T5.

Scheme 6 for Preparing a Compound (I) with T=T (I-T6)

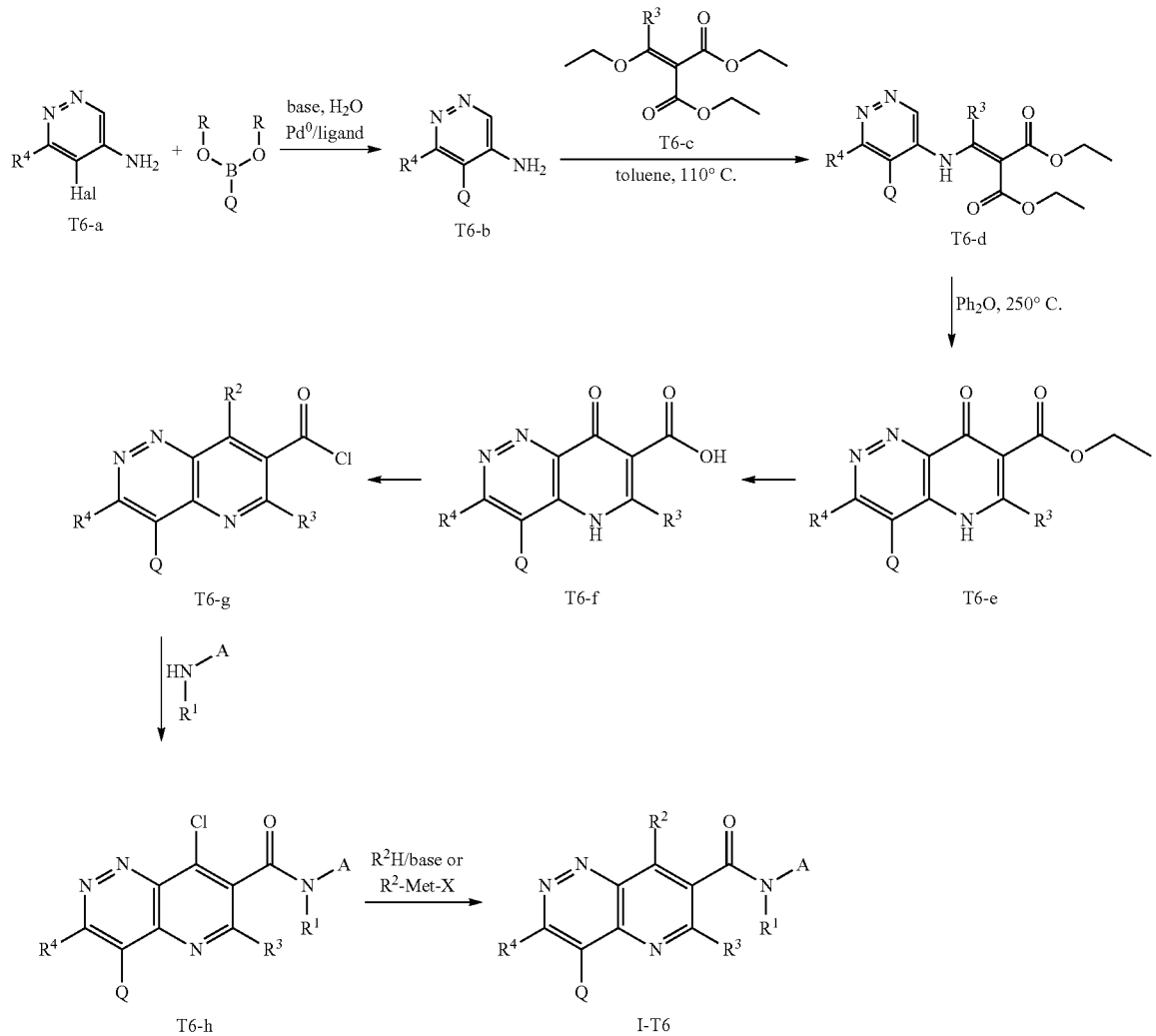

Aminopyridazines T6-a can be converted via a Suzuki cross coupling reaction with boronic acids or boronic esters Q-B(OR)$_2$ (R=H; R=Me or R,R=pinacolate) as described in WO 2014143241 into aryl- or hetaryl-substituted aminopyridazines T6-b. Such aminopyridazines can be readily converted with (alkoxymethylen)malonates T6-c dissolved in the corresponding alcohol solvent or toluene, preferably under boiling conditions, into (pyridazin-4-ylaminomethylene)-malonates T6-d as described with similar reactions in US 20140336182, or without any solvent as described in Journal of the American Chemical Society, 1946, 68, 1204-1208. The ring closure is performed in high boiling solvents, preferably in diphenylether or xylol, to achieve 8-oxo-5,8-dihydropyrido[3,2-c]pyridazine carboxylic esters T6-e as described in WO 2013132376. Intermediate esters T6-e react under hydrolytic conditions to yield 8-oxo-5,8-dihydropyrido[3,2-c]pyridazine-7-carboxylic acids T6-f as described with similar syntheses in WO 20060223843. The carboxylic acids T6-f can be converted into the corresponding acid chlorides T6-g in the presence of chlorination agents like phosphorus oxychloride as described in WO 2006125974 with similar aza-quinolines. The acid chloride can easily be converted with amines R$^1$—NH-A into amides T6-h in the presence of bases like triethylamine. Dependend on the nature of the nucleophile R$^2$H, the 8-chloro-pyrido [3,2-c]pyridazine-7-carboxamides T6-h react with R$^2$H in the presence of a base, e.g. sodium ethylate, sodium methylate, potassium t-butylate, triethylamine N,N-diisopropyl ethylamine, diazabicycloundecan, sodium hydride, lithium hydroxide, sodium hydroxide, potassium hydroxide, potassium carbonate, cesium carbonate, or the like to obtain the final compounds I-T6. Alternatively, T6-h can be converted with certain Grignard- or metal organic compounds R$^2$Met-X, e.g. C$_1$-C$_4$-alkyl-Met-X, C$_3$-C$_6$-cycloalkyl-Met-X, C$_2$-C$_4$-alkenyl-Met-X, C$_3$-C$_6$-cycloalkenyl-Met-X, C$_2$-C$_4$-alkynyl-Met-X or phenyl-C$_1$-C$_4$-alkyl-Met-X (Met=Mg, Zn; X=I, Br, Cl) introducing C$_1$-C$_4$-alkyl, C$_3$-C$_6$-cycloalkyl, C$_2$-C$_4$-alkenyl, C$_3$-C$_6$-cycloalkenyl, C$_2$-C$_4$-alkynyl or phenyl-C$_1$-C$_4$-alkyl, each of which is optionally substituted as defined supra for the R$^2$ group, as described in Tetrahedron Letters, 2000, 41(33), 6387-6391 for example, into final compounds I-T6.

EXPERIMENTAL SECTION—EXAMPLES

Intermediates (T[1])

2-(3,5-Dichlorophenyl)pyridin-3-amine (T1-b-1)

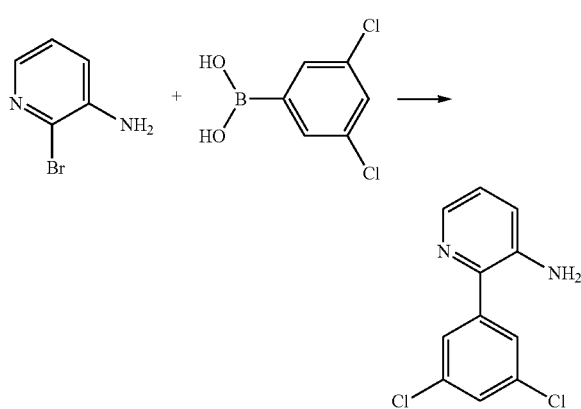

2-Bromopyridin-3-amine, 2.00 g (11.6 mmol), 3,5-dichlorophenylboronic acid, 3.30 g (17.3 mmol), tris(dibenzylideneacetone)dipalladium, 0.50 g (0.6 mmol), tri-tert-butylphosphine tetrafluoroborate, 0.30 g (1.2 mmol), and potassium fluoride, 2.00 g (34.7 mmol), were dissolved in 80 mL of tetrahydrofuran and 20 mL of water. The mixture was stirred at 60° C. overnight. The solvent was removed in vacuo. Water was added, the mixture was extracted with ethyl acetate and the combined organic phases were dried over anhydrous sodium sulfate. The solvent was removed in vacuo and the residue was purified by silica gel column chromatography (petroleum ether/ethyl acetate=10:1) to give 1.40 g (51%) of the product as a yellow solid.

LC-MS (Method M34): $R_t$=0.77 min; m/z=239 (M+1)$^+$.

2-(2,3-Dichlorophenyl)pyridin-3-amine (T1-b-2)

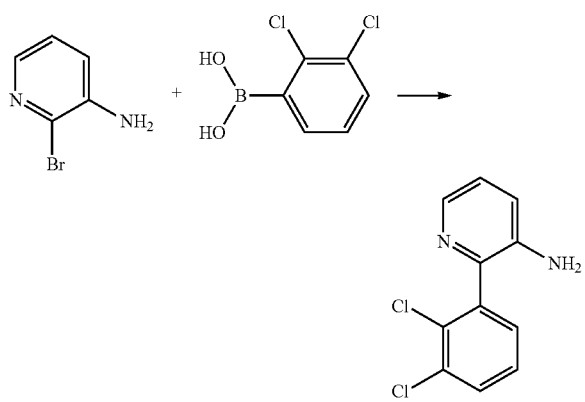

This compound was synthesized by the same method as described in T1-b-1 to give 1.56 g (62%) of the product as a yellow solid.

LC-MS (Method M34): $R_t$=0.82 min; m/z=239 (M+1)$^+$.

Diethyl ({[2-(3,5-dichlorophenyl)pyridin-3-yl]amino}methylene)malonate (T1-d-1)

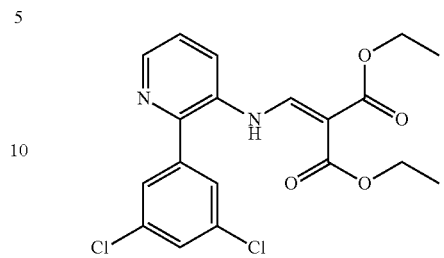

2-(3,5-Dichlorophenyl)pyridin-3-amine, 1.40 g (5.6 mmol) and diethyl 2-(ethoxymethylene)-malonate, 3.80 g (17.6 mmol), were dissolved in 30 mL of toluene. The resulting mixture was stirred at 110° C. for overnight. The solvent was removed in vacuo and the residue was purified by silica gel column chromatography (petroleum ether/ethyl acetate=1:2) to give 2.40 g (40%) of the product as a yellow solid.

LC-MS (Method M20): $R_t$=1.32 min; m/z=409 (M+1)$^+$.

Diethyl ({[2-(2,3-dichlorophenyl)pyridin-3-yl]amino}methylene)malonate (T1-d-2)

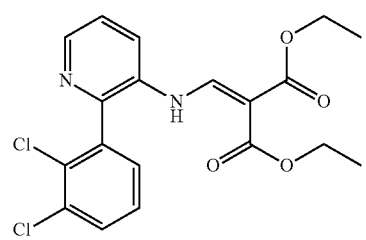 [SMILES: CCOC(=O)C(=CNc1cccnc1-c1cccc(Cl)c1Cl)C(=O)OCC]

This compound was synthesized by the same method as described in T1-d-1 to give 2.10 g (70%) of the product as yellow oil.

LC-MS (Method M20): $R_t$=1.19 min; m/z=409 (M+1)$^+$.

Ethyl 8-(3,5-dichlorophenyl)-4-oxo-1,4-dihydro-1,7-naphthyridine-3-carboxylate (T1-e-1)

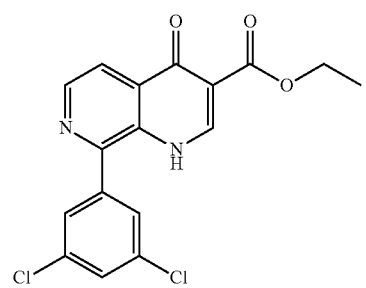 [SMILES: CCOC(=O)c1c[nH]c2c(-c3cc(Cl)cc(Cl)c3)nccc2c1=O]

Diethyl ({[2-(3,5-dichlorophenyl)pyridin-3-yl]amino}methylene)malonate, 2.40 g (5.9 mmol), was dissolved in 50 mL of diphenyl ether. The resulting mixture was stirred at 230° C. for 30 min. After cooling to room temperature, 500 mL of petroleum ether was added and the precipitated solid was collected by filtration to give 460 mg (9%) of the product as a brown solid.

LC-MS (Method M17): $R_t$=0.77 min; m/z=363 (M+1)$^+$.

Ethyl 8-(2,3-dichlorophenyl)-4-oxo-1,4-dihydro-1,7-naphthyridine-3-carboxylate (T1-e-2)

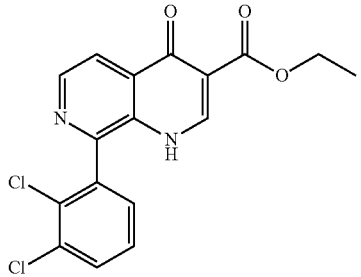 [SMILES: CCOC(=O)c1c[nH]c2c(-c3cccc(Cl)c3Cl)nccc2c1=O]

This compound was synthesized by the same method as described in T1-e-1 to give 460 mg (21%) of the product as a brown solid.

LC-MS (Method M20): $R_t$=0.93 min; m/z=363 (M+1)$^+$.

Ethyl 4-chloro-8-(3,5-dichlorophenyl)-1,7-naphthyridine-3-carboxylate (T1-f-1)

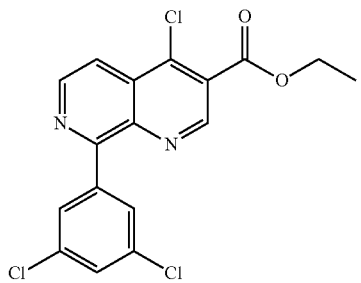 [SMILES: CCOC(=O)c1cnc2c(-c3cc(Cl)cc(Cl)c3)nccc2c1Cl]

Ethyl 8-(3,5-dichlorophenyl)-4-oxo-1,4-dihydro-1,7-naphthyridine-3-carboxylate, 460 mg (1.3 mmol), was dissolved in 10 mL of phosphorus oxychloride. The resulting mixture was stirred at 100° C. for 2 hours. The solvent was removed in vacuo to give 460 mg (crude) of the product as black oil.

LC-MS (Method M20): $R_t$=1.55 min; m/z=381 (M+1)$^+$.

Ethyl 4-chloro-8-(2,3-dichlorophenyl)-1,7-naphthyridine-3-carboxylate (T1-f-2)

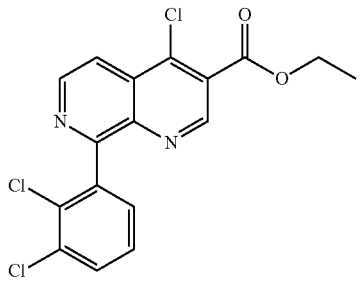 [SMILES: CCOC(=O)c1cnc2c(-c3cccc(Cl)c3Cl)nccc2c1Cl]

This compound was synthesized by the same method as described in T1-f-1 to give 460 mg (55%) of the product as black oil.

LC-MS (Method M3): $R_t$=1.32 min; m/z=381 (M+1)$^+$.

Ethyl 8-(3,5-dichlorophenyl)-4-(dimethylamino)-1,7-naphthyridine-3-carboxylate (T1-g-1)

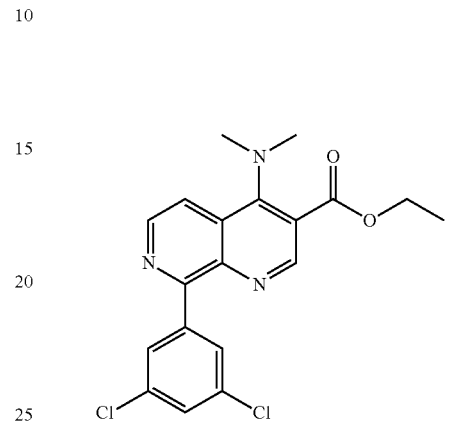

Ethyl 4-chloro-8-(3,5-dichlorophenyl)-1,7-naphthyridine-3-carboxylate, 230 mg (0.6 mmol), was dissolved in 10 mL of tetrahydrofuran. Dimethylamine, 3.0 mL (2M in tetrahydrofuran, 6.0 mmol), was added. The resulting mixture was stirred at room temperature for 1 hour. The solvent was removed in vacuo. Water was added, the mixture was extracted with ethyl acetate and the combined organic phases were dried over anhydrous sodium sulfate. The solvent was removed in vacuo to give 230 mg (crude) of the product as brown oil.

LC-MS (Method M21): $R_t$=1.24 min; m/z=390 (M+1)$^+$.

Ethyl 8-(2,3-dichlorophenyl)-4-(dimethylamino)-1,7-naphthyridine-3-carboxylate (T1-g-2)

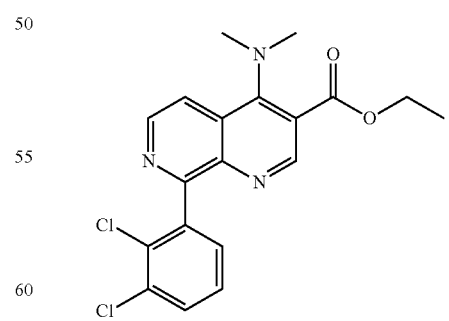

This compound was synthesized by the same method as described in T1-g-1 to give 210 mg (63%) of the product as a brown solid.

LC-MS (Method M3): $R_t$=1.14 min; m/z=390 (M+1)$^+$.

131

Ethyl 8-(3,5-dichlorophenyl)-4-(morpholin-4-yl)-1,7-naphthyridine-3-carboxylate (T1-g-3)

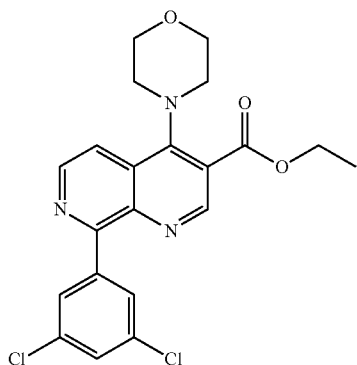 [SMILES: CCOC(=O)c1cnc2c(-c3cc(Cl)cc(Cl)c3)nccc2c1N1CCOCC1]

Ethyl 4-chloro-8-(3,5-dichlorophenyl)-1,7-naphthyridine-3-carboxylate, 260 mg (crude), was dissolved in 5 mL of tetrahydrofuran. Morpholine, 310 mg (5.2 equiv.), was added. The resulting mixture was stirred at room temperature for 1 hour. The solvent was removed in vacuo. Water was added, the mixture was extracted with ethyl acetate and the combined organic phases were dried over anhydrous sodium sulfate to give 230 mg (78%) of the product as a white solid.

LC-MS (Method M21): $R_t$=1.23 min; m/z=432 (M+1)$^+$.

Ethyl 8-(3,5-dichlorophenyl)-4-(morpholin-4-yl)-1,7-naphthyridine-3-carboxylate (T1-g-4)

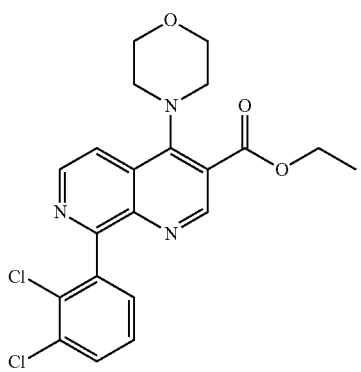 [SMILES: CCOC(=O)c1cnc2c(-c3cccc(Cl)c3Cl)nccc2c1N1CCOCC1]

This compound was synthesized by the same method as described in T1-g-3 to give 200 mg (64%) of the product as a yellow solid.

LC-MS (Method M21): $R_t$=1.19 min; m/z=432 (M+1)$^+$.

132

8-(3,5-Dichlorophenyl)-4-(dimethylamino)-1,7-naphthyridine-3-carboxylic (T1-h-1)

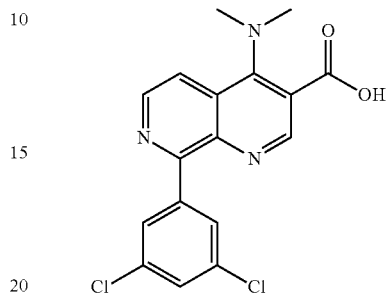

Ethyl 8-(3,5-dichlorophenyl)-4-(dimethylamino)-1,7-naphthyridine-3-carboxylate, 230 mg (0.6 mmol), was dissolved in 4.0 mL of tetrahydrofuran and 1.0 mL of water. Lithium hydroxide, 140 mg (5.9 mmol), was added at room temperature. The resulting mixture was stirred at 60° C. overnight. After cooling to room temperature, the solvent was removed in vacuo. The mixture was extracted with ethyl acetate and the pH of the water phase was adjusted to 7 with 2N hydrogen chloride solution. The precipitate solid was filtered off, washed with water and dried on air to give 130 mg (57%) of the product as a yellow solid.

LC-MS (Method M21): $R_t$=0.81 min; m/z=362 (M+1)$^+$.

8-(2,3-Dichlorophenyl)-4-(dimethylamino)-1,7-naphthyridine-3-carboxylic (T1-h-2)

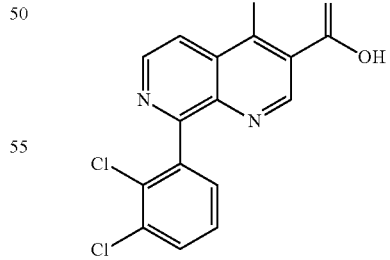

This compound was synthesized by the same method as described in T1-h-1 to give 190 mg (89%) of the product as a yellow solid.

LC-MS (Method M3): $R_t$=0.82 min; m/z=362 (M+1)$^+$.

8-(3,5-Dichlorophenyl)-4-(morpholin-4-yl)-1,7-naphthyridine-3-carboxylic acid (T1-h-3)

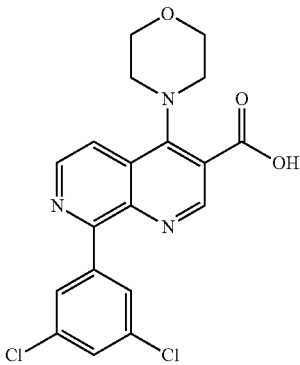 [SMILES: O=C(O)c1cnc2c(-c3cc(Cl)cc(Cl)c3)nccc2c1N1CCOCC1]

This compound was synthesized by the same method as described in T1-h-1 to give 100 mg (44%) of the product as a yellow solid.
LC-MS (Method M21): $R_t$=1.00 min; m/z=404 (M+1)$^+$.

8-(2,3-Dichlorophenyl)-4-(morpholin-4-yl)-1,7-naphthyridine-3-carboxylic acid (T1-h-4)

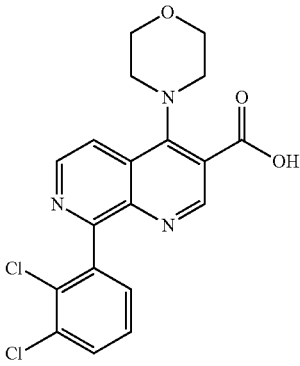 [SMILES: O=C(O)c1cnc2c(-c3cccc(Cl)c3Cl)nccc2c1N1CCOCC1]

This compound was synthesized by the same method as described in T1-h-1 to give 160 mg (73%) of the product as a yellow solid.
LC-MS (Method M3): $R_t$=0.99 min; m/z=404 (M+1)$^+$.

Examples (T$^1$)

Example T1-1

8-(3,5-Dichlorophenyl)-N-[(4S)-3,4-dihydro-2H-chromen-4-yl]-4-(dimethylamino)-1,7-naphthyridine-3-carboxamide

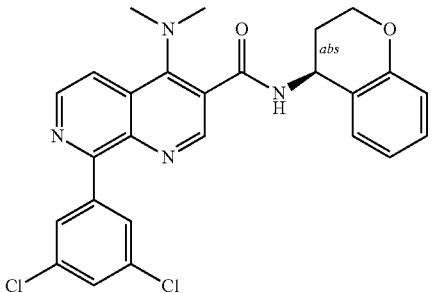 [SMILES: CN(C)c1c(C(=O)N[C@H]2CCOc3ccccc32)cnc2c(-c3cc(Cl)cc(Cl)c3)nccc12]

8-(3,5-Dichlorophenyl)-4-(dimethylamino)-1,7-naphthyridine-3-carboxylic acid, 120 mg (0.3 mmol), (S)-chroman-4-amine, 60 mg (0.4 mmol), HATU, 189 mg (0.5 mmol), N,N-diisopropylethylamine, 129 mg (1.0 mmol), were dissolved in 3 mL of N,N-dimethylformamide. The resulting mixture was stirred at room temperature for 2 hours. The solvent was removed in vacuo and the residue was purified by preparative HPLC to give 36 mg (20%) of the product as a yellow solid.
LC-MS (Method M30): $R_t$=1.61 min; m/z=493 (M+1)$^+$.
$^1$H-NMR (400 MHz, DMSO-d$_6$): δ [ppm]=2.05-2.08 (m, 1H), 2.19-2.24 (m, 1H), 3.11 (s, 6H), 4.22-4.31 (m, 2H), 5.25 (q, 1H), 6.80 (d, 1H), 6.94 (t, 1H), 7.18 (t, 1H), 7.38 (d, 1H), 7.73 (s, 1H), 8.06-8.09 (m, 3H), 8.65 (d, 1H), 8.74 (s, 1H), 9.18 (d, 1H).

Example T1-2

8-(2,3-Dichlorophenyl)-N-[(4S)-3,4-dihydro-2H-chromen-4-yl]-4-(dimethylamino)-1,7-naphthyridine-3-carboxamide

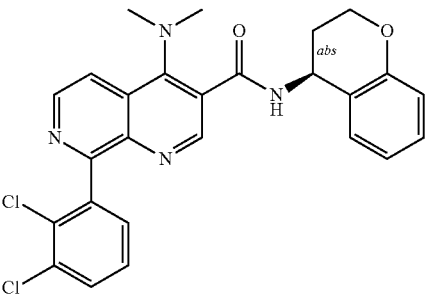 [SMILES: CN(C)c1c(C(=O)N[C@H]2CCOc3ccccc32)cnc2c(-c3cccc(Cl)c3Cl)nccc12]

This compound was synthesized by the same method as described in example T1-1 to give 74 mg (29%) of the product as a yellow solid.
LC-MS (Method M36): $R_t$=1.20 min; m/z=493 (M+1)$^+$.
$^1$H-NMR (400 MHz, DMSO-d$_6$): δ [ppm]=2.01-2.07 (m, 1H), 2.17-2.20 (m, 1H), 3.16 (s, 6H), 4.17-4.29 (m, 2H), 5.22 (q, 1H), 6.79 (d, 1H), 6.92 (t, 1H), 7.14-7.19 (m, 1H), 7.34 (d, 1H), 7.40-7.49 (m, 2H), 7.7-7.8 (m, 1H), 8.13 (d, 1H), 8.57 (s, 1H), 8.64 (d, 1H), 9.16 (d, 1H).

Example T1-3

8-(3,5-Dichlorophenyl)-N-[(4S)-3,4-dihydro-2H-chromen-4-yl]-4-(morpholin-4-yl)-1,7-naphthyridine-3-carboxamide

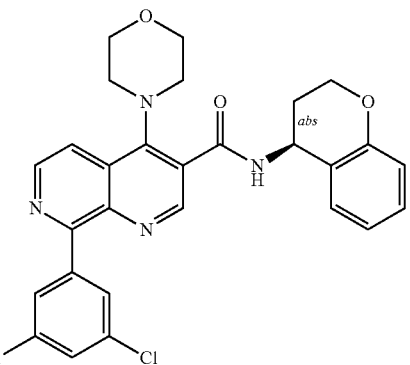

This compound was synthesized by the same method as described in example T1-1 to give 78 mg (57%) of the product as a light yellow solid.

LC-MS (Method M35): R$_t$=1.85 min; m/z=535 (M+1)$^+$.

$^1$H-NMR (400 MHz, DMSO-d$_6$): δ [ppm]=2.07-2.11 (m, 1H), 2.20-2.27 (m, 1H), 3.31-3.40 (m, 4H), 3.87-3.90 (m, 4H), 4.24-4.30 (m, 2H), 5.27 (q, 1H), 6.81 (d, 1H), 6.95 (t, 1H), 7.19 (t, 1H), 7.41 (d, 1H), 7.74 (t, 1H), 8.06-8.10 (m, 3H), 8.71 (d, 1H), 8.83 (s, 1H), 9.28 (d, 1H).

Example T1-4

8-(2,3-Dichlorophenyl)-N-[(4S)-3,4-dihydro-2H-chromen-4-yl]-4-(morpholin-4-yl)-1,7-naphthyridine-3-carboxamide

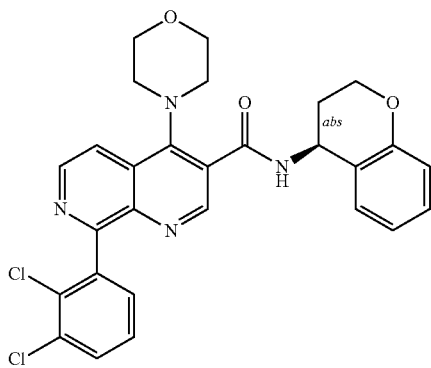 [SMILES: O=C(N[C@H]1CCOc2ccccc21)c1cnc2c(-c3cccc(Cl)c3Cl)nccc2c1N1CCOCC1]

This compound was synthesized by the same method as described in example T1-1 to give 59 mg (29%) of the product as a yellow solid.

LC-MS (Method M37): R$_t$=1.60 min; m/z=535 (M+1)$^+$.

$^1$H-NMR (400 MHz, DMSO-d$_6$): δ [ppm]=2.03-2.08 (m, 1H), 2.18-2.23 (m, 1H), 3.32-3.33 (m, 4H), 3.88 (m, 4H), 4.22-4.48 (m, 2H), 5.24 (q, 1H), 6.78-6.80 (m, 1H), 6.91 (t, 1H), 7.11-7.20 (m, 1H), 7.35-7.51 (m, 3H), 7.75-7.78 (m, 1H), 8.08 (d, 1H), 8.67-8.69 (m, 2H), 9.25 (d, 1H).

Intermediates (T$^2$)

3-(2,3-Dichlorophenyl)pyridin-4-amine (T2-b-1)

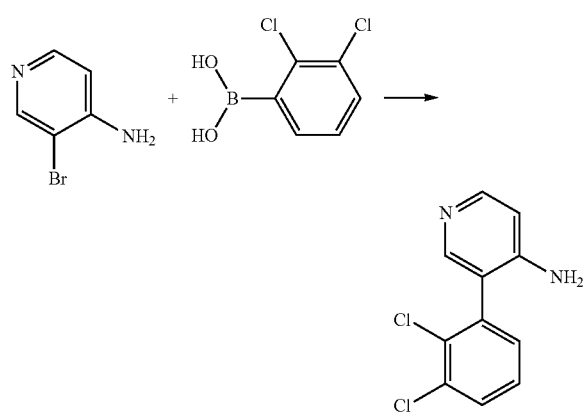

3-Bromopyridin-4-amine, 2.00 g (11.6 mmol), 2,3-dichlorophenylboronic acid, 3.30 g (17.3 mmol), tris(dibenzylideneacetone)dipalladium, 530 mg (0.6 mmol), tri-tert-butylphosphine tetrafluoroborate, 335 mg (1.2 mmol), and potassium fluoride, 2.00 g (34.7 mmol), were dissolved in 40 mL of tetrahydrofuran and 10 mL of water. The mixture was stirred at 110° C. overnight. The solvent was removed in vacuo. Water was added, the mixture was extracted with ethyl acetate and the combined organic phase was dried over anhydrous sodium sulfate. The solvent was removed in vacuo and the residue was purified with silica gel column chromatography (dichloromethane/methanol=20:1) to give 1.90 g (59%) of the product as a yellow solid.

LC-MS (Method M33): R$_t$=1.22 min; m/z=239 (M+1)$^+$.

Diethyl ({[3-(2,3-dichlorophenyl)pyridin-4-yl]amino}methylene)malonate (T2-d-1)

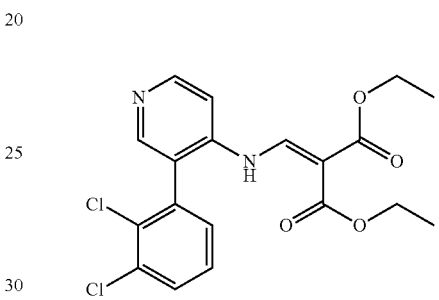

3-(2,3-Dichlorophenyl)pyridin-4-amine, 1.90 g (8.0 mmol) and diethyl 2-(ethoxymethylene)malonate, 5.70 g (23.8 mmol), were dissolved in 30 mL of toluene. The resulting mixture was stirred at 110° C. overnight. The solvent was removed in vacuo and the residue was purified with silica gel column chromatography (petroleum ether/ethyl acetate=1:2) to give 1.10 g (33%) of the product as yellow oil.

LC-MS (Method M33): R$_t$=1.52 min; m/z=409 (M+1)$^+$.

Ethyl 8-(2,3-dichlorophenyl)-4-oxo-1,4-dihydro-1,6-naphthyridine-3-carboxylate (T2-e-1)

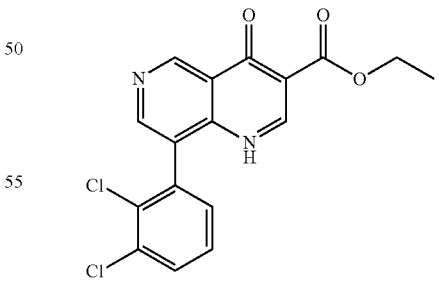

1000 mL of diphenyl ether was placed in to a three-necked flask, diethyl ({[3-(2,3-dichlorophenyl)pyridin-4-yl]amino}methylene)malonate, 1.00 g (2.4 mmol), dissolved in 100 mL of diphenyl ether, was added at reflux. The resulting mixture was stirred at reflux for 10 min. After cooling to room temperature, the reaction system was washed five times with 4N hydrogen chloride solution. The aqueous phase was lyophilized and then purified with C18 reversed phase column to give 540 mg (61%) of the product as a yellow solid.

LC-MS (Method M31): $R_t$=1.93 min; m/z=363 (M+1)$^+$.

8-(2,3-Dichlorophenyl)-4-oxo-1,4-dihydro-1,6-naphthyridine-3-carboxylic acid (T2-f-1)

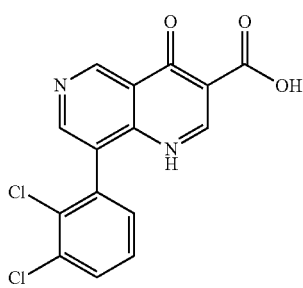

Ethyl 8-(2,3-dichlorophenyl)-4-oxo-1,4-dihydro-1,6-naphthyridine-3-carboxylate, 540 mg (1.5 mmol), was dissolved in 16 mL of tetrahydrofuran and 4 mL of water. Lithium hydroxide, 625 mg (14.9 mmol), was added at room temperature. The resulting mixture was stirred at 60° C. overnight. After cooling to room temperature, the solvent was removed in vacuo. The mixture was extracted with ethyl acetate and the pH of the water phase was adjusted to 7 with 2N hydrogen chloride solution. The precipitated solid was filtered off, washed with water and dried on air to give 300 mg (50%) of the product as a white solid.

LC-MS (Method M17): $R_t$=0.80 min; m/z=335 (M+1)$^+$.

4-Chloro-8-(2,3-dichlorophenyl)-1,6-naphthyridine-3-carbonyl chloride (T2-g-1)

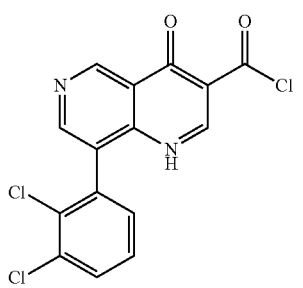

8-(2,3-Dichlorophenyl)-4-oxo-1,4-dihydro-1,6-naphthyridine-3-carboxylic acid, 250 mg (0.8 mmol), was dissolved in 5 mL of toluene. N,N-Diisopropylethylamine, 289 mg (2.2 mmol), was added at room temperature. The resulting mixture was stirred at 60° C. for 1 hour. Phosphorus oxychloride, 572 mg (3.7 mmol), was added at 60° C. The resulting mixture was stirred at 60° C. for 30 minutes. The solvent was removed in vacuo to give 250 mg (crude) of the product as brown oil. The residue was used directly to the next step without further purification.

4-Chloro-8-(2,3-dichlorophenyl)-N-[(4S)-3,4-dihydro-2H-chromen-4-yl]-1,6-naphthyridine-3-carboxamide (T2-h-2)

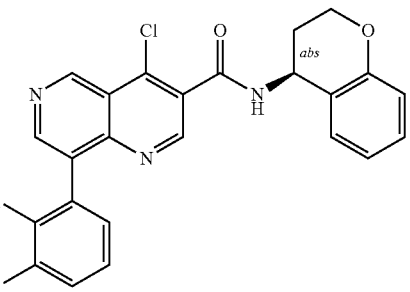

4-Chloro-8-(2,3-dichlorophenyl)-1,6-naphthyridine-3-carbonyl chloride, 250 mg (0.7 mmol) and (S)-chroman-4-amine, 120 mg (0.8 mmol), were dissolved in 5 mL of dichloromethane. Triethylamine, 340 mg (3.4 mmol), was added at room temperature. The resulting mixture was stirred at room temperature for 30 minutes. The solvent was removed in vacuo to give 250 mg (crude) of the product as brown oil.

LC-MS (Method M17): $R_t$=1.06; m/z=484 (M+1)$^+$.

Diethyl {[(3-bromopyridin-4-yl)amino]methylene}malonate (T2-i-1)

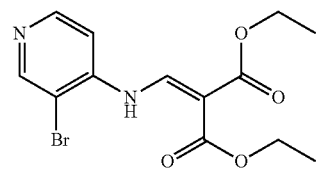 [SMILES: CCOC(=O)C(=CNc1ccncc1Br)C(=O)OCC]

3-Bromopyridin-4-amine, 2.00 g (11.6 mmol) and diethyl 2-(ethoxymethylene)malonate, 7.49 g (34.7 mmol), were dissolved in 50 mL of toluene. The resulting mixture was stirred at 110° C. overnight. After cooling to room temperature, the solvent was removed in vacuo. The residue was purified with silica gel column chromatography (petroleum ether/ethyl acetate=2:3) to give 3.50 g (88%) of the product as a brown solid.

LC-MS (Method M20): $R_t$=0.86 min; m/z=343/345 (M+1)$^+$.

Ethyl 8-bromo-4-oxo-1,4-dihydro-1,6-naphthyridine-3-carboxylate (T2-j-1)

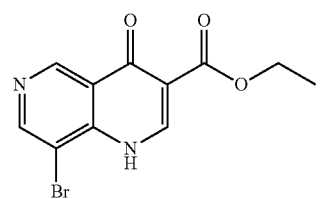 [SMILES: CCOC(=O)c1c[nH]c2c(Br)cncc2c1=O]

Diethyl {[(3-bromopyridin-4-yl)amino]methylene}malonate, 3.00 g (8.7 mmol), was dissolved in 50 mL of diphenyl ether. The resulting mixture was stirred at 230° C. for 40 min. After cooling to room temperature, 500 mL of petroleum ether was added, the precipitated solid was collected by filtration to give 1.42 g (50%) of the product as a brown solid.

LC-MS (Method M12): $R_f$=0.59 min; m/z=297/299 (M+1)$^+$.

8-Bromo-4-oxo-1,4-dihydro-1,6-naphthyridine-3-carboxylic acid (T2-k-1)

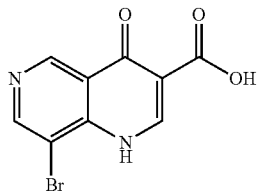 [SMILES: O=C(O)c1c[nH]c2c(Br)cncc2c1=O]

Ethyl 8-bromo-4-oxo-1,4-dihydro-1,6-naphthyridine-3-carboxylate, 1.42 g (4.8 mmol), was dissolved in 40.0 mL of tetrahydrofuran and 10 mL of water. Lithium hydroxide, 1.15 g (47.8 mmol), was added at room temperature. The resulting mixture was stirred at 65° C. overnight. After cooling to room temperature, the solvent was removed in vacuo. The mixture was extracted with ethyl acetate and the pH of the water phase was adjusted to 7 with 2N hydrogen chloride solution. The precipitated solid was filtered off, washed with water and dried on air to afford 1.10 g (86%) of the product as a white solid.

LC-MS (Method M12): $R_f$=0.56 min; m/z=269/271 (M+1)$^+$.

8-Bromo-N-[(4S)-3,4-dihydro-2H-chromen-4-yl]-4-oxo-1,4-dihydro-1,6-naphthyridine-3-carboxamide (T2-l-1)

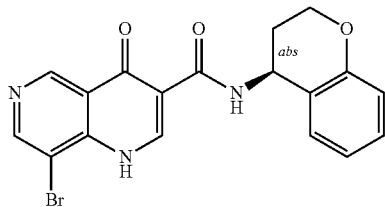 [SMILES: O=C(N[C@H]1CCOc2ccccc21)c1c[nH]c2c(Br)cncc2c1=O]

8-Bromo-4-oxo-1,4-dihydro-1,6-naphthyridine-3-carboxylic acid, 600 mg (2.2 mmol), (S)-chroman-4-amine, 400 mg (2.7 mmol), HATU, 1.27 g (3.3 mmol), N,N-diisopropylethylamine, 865 mg (6.7 mmol), were dissolved in 10 mL of N,N-dimethylformamide. The resulting mixture was stirred at room temperature for 2 hours. The reaction was quenched with saturated sodium chloride solution. The precipitation was collected by filtration, washed with water and dried in vacuo to give 650 mg (73%) of the product as a white solid.

LC-MS (Method M20): $R_f$=0.94 min; m/z=400/402 (M+1)$^+$.

8-(3,5-Dichlorophenyl)-N-[(4S)-3,4-dihydro-2H-chromen-4-yl]-4-oxo-1,4-dihydro-1,6-naphthyridine-3-carboxamide (T2-m-1)

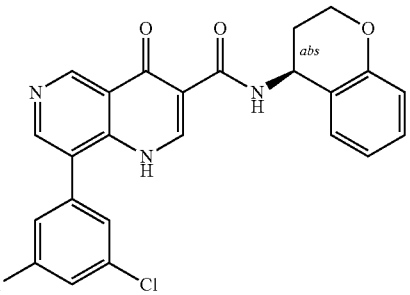

8-Bromo-N-[(4S)-3,4-dihydro-2H-chromen-4-yl]-4-oxo-1,4-dihydro-1,6-naphthyridine-3-carboxamide, 450 mg (1.1 mmol), 3,5-dichlorophenylboronic acid, 322 mg (1.7 mmol), tris(dibenzylideneacetone)dipalladium, 52 mg (0.06 mmol), tri-tert-butylphosphine tetrafluoroborate, 33 mg (0.1 mmol), and potassium fluoride, 196 mg (3.4 mmol), were dissolved in 8 mL of tetrahydrofuran and 2 mL of water. The mixture was stirred at 60° C. overnight. The solvent was removed in vacuo. After cooling to room temperature, water was added, the mixture was extracted with ethyl acetate and the combined organic phases were dried over anhydrous sodium sulfate. The solvent was removed in vacuo and the residue was purified with silica gel column chromatography (petroleum ether/ethyl acetate=20:1) to give 420 mg (40%) of the product as a yellow solid.

LC-MS (Method M29): $R_f$=3.21 min; m/z=466 (M+1)$^+$.
$^1$H-NMR (300 MHz, DMSO-d$_6$): δ [ppm]=2.04-2.09 (m, 1H), 2.20-2.27 (m, 1H), 4.15-4.20 (m, 1H), 4.29-4.34 (m, 1H), 5.24 (q, 1H), 6.82-6.93 (m, 2H), 7.18-7.26 (m, 2H), 7.70 (d, 2H), 7.84 (d, 1H), 8.64-8.68 (m, 2H), 9.39 (s, 1H), 10.10 (d, 1H), 11.98-11.99 (m, 1H).

8-(2,3-Dichlorophenyl)-N-[(4S)-3,4-dihydro-2H-chromen-4-yl]-4-oxo-1,4-dihydro-1,6-naphthyridine-3-carboxamide (T2-m-2)

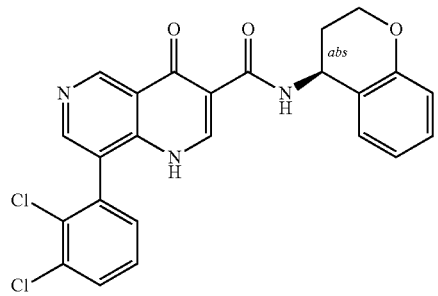 [SMILES: O=C(N[C@H]1CCOc2ccccc21)c1c[nH]c2c(-c3cccc(Cl)c3Cl)cncc2c1=O]

This compound was synthesized by the same method as described with T2-m-1 to give 460 mg (70%) of the product as a yellow solid.

LC-MS (Method M30): $R_f$=1.73 min; m/z=466 (M+1)$^+$.
$^1$H-NMR (300 MHz, DMSO-d$_6$): δ [ppm]=2.03-2.08 (m, 1H), 2.18-2.24 (m, 1H), 4.14-4.20 (m, 1H), 4.28-4.35 (m, 1H), 5.23 (q, 1H), 6.82-6.93 (m, 2H), 7.18-7.27 (m, 2H), 7.54-7.63 (m, 2H), 7.90 (d, 1H), 8.62-8.66 (m, 2H), 9.43 (s, 1H), 10.06 (d, 1H), 12.02 (br, 1H).

4-Chloro-8-(3,5-dichlorophenyl)-N-[(4S)-3,4-dihydro-2H-chromen-4-yl]-1,6-naphthyridine-3-carboxamide (T2-h-1)

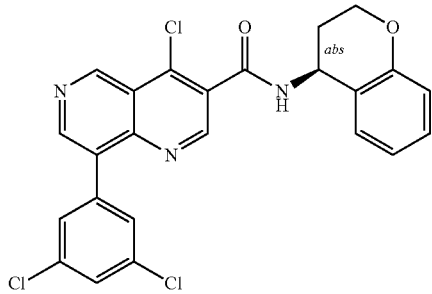 [SMILES: O=C(N[C@H]1CCOc2ccccc21)c1cnc2c(-c3cc(Cl)cc(Cl)c3)cncc2c1Cl]

8-(3,5-Dichlorophenyl)-N-[(4S)-3,4-dihydro-2H-chromen-4-yl]-4-oxo-1,4-dihydro-1,6-naphthyridine-3-carboxamide, 200 mg (0.4 mmol), N,N-diisopropylethylamine, 166 mg (1.29 mmol), were dissolved in 10 mL of toluene. The resulting mixture was stirred at 80° C. for 1 hour. After cooling to room temperature, phosphorus oxychloride, 329 mg (2.1 mmol), was added dropwise. The resulting mixture was stirred at room temperature for 10 min. The solvent was removed in vacuo to give 200 mg (crude) of the product as brown oil which was used without further purification in the next step.

LC-MS (Method M2): $R_t$=2.71 min; m/z=484 (M+1)$^+$.

4-Chloro-8-(2,3-dichlorophenyl)-N-[(4S)-3,4-dihydro-2H-chromen-4-yl]-1,6-naphthyridine-3-carboxamide (T2-h-2)

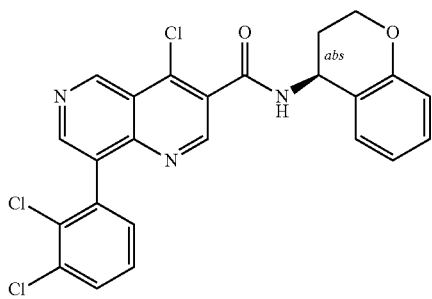 [SMILES: O=C(N[C@H]1CCOc2ccccc21)c1cnc2c(-c3cccc(Cl)c3Cl)cncc2c1Cl]

This compound was synthesized by the same method as described with T2-h-1 to give 300 mg (crude) of the product as orange oil which was used without further purification in the next step.

LC-MS (Method M20): $R_t$=1.17 min; m/z=484 (M+1)$^+$.

Examples (T²)

Example T2-1

8-(3,5-Dichlorophenyl)-N-[(4S)-3,4-dihydro-2H-chromen-4-yl]-4-(dimethylamino)-1,6-naphthyridine-3-carboxamide

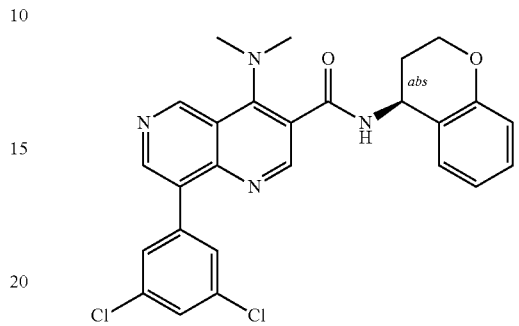

(4-Chloro-8-(3,5-dichlorophenyl)-N-[(4S)-3,4-dihydro-2H-chromen-4-yl]-1,6-naphthyridine-3-carboxamide, 100 mg (0.2 mmol), was dissolved in 5 mL of tetrahydrofuran. Dimethylamine, 1.0 mL (2M in tetrahydrofuran, 2.1 mmol), was added. The resulting mixture was stirred at room temperature for 1 hour. The solvent was removed in vacuo. Water was added, the mixture was extracted with ethyl acetate and the combined organic phases were dried over anhydrous sodium sulfate. The solvent was removed in vacuo. The residue was purified by preparative HPLC to give 8.8 mg (8.1%) of the product as a yellow solid.

LC-MS (Method M29): $R_t$=2.62 min; m/z=493 (M+1)$^+$.
$^1$H-NMR (400 MHz, DMSO-d$_6$): δ [ppm]=2.02-2.07 (m, 1H), 2.19-2.22 (m, 1H), 3.20 (s, 6H), 4.21-4.28 (m, 2H), 5.24 (q, 1H), 6.80 (d, 1H), 6.93 (t, 1H), 7.17 (t, 1H), 7.37 (d, 1H), 7.68 (d, 1H), 7.37 (d, 2H), 8.73 (d, 2H), 9.13 (d, 1H), 9.54 (s, 1H).

Example T2-2

8-(2,3-Dichlorophenyl)-N-[(4S)-3,4-dihydro-2H-chromen-4-yl]-4-(dimethylamino)-1,6-naphthyridine-3-carboxamide

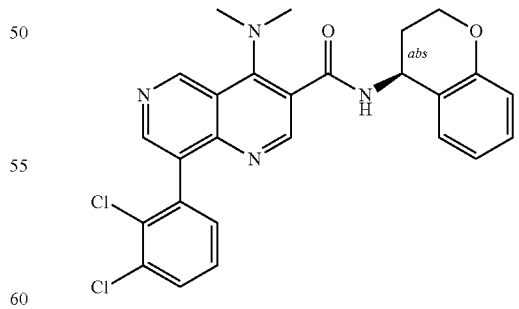

This compound was synthesized by the same method as described in example T2-1 to give 19.4 mg (12%) of the product as a yellow solid LC-MS (Method M14): $R_t$=1.30 min; m/z=493 (M+1)$^+$.
$^1$H-NMR (400 MHz, DMSO-d$_6$): δ [ppm]=2.02-2.05 (m, 1H), 2.16-2.23 (m, 1H), 3.42 (s, 6H), 4.15-4.30 (m, 2H), 5.19 (q, 1H), 6.80 (d, 1H), 6.90 (t, 1H), 7.18 (t, 1H), 7.33 (d, 1H), 7.47-7.56 (m, 2H), 7.83 (d, 1H), 8.49 (s, 1H), 8.68 (s, 1H), 9.23 (s, 1H), 9.65 (s, 1H).

Example T2-3

8-(2,3-Dichlorophenyl)-N-[(4S)-3,4-dihydro-2H-chromen-4-yl]-4-(morpholin-4-yl)-1,6-naphthyridine-3-carboxamide

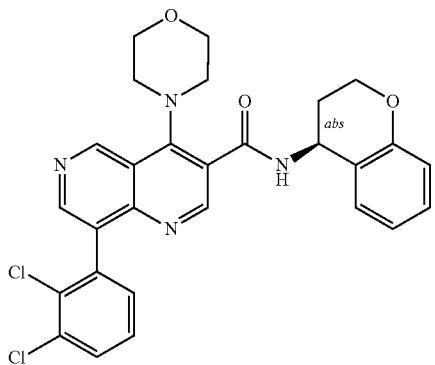

4-Chloro-8-(2,3-dichlorophenyl)-N-[(4S)-3,4-dihydro-2H-chromen-4-yl]-1,6-naphthyridine-3-carboxamide, 250 mg (crude), was dissolved in 5 mL of tetrahydrofuran. Morpholine, 450 mg (5.2 mmol), was added. The resulting mixture was stirred at room temperature for 1 hour. The solvent was removed in vacuo. Water was added, the mixture was extracted with ethyl acetate and the combined organic phases were dried over anhydrous sodium sulfate. The solvent was removed in vacuo. The residue was purified by preparative HPLC to give 86.8 mg (31%) of the product as a white solid.

LC-MS (Method M33): $R_t$=3.34 min; m/z=535 (M+1)$^+$.

$^1$H-NMR (400 MHz, DMSO-d$_6$): δ [ppm]=2.03-2.07 (m, 1H), 2.19-2.23 (m, 1H), 3.40-3.44 (m, 4H), 3.90-3.92 (m, 4H), 4.20-4.30 (m, 2H), 5.23 (q, 1H), 6.79 (d, 1H), 6.91 (t, 1H), 7.17 (t, 1H), 7.35-7.50 (m, 3H), 7.77 (d, 1H), 8.65 (s, 1H), 8.75 (s, 1H), 9.22 (d, 1H), 9.58 (s, 1H).

Example T2-4

8-(3,5-Dichlorophenyl)-N-[(4S)-3,4-dihydro-2H-chromen-4-yl]-4-(morpholin-4-yl)-1,6-naphthyridine-3-carboxamide

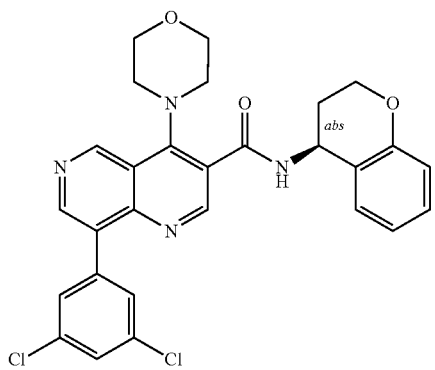

This compound was synthesized by the same method as described in example T2-3 to give 14.1 mg (12%) of the product as a white solid.

LC-MS (Method M29): $R_t$=1.77 min; m/z=535 (M+1)$^+$.

$^1$H-NMR (300 MHz, DMSO-d$_6$): δ [ppm]=2.04-2.28 (m, 2H), 3.39-3.40 (m, 4H), 3.89-3.92 (m, 4H), 4.22-4.26 (m, 2H), 5.24 (q, 1H), 6.81 (d, 1H), 6.94 (t, 1H), 7.18 (t, 1H), 7.39 (d, 1H), 7.70-7.75 (m, 3H), 8.81 (s, 1H), 8.86 (s, 1H), 9.24 (d, 1H), 9.54 (s, 1H).

Intermediates (T$^3$)

4-(3,5-Dichlorophenyl)pyridin-3-amine (T3-b-1)

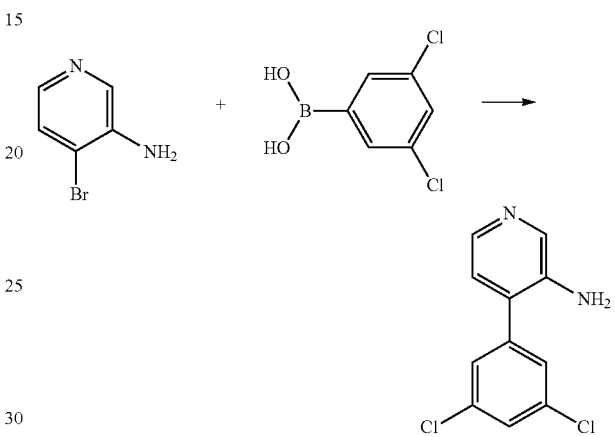

4-Bromopyridin-3-amine, 2.00 g (11.6 mmol), 3,5-dichlorophenylboronic acid, 3.30 g (17.3 mmol), tris(dibenzylideneacetone)dipalladium, 265 mg (0.3 mmol), tri-tert-butylphosphine tetrafluoroborate, 168 mg (0.6 mmol), and potassium fluoride, 2.00 g (34.7 mmol), were dissolved in 16 mL of tetrahydrofuran and 4 mL of water. The mixture was stirred at 60° C. overnight. The solvent was removed in vacuo. Water was added, the mixture was extracted with ethyl acetate and the combined organic phases were dried over anhydrous sodium sulfate. The solvent was removed in vacuo and the residue was purified by silica gel column chromatography (dichloromethane/methanol=20:1) to give 2.96 g (91%) of the product as a yellow solid.

LC-MS (Method M16): $R_t$=0.74 min; m/z=239 (M+1)$^+$.

4-(2,3-Dichlorophenyl)pyridin-3-amine (T3-b-2)

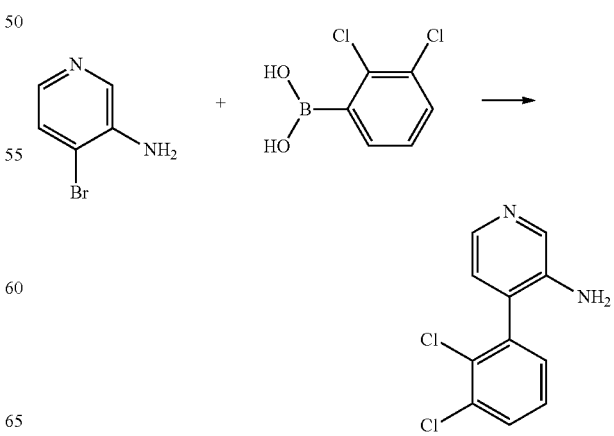

This compound was synthesized by the same method as described in example T3-b-1 to give 2.36 g (79%) of the product as a yellow solid.

LC-MS (Method M3): $R_t$=0.68 min; m/z=239 (M+1)$^+$.

Diethyl ({[4-(3,5-dichlorophenyl)pyridin-3-yl]amino}methylene)malonate (T3-d-1)

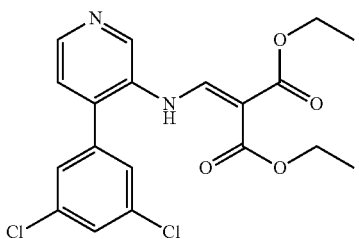 [SMILES: CCOC(=O)C(=CNc1cnccc1-c1cc(Cl)cc(Cl)c1)C(=O)OCC]

4-(3,5-Dichlorophenyl)pyridin-3-amine, 2.96 g (12.4 mmol) and diethyl 2-(ethoxymethylene)malonate, 8.02 g (37.1 mmol), were dissolved in 30 mL of toluene. The resulting mixture was stirred at 110° C. overnight. The solvent was removed in vacuo and the residue was purified by silica gel column chromatography (petroleum ether/ethyl acetate=1:2) to give 3.90 g (63%) of the product as a white solid.

LC-MS (Method M16): $R_t$=1.30 min; m/z=409 (M+1)$^+$.

Diethyl ({[4-(2,3-dichlorophenyl)pyridin-3-yl]amino}methylene)malonate (T3-d-2)

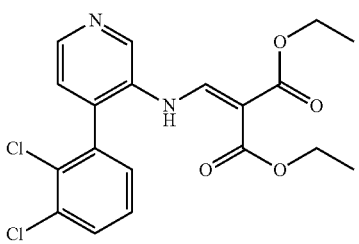

This compound was synthesized by the same method as described in example T3-d-1 to give 3.0 g (67%) of the product as a white solid.

LC-MS (Method M3): $R_t$=1.24 min; m/z=409 (M+1)$^+$.

Ethyl 8-(3,5-dichlorophenyl)-4-oxo-1,4-dihydro-1,5-naphthyridine-3-carboxylate (T3-e-1)

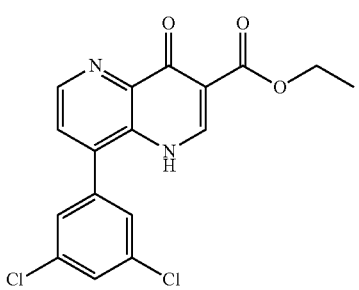 [SMILES: CCOC(=O)c1c[nH]c2c(-c3cc(Cl)cc(Cl)c3)ccnc2c1=O]

100 mL of diphenyl ether were placed into a three-necked flask, diethyl diethyl ({[4-(3,5-dichlorophenyl)pyridin-3-yl]amino}methylene)malonate, 3.90 g (9.5 mmol), dissolved in 50 mL of diphenyl ether, was added at reflux. The resulting mixture was stirred at reflux for 5 min. After cooling to room temperature, the reaction mixture was washed five times with 4N hydrogen chloride solution. The aqueous phase was lyophilized and then purified with C18 reversed phase column chromatography (acetonitrile/water=2:3) to give 300 mg (9%) of the product as a yellow solid.

LC-MS (Method M17): $R_t$=0.83 min; m/z=363 (M+1)$^+$.

Ethyl 8-(2,3-dichlorophenyl)-4-oxo-1,4-dihydro-1,5-naphthyridine-3-carboxylate (T3-e-2)

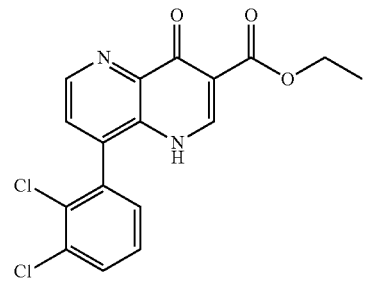 [SMILES: CCOC(=O)c1c[nH]c2c(-c3cccc(Cl)c3Cl)ccnc2c1=O]

This compound was synthesized by the same method as described in example T3-e-1 to give 300 mg (11%) of the product as a yellow solid.

LC-MS (Method M5): $R_t$=0.98 min; m/z=363 (M+1)$^+$.

8-(3,5-Dichlorophenyl)-4-oxo-1,4-dihydro-1,5-naphthyridine-3-carboxylic acid (T3-f-1)

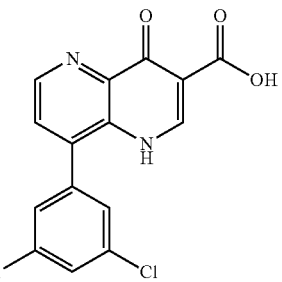

Ethyl 8-(3,5-dichlorophenyl)-4-oxo-1,4-dihydro-1,5-naphthyridine-3-carboxylate, 270 mg (0.7 mmol), was dissolved in 8.0 mL of tetrahydrofuran and 2.0 mL of water. Lithium hydroxide, 312 mg (7.4 mmol), was added at room temperature. The resulting mixture was stirred at 60° C. overnight. After cooling to room temperature, the solvent was removed in vacuo. Water was added, the mixture was extracted with ethyl acetate. The pH of the water phase was adjusted to 7 with 2N hydrogen chloride solution. The precipitate solid was filtered off, washed with water and dried in vacuo to give 180 mg (73%) of the product as a yellow solid.

LC-MS (Method M25): $R_t$=0.89 min; m/z=335 (M+1)$^+$.

8-(2,3-Dichlorophenyl)-4-oxo-1,4-dihydro-1,5-naphthyridine-3-carboxylic acid (T3-f-2)

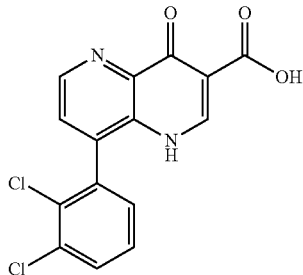 [SMILES: O=C(O)c1c[nH]c2c(-c3cccc(Cl)c3Cl)ccnc2c1=O]

This compound was synthesized by the same method as described in example 1 (step 4) to give 200 mg (69%) of the product as a yellow solid.

LC-MS (Method M4): $R_t$=0.81 min; m/z=335 (M+1)$^+$.

4-Chloro-8-(3,5-dichlorophenyl)-1,5-naphthyridine-3-carbonyl chloride (T3-g-1)

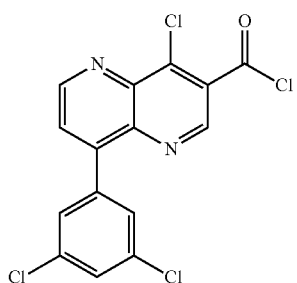 [SMILES: O=C(Cl)c1cnc2c(-c3cc(Cl)cc(Cl)c3)ccnc2c1Cl]

8-(3,5-Dichlorophenyl)-4-oxo-1,4-dihydro-1,5-naphthyridine-3-carboxylic acid, 160 mg (0.5 mmol), was dissolved in 5 mL of toluene. N,N-Diisopropylethylamine, 185 mg (1.4 mmol), was added at room temperature. The resulting mixture was stirred at 60° C. for 1 hour. Phosphorus oxychloride, 366 mg (2.4 mmol), was added at 60° C. The resulting mixture was stirred at 60° C. for 30 min. The solvent was removed in vacuo to give 160 mg (crude) of the product as a brown oil. The residue was used directly in the next step without any purification.

4-Chloro-8-(2,3-dichlorophenyl)-1,5-naphthyridine-3-carbonyl chloride (T3-g-2)

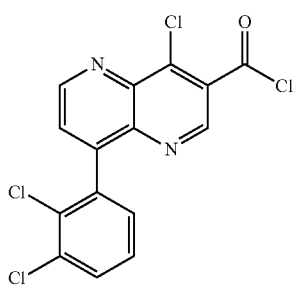 [SMILES: O=C(Cl)c1cnc2c(-c3cccc(Cl)c3Cl)ccnc2c1Cl]

This compound was synthesized by the same method as described in example T3-g-1 to give 200 mg (crude) of the product as a brown oil. The residue was used directly to the next step without further purification.

4-Chloro-8-(3,5-dichlorophenyl)-N-[(4S)-3,4-dihydro-2H-chromen-4-yl]-1,5-naphthyridine-3-carboxamide (T3-h-1)

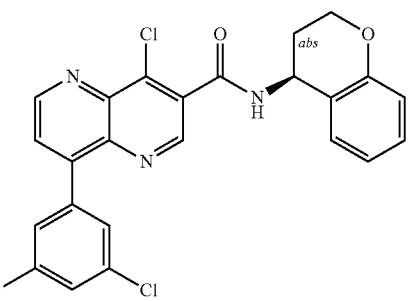

4-Chloro-8-(3,5-dichlorophenyl)-1,5-naphthyridine-3-carbonyl chloride, 160 mg (0.4 mmol) and (S)-chroman-4-amine, 77 mg (0.5 mmol), were dissolved in 5 mL of dichloromethane. Triethylamine, 218 mg (2.2 mmol), was added at room temperature. The resulting mixture was stirred at room temperature for 30 min. The solvent was removed in vacuo to give 160 mg (crude) of the product as a brown oil.

LC-MS (Method M17): $R_t$=1.29 min; m/z=484 (M+1)$^+$.

4-Chloro-8-(2,3-dichlorophenyl)-N-[(4S)-3,4-dihydro-2H-chromen-4-yl]-1,5-naphthyridine-3-carboxamide (T3-h-2)

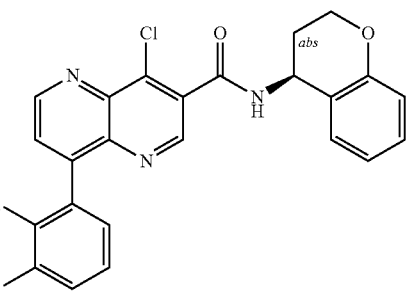

This compound was synthesized by the same method as described in example T3-h-1 to give 200 mg (crude) of the product as a brown oil.

LC-MS (Method M27): $R_t$=1.29 min; m/z=484 (M+1)$^+$.

Examples (T³)

Example T3-1

8-(3,5-Dichlorophenyl)-N-[(4S)-3,4-dihydro-2H-chromen-4-yl]-4-(dimethylamino)-1,5-naphthyridine-3-carboxamide

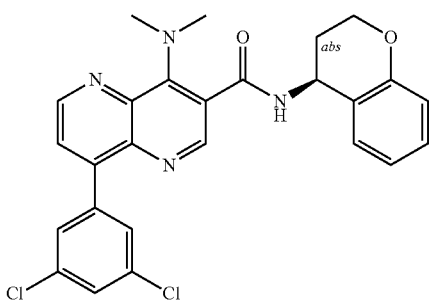 [SMILES: CN(C)c1c(C(=O)N[C@H]2CCOc3ccccc32)cnc2c(-c3cc(Cl)cc(Cl)c3)ccnc12]

4-Chloro-8-(2,3-dichlorophenyl)-N-[(4S)-3,4-dihydro-2H-chromen-4-yl]-1,5-naphthyridine-3-carboxamide (T3-h-2) 80 mg (crude), was dissolved in 10 mL of tetrahydrofuran at room temperature. Dimethylamine, 1.7 mL (1 M in tetrahydrofuran, 1.7 mmol), was added at room temperature. The resulting mixture was stirred for 2 hours at room temperature. The solvent was removed in vacuo. Water was added, the resulting mixture was extracted with ethyl acetate and the combined organic phases were dried over anhydrous sodium sulfate. The solvent was removed in vacuo and the residue was purified by preparative HPLC to give 12 mg (14.5%) of the product as a light yellow solid.

LC-MS (Method M26): $R_t$=1.99 min; m/z=493 (M+1)⁺.
¹H-NMR (300 MHz, DMSO-$d_6$): δ [ppm]=2.02-2.08 (m, 1H), 2.15-2.20 (m, 1H), 3.31 (s, 6H), 4.23-4.26 (m, 2H), 5.23 (q, 1H), 6.79 (d, 1H), 6.92 (t, 1H), 7.16 (t, 1H), 7.33 (d, 1H), 7.73-7.77 (m, 4H), 8.57 (s, 1H), 8.89 (d, 1H), 9.09 (d, 1H).

Example T3-2

8-(3,5-Dichlorophenyl)-N-[(4S)-3,4-dihydro-2H-chromen-4-yl]-4-(morpholin-4-yl)-1,5-naphthyridine-3-carboxamide

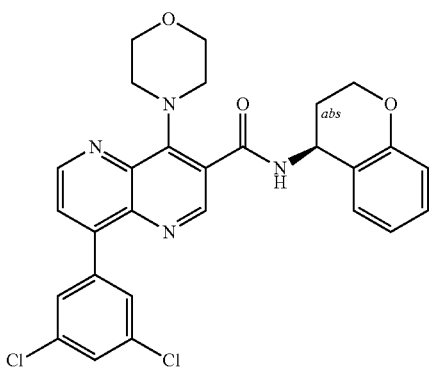 [SMILES: O=C(N[C@H]1CCOc2ccccc21)c1cnc2c(-c3cc(Cl)cc(Cl)c3)ccnc2c1N1CCOCC1]

This compound was synthesized by the same method as described in the example T3-1 to give 8.4 mg (9%) of the product as a light yellow solid.

LC-MS (Method M24): $R_t$=1.46 min; m/z=535 (M+1)⁺.
¹H-NMR (300 MHz, DMSO-$d_6$): δ [ppm]=2.05-2.21 (m, 2H), 3.63-3.65 (m, 4H), 3.82-3.84 (m, 4H), 4.23-4.29 (m, 2H), 5.25 (q, 1H), 6.79 (d, 1H), 6.92 (t, 1H), 7.17 (t, 1H), 7.37 (d, 1H), 7.45-7.48 (m, 3H), 7.81 (d, 1H), 8.68 (s, 1H), 8.94 (d, 1H), 9.17 (d, 1H).

Example T3-3

8-(2,3-Dichlorophenyl)-N-[(4S)-3,4-dihydro-2H-chromen-4-yl]-4-(dimethylamino)-1,5-naphthyridine-3-carboxamide

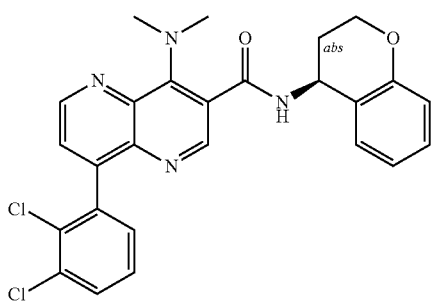 [SMILES: CN(C)c1c(C(=O)N[C@H]2CCOc3ccccc32)cnc2c(-c3cccc(Cl)c3Cl)ccnc12]

This compound was synthesized by the same method as described in example T3-1 to give 20.0 mg (20%) of the product as a light yellow solid.

LC-MS (Method M28): $R_t$=1.23 min; m/z=493 (M+1)⁺.
¹H-NMR (300 MHz, DMSO-$d_6$): δ [ppm]=1.99-2.05 (m, 1H), 2.15-2.22 (m, 1H), 3.31 (s, 6H), 4.23-4.27 (m, 2H), 5.23 (q, 1H), 6.79 (d, 1H), 6.90 (t, 1H), 7.16 (t, 1H), 7.31-7.37 (m, 2H), 7.47 (t, 1H), 7.64 (d, 1H), 7.74 (d, 1H), 8.46 (s, 1H), 8.92 (d, 1H), 9.05 (d, 1H).

Example T3-4

8-(2,3-Dichlorophenyl)-N-[(4S)-3,4-dihydro-2H-chromen-4-yl]-4-(morpholin-4-yl)-1,5-naphthyridine-3-carboxamide

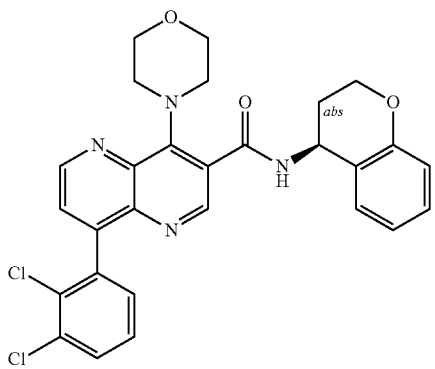 [SMILES: O=C(N[C@H]1CCOc2ccccc21)c1cnc2c(-c3cccc(Cl)c3Cl)ccnc2c1N1CCOCC1]

This compound was synthesized by the same method as described in the example T3-1 to give 17.8 mg (16%) of the product as a light yellow solid.

LC-MS (Method M28): $R_t$=1.52 min; m/z=535 (M+1)⁺.
¹H-NMR (300 MHz, DMSO-$d_6$): δ [ppm]=2.06-2.07 (m, 1H), 2.17-2.22 (m, 1H), 3.64-3.66 (m, 4H), 3.82-3.83 (m, 4H), 4.23-4.28 (m, 2H), 5.24 (q, 1H), 6.79 (d, 1H), 6.91 (t, 1H), 7.16 (t, 1H), 7.33-7.38 (m, 2H), 7.49 (t, 1H), 7.68 (d, 1H), 7.76 (d, 1H), 8.57 (s, 1H), 8.97 (d, 1H), 9.15 (d, 1H).

Intermediates (T⁴)

4-Chloro-6-(3,5-dichlorophenyl)pyrimidin-5-amine (T4-b-1)

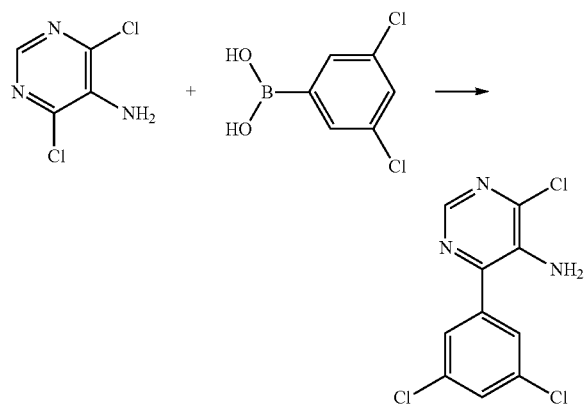

To a stirred solution of 4,6-dichloropyrimidin-5-amine (12.5 g, 76.2 mmol) and (3,5-dichlorophenyl)boronic acid (11.28 g, 59 mmol) in dioxane (275 mL) was added a 2 M aqueous potassium carbonate solution (120 mL, 250 mmol) and (2.75 g, 2.38 mmol) tetrakis(triphenyl-phosphine)palladium(0). The mixture was purged with argon and heated to 90° C. for 14 hours. After cooling to ambient temperature and evaporation of solvents the remaining material was dissolved in dichloromethane (500 mL), washed with brine (250 mL), dried over sodium sulfate and reduced in vacuo again. The remaining solid was triturated in dichloromethane, filtered off and washed with petrol ether and air-dried to afford 4.26 g of the title compound as solid. Further amounts can be obtained from the mother liquor after evaporation of solvents and flash chromatography to afford another 1.46 g of the title compound.

¹H NMR (400 MHz, CD₃CN) NMR Peaklist:
δ=8.6084 (0.4); 8.3369 (10.5); 7.7350 (0.8); 7.7303 (0.9); 7.6528 (13.7); 7.6481 (16.0); 7.5954 (4.8); 7.5907 (7.6); 7.5861 (4.0); 5.4476 (1.2); 4.8312 (2.8); 3.6002 (0.6); 2.1641 (110.8); 2.1139 (0.4); 2.1077 (0.4); 1.9644 (1.8); 1.9581 (3.5); 1.9581 (3.5); 1.9526 (22.8); 1.9464 (42.4); 1.9403 (58.5); 1.9341 (40.9); 1.9280 (21.2); 1.7687 (0.3); 0.1460 (0.7); 0.0078 (7.0); −0.0003 (143.1); −0.1497 (0.7)

Methyl 5-amino-6-(3,5-dichlorophenyl)pyrimidine-4-carboxylate (T4-c-1)

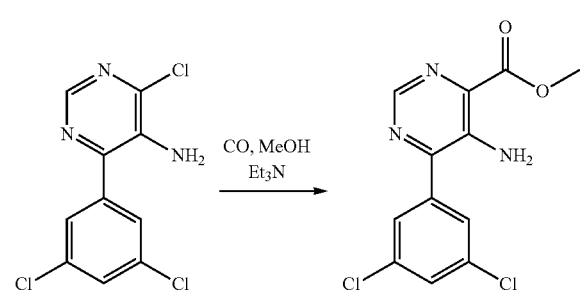 [SMILES: Nc1c(Cl)ncnc1-c1cc(Cl)cc(Cl)c1 ; COC(=O)c1ncnc(-c2cc(Cl)cc(Cl)c2)c1N]

An autoclave was charged with 4-chloro-6-(3,5-dichlorophenyl)pyrimidin-5-amine (5.72 g, 20.8 mmol), methanol (280 mL) and triethylamine (4.46 g, 44 mmol). It was then purged with argon, followed by addition of [1,1'-bis(diphenylphosphino)ferrocene]dichloropalladium(II) (1.53 g, 2.09 mmol). The autoclave atmosphere was purged twice with 10 bar carbon monoxide and stirred under 5 bar pressure of carbon monoxide at 50° C. for 18 hours. The autoclave was allowed to cool to ambient temperature, the pressure was released and the reaction mixture was evaporated in vacuo. The remaining material was purified by flash chromatography (silica gel cartridge 12 g, gradient of ethyl acetate in cyclohexane—5%-95% v/v). 3.93 g of the title compound were obtained.

¹H NMR (400 MHz, CD₃CN) NMR Peaklist:
δ=8.5682 (4.4); 7.6344 (3.7); 7.6298 (7.1); 7.6207 (2.7); 7.6167 (2.2); 7.6114 (0.9); 6.1151 (0.9); 3.9277 (16.0); 2.4658 (0.4); 2.1813 (92.7); 1.9718 (0.4); 1.9647 (1.1); 1.9585 (2.2); 1.9528 (15.0); 1.9467 (27.8); 1.9405 (38.4); 1.9343 (26.2); 1.9281 (13.4); 0.1461 (0.5); 0.0079 (5.1); −0.0002 (102.0); −0.0086 (4.1); −0.1496 (0.5)

Methyl 4-(3,5-dichlorophenyl)-8-oxo-5,8-dihydropyrido[3,2-d]pyrimidine-7-carboxylate (T4-e-1)

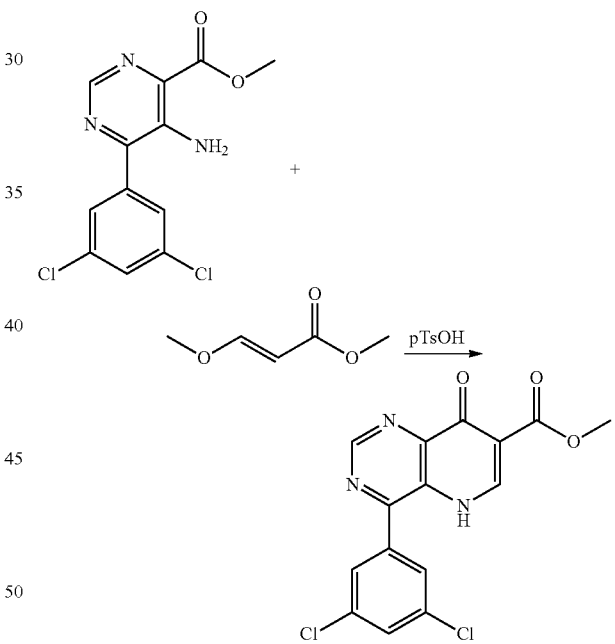

A mixture of methyl 5-amino-6-(3,5-dichlorophenyl)pyrimidine-4-carboxylate (1 g, 3.29 mmol) and p-toluene sulfonic acid hydrate (81.3 mg, 0.42 mmol) in xylene (80 mL) was prepared and 40 mL xylene allowed to distill off under argon. Methyl (2E)-3-methoxyacrylate (572 mg, 4.9 mmol) was added and further 20 mL solvent were allowed to distill off. The remaining mixture was heated to reflux for 2 hours. Xylene (40 mL) and methyl (2E)-3-methoxyacrylate (572 mg, 4.9 mmol) were added and 40 mL of solvents were distilled off within 1 hour. The addition of xylene and methyl (2E)-3-methoxyacrylate, followed by distillation of the solvent was repeated once again. Then, the reaction mixture was kept at ambient temperature overnight and treated with 1M potassium t-butylate (5 mL, 5 mmol in tetrahydrofurane) and stirred at 80° C. for 3 hours. The reaction mixture was cooled to ambient temperature und neutralized with glacial acetic acid and evaporated in vacuo. The remaining solid was triturated in glacial acetic acid and filtered off. The solid was washed with acetic acid, followed by water and dried in an desiccator over sulfuric acid to afford 528 mg of the title compound.

¹H NMR (400 MHz, DMSO-d6) NMR Peaklist:

δ=12.1844 (0.4); 12.1612 (0.4); 12.1560 (0.4); 12.1378 (0.4); 12.1283 (0.4); 12.1003 (0.4); 12.0909 (0.5); 12.0611 (0.4); 12.0376 (0.4); 12.0210 (0.3); 9.2667 (4.6); 8.5652 (4.0); 8.4972 (0.4); 8.0140 (8.5); 7.8870 (5.1); 4.0136 (0.4); 3.9796 (0.4); 3.7912 (16.0); 3.7025 (0.7); 3.6821 (0.6); 3.6748 (0.5); 3.6349 (0.5); 3.6071 (0.6); 3.5829 (0.5); 3.5598 (0.6); 3.5418 (0.6); 3.5368 (0.6); 3.4934 (0.8); 3.3240 (10.1); 3.2140 (1.3); 3.1102 (0.5); 3.0507 (0.4); 3.0424 (0.4); 2.9703 (0.4); 2.9348 (0.4); 2.8559 (0.6); 2.8507 (0.5); 2.8363 (0.6); 2.8280 (0.6); 2.7080 (1.4); 2.6730 (2.6); 2.6688 (2.7); 2.5022 (168.9); 2.3323 (2.3); 2.2539 (1.7); 2.1681 (0.4); 2.1523 (0.4); 1.9857 (0.4); 0.1400 (0.5); 0.1290 (0.5); 0.1005 (0.7); −0.0004 (30.3)

4-(3,5-Dichlorophenyl)-8-oxo-5,8-dihydropyrido[3,2-d]pyrimidine-7-carboxylic acid (T4-f-1)

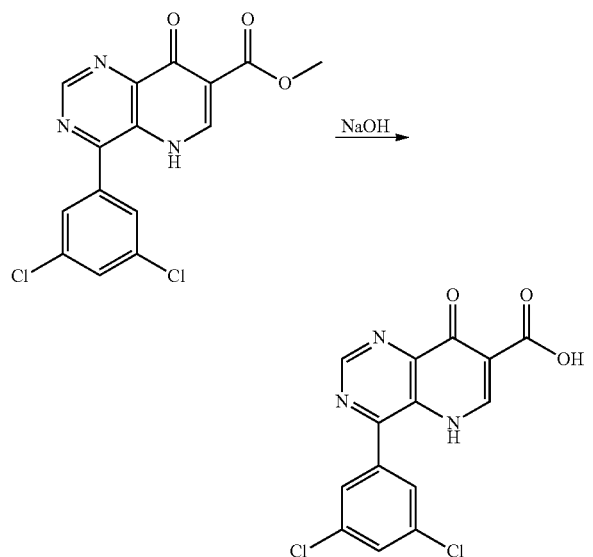

(250 mg, 0.71 mmol) Methyl 4-(3,5-dichlorophenyl)-8-oxo-5,8-dihydropyrido[3,2-d]pyrimidine-7-carboxylate and sodium hydroxide (102 mg, 2.55 mmol) in water (15 mL) were refluxed for 22 hours. The reaction mixture was cooled and the suspension filtered by suction. The filter residue was washed with a small amount of water. The combined filtrates were acidified with acetic acid, and the product precipitated after the addition of some ethyl acetate. The solids were filtered off, washed with ethyl acetate and water and dried in a dessicator over sulfuric acid to afford 125 mg of the title compound.

¹H NMR (400 MHz, DMSO-d6) NMR Peaklist:

δ=9.4552 (0.8); 9.4143 (9.9); 8.7817 (0.5); 8.7307 (9.6); 8.3910 (0.5); 8.3158 (0.4); 8.0823 (0.4); 7.9650 (16.0); 7.9448 (12.1); 7.8925 (0.4); 7.8871 (0.3); 4.7406 (0.3); 4.6683 (0.4); 4.6475 (0.4); 4.6429 (0.3); 4.6323 (0.4); 4.6242 (0.4); 4.6074 (0.3); 4.5946 (0.4); 4.5679 (0.4); 4.5355 (0.4); 4.5192 (0.4); 4.5058 (0.4); 4.5040 (0.4); 4.4750 (0.4); 4.4600 (0.5); 4.4393 (0.4); 4.420393 (0.4); 4.4208 (0.4); 4.3917 (0.6); 4.3818 (0.6); 4.3478 (0.6); 4.3289 (0.6); 4.3186 (0.6); 4.3055 (0.5); 4.2824 (0.6); 4.2673 (0.6); 4.2346 (0.7); 4.2035 (0.8); 4.2006 (0.7); 4.1870 (0.7); 4.1702 (0.7); 4.1397 (0.8); 4.1162 (0.8); 4.1023 (0.9); 4.0929 (0.9); 4.0826 (0.9); 4.0736 (0.9); 4.0642 (1.0); 4.0495 (1.0); 4.0426 (1.0); 3.9996 (1.1); 3.9954 (1.1); 3.9814 (1.2); 3.9695 (1.2); 3.9196 (1.4); 3.9107 (1.5); 3.8791 (1.6); 3.8665 (1.7); 3.8264 (2.0); 3.8158 (2.0); 3.8050 (2.2); 3.7605 (2.6); 3.5606 (5.6); 3.5545 (5.7); 3.5344 (5.9); 3.5057 (5.9); 3.4894 (5.8); 3.3851 (4.3); 3.3242 (3.2); 3.2824 (2.7); 3.2439 (2.3); 3.2274 (2.1); 3.2134 (2.0); 3.2077 (1.9); 3.1987 (1.9); 3.1939 (1.8); 3.1667 (1.7); 3.1225 (1.4); 3.1196 (1.4); 3.1115 (1.5); 3.0976 (1.4); 2.9984 (1.2); 2.9819 (1.2); 2.9617 (1.1); 2.9556 (1.1); 2.9335 (1.2); 2.9178 (1.1); 2.9005 (1.2); 2.8700 (1.2); 2.8653 (1.2); 2.8599 (1.2); 2.8424 (1.3); 2.8019 (1.3); 2.7898 (1.3); 2.7362 (1.7); 2.6709 (6.0); 2.6432 (3.4); 2.5015 (616.2); 2.3276 (4.2); 2.2651 (0.5); 2.2588 (0.5); 2.2501 (0.4); 2.2079 (0.3); 1.9082 (2.2); 1.3579 (0.3); 1.3411 (0.3); 1.3264 (0.3); 1.3037 (0.4); 1.2823 (0.5); 1.2747 (0.6); 1.2353 (3.2); 1.2025 (0.7); 1.1808 (0.4); 1.1737 (0.4); 1.1509 (0.3); 1.1232 (0.4); 1.1116 (0.4); 1.0978 (0.4); 1.0773 (0.4); 0.9278 (0.3); 0.8832 (0.4); 0.8491 (0.6); 0.8357 (0.6); 0.8260 (0.5); −0.0004 (8.0)

8-Chloro-4-(3,5-dichlorophenyl)pyrido[3,2-d]pyrimidine-7-carbonyl chloride (T4-g-1)

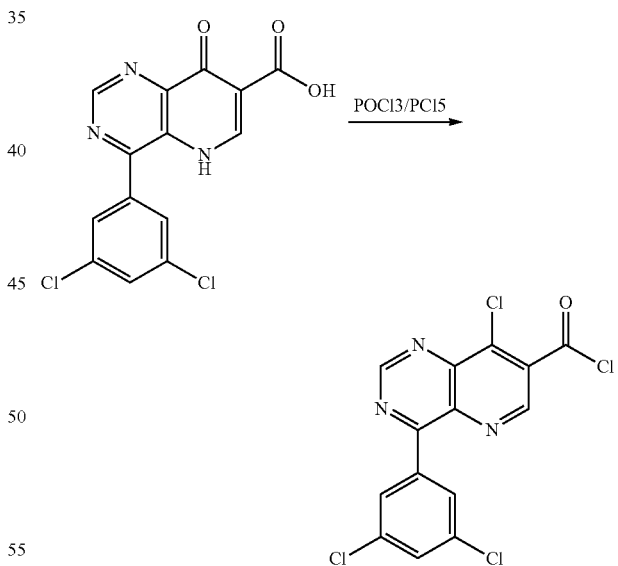

A stirred mixture of 4-(3,5-dichlorophenyl)-8-oxo-5,8-dihydropyrido[3,2-d]pyrimidine-7-carboxylic acid (105 mg, 0.312 mmol) and phosphorus oxychloride (291 μL, 3.12 mmol) was heated to reflux fo 1 hour, and phosphorus pentachloride (260 mg, 1.25 mmol) was subsequently added. The mixture was heated to reflux further 2.5 hours, then reduced in vacuo. Toluene (1 mL) was added and the mixture was reduced in vacuo again to afford 116 mg of the title compound. The material was used as such in the subsequent step.

8-Chloro-4-(3,5-dichlorophenyl)-N-[(4S)-3,4-di-hydro-2H-chromen-4-yl]pyrido[3,2-d]pyrimidine-7-carboxamide (T4-h-1)

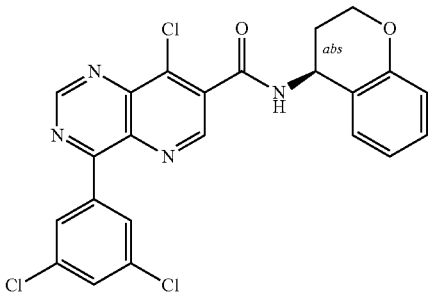 [SMILES: O=C(N[C@H]1CCOc2ccccc21)c1cnc2c(-c3cc(Cl)cc(Cl)c3)ncnc2c1Cl]

A solution of 8-chloro-4-(3,5-dichlorophenyl)pyrido[3,2-d]pyrimidine-7-carbonyl chloride (116 mg, 0.31 mmol) in chloroform (10 mL) was cooled to −5° C. Subsequently, a solution of (S)-chroman-4-amine hydrochloride (58 mg, 0.31 mmol) and triethylamine (87 µL, 0.62 mmol) in chloroform (2 mL) was added dropwise. The mixture was stirred for further 60 minutes at −5° C., then diluted with a further volume of chloroform. The organic layer was washed with 5% aqueous monosodium phosphate followed by a wash with brine. The organic layer was separated, dried over sodium sulfate and reduced in vacuo to afford 120 mg of the title compound. The material was used as such in the subsequent step.

Examples (T⁴)

Example T4-1

4-(3,5-Dichlorophenyl)-N-[(4S)-3,4-dihydro-2H-chromen-4-yl]-8-(dimethylamino)-pyrido[3,2-d]pyrimidine-7-carboxamide

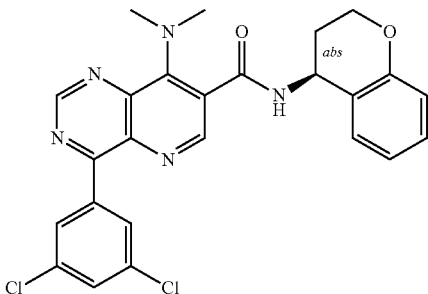 [SMILES: CN(C)c1c(C(=O)N[C@H]2CCOc3ccccc32)cnc2c(-c3cc(Cl)cc(Cl)c3)ncnc12]

To a stirred solution of 8-chloro-4-(3,5-dichlorophenyl)-N-[(4S)-3,4-dihydro-2H-chromen-4-yl]pyrido[3,2-d]pyrimidine-7-carboxamide (71 mg, 0.14 mmol) in tetrahydrofuran (20 mL) were added trimethylamine (61 µL, 0.437 mmol) at 0° C. and dropwise a 2M dimethylamine solution in tetrahydrofurane (219 µL, 0.437 mmol). The reaction mixture was allowed to warm to ambient temperature for 1.5 hours and diluted with dichloromethane. The mixture was washed with 5% aqueous monosodium phosphate followed by a wash with brine. The separated organic layer was dried over sodium sulfate and the solvents removed in vacuo. The remaining residue was purified by flash chromatography (silica gel cartridge 15 g, gradient of ethyl acetate in cyclohexane—10%-30% v/v), and 60.9 mg of the title compound were obtained.

LC-MS (Method L1): $R_t$=1.58 min; m/z=494 (M+1)⁺.

¹H NMR (400 MHz, CD₃CN) NMR Peaklist:

δ=9.2386 (2.6); 8.6644 (2.4); 8.2811 (2.6); 8.2763 (2.6); 7.6454 (0.9); 7.6405 (1.6); 7.6356 (0.9); 7.3788 (0.6); 7.3622 (0.6); 7.2063 (0.3); 7.1852 (0.6); 7.1679 (0.4); 6.9507 (0.5); 6.9323 (0.8); 6.9162 (0.4); 6.8303 (0.8); 6.8088 (0.7); 5.4466 (0.7); 5.3040 (0.4); 5.2867 (0.4); 4.3127 (0.4); 4.3039 (0.4); 4.2962 (0.4); 4.2875 (0.3); 4.2545 (0.4); 4.2473 (0.5); 4.2315 (0.4); 4.2244 (0.6); 3.7967 (0.6); 3.3678 (16.0); 2.4629 (0.4); 2.2848 (0.4); 2.2747 (0.4); 2.2624 (0.5); 2.2480 (0.4); 2.1473 (61.9); 2.1131 (1.2); 2.1069 (1.2); 2.1007 (0.9); 2.0950 (0.5); 1.9637 (3.8); 1.9576 (6.6); 1.9518 (52.1); 1.9456 (97.7); 1.9395 (135.7); 1.9333 (92.8); 1.9271 (47.4); 1.7740 (0.5); 1.7679 (0.7); 1.7617 (0.5); 1.2702 (2.0); 0.1460 (1.7); 0.0902 (1.5); 0.0847 (1.2); 0.0780 (1.0); 0.0521 (0.9); 0.0079 (16.0); −0.0002 (388.0); −0.0086 (15.9); −0.1495 (1.7)

Example T4-2

4-(3,5-Dichlorophenyl)-N-[(4S)-3,4-dihydro-2H-chromen-4-yl]-8-(morpholin-4-yl)pyrido[3,2-d]pyrimidine-7-carboxamide

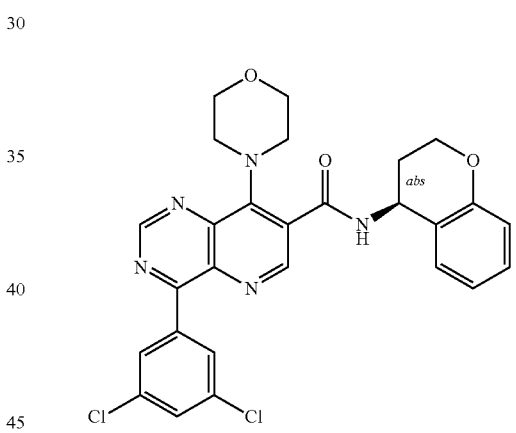

The title compound was prepared in an analoguous way as described for T4-1.

LC-MS (Method L2): $R_t$=1.64 min; m/z=536 (M+1)⁺.

¹H NMR (400 MHz, DMSO-d6) NMR Peaklist:

δ=16.8598 (0.4); 9.3671 (14.9); 9.2292 (4.0); 9.2090 (3.8); 8.7746 (14.1); 8.3142 (1.3); 8.2962 (15.9); 8.2916 (16 0.0); 7.8651 (4.7); 7.8603 (8.3); 7.3908 (3.6); 7.3726 (4.1); 7.2010 (2.0); 7.1818 (3.9); 7.1633 (2.4); 6.9600 (2.7); 6.9408 (4.7); 6.9223 (2.3); 6.8172 (5.0); 6.7967 (4.9); 5.2719 (1.0); 5.2591 (2.5); 5.2410 (2.4); 5.2271 (1.0); 4.3086 (1.1); 4.2950 (2.2); 4.2792 (2.8); 4.2719 (3.3); 4.2429 (2.5); 4.2214 (1.1); 3.9161 (0.5); 3.8573 (7.8); 3.8499 (11.8); 3.8379 (9.5); 3.8081 (0.5); 3.7043 (0.5); 3.6730 (9.4); 3.6628 (11.1); 3.3795 (0.5); 3.3473 (1.7); 3.3188 (397.9); 2.6705 (4.1); 2.6143 (0.5); 2.5939 (0.5); 2.5055 (532.4); 2.5015 (671.9); 2.4976 (498.7); 2.3281 (4.0); 2.3052 (0.5); 2.2558 (1.0); 2.2437 (1.3); 2.2331 (1.5); 2.2225 (1.6); 2.2096 (1.7); 2.1960 (1.4); 2.1173 (1.0); 2.1093 (1.3); 2.1012 (1.7); 2.0945 (1.9); 2.0809 (1.6); 2.0661 (1.3); 2.0591 (1.4); 1.9882 (0.8); 1.3981 (2.0);

1.2348 (6.6); 1.1749 (0.5); 1.1067 (0.5); 0.8539 (0.8); 0.8302 (0.5); 0.1461 (1.6); 0.0377 (0.5); −0.0002 (324.9); −0.1497 (1.6); −0.7272 (0.5)

Intermediates (T5)

2-Amino-N'-(2-bromophenyl)-2-oxoacetohydrazonoyl cyanide (T5-b-1)

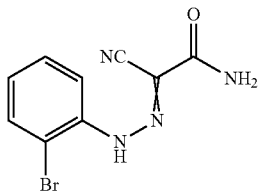 [SMILES: N#CC(=NNc1ccccc1Br)C(N)=O]

To a stirred solution of 2-bromoaniline (10.0 g, 58 mmol) in acetic acid (30 mL) were added water (18 mL) and hydrochloric acid (18.2 g, 174 mmol, 15 mL) at room temperature. The resulting mixture was cooled to −10° C. A solution of sodium nitrite (4.4 g, 64 mmol) in water (18 mL) was added dropwise at such a rate that the internal temperature did not exceed 0° C. The resulting orange solution was stirred at temperatures between −5° C. and −10° C. for 30 min. At −10° C. this solution was added over a period of 10 min to a stirred solution of 2-cyanoacetamide (6.1 g, 73 mmol) and sodium acetate (7.6 g, 93 mmol) in a mixture of ethanol (135 mL) and water (360 mL). The resulting yellow suspension was stirred for 18 hours at 0° C. while warming up to room temperature. The reaction mixture was cooled to 0° C. The solid was filtered off, washed with ice-water (1000 mL) and dried in vacuo. 15.1 g (60 mmol, 98% of theory) of the title compound were obtained (cis/trans mixture).

LC-MS (Method L3): $R_t$=1.84 min; m/z=267/269 (M+1)$^+$.

$^1$H NMR (400 MHz, DMSO-d6) δ 10.02 (s, 1H), 8.02-7.91 (m, 2H), 7.73-7.57 (m, 2H), 7.48-7.35 (m, 1H), 7.09 (td, J=8.0, 1.5 Hz, 1H).

4-Amino-8-bromocinnoline-3-carboxamide hydrochloride (T5-c-1)

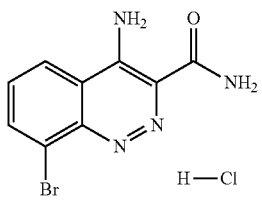

A suspension of 2-amino-N'-(2-bromophenyl)-2-oxoacetohydrazonoyl cyanide (5.00 g, 18.72 mmol) in chlorobenzene (37 mL) was added under stirring to aluminium chloride (11.23 g, 84.00 mmol). The resulting suspension was stirred under nitrogen atmosphere at 130° C. for 1 h and was allowed to cool to room temperature overnight. Hydrochloric acid (2 M; 50 mL) was carefully added under stirring. The resulting mixture was stirred at 100° C. for 1 h and subsequently cooled to room temperature. The formed precipitate was collected by filtration, washed with water (50 mL) and dried in vacuo.

Trituration in ethyl acetate afforded 4.97 g (16.37 mmol, 87% of theory) of the title compound.

LC-MS (Method L3): $R_t$=1.10 min, m/z=267/269 (M+H)$^+$[free amine].

8-Bromo-4-hydroxycinnoline-3-carboxylic acid (T5-d-1)

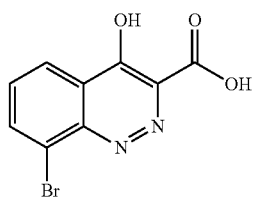 [SMILES: O=C(O)c1nnc2c(Br)cccc2c1O]

A mixture of 4-amino-8-bromocinnoline-3-carboxamide hydrochloride (1.00 g, 3.29 mmol) and aqueous potassium hydroxide (15 g, 66 mmol; 25%) in 1,4-dioxane (10 mL) was stirred at 100° C. overnight. The reaction mixture was cooled to room temperature and was slowly poured out into hydrochloric acid (1 M, 350 mL). The resulting suspension was stirred for 15 minutes. The precipitate was collected by filtration and dried on air to afford 0.71 g (2.64 mmol, 80% of theory) of the title compound.

LC-MS (Method L3): $R_t$=1.60 min; m/z=269/271 (M+H)$^+$.

$^1$H NMR (400 MHz, DMSO-d6) δ 14.16 (s, 2H), 8.33-8.18 (m, 2H), 7.55 (t, J=7.9 Hz, 1H).

8-Bromo-4-chlorocinnoline-3-carbonyl chloride (T5-e-1)

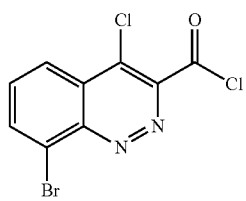 [SMILES: O=C(Cl)c1nnc2c(Br)cccc2c1Cl]

Under a nitrogen atmosphere a suspension of 8-bromo-4-hydroxycinnoline-3-carboxylic acid (0.61 g, 2.27 mmol) in phosphorus oxychloride (3.48 g, 22.67 mmol, 2.11 mL) was stirred at 110° C. for 2 hours. The resulting green solution was allowed to cool to room temperature and was concentrated in vacuo. The crude product was handled under an argon atmosphere. The material was co-evaporated with dry dichloromethane to afford the crude title compound. The material was kept under an argon atmosphere and was used as such in the subsequent step.

(8-Bromo-4-chloro-N-[(4S)-3,4-dihydro-2H-chromen-4-yl]cinnoline-3-carboxamide (T5-f-1)

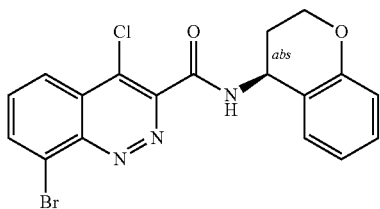 [SMILES: O=C(N[C@H]1CCOc2ccccc21)c1nnc2c(Br)cccc2c1Cl]

Under a nitrogen atmosphere to a stirred solution of crude 8-bromo-4-chlorocinnoline-3-carbonyl chloride (2.27 mmol) in dichloromethane (25 mL) were added triethylamine (688 mg, 6.80 mmol, 0.95 mL) and (S)-chroman-4-amine hydrochloride (463 mg, 2.49 mmol). The resulting mixture was stirred at room temperature for 2 hours. The reaction mixture was washed with hydrochloric acid (1 M, 20 mL). The aqueous layer was extracted with dichloromethane (2×20 mL). Combined organic layers were dried with sodium sulfate and concentrated in vacuo. 922 mg (2.20 mmol, 97% of theory) of the title compound were obtained.

LC-MS (Method L3): $R_t$=2.07 min; m/z=418/420 (M+1)$^+$.

$^1$H NMR (400 MHz, DMSO-d6) δ 9.48 (d, J=8.3 Hz, 1H), 8.49 (dd, J=7.5, 1.1 Hz, 1H), 8.36 (dd, J=8.5, 1.1 Hz, 1H), 7.99 (dd, J=8.5, 7.5 Hz, 1H), 7.43-7.34 (m, 1H), 7.24-7.14 (m, 1H), 6.95 (td, J=7.5, 1.2 Hz, 1H), 6.81 (dd, J=8.2, 1.1 Hz, 1H), 5.38 (q, J=6.0 Hz, 1H), 4.40-4.19 (m, 2H), 2.32-2.19 (m, 1H), 2.19-2.05 (m, 1H).

8-Bromo-N-[(4S)-3,4-dihydro-2H-chromen-4-yl]-4-(dimethylamino)cinnoline-3-carboxamide (T5-g-1)

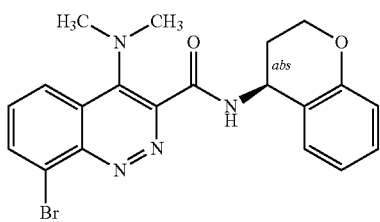 [SMILES: CN(C)c1c(C(=O)N[C@H]2CCOc3ccccc32)nnc2c(Br)cccc12]

To a stirred solution of (8-bromo-4-chloro-N-[(4S)-3,4-dihydro-2H-chromen-4-yl]cinnoline-3-carboxamide (400 mg, 0.96 mmol) in tetrahydrofuran (5 mL) under a nitrogen atmosphere were added triethylamine (193 mg, 1.91 mmol, 0.27 mL) and a solution of dimethylamine in tetrahydrofuran (2 M; 1.05 mmol, 0.53 mL). The resulting mixture was stirred at room temperature in a closed vessel for 72 h. Volatiles were removed in vacuo. Purification by flash column chromatography (gradient heptane/5%-100% ethyl acetate) afforded 340 mg (0.80 mmol, 83% of theory) of the title compound.

LC-MS (Method L3): $R_t$=1.70 min; m/z=427/429 (M+1)$^+$.

$^1$H NMR (400 MHz, DMSO-d6) δ 9.23 (d, J=8.3 Hz, 1H), 8.27-8.18 (m, 2H), 7.62 (dd, J=8.5, 7.5 Hz, 1H), 7.38 (d, J=6.8 Hz, 1H), 7.23-7.15 (m, 1H), 6.94 (td, J=7.5, 1.2 Hz, 1H), 6.81 (dd, J=8.2, 1.1 Hz, 1H), 5.33 (q, J=5.9 Hz, 1H), 4.36-4.21 (m, 2H), 3.17 (s, 6H), 2.28-2.17 (m, 1H), 2.14-2.02 (m, 1H).

8-Bromo-N-[(4S)-3,4-dihydro-2H-chromen-4-yl]-4-methoxycinnoline-3-carboxamide (T5-g-2)

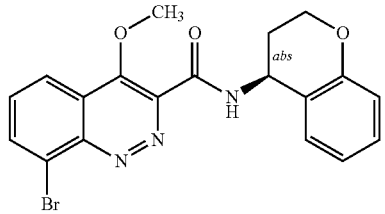 [SMILES: COc1c(C(=O)N[C@H]2CCOc3ccccc32)nnc2c(Br)cccc12]

To a stirred solution of (8-bromo-4-chloro-N-[(4S)-3,4-dihydro-2H-chromen-4-yl]cinnoline-3-carboxamide (400 mg, 0.96 mmol) in a mixture of methanol (5 mL) and tetrahydrofuran (1 mL) under a nitrogen atmosphere was added sodium tert-butoxide (96 mg, 1.00 mmol). The resulting mixture was stirred at room temperature in a closed vessel overnight. Under stirring the reaction mixture was added to hydrochloric acid (1 M, 20 mL). The resulting suspension was stirred for 10 minutes. The precipitate was collected by filtration, was washed with water (20 mL) and dried on air. Purification by flash column chromatography (gradient heptane/5%-100% ethyl acetate) afforded 260 mg (0.63 mmol, 66% of theory) of the title compound.

LC-MS (Method L3): $R_t$=2.03 min; m/z=414/416 (M+1)$^+$.

$^1$H NMR (400 MHz, DMSO-d6) δ 9.48 (d, J=8.3 Hz, 1H), 8.39-8.25 (m, 2H), 7.78 (dd, J=8.5, 7.4 Hz, 1H), 7.41-7.34 (m, 1H), 7.25-7.15 (m, 1H), 7.00-6.90 (m, 1H), 6.82 (dd, J=8.2, 1.1 Hz, 1H), 5.44-5.33 (m, 1H), 4.35-4.26 (m, 2H), 4.24 (s, 3H), 2.30-2.18 (m, 1H), 2.18-2.06 (m, 1H).

Examples (T$^5$)

Example T5-1

8-(3,5-Dichlorophenyl)-N-[(4S)-3,4-dihydro-2H-chromen-4-yl]-4-(dimethylamino)cinnoline-3-carboxamide

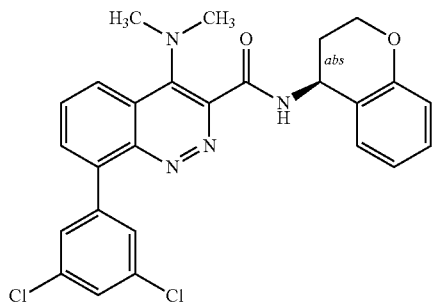 [SMILES: CN(C)c1c(C(=O)N[C@H]2CCOc3ccccc32)nnc2c(-c3cc(Cl)cc(Cl)c3)cccc12]

A stirred mixture of 8-bromo-N-[(4S)-3,4-dihydro-2H-chromen-4-yl]-4-(dimethylamino)cinnoline-3-carboxamide (65 mg, 0.15 mmol), (3,5-dichlorophenyl)boronic acid (32 mg, 0.17 mmol) and sodium carbonate (32 mg, 0.30 mmol) in 1,4-dioxane (1 mL) and water (0.15 mL) was sparged with nitrogen. [1,1'-Bis(diphenylphosphino)ferrocene]dichloropalladium(II) (7 mg, 0.01 mmol) was added and the resulting mixture was stirred at 60° C. for 4 hours under nitrogen atmosphere in a closed vessel. The reaction mixture was cooled to room temperature and was concentrated in vacuo. Purification by flash column chromatography (gradient heptane/5%-100% ethyl acetate) afforded 68 mg (0.14 mmol, 91% of theory) of the title compound.

LC-MS (Method L4): $R_t$=3.51 min; m/z=493/495 $(M+1)^+$.

$^1$H NMR (400 MHz, DMSO-d6) δ 9.23 (d, J=8.4 Hz, 1H), 8.29 (dd, J=8.6, 1.2 Hz, 1H), 7.93 (dd, J=7.1, 1.2 Hz, 1H), 7.83 (dd, J=8.6, 7.1 Hz, 1H), 7.76-7.67 (m, 3H), 7.36 (d, J=7.6 Hz, 1H), 7.22-7.11 (m, 1H), 6.97-6.89 (m, 1H), 6.80 (dd, J=8.2, 1.0 Hz, 1H), 5.33 (q, J=6.0 Hz, 1H), 4.29 (q, J=6.6, 6.1 Hz, 2H), 3.17 (s, 6H), 2.27-2.15 (m, 1H), 2.15-2.02 (m, 1H).

Example T5-2

8-(3-Chlorophenyl)-N-[(4S)-3,4-dihydro-2H-chromen-4-yl]-4-(dimethylamino)cinnoline-3-carboxamide

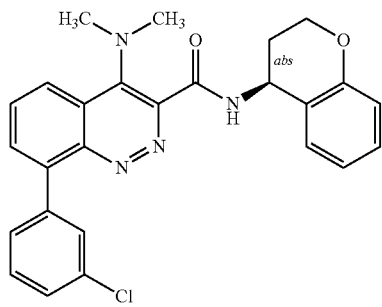 [SMILES: CN(C)c1c(C(=O)N[C@H]2CCOc3ccccc32)nnc2c(-c3cccc(Cl)c3)cccc12]

A stirred mixture of 8-bromo-N-[(4S)-3,4-dihydro-2H-chromen-4-yl]-4-(dimethylamino)cinnoline-3-carboxamide (65 mg, 0.15 mmol), (3-chlorophenyl)boronic acid (26 mg, 0.17 mmol) and sodium carbonate (32 mg, 0.30 mmol) in 1,4-dioxane (1 mL) and water (0.15 mL) was sparged with nitrogen. [1,1'-Bis(diphenylphosphino)ferrocene]dichloropalladium(II) (7 mg, 0.01 mmol) was added and the resulting mixture was stirred at 60° C. for 4 hours under nitrogen atmosphere. The reaction mixture was cooled to room temperature and was concentrated in vacuo. Purification by flash column chromatography (gradient heptane/5%-100% ethyl acetate) afforded 51 mg (0.11 mmol, 73% of theory) of the title compound.

LC-MS LC-MS (Method L4): $R_t$=3.10 min; m/z=459/461 $(M+1)^+$.

$^1$H NMR (400 MHz, DMSO-d6) δ 9.21 (d, J=8.4 Hz, 1H), 8.26 (dd, J=8.3, 1.5 Hz, 1H), 7.92-7.79 (m, 2H), 7.73 (q, J=1.4 Hz, 1H), 7.67-7.58 (m, 1H), 7.58-7.48 (m, 2H), 7.36 (d, J=7.6 Hz, 1H), 7.22-7.12 (m, 1H), 6.97-6.88 (m, 1H), 6.80 (dd, J=8.2, 1.1 Hz, 1H), 5.33 (q, J=6.0 Hz, 1H), 4.29 (t, J=5.5 Hz, 2H), 3.16 (s, 6H), 2.28-2.16 (m, 1H), 2.15-2.02 (m, 1H).

Example T5-3

8-(2,3-Dichlorophenyl)-N-[(4S)-3,4-dihydro-2H-chromen-4-yl]-4-(dimethylamino)cinnoline-3-carboxamide

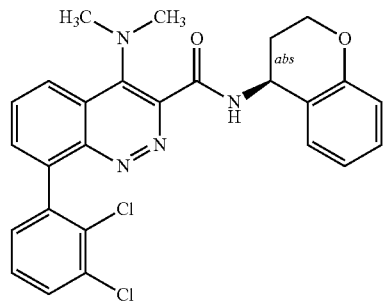 [SMILES: CN(C)c1c(C(=O)N[C@H]2CCOc3ccccc32)nnc2c(-c3cccc(Cl)c3Cl)cccc12]

A stirred mixture of 8-bromo-N-[(4S)-3,4-dihydro-2H-chromen-4-yl]-4-(dimethylamino)cinnoline-3-carboxamide (65 mg, 0.15 mmol), (2,3-dichlorophenyl)boronic acid (32 mg, 0.17 mmol) and sodium carbonate (32 mg, 0.30 mmol) in 1,4-dioxane (1 mL) and water (0.15 mL) was sparged with nitrogen. [1,1'-Bis(diphenylphosphino)ferrocene]dichloropalladium(II) (7 mg, 0.01 mmol) was added and the resulting mixture was stirred at 60° C. for 4 hours under nitrogen atmosphere. The reaction mixture was cooled to room temperature and was concentrated in vacuo. Purification by flash column chromatography (gradient heptane/5%-100% ethyl acetate) afforded 60 mg (0.12 mmol, 80% of theory) of the title compound.

LC-MS (Method L4): $R_t$=3.17 min; m/z=493/495 $(M+1)^+$.

$^1$H NMR (400 MHz, DMSO-d6) δ 9.19 (dd, J=12.0, 8.4 Hz, 1H), 8.32 (dd, J=8.6, 1.3 Hz, 1H), 7.84 (dd, J=8.6, 7.0 Hz, 1H), 7.80-7.71 (m, 2H), 7.54-7.37 (m, 2H), 7.33 (t, J=6.5 Hz, 1H), 7.21-7.11 (m, 1H), 6.90 (t, J=7.5 Hz, 1H), 6.79 (d, J=7.9 Hz, 1H), 5.31 (d, J=6.1 Hz, 1H), 4.27 (t, J=5.1 Hz, 2H), 3.18 (s, 6H), 2.26-2.13 (m, 1H), 2.12-1.99 (m, 1H).

Example T5-4

8-(3,4-Difluorophenyl)-N-[(4S)-3,4-dihydro-2H-chromen-4-yl]-4-(dimethylamino)cinnoline-3-carboxamide

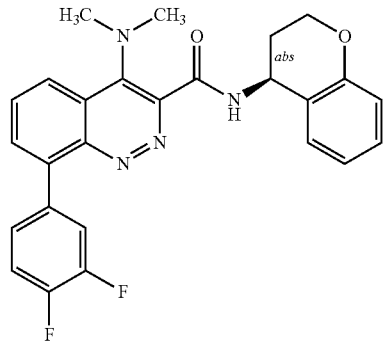 [SMILES: CN(C)c1c(C(=O)N[C@H]2CCOc3ccccc32)nnc2c(-c3ccc(F)c(F)c3)cccc12]

A stirred mixture of 8-bromo-N-[(4S)-3,4-dihydro-2H-chromen-4-yl]-4-(dimethylamino)cinnoline-3-carboxamide (65 mg, 0.15 mmol), (3,4-difluorophenyl)boronic acid (26 mg, 0.17 mmol) and sodium carbonate (32 mg, 0.30 mmol) in 1,4-dioxane (1 mL) and water (0.15 mL) was sparged with nitrogen. [1,1'-Bis(diphenylphosphino)ferrocene]dichloropalladium(II) (7 mg, 0.01 mmol) was added and the resulting mixture was stirred at 60° C. for 4 hours under nitrogen atmosphere. The reaction mixture was cooled to room temperature and was concentrated in vacuo. Purification by flash column chromatography (gradient heptane/5%-100% ethyl acetate) afforded 60 mg (0.12 mmol, 80% of theory) of the title compound.

LC-MS (Method L4): $R_t$=3.03 min; m/z=461 (M+1)$^+$.

$^1$H NMR (400 MHz, DMSO-d6) δ 9.21 (d, J=8.4 Hz, 1H), 8.26 (dd, J=8.4, 1.5 Hz, 1H), 7.92-7.72 (m, 3H), 7.63-7.48 (m, 2H), 7.36 (d, J=7.6 Hz, 1H), 7.22-7.13 (m, 1H), 6.97-6.88 (m, 1H), 6.80 (dd, J=8.2, 1.1 Hz, 1H), 5.33 (q, J=6.0 Hz, 1H), 4.36-4.22 (m, 2H), 3.16 (s, 6H), 2.27-2.14 (m, 1H), 2.14-2.01 (m, 1H).

Example T5-5

8-(3,5-Dichlorophenyl)-N-[(4S)-3,4-dihydro-2H-chromen-4-yl]-4-methoxycinnoline-3-carboxamide

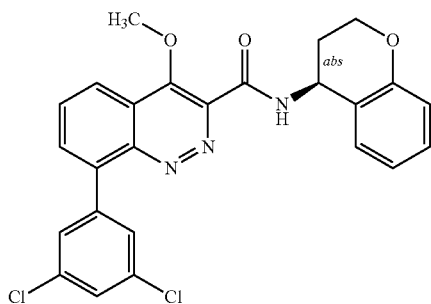 [SMILES: COc1c(C(=O)N[C@H]2CCOc3ccccc32)nnc2c(-c3cc(Cl)cc(Cl)c3)cccc12]

A stirred mixture of 8-bromo-N-[(4S)-3,4-dihydro-2H-chromen-4-yl]-4-methoxycinnoline-3-carboxamide, (3,5-dichlorophenyl)boronic acid (25 mg, 0.13 mmol) and sodium carbonate (26 mg, 0.24 mmol) in 1,4-dioxane (1 mL) and water (0.15 mL) was sparged with nitrogen. [1,1'-Bis(diphenylphosphino)ferrocene]dichloropalladium(II) (5 mg, 0.01 mmol) was added and the resulting mixture was stirred at 60° C. for 4 hours under nitrogen atmosphere in a closed vessel. The reaction mixture was cooled to room temperature, was diluted with ethyl acetate (1 mL), filtered and concentrated in vacuo. Purification by flash column chromatography (gradient heptane/5%-100% ethyl acetate) afforded 39 mg (0.08 mmol, 67% of theory) of the title compound.

LC-MS (Method L4): $R_t$=4.20 min; m/z=480/482 (M+1).

$^1$H NMR (400 MHz, DMSO-d6) δ 9.50 (d, J=8.4 Hz, 1H), 8.38 (dd, J=8.4, 1.3 Hz, 1H), 8.07 (dd, J=7.2, 1.3 Hz, 1H), 7.98 (dd, J=8.4, 7.2 Hz, 1H), 7.78 (d, J=1.9 Hz, 2H), 7.74 (t, J=1.9 Hz, 1H), 7.35 (d, J=7.6 Hz, 1H), 7.23-7.13 (m, 1H), 6.99-6.88 (m, 1H), 6.81 (dd, J=8.2, 1.1 Hz, 1H), 5.38 (q, J=6.1 Hz, 1H), 4.29 (t, J=5.3 Hz, 2H), 4.25 (s, 3H), 2.28-2.18 (m, 1H), 2.18-2.07 (m, 1H).

Example T5-6

8-(3-Chlorophenyl)-N-[(4S)-3,4-dihydro-2H-chromen-4-yl]-4-methoxycinnoline-3-carboxamide

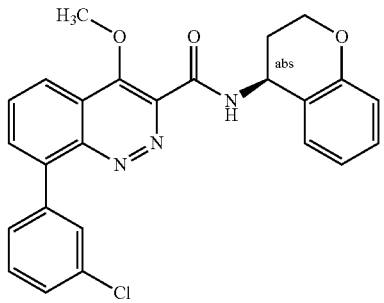 [SMILES: COc1c(C(=O)N[C@H]2CCOc3ccccc32)nnc2c(-c3cccc(Cl)c3)cccc12]

A stirred mixture of 8-bromo-N-[(4S)-3,4-dihydro-2H-chromen-4-yl]-4-methoxycinnoline-3-carboxamide, (3-chlorophenyl)boronic acid (21 mg, 0.13 mmol) and sodium carbonate (26 mg, 0.24 mmol) in 1,4-dioxane (1 mL) and water (0.15 mL) was sparged with nitrogen. [1,1'-Bis(diphenylphosphino)ferrocene]dichloropalladium(II) (5 mg, 0.01 mmol) was added and the resulting mixture was stirred at 60° C. for 4 hours under nitrogen atmosphere in a closed vessel. The reaction mixture was cooled to room temperature, was diluted with ethyl acetate (1 mL), filtered and concentrated in vacuo. Purification by flash column chromatography (gradient heptane/5%-100% ethyl acetate) afforded 32 mg (0.07 mmol, 60% of theory) of the title compound.

LC-MS (Method L4): $R_t$=4.05 min; m/z=446/448 (M+1)$^+$.

$^1$H NMR (400 MHz, DMSO-d6) δ 9.47 (d, J=8.4 Hz, 1H), 8.35 (dd, J=8.1, 1.7 Hz, 1H), 8.06-7.94 (m, 2H), 7.79 (q, J=1.3 Hz, 1H), 7.71-7.62 (m, 1H), 7.57-7.53 (m, 2H), 7.35 (d, J=7.6 Hz, 1H), 7.24-7.12 (m, 1H), 6.98-6.87 (m, 1H), 6.81 (dd, J=8.2, 1.1 Hz, 1H), 5.38 (q, J=6.1 Hz, 1H), 4.29 (t, J=5.4 Hz, 2H), 4.25 (s, 3H), 2.29-2.18 (m, 1H), 2.18-2.06 (m, 1H).

Example T5-7

8-(2,3-Dichlorophenyl)-N-[(4S)-3,4-dihydro-2H-chromen-4-yl]-4-methoxycinnoline-3-carboxamide

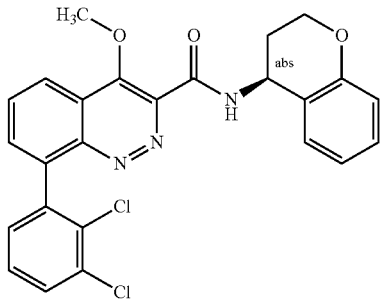 [SMILES: COc1c(C(=O)N[C@H]2CCOc3ccccc32)nnc2c(-c3cccc(Cl)c3Cl)cccc12]

A stirred mixture of 8-bromo-N-[(4S)-3,4-dihydro-2H-chromen-4-yl]-4-methoxycinnoline-3-carboxamide, (2,3-dichlorophenyl)boronic acid (25 mg, 0.13 mmol) and sodium carbonate (26 mg, 0.24 mmol) in 1,4-dioxane (1 mL) and water (0.15 mL) was sparged with nitrogen. [1,1′-Bis(diphenylphosphino)ferrocene]dichloropalladium(II) (5 mg, 0.01 mmol) was added and the resulting mixture was stirred at 60° C. for 4 hours under nitrogen atmosphere in a closed vessel. The reaction mixture was cooled to room temperature, was diluted with ethyl acetate (1 mL), filtered and concentrated in vacuo. Purification by flash column chromatography (gradient heptane/5%-100% ethyl acetate) and preparative HPLC afforded 32 mg (0.07 mmol, 55% of theory) of the title compound.

LC-MS (Method L4): $R_t$=3.99 min; m/z=480/482 (M+1)$^+$.

$^1$H NMR (400 MHz, DMSO-d6) δ 9.50-9.39 (m, 1H), 8.39 (dd, J=8.4, 1.3 Hz, 1H), 7.99 (dd, J=8.4, 7.1 Hz, 1H), 7.91 (d, J=6.8 Hz, 1H), 7.78 (dd, J=7.8, 1.8 Hz, 1H), 7.56-7.43 (m, 2H), 7.33 (dd, J=7.1, 3.2 Hz, 1H), 7.22-7.11 (m, 1H), 6.96-6.87 (m, 1H), 6.80 (d, J=8.1 Hz, 1H), 5.36 (q, J=6.1 Hz, 1H), 4.25 (s, 5H), 2.28-2.15 (m, 1H), 2.15-2.03 (m, 1H).

Example T5-8

8-(3,4-Difluorophenyl)-N-[(4S)-3,4-dihydro-2H-chromen-4-yl]-4-methoxycinnoline-3-carboxamide

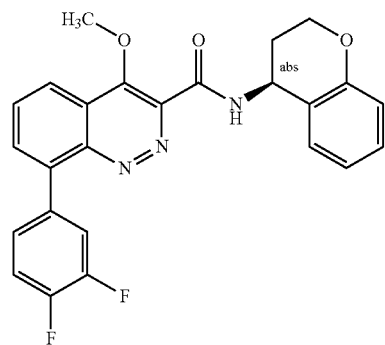 [SMILES: COc1c(C(=O)N[C@H]2CCOc3ccccc32)nnc2c(-c3ccc(F)c(F)c3)cccc12]

A stirred mixture of 8-bromo-N-[(4S)-3,4-dihydro-2H-chromen-4-yl]-4-methoxycinnoline-3-carboxamide (50 mg, 0.12 mmol), (3,4-difluorophenyl)boronic acid (21 mg, 0.13 mmol) and sodium carbonate (26 mg, 0.24 mmol) in 1,4-dioxane (1 mL) and water (0.15 mL) was sparged with nitrogen. [1,1′-Bis(diphenylphosphino)ferrocene]dichloropalladium(II) (5 mg, 0.01 mmol) was added and the resulting mixture was stirred at 60° C. for 4 hours under nitrogen atmosphere in a closed vessel. The reaction mixture was cooled to room temperature, was diluted with ethyl acetate (1 mL), filtered and concentrated in vacuo. Purification by flash column chromatography (gradient heptane/5%-100% ethyl acetate) and preparative HPLC afforded 30 mg (0.07 mmol, 55% of theory) of the title compound.

LC-MS (Method L4): $R_t$=3.87 min; m/z=448 (M+1)$^+$.

$^1$H NMR (400 MHz, DMSO-d6) δ 9.46 (d, J=8.4 Hz, 1H), 8.35 (dd, J=8.2, 1.6 Hz, 1H), 8.07-7.93 (m, 2H), 7.89-7.78 (m, 1H), 7.65-7.54 (m, 2H), 7.35 (d, J=6.9 Hz, 1H), 7.23-7.14 (m, 1H), 6.98-6.88 (m, 1H), 6.81 (dd, J=8.2, 1.1 Hz, 1H), 5.43-5.33 (m, 1H), 4.29 (t, J=5.4 Hz, 2H), 4.25 (s, 3H), 2.29-2.18 (m, 1H), 2.18-2.06 (m, 1H).

Intermediates (T$^6$)

5-(2,3-Dichlorophenyl)pyridazin-4-amine (T6-b-1)

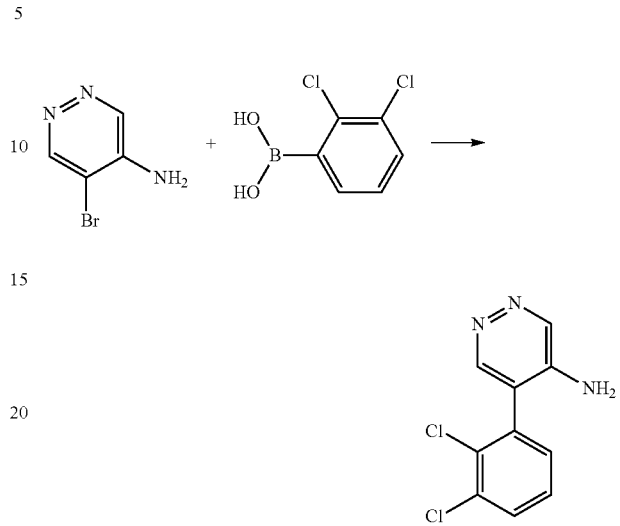

5-Bromopyridazin-4-amine, 2.00 g (11.5 mmol), 2,3-dichlorophenylboronic acid, 3.30 g (17.2 mmol), tris(dibenzylideneacetone)dipalladium, 265 mg (0.3 mmol), tri-tert-butylphosphine tetrafluoroborate, 167 mg (0.6 mmol), and potassium fluoride, 2.00 g (34.7 mmol), were dissolved in 16 mL of tetrahydrofuran and 4 mL of water. The mixture was stirred at 60° C. overnight. The solvent was removed in vacuo. Water was added, the mixture was extracted with ethyl acetate and the combined organic phase was dried over anhydrous sodium sulfate. The solvent was removed in vacuo and the residue was purified with silica gel column chromatograph (dichloromethane/methanol=20:1) to give 2.1 g (75%) of the product as a yellow solid.

LC-MS (Method M1): $R_t$=0.91 min; m/z=240 (M+1)$^+$.

Diethyl ({[5-(2,3-dichlorophenyl)pyridazin-4-yl]amino}methylene)malonate (T6-d-2)

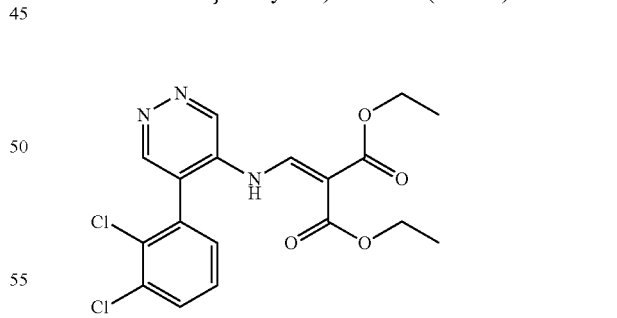

5-(2,3-Dichlorophenyl)pyridazin-4-amine, 2.10 g (8.8 mmol) and diethyl 2-(ethoxymethylene)malonate, 5.70 g (26.2 mmol), were dissolved in 30 mL of toluene. The resulting mixture was stirred at 110° C. overnight. The solvent was removed in vacuo and the residue was purified with silica gel column chromatograph (petroleum ether/ethyl acetate=1:2) to give 1.7 g (46%) of the product as a white solid.

LC-MS (Method M2): $R_t$=2.21 min; m/z=410 (M+1)$^+$.

Ethyl 4-(2,3-dichlorophenyl)-8-oxo-5,8-dihydropyrido[3,2-c]pyridazine-7-carboxylate (T6-e-1)

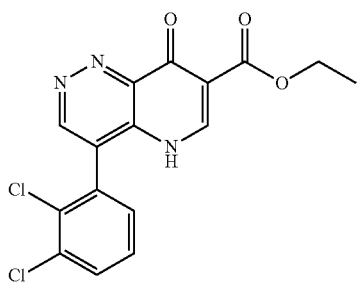 [SMILES: CCOC(=O)c1c[nH]c2c(-c3cccc(Cl)c3Cl)cnnc2c1=O]

100 mL of diphenyl ether were placed into a three-necked flask, diethyl ({[5-(2,3-dichlorophenyl)pyridazin-4-yl]amino}methylene)malonate, 1.70 g (4.1 mmol), dissolved in 50 mL of diphenyl ether, was added at reflux. The resulting mixture was stirred at reflux for 15 min. After cooling to room temperature, the reaction mixture was washed five times with 4N hydrogen chloride solution. The aqueous phase was lyophilized and then purified with C18 reversed phase column (acetonitrile/water=2:3) to give 280 mg (15%) of the product as a yellow solid.

LC-MS (Method M3): $R_t$=0.87 min; m/z=364 (M+1)$^+$.

4-(2,3-Dichlorophenyl)-8-oxo-5,8-dihydropyrido[3,2-c]pyridazine-7-carboxylic acid (T6-f-1)

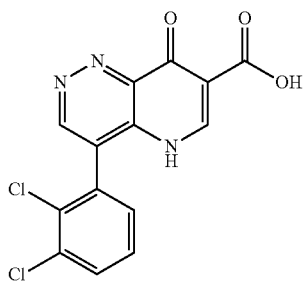 [SMILES: O=C(O)c1c[nH]c2c(-c3cccc(Cl)c3Cl)cnnc2c1=O]

Ethyl 4-(2,3-dichlorophenyl)-8-oxo-5,8-dihydropyrido[3,2-c]pyridazine-7-carboxylate, 280 mg (0.8 mmol), was dissolved in 5 mL of tetrahydrofuran and 5 mL of water. Lithium hydroxide, 55 mg (2.3 mmol), was added at room temperature. The resulting mixture was stirred at 60° C. overnight. After cooling to room temperature, the solvent was removed in vacuo. Water was added, the mixture was extracted with ethyl acetate. The pH of the water phase was adjusted to 7 with 2N hydrogen chloride solution. The precipitate solid was filtered off, washed with water and dried in vacuo to give 150 mg (56%) of the product as a yellow solid.

LC-MS (Method M4): $R_t$=0.78 min; m/z=336 (M+1)$^+$.

8-Chloro-4-(2,3-dichlorophenyl)pyrido[3,2-c]pyridazine-7-carbonyl chloride (T6-g-1)

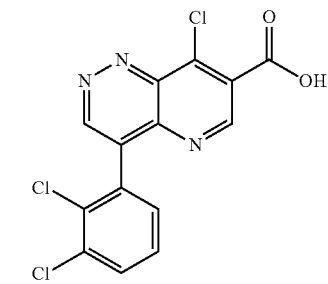 [SMILES: O=C(O)c1cnc2c(-c3cccc(Cl)c3Cl)cnnc2c1Cl]

4-(2,3-Dichlorophenyl)-8-oxo-5,8-dihydropyrido[3,2-c]pyridazine-7-carboxylic acid, 150 mg (0.5 mmol), was dissolved in 5 mL of toluene. N,N-Diisopropylethylamine, 173 mg (1.3 mmol), was added at room temperature. The resulting mixture was stirred at 60° C. for 1 hour. Phosphorus oxychloride, 684 mg (4.5 mmol), was added at 60° C. The resulting mixture was stirred at 60° C. for 30 min. The solvent was removed in vacuo to give 150 mg (crude) of the product as a brown oil. The residue was used directly to the next step without further purification.

8-Chloro-4-(2,3-dichlorophenyl)-N-[(4S)-3,4-dihydro-2H-chromen-4-yl]pyrido[3,2-c]pyridazine-7-carboxamide (T6-h-1)

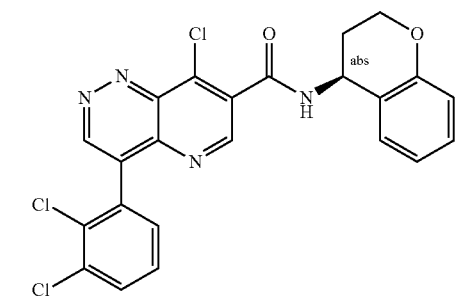

8-Chloro-4-(2,3-dichlorophenyl)pyrido[3,2-c]pyridazine-7-carbonyl chloride, 150 mg (0.4 mmol), and (S)-chroman-4-amine, 72 mg (0.5 mmol), were dissolved in 5 mL of dichloromethane. Triethylamine, 203 mg (2.0 mmol), was added at room temperature. The resulting mixture was stirred at room temperature for 30 min. The solvent was removed in vacuo to give 150 mg (crude) of the product as a brown oil.

LC-MS (Method M5): $R_t$=1.20 min; m/z=485 (M+1)$^+$.

Examples (T6)

Example T6-1

4-(2,3-Dichlorophenyl)-N-[(4S)-3,4-dihydro-2H-chromen-4-yl]-8-(dimethylamino)pyrido[3,2-c]pyridazine-7-carboxamide

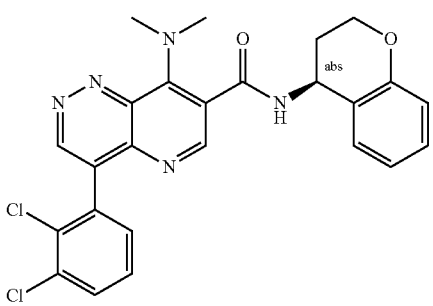 [SMILES: CN(C)c1c(C(=O)N[C@H]2CCOc3ccccc32)cnc2c(-c3cccc(Cl)c3Cl)cnnc12]

8-Chloro-4-(2,3-dichlorophenyl)-N-[(4S)-3,4-dihydro-2H-chromen-4-yl]pyrido[3,2-c]pyridazine-7-carboxamide (T6-h-1) 75 mg (crude), was dissolved in 10 mL of tetrahydrofuran. Dimethylamine, 1.6 mL (1 M in THF, 1.6 mmol), was added at room temperature. The resulting mixture was stirred for 2 hours at room temperature. The solvent was removed in vacuo. Water was added, the resulting mixture was extracted with ethyl acetate and the combined organic phase was dried over anhydrous sodium sulfate. The solvent was removed under vacuum and the residue was purified by preparative HPLC to give 3.3 mg (4.2%) of the product as a yellow solid.

LC-MS (Method M6): $R_t$=1.51 min; m/z=494 (M+1)$^+$.
$^1$H-NMR (300 MHz, DMSO-d$_6$): δ [ppm]=2.02-2.05 (m, 1H), 2.15-2.17 (m, 1H), 3.48 (s, 6H), 4.26-4.27 (m, 2H), 5.20-5.22 (m, 1H), 6.79 (d, 1H), 6.91 (t, 1H), 7.16 (t, 1H), 7.33 (d, 1H), 7.47-7.52 (m, 2H), 7.78 (d, 1H), 8.58 (s, 1H), 9.12 (d, 1H), 9.40 (s, 1H).

Example T6-2

4-(2,3-Dichlorophenyl)-N-[(4S)-3,4-dihydro-2H-chromen-4-yl]-8-(morpholin-4-yl)pyrido[3,2-c]pyridazine-7-carboxamide

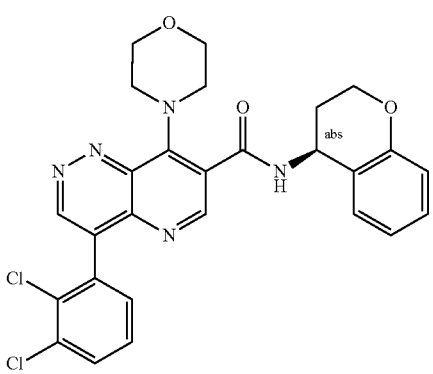 [SMILES: O=C(N[C@H]1CCOc2ccccc21)c1cnc2c(-c3cccc(Cl)c3Cl)cnnc2c1N1CCOCC1]

8-Chloro-4-(2,3-dichlorophenyl)-N-[(4S)-3,4-dihydro-2H-chromen-4-yl]pyrido[3,2-c]pyridazine-7-carboxamide (T6-h-1) 75 mg (crude), was dissolved in 10 mL of tetrahydrofuran. Dimethylamine, 1.6 mL (1 M in THF, 1.6 mmol), was added at room temperature. The resulting mixture was stirred for 2 hours at room temperature. The solvent was removed in vacuo. Water was added, the resulting mixture was extracted with ethyl acetate and the combined organic phase was dried over anhydrous sodium sulfate. The solvent was removed under vacuum and the residue was purified by preparative HPLC to give 4.2 mg (4%) of the product as a yellow solid.

LC-MS (Method M7): $R_t$=1.73 min; m/z=536 (M+1)$^+$.
$^1$H-NMR (300 MHz, DMSO-d$_6$): δ [ppm]=2.08-2.09 (m, 1H), 2.21-2.27 (m, 1H), 3.82-3.84 (m, 4H), 3.88-3.40 (m, 4H), 4.23-4.29 (m, 2H), 5.22-5.25 (m, 1H), 6.79 (d, 1H), 6.92 (t, 1H), 7.16 (t, 1H), 7.35 (d, 1H), 7.45-7.55 (m, 2H), 7.82 (d, 1H), 8.69 (s, 1H), 9.18 (d, 1H), 9.47 (s, 1H).

Example T6-3

4-(3,5-Dichlorophenyl)-N-[(4S)-3,4-dihydro-2H-chromen-4-yl]-8-(dimethylamino)pyrido[3,2-c]pyridazine-7-carboxamide

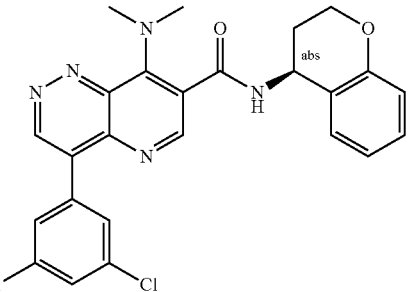

This compound was synthesized by the same method as described in the example T6-1 to give 9.7 mg (9%) of the product as a yellow solid.

LC-MS (Method M7): $R_t$=1.65 min; m/z=494 (M+1)$^+$.
$^1$H-NMR (300 MHz, CD$_3$OD): δ [ppm]=2.14-2.20 (m, 1H), 2.24-2.31 (m, 1H), 3.54 (s, 6H), 4.20-4.30 (m, 2H), 5.29 (q, 1H), 6.78 (d, 1H), 6.91 (t, 1H), 7.15 (t, 1H), 7.32 (d, 1H), 7.58 (d, 1H), 7.77 (d, 2H), 8.61 (s, 1H), 9.32 (d, 1H).

Example T6-4

4-(3,5-Dichlorophenyl)-N-[(4S)-3,4-dihydro-2H-chromen-4-yl]-8-(morpholin-4-yl)pyrido[3,2-c]pyridazine-7-carboxamide

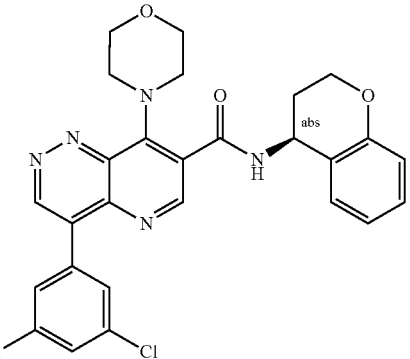

This compound was synthesized by the same method as described in the example T6-2 to give 9 mg (10%) of the product as a yellow solid.

LC-MS (Method M11): R$_t$=1.70 min; m/z=536 (M+1)$^+$.
$^1$H-NMR (400 MHz, DMSO-d$_6$): δ [ppm]=2.07-2.11 (m, 1H), 2.21-2.27 (m, 1H), 3.80-3.81 (m, 4H), 3.90-3.91 (m, 4H), 4.23-4.33 (m, 2H), 5.26 (q, 1H), 6.82 (d, 1H), 6.95 (t, 1H), 7.19 (t, 1H), 7.39 (d, 1H), 7.80 (s, 1H), 7.93 (s, 2H), 8.81 (s, 1H), 9.20 (d, 1H), 9.61 (s, 1H).

TABLE 1

Examples T1-5 to T1-15, T2-5 to T2-12 and T3-5 to T3-20

| Example No | Structure | IUPAC Name |
|---|---|---|
| T1-5 | 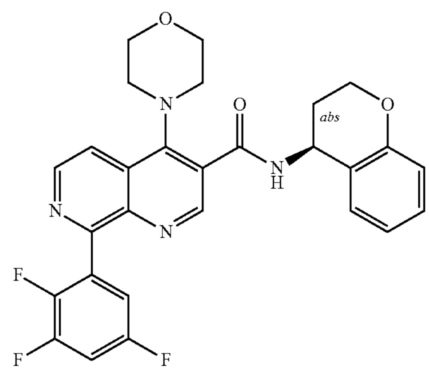 [SMILES: O=C(N[C@H]1CCOc2ccccc21)c1cnc2c(-c3cc(F)cc(F)c3F)nccc2c1N1CCOCC1] | N-[(4S)-3,4-dihydro-2H-1-benzopyran-4-yl]-4-(morpholin-4-yl)-8-(2,3,5-trifluorophenyl)-1,7-naphthyridine-3-carboxamide |
| T1-6 | 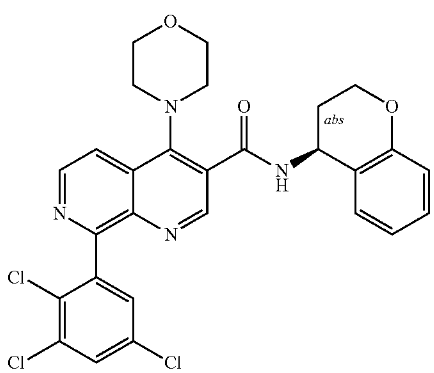 [SMILES: O=C(N[C@H]1CCOc2ccccc21)c1cnc2c(-c3cc(Cl)cc(Cl)c3Cl)nccc2c1N1CCOCC1] | N-[(4S)-3,4-dihydro-2H-chromen-4-yl]-4-(morpholin-4-yl)-8-(2,3,5-trichlorophenyl)-1,7-naphthyridine-3-carboxamide |
| T1-7 | 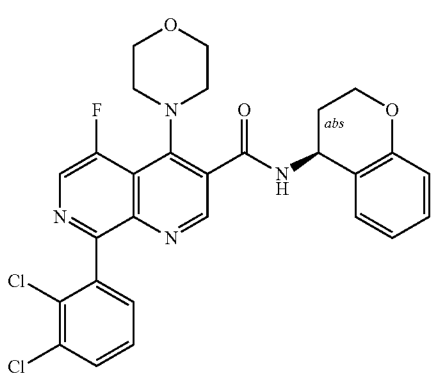 [SMILES: O=C(N[C@H]1CCOc2ccccc21)c1cnc2c(-c3cccc(Cl)c3Cl)ncc(F)c2c1N1CCOCC1] | 8-(2,3-dichlorophenyl)-N-[(4S)-3,4-dihydro-2H-1-benzopyran-4-yl]-5-fluoro-4-(morpholin-4-yl)-1,7-naphthyridine-3-carboxamide |

TABLE 1-continued

Examples T1-5 to T1-15, T2-5 to T2-12 and T3-5 to T3-20

| Example No | Structure | IUPAC Name |
|---|---|---|
| T1-8 | 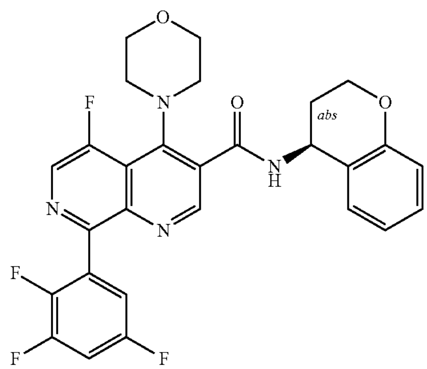 [SMILES: O=C(N[C@H]1CCOc2ccccc21)c1cnc2c(-c3cc(F)cc(F)c3F)ncc(F)c2c1N1CCOCC1] | N-[(4S)-3,4-dihydro-2H-1-benzopyran-4-yl]-5-fluoro-4-(morpholin-4-yl)-8-(2,3,5-trifluorophenyl)-1,7-naphthyridine-3-carboxamide |
| T1-9 | 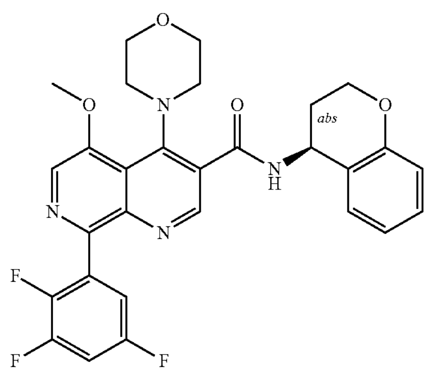 [SMILES: COc1cnc(-c2cc(F)cc(F)c2F)c2ncc(C(=O)N[C@H]3CCOc4ccccc43)c(N3CCOCC3)c12] | N-[(4S)-3,4-dihydro-2H-1-benzopyran-4-yl]-5-methoxy-4-(morpholin-4-yl)-8-(2,3,5-trifluorophenyl)-1,7-naphthyridine-3-carboxamide |
| T1-10 | 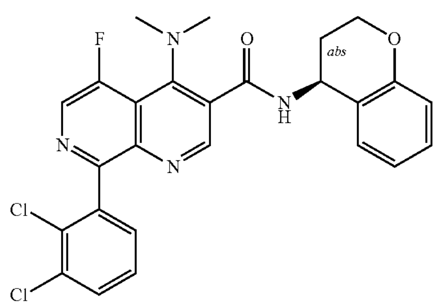 [SMILES: CN(C)c1c(C(=O)N[C@H]2CCOc3ccccc32)cnc2c(-c3cccc(Cl)c3Cl)ncc(F)c12] | 8-(2,3-dichlorophenyl)-N-[(4S)-3,4-dihydro-2H-1-benzopyran-4-yl]-4-(dimethylamino)-5-fluoro-1,7-naphthyridine-3-carboxamide |
| T1-11 | 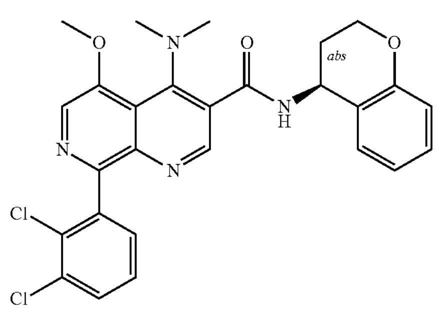 [SMILES: COc1cnc(-c2cccc(Cl)c2Cl)c2ncc(C(=O)N[C@H]3CCOc4ccccc43)c(N(C)C)c12] | 8-(2,3-dichlorophenyl)-N-[(4S)-3,4-dihydro-2H-1-benzopyran-4-yl]-4-(dimethylamino)-5-methoxy-1,7-naphthyridine-3-carboxamide |

TABLE 1-continued

Examples T1-5 to T1-15, T2-5 to T2-12 and T3-5 to T3-20

| Example No | Structure | IUPAC Name |
|---|---|---|
| T1-12 | 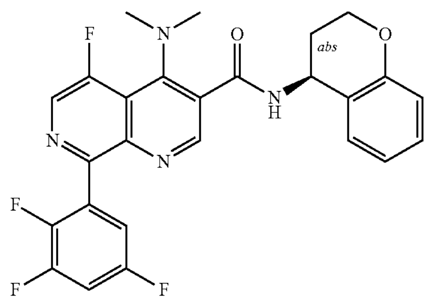 [SMILES: CN(C)c1c(C(=O)N[C@H]2CCOc3ccccc32)cnc2c(-c3cc(F)cc(F)c3F)ncc(F)c12] | N-[(4S)-3,4-dihydro-2H-1-benzopyran-4-yl]-4-(dimethylamino)-5-fluoro-8-(2,3,5-trifluorophenyl)-1,7-naphthyridine-3-carboxamide |
| T1-13 | 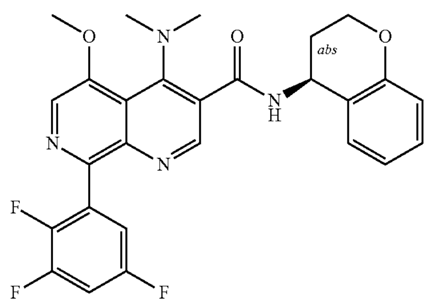 [SMILES: COc1cnc(-c2cc(F)cc(F)c2F)c2ncc(C(=O)N[C@H]3CCOc4ccccc43)c(N(C)C)c12] | N-[(4S)-3,4-dihydro-2H-1-benzopyran-4-yl]-4-(dimethylamino)-5-methoxy-8-(2,3,5-trifluorophenyl)-1,7-naphthyridine-3-carboxamide |
| T1-14 | 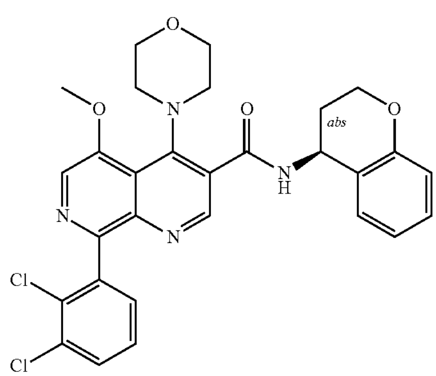 [SMILES: COc1cnc(-c2cccc(Cl)c2Cl)c2ncc(C(=O)N[C@H]3CCOc4ccccc43)c(N3CCOCC3)c12] | 8-(2,3-dichlorophenyl)-N-[(4S)-3,4-dihydro-2H-1-benzopyran-4-yl]-5-methoxy-4-(morpholin-4-yl)-1,7-naphthyridine-3-carboxamide |
| T1-15 | 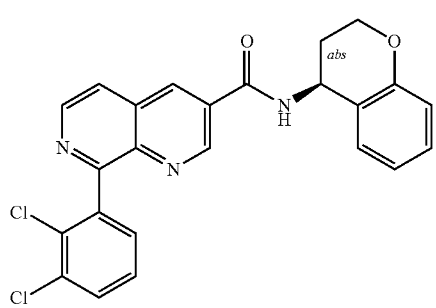 [SMILES: O=C(N[C@H]1CCOc2ccccc21)c1cnc2c(-c3cccc(Cl)c3Cl)nccc2c1] | 8-(2,3-dichlorophenyl)-N-[(4S)-3,4-dihydro-2H-chromen-4-yl]-1,7-naphthyridine-3-carboxamide |

TABLE 1-continued

Examples T1-5 to T1-15, T2-5 to T2-12 and T3-5 to T3-20

| Example No | Structure | IUPAC Name |
|---|---|---|
| T2-5 | 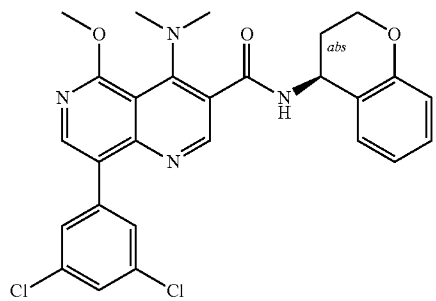 [SMILES: COc1ncc(-c2cc(Cl)cc(Cl)c2)c2ncc(C(=O)N[C@H]3CCOc4ccccc43)c(N(C)C)c12] | 8-(3,5-dichlorophenyl)-N-[(4S)-3,4-dihydro-2H-1-benzopyran-4-yl]-4-(dimethylamino)-5-methoxy-1,6-naphthyridine-3-carboxamide |
| T2-6 | 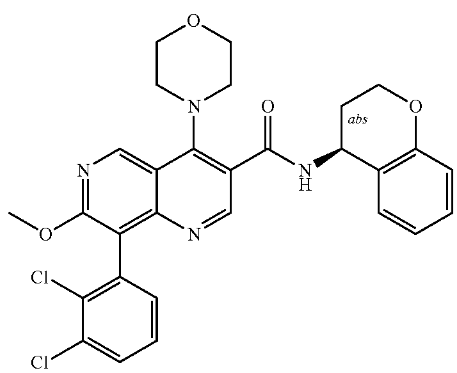 [SMILES: COc1ncc2c(N3CCOCC3)c(C(=O)N[C@H]3CCOc4ccccc43)cnc2c1-c1cccc(Cl)c1Cl] | 8-(2,3-dichlorophenyl)-N-[(4S)-3,4-dihydro-2H-1-benzopyran-4-yl]-7-methoxy-4-(morpholin-4-yl)-1,6-naphthyridine-3-carboxamide |
| T2-7 | 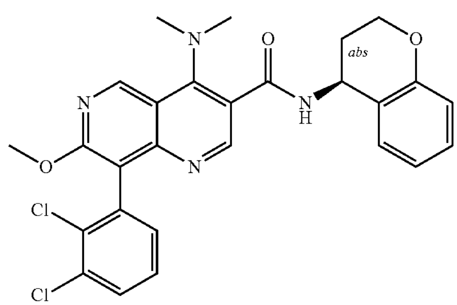 [SMILES: COc1ncc2c(N(C)C)c(C(=O)N[C@H]3CCOc4ccccc43)cnc2c1-c1cccc(Cl)c1Cl] | 8-(2,3-dichlorophenyl)-N-[(4S)-3,4-dihydro-2H-1-benzopyran-4-yl]-4-(dimethylamino)-7-methoxy-1,6-naphthyridine-3-carboxamide |
| T2-8 | 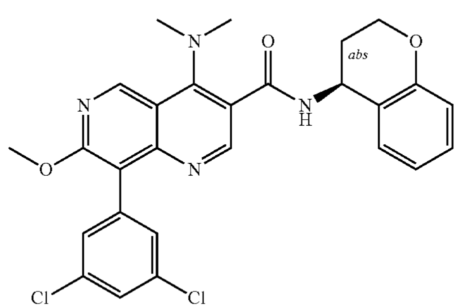 [SMILES: COc1ncc2c(N(C)C)c(C(=O)N[C@H]3CCOc4ccccc43)cnc2c1-c1cc(Cl)cc(Cl)c1] | 8-(3,5-dichlorophenyl)-N-[(4S)-3,4-dihydro-2H-1-benzopyran-4-yl]-4-(dimethylamino)-7-methoxy-1,6-naphthyridine-3-carboxamide |

TABLE 1-continued

Examples T1-5 to T1-15, T2-5 to T2-12 and T3-5 to T3-20

| Example No | Structure | IUPAC Name |
|---|---|---|
| T2-9 | 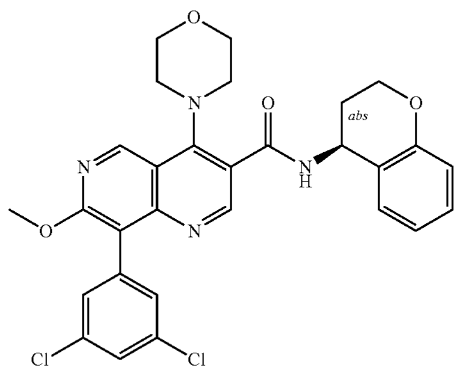 [SMILES: COc1ncc2c(N3CCOCC3)c(C(=O)N[C@H]3CCOc4ccccc43)cnc2c1-c1cc(Cl)cc(Cl)c1] | 8-(3,5-dichlorophenyl)-N-[(4S)-3,4-dihydro-2H-1-benzopyran-4-yl]-7-methoxy-4-(morpholin-4-yl)-1,6-naphthyridine-3-carboxamide |
| T2-10 | 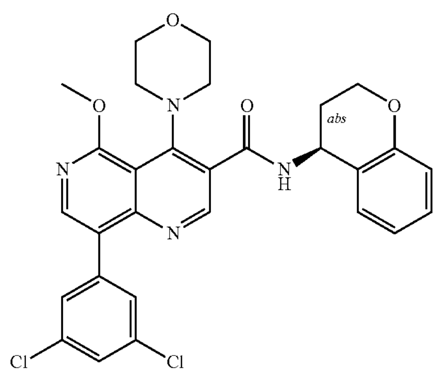 [SMILES: COc1ncc(-c2cc(Cl)cc(Cl)c2)c2ncc(C(=O)N[C@H]3CCOc4ccccc43)c(N3CCOCC3)c12] | 8-(3,5-dichlorophenyl)-N-[(4S)-3,4-dihydro-2H-1-benzopyran-4-yl]-5-methoxy-4-(morpholin-4-yl)-1,6-naphthyridine-3-carboxamide |
| T2-11 | 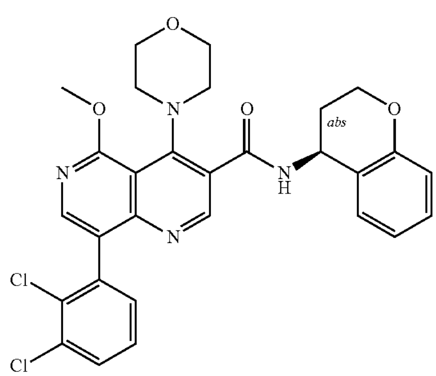 [SMILES: COc1ncc(-c2cccc(Cl)c2Cl)c2ncc(C(=O)N[C@H]3CCOc4ccccc43)c(N3CCOCC3)c12] | 8-(2,3-dichlorophenyl)-N-[(4S)-3,4-dihydro-2H-1-benzopyran-4-yl]-5-methoxy-4-(morpholin-4-yl)-1,6-naphthyridine-3-carboxamide |
| T2-12 | 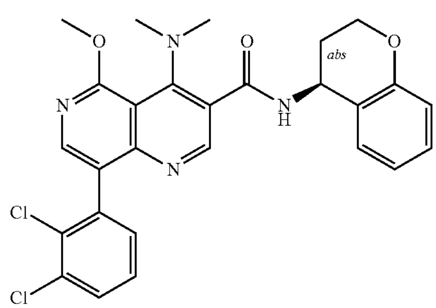 [SMILES: COc1ncc(-c2cccc(Cl)c2Cl)c2ncc(C(=O)N[C@H]3CCOc4ccccc43)c(N(C)C)c12] | 8-(2,3-dichlorophenyl)-N-[(4S)-3,4-dihydro-2H-1-benzopyran-4-yl]-4-(dimethylamino)-5-methoxy-1,6-naphthyridine-3-carboxamide |

TABLE 1-continued

Examples T1-5 to T1-15, T2-5 to T2-12 and T3-5 to T3-20

| Example No | Structure | IUPAC Name |
| --- | --- | --- |
| T3-5 | 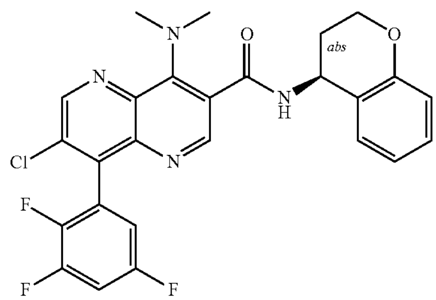 [SMILES: CN(C)c1c(C(=O)N[C@H]2CCOc3ccccc32)cnc2c(-c3cc(F)cc(F)c3F)c(Cl)cnc12] | 7-chloro-N-[(4S)-3,4-dihydro-2H-1-benzopyran-4-yl]-4-(dimethylamino)-8-(2,3,5-trifluorophenyl)-1,5-naphthyridine-3-carboxamide |
| T3-6 | 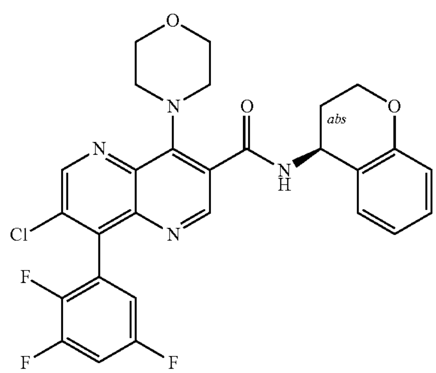 [SMILES: O=C(N[C@H]1CCOc2ccccc21)c1cnc2c(-c3cc(F)cc(F)c3F)c(Cl)cnc2c1N1CCOCC1] | 7-chloro-N-[(4S)-3,4-dihydro-2H-1-benzopyran-4-yl]-4-(morpholin-4-yl)-8-(2,3,5-trifluorophenyl)-1,5-naphthyridine-3-carboxamide |
| T3-7 | 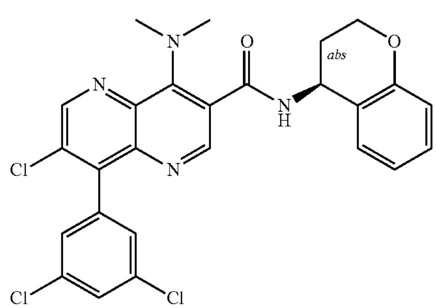 [SMILES: CN(C)c1c(C(=O)N[C@H]2CCOc3ccccc32)cnc2c(-c3cc(Cl)cc(Cl)c3)c(Cl)cnc12] | 7-chloro-8-(3,5-dichlorophenyl)-N-[(4S)-3,4-dihydro-2H-1-benzopyran-4-yl]-4-(dimethylamino)-1,5-naphthyridine-3-carboxamide |
| T3-8 | 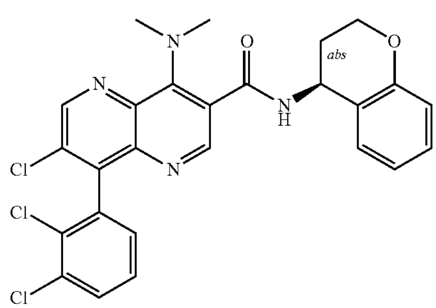 [SMILES: CN(C)c1c(C(=O)N[C@H]2CCOc3ccccc32)cnc2c(-c3cccc(Cl)c3Cl)c(Cl)cnc12] | 7-chloro-8-(2,3-dichlorophenyl)-N-[(4S)-3,4-dihydro-2H-1-benzopyran-4-yl]-4-(dimethylamino)-1,5-naphthyridine-3-carboxamide |

TABLE 1-continued

Examples T1-5 to T1-15, T2-5 to T2-12 and T3-5 to T3-20

| Example No | Structure | IUPAC Name |
|---|---|---|
| T3-9 | 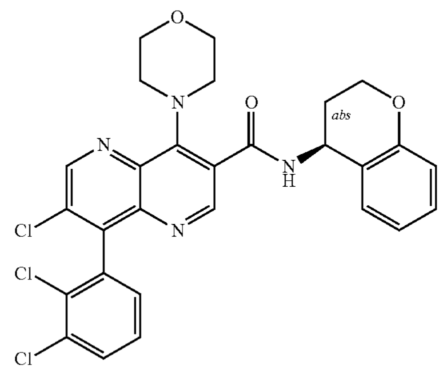 [SMILES: O=C(N[C@H]1CCOc2ccccc21)c1cnc2c(-c3cccc(Cl)c3Cl)c(Cl)cnc2c1N1CCOCC1] | 7-chloro-8-(2,3-dichlorophenyl)-N-[(4S)-3,4-dihydro-2H-1-benzopyran-4-yl]-4-(morpholin-4-yl)-1,5-naphthyridine-3-carboxamide |
| T3-10 | 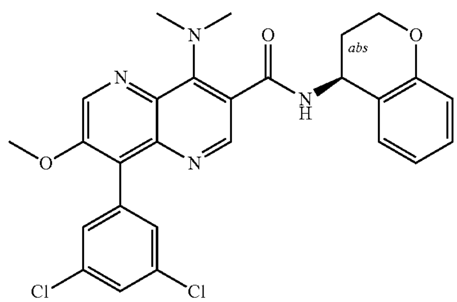 [SMILES: COc1cnc2c(N(C)C)c(C(=O)N[C@H]3CCOc4ccccc43)cnc2c1-c1cc(Cl)cc(Cl)c1] | 8-(3,5-dichlorophenyl)-N-[(4S)-3,4-dihydro-2H-1-benzopyran-4-yl]-4-(dimethylamino)-7-methoxy-1,5-naphthyridine-3-carboxamide |
| T3-11 | 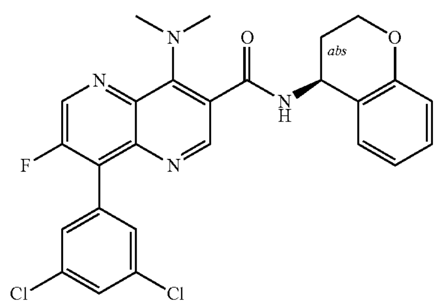 [SMILES: CN(C)c1c(C(=O)N[C@H]2CCOc3ccccc32)cnc2c(-c3cc(Cl)cc(Cl)c3)c(F)cnc12] | 8-(3,5-dichlorophenyl)-N-[(4S)-3,4-dihydro-2H-1-benzopyran-4-yl]-4-(dimethylamino)-7-fluoro-1,5-naphthyridine-3-carboxamide |
| T3-12 | 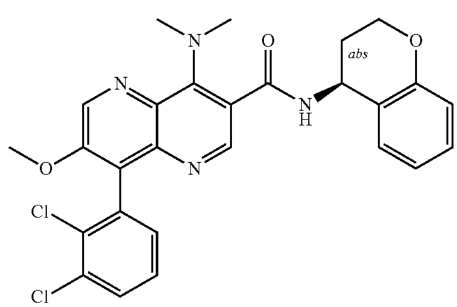 [SMILES: COc1cnc2c(N(C)C)c(C(=O)N[C@H]3CCOc4ccccc43)cnc2c1-c1cccc(Cl)c1Cl] | 8-(2,3-dichlorophenyl)-N-[(4S)-3,4-dihydro-2H-1-benzopyran-4-yl]-4-(dimethylamino)-7-methoxy-1,5-naphthyridine-3-carboxamide |

TABLE 1-continued

Examples T1-5 to T1-15, T2-5 to T2-12 and T3-5 to T3-20

| Example No | Structure | IUPAC Name |
|---|---|---|
| T3-14 | 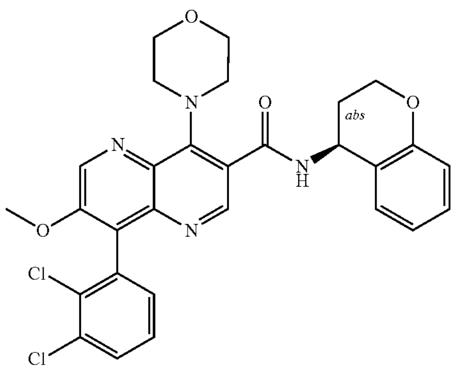 [SMILES: COc1cnc2c(N3CCOCC3)c(C(=O)N[C@H]3CCOc4ccccc43)cnc2c1-c1cccc(Cl)c1Cl] | 8-(2,3-dichlorophenyl)-N-[(4S)-3,4-dihydro-2H-1-benzopyran-4-yl]-7-methoxy-4-(morpholin-4-yl)-1,5-naphthyridine-3-carboxamide |
| T3-15 | 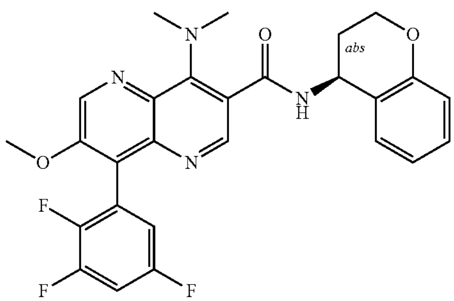 [SMILES: COc1cnc2c(N(C)C)c(C(=O)N[C@H]3CCOc4ccccc43)cnc2c1-c1cc(F)cc(F)c1F] | N-[(4S)-3,4-dihydro-2H-1-benzopyran-4-yl]-4-(dimethylamino)-7-methoxy-8-(2,3,5-trifluorophenyl)-1,5-naphthyridine-3-carboxamide |
| T3-16 | 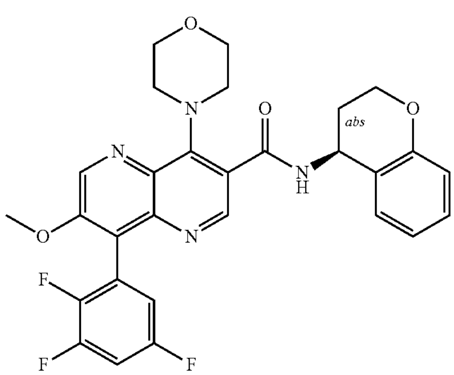 | N-[(4S)-3,4-dihydro-2H-1-benzopyran-4-yl]-7-methoxy-4-(morpholin-4-yl)-8-(2,3,5-trifluorophenyl)-1,5-naphthyridine-3-carboxamide |
| T3-17 | 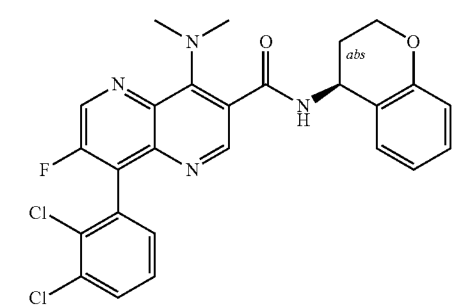 | 8-(2,3-dichlorophenyl)-N-[(4S)-3,4-dihydro-2H-1-benzopyran-4-yl]-4-(dimethylamino)-7-fluoro-1,5-naphthyridine-3-carboxamide |

TABLE 1-continued

Examples T1-5 to T1-15, T2-5 to T2-12 and T3-5 to T3-20

| Example No | Structure | IUPAC Name |
|---|---|---|
| T3-18 | 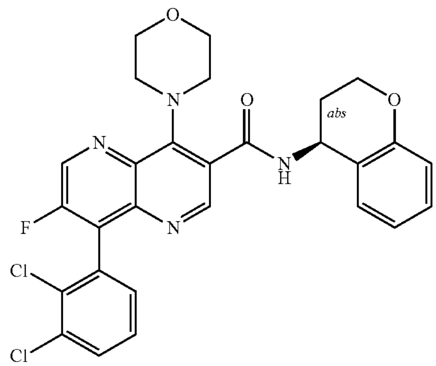 [SMILES: O=C(N[C@H]1CCOc2ccccc21)c1cnc2c(-c3cccc(Cl)c3Cl)c(F)cnc2c1N1CCOCC1] | 8-(2,3-dichlorophneyl)-N-[(4S)-3,4-dihydro-2H-1-benzopyran-4-yl]-7-fluoro-4-(morpholin-4-yl)-1,5-naphthyridine-3-carboxamide |
| T3-19 | 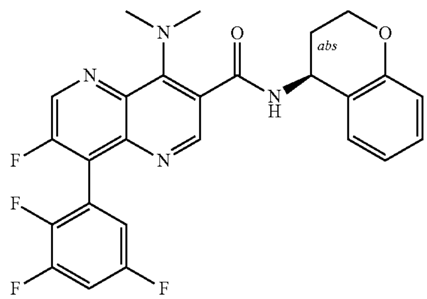 [SMILES: CN(C)c1c(C(=O)N[C@H]2CCOc3ccccc32)cnc2c(-c3cc(F)cc(F)c3F)c(F)cnc12] | N-[(4S)-3,4-dihydro-2H-1-benzopyran-4-yl]-4-(dimethylamino)-7-fluoro-8-(2,3,5-trifluorophenyl)-1,5-naphthyridine-3-carboxamide |
| T3-20 | 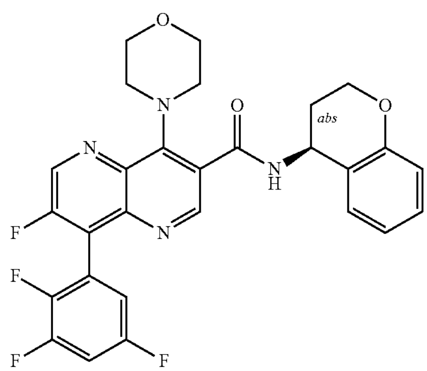 [SMILES: O=C(N[C@H]1CCOc2ccccc21)c1cnc2c(-c3cc(F)cc(F)c3F)c(F)cnc2c1N1CCOCC1] | N-[(4S)-3,4-dihydro-2H-1-benzopyran-4-yl]-7-fluoro-4-(morpholin-4-yl)-8-(2,3,5-trifluorophenyl)-1,5-naphthyridine-3-carboxamide |

TABLE 2

Analytical Data for Examples T1-5 to T1-15, T2-5 to T2-12 and T3-5 to T3-20

| Example No | LC-MS | NMR |
|---|---|---|
| T1-5 | MS (ESIpos): m/z = 521(M + H)+. LC-MS (Method M125): Rt = 2.86 min. | 1H-NMR (400 MHz, DMSO-d6): δ [ppm] = 2.04-2.08 (m, 1H), 2.20-2.25 (m, 1H), 3.32 (s, 4H), 3.89 (t, 4H), 4.20-4.31 (m, 2H), 5.25 (q, 1H), 6.79-6.81 (m, 1H), 6.91-6.95 (m, 1H), 7.16-7.20 (m, 1H), 7.31-7.39 (m, 2H), 7.67-7.70 (m, 1H), 8.11 (d, 1H), 8.70-8.75 (m, 2H), 9.26-9.28 (m, 1H). |
| T1-6 | MS (ESIpos): m/z = 569 (M + H)+. LC-MS (Method M7): Rt = 1.91 min. | 1H-NMR (400 MHz, DMSO-d6): δ [ppm] = 2.06-2.08 (m, 1H), 2.19-2.33 (m, 1H), 3.32 (s, 4H), 3.89 (t, 4H), 4.20-4.30 (m, 2H), 5.24 (q, 1H), 6.78-6.80 (m, 1H), 6.90-6.93 (m, 1H), 7.15-7.19 (m, 1H), 7.36-7.38 (m, 1H), 7.58 (d, 1H), 7.99 (d, 1H), 8.10 (d, 1H), 8.70-8.71 (m, 2H), 9.26 (d, 1H). |
| T1-7 | MS (ESIpos): m/z = 553 (M + H)+. LC-MS (Method M96): Rt = 1.82 min. | 1H-NMR (300 MHz, DMSO-d6): δ [ppm] = 2.02-2.08 (m, 1H), 2.18-2.24 (m, 1H), 3.32 (s, 4H), 3.80 (t, 4H), 4.22-4.30 (m, 2H), 5.30 (q, 1H), 6.79-6.81 (m, 1H), 6.89-6.94 (m, 1H), 7.15-7.20 (m, 1H), 7.37-7.42 (m, 2H), 7.47-7.52 (m, 1H), 7.75-7.78 (m, 1H) 8.65 (d, 1H), 8.71 (s, 1H), 9.29 (s, 1H). |

TABLE 2-continued

Analytical Data for Examples T1-5 to T1-15, T2-5 to T2-12 and T3-5 to T3-20

| Example No | LC-MS | NMR |
|---|---|---|
| T1-8 | MS (ESIpos): m/z = 539 (M + H)+. LC-MS (Method M127): Rt = 2.11 min. | 1H-NMR (300 MHz, DMSO-d6): δ [ppm] = 2.04-2.09 (m, 1H), 2.19-2.27 (m, 1H), 3.30-3.33(m, 4H), 3.79-3.80 (m, 4H), 4.22-4.29 (m, 2H), 5.24 (q, 1H), 6.79-6.82 (m, 1H), 6.90-6.95 (m, 1H), 7.15-7.21 (m, 1H), 7.29-7.33(m, 1H), 7.38-7.40 (m, 1H), 7.70-7.72 (m, 1H), 8.68 (d, 1H), 8.76 (s, 1H), 9.31 (d, 1H). |
| T1-9 | MS (ESIpos): m/z = 551 (M + H)+. LC-MS (Method M128): Rt = 2.65 min. | 1H-NMR (400 MHz, DMSO-d6): δ [ppm] = 2.03-2.08 (m, 1H), 2.18 -2.23 (m, 1H), 3.22-3.33(m, 4H), 3.78-3.80(m, 4H), 4.12(s, 3H), 4.20-4.30 (m, 2H), 5.23 (q, 1H), 6.78-6.80 (m, 1H), 6.91-6.95 (m, 1H), 7.15-7.20 (m, 1H), 7.22-7.26 (m, 1H), 7.37-7.40 (m, 1H), 7.61-7.66 (m, 1H), 8.38 (s, 1H), 8.63 (s, 1H), 9.22 (d, 1H). |
| T1-10 | MS (ESIpos): m/z = 511 (M + H)+. LC-MS (Method M52): Rt = 1.72 min. | 1H-NMR (300 MHz, DMSO-d6): δ [ppm] = 2.00-2.07 (m, 1H), 2.16-2.22 (m, 1H), 3.03 (d, 6H), 4.21-4.30 (m, 2H), 5.22 (q, 1H), 6.78-6.81 (m, 1H), 6.88-6.93 (m, 1H), 7.15-7.20 (m, 1H), 7.34-7.42 (m, 2H), 7.46-7.51 (m, 1H), 7.74-7.77 (m, 1H), 8.57-8.60 (m, 2H), 9.21 (d, 1H). |
| T1-11 | MS (ESIpos): m/z = 523 (M + H)+. LC-MS (Method M58): Rt = 1.74 min. | 1H-NMR (300 MHz, DMSO-d6): δ [ppm] = 1.99-2.07 (m, 1H), 2.15-2.22 (m, 1H), 2.98 (s, 6H), 4.10 (s, 3H), 4.20-4.27 (m, 2H), 5.22 (q, 1H), 6.78-6.80 (m, 1H), 6.88-6.93 (m, 1H), 7.14-7.19 (m, 1H), 7.33-7.38 (m, 2H), 7.43-7.48 (m, 1H), 7.70-7.73 (m, 1H) 8.27 (s, 1H), 8.47 (s, 1H), 9.10 (d, 1H). |
| T1-12 | MS (ESIpos): m/z = 497 (M + H)+. LC-MS (Method M127): Rt = 2.23 min. | 1H-NMR (300 MHz, DMSO-d6): δ [ppm] = 2.06-2.08 (m, 1H), 2.18-2.27 (m, 1H), 3.03 (d, 6H), 4.21-4.28 (m, 2H), 5.22 (q, 1H), 6.79-6.81 (m, 1H), 6.89-7.15 (m, 1H), 7.16-7.20 (m, 1H), 7.28-7.31 (m, 1H), 7.35-7.37 (m, 1H), 7.67-7.71 (m, 1H), 8.61 (d, 1H), 8.65 (s, 1H), 9.23 (d, 1H). |
| T1-13 | MS (ESIpos): m/z = 509 (M + H)+. LC-MS (Method M58): Rt = 1.73 min. | 1H-NMR (300 MHz, DMSO-d6): δ [ppm] = 2.01-2.07 (m, 1H), 2.15 -2.20 (m, 1H), 3.34 (s, 6H), 4.11 (s, 4H), 4.22-4.28 (m, 1H), 5.24 (q, 1H), 6.78-6.81 (m, 1H), 6.89-6.94 (m, 1H), 7.14-7.26 (m, 2H), 7.35 (d, 1H), 7.59-7.65 (m, 1H), 8.31 (s, 1H), 8.52 (s, 1H), 9.13 (d, 1H). |
| T1-14 | MS (ESIpos): m/z = 565 (M + H)+. LC-MS (Method M125): Rt = 2.83 min. | 1H-NMR (300 MHz, DMSO-d6): δ [ppm] = 2.02-2.08 (m, 1H), 2.17-2.22 (m, 1H), 3.21-3.33 (m, 4H), 3.78-3.81 (m, 4H), 4.13(s, 3H), 4.15-4.28 (m, 2H), 5.24 (q, 1H), 6.78-6.81 (m, 1H), 6.89-6.94 (m, 1H), 7.14-7.20 (m, 1H), 7.35-7.38 (m, 2H), 7.43-7.48 (m, 1H), 7.71-7.74 (m, 1H), 8.33 (s, 1H), 8.58 (s, 1H), 9.19 (d, 1H). |
| T1-15 | MS (ESIpos): m/z (M + H)+ 450.0; 451.9 | 1H-NMR(600.1 MHz, d6-DMSO): δ [ppm] = 9.3675 (5.6); 9.3541 (5.6); 9.3139 (12.1); 9.3103 (12.4); 9.1564 (0.5); 9.1358 (0.4); 8.9923 (0.4); 8.9889 (0.4); 8.9759 (11.7); 8.9723 (11.7); 8.7852 (9.4); 8.7759 (10.0); 8.1320 (11.2); 8.1227 (10.9); 7.8178 (0.4); 7.8030 (5.9); 7.7995 (5.3); 7.7908 (5.8); 7.7871 (6.5); 7.5991 (0.4); 7.5856 (0.3); 7.5368 (3.5); 7.5242 (10.0); 7.5117 (16.0); 7.5079 (9.3); 7.4988 (2.6); 7.4953 (1.6); 7.3889 (0.4); 7.3794 (0.4); 7.3625 (0.3); 7.2809 (5.6); 7.2683 (5.9); 7.2017 (2.8); 7.1995 (2.9); 7.1877 (5.7); 7.1760 (3.3); 7.1738 (3.2); 7.1462 (0.4); 7.1336 (0.6); 7.1209 (0.4); 6.9130 (3.8); 6.9113 (4.1); 6.8990 (7.1); 6.8882 (3.4); 6.8865 (3.6); 6.8620 (0.4); 6.8493 (0.4); 6.8354 (7.4); 6.8341 (7.4); 6.8217 (6.8); 6.8203 (6.7); 6.7661 (0.6); 6.7527 (0.6); 5.7562 (4.2); 5.3399 (1.7); 5.3293 (3.6); 5.3171 (3.5); 5.3069 (1.6); 4.3318 (1.0); 4.3265 (1.4); 4.3192 (1.1); 4.3132 (4.3); 4.3078 (3.5); 4.3000 (5.5); 4.2941 (5.2); 4.2876 (3.4); 4.2814 (3.7); 4.2744 (0.9); 4.2690 (1.3); 4.2630 (0.9); 3.8747 (1.7); 3.3175 (298.2); 3.3042 (3.9); 3.0969 (0.7); 2.8900 (0.4); 2.8754 (0.5); 2.6161 (2.4); 2.6131 (3.3); 2.6101 (2.5); 2.5221 (6.8); 2.5190 (9.0); 2.5159 (10.3); 2.5041 (407.2); 2.5011 (550.0); 2.4981 (416.4); 2.3880 (2.4); 2.3850 (3.3); 2.3821 (2.5); 2.2158 (0.9); 2.2100 (1.2); 2.2070 (1.1); 2.2014 (1.6); 2.1931 (2.1); 2.1869 (2.3); 2.1839 (2.0); 2.1782 (2.1); 2.1742 (1.7); 2.1717 (1.7); 2.1653 (1.2); 2.1176 (1.4); 2.1121 (1.6); 2.1070 (2.5); 2.1013 (2.6); 2.0956 (2.2); 2.0900 (2.1); 2.0837 (2.0); 2.0785 (1.6); 2.0726 (1.1); 2.0673 (0.8); 1.3512 (0.4); 1.2982 (0.9); 1.2701 (0.4); 1.2584 (1.6); 1.2350 (2.2); 1.1404 (0.6); 0.8531 (0.4); 0.0053 (1.3); -0.0001 (34.4); -0.0056 (1.2) |
| T2-5 | MS (ESIpos): m/z = 523 (M + H)+. LC-MS (Method M59): Rt = 1.33 min. | 1H-NMR (400 MHz, DMSO-d6): δ [ppm] = 2.01-2.07 (m, 1H), 2.15-2.21(m, 1H), 3.02 (s, 6H), 4.07-4.14 (m, 3H), 4.20-4.29 (m, 2H), 5.20 (q, 1H), 6.79-6.81 (m, 1H), 6.90-6.94 (m, 1H), 7.15-7.19 (m, 1H), 7.34-7.36 (m, 1H), 7.60-7.62 (m, 1H), 7.64 (d, 2H), 8.21 (s, 1H), 8.52 (s, 1H), 9.07 (d, 1H). |

TABLE 2-continued

Analytical Data for Examples T1-5 to T1-15, T2-5 to T2-12 and T3-5 to T3-20

| Example No | LC-MS | NMR |
|---|---|---|
| T2-6 | MS (ESIpos): m/z = 565 (M + H)+; LC-MS (Method YCT 20): Rt = 2.29 min. | 1H-NMR (400 MHz, DMSO-d6): δ [ppm] = 1.98-2.07 (m, 1H), 2.18-2.27 (m, 1H), 3.38-3.42 (m, 4H), 3.88-3.90 (m, 4H), 3.97 (s, 3H), 4.22-4.27 (m, 2H), 5.21-5.23 (m, 1H), 6.78 (d, 1H), 6.90 (t, 1H), 7.16 (t, 1H), 7.26-7.35 (m, 2H), 7.44 (m, 1H), 7.68 (d, 1H), 8.60 (s, 1H), 9.13 (d, 1H), 9.30 (s, 1H). |
| T2-7 | MS (ESIpos): m/z = 523 (M + H)+; LC-MS (Method YCT 19): Rt = 2.67 min. | 1H-NMR (300 MHz, DMSO-d6): δ [ppm] = 1.97-2.03 (m, 1H), 2.15-2.17 (m, 1H), 3.18-3.19 (m, 6H), 3.98 (s, 3H), 4.22-4.25 (m, 2H), 5.10-5.21 (m, 1H), 6.77-6.79 (m, 1H), 6.88-6.92 (m, 1H), 7.13-7.18 (m, 1H), 7.31-7.34 (m, 2H), 7.40-7.41 (m, 1H), 7.59-7.60 (m, 1H), 8.53 (s, 1H), 9.02-9.05 (m, 1H), 9.31 (s, 1H). |
| T2-8 | MS (ESIpos): m/z = 523 (M + H)+; LC-MS (Method M127): Rt = 2.67 min. | 1H-NMR (300 MHz, DMSO-d6): δ [ppm] = 1.97-2.03 (m, 1H), 2.15-2.17 (m, 1H), 3.18-3.19 (m, 6H), 3.98 (s, 3H), 4.22-4.25 (m, 2H), 5.10-5.21 (m, 1H), 6.77-6.79 (m, 1H), 6.88-6.92 (m, 2H), 7.13-7.18 (m, 1H), 7.31-7.34 (m, 2H), 7.40-7.41 (m, 1H), 7.59-7.60 (m, 1H), 8.53 (s, 1H), 9.02-9.05 (m, 1H), 9.31 (s, 1H). |
| T2-9 | MS (ESIpos): m/z = 565 (M + H)+; LC-MS (Method M128): Rt = 2.29 min. | 1H-NMR (300 MHz, DMSO-d6): δ [ppm] = 1.23-1.31 (m, 1H), 1.98-2.07 (m, 1H), 2.18-2.27 (m, 1H), 3.32-3.37 (m, 3H), 3.87-3.93 (m, 3H), 4.18-4.19 (m, 3H), 4.22-4.30 (m, 2H), 5.20-5.23 (m, 1H), 6.77-6.80 (m, 1H), 6.89-6.94 (m, 1H), 7.14-7.19 (m, 1H), 7.34-7.37 (m, 1H), 7.42-7.43 (m, 3H), 7.60-7.62 (m, 1H), 8.66 (s, 1H), 9.10-9.15 (m, 1H), 9.30 (s, 1H). |
| T2-10 | MS (ESIpos): m/z = 565 (M + H)+. LC-MS (Method M43): Rt = 2.00 min. | 1H-NMR (300 MHz, DMSO-d6): δ [ppm] = 2.02-2.06 (m, 1H), 2.15-2.24 (m, 1H), 3.28 (s, 4H), 3.78 (s, 4H), 4.09 (s, 3H), 4.18-4.28 (m, 2H), 5.20 (q, 1H), 6.77-6.79 (m, 1H), 6.89-6.93 (m, 1H), 7.13-7.18 (m, 1H), 7.34-7.37 (m, 1H), 7.59 (s, 3H), 8.25 (s, 1H), 8.64 (s, 1H), 9.12 (d, 1H). |
| T2-11 | MS (ESIpos): m/z = 565 (M + H)+. LC-MS (Method M52): Rt = 1.52 min. | 1H-NMR (300 MHz, DMSO-d6): δ [ppm] = 2.05-2.19 (m, 2H), 3.28-3.31 (m, 4H), 3.81 (s, 4H), 4.12 (s, 3H), 4.19-4.27 (m, 2H), 5.20 (q, 1H), 6.77-6.80 (m, 1H), 6.88-6.93 (m, 1H), 7.13-7.19 (m, 1H), 7.34-7.46 (m, 3H), 7.67-7.71 (m, 1H), 8.11 (s, 1H), 8.57 (s, 1H), 9.16 (d, 1H). |
| T2-12 | MS (ESIpos): m/z = 523 (M + H)+. LC-MS (Method MY-15): Rt = 1.13 min. | LC-MS (Method Y-15): Rt = 1.13 min. 1H-NMR (300 MHz, DMSO-d6): δ [ppm] = 2.02-2.03 (m, 2H), 3.02 (s, 6H), 4.10 (s, 3H), 4.19-4.29 (m, 2H), 5.21 (q, 1H), 6.77-6.79 (m, 1H), 6.87-6.92 (m, 1H), 7.13-7.18 (m, 1H), 7.31-7.45 (m, 3H), 7.67-7.70 (m, 1H), 8.04 (s, 1H), 8.43 (s, 1H), 9.05 (d, 1H). |
| T3-5 | MS (ESIpos): m/z = 513 (M + H)+. LC-MS (Method M68): Rt = 1.91 min. | 1H-NMR (400 MHz, DMSO-d6): δ [ppm] = 1.93-1.97 (m, 1H), 2.10-2.13 (m, 1H), 3.24 (s, 6H), 4.13-4.21 (m, 2H), 5.14-5.15 (m, 1H), 6.70-6.72 (m, 1H), 6.83 (t, 1H), 7.07-7.10 (m, 1H), 7.17-7.26 (m, 2H), 7.61-7.69 (m, 1H), 8.42 (s, 1H), 8.94-9.00 (m, 2H). |
| T3-6 | MS (ESIpos): m/z = 555 (M + H)+. LC-MS (Method M68): Rt = 1.89 min. | 1H-NMR (300 MHz, DMSO-d6): δ [ppm] = 2.05-2.07 (m, 1H), 2.19-2.21 (m, 1H), 3.64 (s, 4H), 3.82 (s, 4H), 4.22-4.28 (m, 2H), 5.21-5.24 (m, 1H), 6.79 (d, 1H), 6.91 (t, 1H), 7.14-7.18 (m, 1H), 7.287.29 (m, 1H), 7.33-7.35 (m, 1H), 7.73-7.74 (m, 1H), 8.59 (d, 1H), 9.08(s, 1H), 9.12-9.14 (d, 1H). |
| T3-7 | MS(ESIpos): m/z = 527 (M + H)+. LC-MS (Method M130): Rt = 2.01 min. | 1H-NMR (400 MHz, DMSO-d6): δ [ppm] = 2.00-2.05 (m, 1H), 2.15-2.21 (m, 1H), 3.29 (s, 6H), 4.20-4.29 (m, 2H), 5.19-5.24 (m, 1H), 6.79 (d, 1H), 6.90 (t, 1H), 7.16 (t, 1H), 7.32 (d, 1H), 7.46 (s, 2H) 7.74 (s, 1H), 8.49 (s, 1H), 8.97 (s, 1H), 9.07 (d, 1H). |
| T3-8 | MS(ESIpos): m/z = 528 (M + H)+. LC-MS (Method M130): Rt = 1.91 min. | 1H-NMR (400 MHz, DMSO-d6): δ [ppm] = 1.99-2.04 (m, 1H), 2.15-2.21 (m, 1H), 3.31-3.33 (m, 6H), 4.22-4.28 (m, 2H), 5.21 (q, 1H), 6.77-6.79 (m, 1H), 6.87-6.91 (m, 1H), 7.13-7.17 (m, 1H), 7.31-7.36 (m, 2H), 7.49-7.54 (m, 1H) 7.76-7.78 (m, 1H), 8.45 (d, 1H), 8.99 (s, 1H), 9.06 (d, 1H). |
| T3-9 | MS(ESIpos): m/z = 570 (M + H)+. LC-MS (Method M130): Rt = 1.79 min. | 1H-NMR (400 MHz, DMSO-d6): δ [ppm] = 2.01-2.05 (m, 1H), 2.18-2.50 (m, 1H), 3.64 (s, 4H), 3.82-3.90 (m, 4H), 4.20-4.30 (m, 2H), 5.22 (q, 1H), 6.78-6.80 (m, 1H), 6.88-6.92 (m, 1H), 7.14-7.18 (m, 1H), 7.32-7.37 (m, 2H), 7.50-7.55 (m, 1H), 7.77-7.79 (m, 1H), 8.55 (d, 1H), 9.06 (s, 1H), 9.12 (d, 1H). |
| T3-10 | MS (ESIpos): m/z = 524 (M + H)+. LC-MS (Method M68): Rt = 1.92 min. | 1H-NMR (400 MHz, DMSO-d6): δ [ppm] = 1.98-2.04 (m, 1H), 2.15-2.18 (m, 1H), 3.33 (s, 6H), 4.03-4.04 (s, 3H), 4.21-4.29 (m, 2H), 5.19-5.24 (m, 1H), 6.78 (d, 1H), 6.90 (t, 1H), 7.14-7.17 (m, 2H), 7.31-7.38 (m, 2H), 7.64 (s, 1H), 8.43 (s, 1H), 8.98-9.00 (m, 2H). |
| T3-11 | MS (ESIpos): m/z = 512 (M + H)+. LC-MS (Method M68): Rt = 1.82 min. | 1H-NMR (400 MHz, DMSO-d6): δ [ppm] = 1.98-2.07 (m, 1H), 2.18-2.50 (m, 1H), 6.27 (d, 6H), 4.21-4.29 (m, 2H), 5.21-5.24 (m, 1H), 6.79 (d, 1H), 6.91 (t, 1H), 7.14-7.18 (m, 1H), 7.32-7.34 (m, 2H), 7.60 (m, 1H), 7.75 (t, 1H), 8.53 (s, 1H), 9.00 (s, 1H), 9.06 (d, 1H). |

TABLE 2-continued

Analytical Data for Examples T1-5 to T1-15, T2-5 to T2-12 and T3-5 to T3-20

| Example No | LC-MS | NMR |
|---|---|---|
| T3-12 | MS (ESIpos): m/z = 524 (M + H)+. LC-MS (Method M68): Rt = 1.79 min. | 1H-NMR (400 MHz, DMSO-d6): δ [ppm] = 1.98-2.07 (m, 1H), 2.18-2.50 (m, 1H), 3.33 (d, 6H), 4.02-4.28 (m, 5H), 5.21-5.24 (m, 1H), 6.79 (d, 1H), 6.91 (t, 1H), 7.14-7.18 (m, 1H), 7.32-7.34 (m, 2H), 7.60 (m, 1H), 7.75 (t, 1H), 8.39 (s, 1H), 8.97-9.00 (m, 2H). |
| T3-14 | MS (ESIpos): m/z = 566 (M + H)+. LC-MS (Method M68): Rt = 1.79 min. | 1H-NMR (300 MHz, DMSO-d6): δ [ppm] = 1.98-2.07 (m, 1H), 2.18-2.50 (m, 1H), 3.65(s, 4H), 3.82 (s, 4H), 4.03-4.26 (m, 3H), 4.30-4.31 (m, 2H), 5.23-5.25 (m, 1H), 6.789 (d, 1H), 6.91 (t, 1H), 7.15 (t, 1H), 7.16-7.19 (m, 1H), 7.23-7.28 (m, 1H), 7.42-7.48 (m, 1H), 7.71-7.72 (m, 1H), 8.51 (s, 1H), 9.07-9.12 (m, 2H) |
| T3-15 | MS (ESIpos): m/z = 509 (M + H)+. LC-MS (Method M68): Rt = 1.74 min. | 1H-NMR (400 MHz, DMSO-d6): δ [ppm] = 1.98-2.04 (m, 1H), 2.15-2.18 (m, 1H), 3.32 (d, 6H), 4.05 (s, 3H), 4.20-4.28 (m, 2H), 5.21-5.22 (m, 1H), 6.77-6.79 (m, 1H), 6.90 (t, 1H), 7.19-7.17 (m, 2H), 7.32 (d, 1H), 7.57-7.64 (m, 1H), 8.42 (s, 1H), 8.98-9.00 (m, 2H). |
| T3-16 | MS (ESIpos): m/z = 551 (M + H)+. LC-MS (Method M68): Rt = 1.73 min. | 1H-NMR (300 MHz, DMSO-d6): δ [ppm] = 1.98-2.22 (m, 2H), 3.34(s, 4H), 3.64 (s, 4H), 4.07-4.08 (m, 3H), 4.21-4.29 (m, 2H), 5.22-5.26 (m, 1H), 6.79 (d, 1H), 6.88-6.93 (m, 1H), 7.10-7.18 (m, 2H), 7.34 (d, 1H), 7.60-7.65 (m, 1H), 8.55 (s, 1H), 9.07-9.11(m, 2H) |
| T3-17 | MS(ESIpos): m/z = 512 (M + H)+. LC-MS (Method M92): Rt = 2.06 min. | 1H-NMR (400 MHz, DMSO-d6): δ [ppm] = 1.99-2.03 (m, 1H), 2.15-2.21 (m, 1H), 3.31 (s, 6H), 4.20-4.28 (m, 2H), 5.20-5.22 (m, 1H), 6.78 (d, 1H), 6.89 (t, 1H), 7.15 (t, 1H), 7.31 (d, 1H), 7.39-7.44 (m, 1H), 7.49-7.54 (m, 1H), 7.78-7.80 (m, 1H), 8.46 (d, 1H), 9.03-9.05 (m, 2H) |
| T3-18 | MS (ESIpos): m/z = 535 (M + H)+. LC-MS (Method M92): Rt = 1.97 min. | 1H-NMR (300 MHz, DMSO-d6): δ [ppm] = 2.02-2.07 (m, 1H), 2.19-2.21 (m, 1H), 3.64 (s, 4H), 3.82 (s, 4H), 4.19-4.29 (m, 2H), 5.20-5.25 (m, 1H), 6.79 (d, 1H), 6.90 (t, 1H), 7.16 (t, 1H), 7.32-7.55 (m, 3H), 7.79-7.81 (m, 1H), 8.57 (d, 1H), 9.11-9.13 (m, 2H) |
| T3-19 | MS (ESIpos): m/z = 497 (M + H)+. LC-MS (Method M119): Rt = 1.29 min. | 1H-NMR (300 MHz, DMSO-d6): δ [ppm] = 1.98-2.07 (m, 1H), 2.18-2.50 (m, 1H), 3.30-3.33 (d, 6H), 4.22-4.27 (m, 1H), 5.21-5.22 (m, 1H), 6.78 (d, 1H), 6.88 (t, 1H), 7.14-7.18 (m, 1H), 7.32-7.34 (m, 2H), 7.74-7.77 (m, 1H), 8.51 (s, 1H), 9.05-9.07 (m, 2H). |
| T3-20 | MS (ESIpos): m/z = 539 (M + H)+. LC-MS (Method M68): Rt = 1.79 min. | 1H-NMR (300 MHz, DMSO-d6): δ [ppm] = 1.98-2.07 (m, 1H), 2.18-2.50 (m, 1H), 3.64(s, 4H), 3.82 (s, 4H), 4.20-4.28 (m, 2H), 5.23 (s, 1H), 6.79 (d, 1H), 6.90 (t, 1H), 7.17 (t, 1H), 7.34-7.36 (m, 2H), 7.73-7.80 (m, 1H), 8.62 (s, 1H), 9.12-9.15 (m, 2H) |

EXPERIMENTAL SECTION—BIOLOGICAL ASSAYS

Examples were tested in selected biological assays one or more times. When tested more than once, data are reported as either average values or as median values, wherein
  the average value, also referred to as the arithmetic mean value, represents the sum of the values obtained divided by the number of times tested, and
  the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values or median values calculated utilizing data sets obtained from testing of one or more synthetic batch.

The in vitro activity of the compounds of the present invention can be demonstrated in the following assays:

In Vitro Assay 1: *C. elegans* Slo-1a—Action at a Recombinant *C. elegans* Cell Line Generation of a Stable *C. elegans* CHO Cell Line A CHO cell line was obtained from ATCC, code ATCC CRL-9096. For transfection with plasmid DNA to express *C. elegans* Slo-1a (accession number AAL28102) CHO cells were passaged to 40% confluence before adding the transfection solution to the cell culture. The transfection solution included 300 μL OptiMEM (Life Technologies, Nr.: 31985), 2 μL (=6 μg) of plasmid DNA containing the *C. elegans* Slo 1a gene and 9 μL FugeneHD (Promega, Nr.: E2311), and was added to the cells prior to incubation for 48 hours at 37° C., 5% $CO_2$. The transfection medium was exchanged for the selection medium which contains additional G418 (2 mg/ml, Invitrogen, Nr.: 10131) and the cells were seeded into 384 well plates (300 cells/well). After a few weeks, the remaining surviving cells were tested with a voltage sensitive dye (Membrane Potential Assay Kit, Molecular Devices Nr.: R8034) for K+ channel expression. Positive cell clones were purified by the limited dilution technique. For this the clone with the highest and most robust signal in the voltage sensitive dye assay was further subcloned (incubated) in 384 well plates (0.7 cells/well) in order to obtain clonal purity. This generated a final stable CHO cell line expressing the *C. elegans* Slo-1a.

Cell Culture Conditions

Cells were cultured at 37° C. and 5% $CO_2$ in MEMalpha with Gutamax I (Invitrogen, Nr.: 32571), supplemented with 10% (v/v) heat inactivated fetal bovine serum (Invitrogen, Nr.: 10500), G418 (1 mg/ml, Invitrogen, Nr.: 10131). Cells were detached using Accutase (Sigma, Nr.: A6964).

Membrane Potential Measurements

Laboratory compound testing was performed on 384-well microtiter plates (MTPs, Greiner, Nr.: 781092). 8000 cells/well were plated onto 384-well MTPs and cultured for 20 to 24 hours at 37° C. and 5% $CO_2$. After removal of the cell culture medium, the cells were washed once with tyrode (150 mM NaCl, 0.3 mM KCl, 2 mM $CaCl_2$, 1 mM $MgCl_2$, 0.8 mM $NaH_2PO_4$, 5 mM Glucose, 28 mM Hepes, pH 7.4) and then loaded with the voltage sensitive dye of the Membrane Potential Assay Kit diluted in tyrode for 1 h at room temperature.

After starting the measurement of fluorescence using a FLIPR Tetra (Molecular Devices, Exc. 510-545 nm, Emm. 565-625 nm), test compounds were added followed by the addition of KCl tyrode (final assay concentration: 70 mM KCl, 2 mM $CaCl_2$, 1 mM $MgCl_2$, 0.8 mM $NaH_2PO_4$, 5 mM Glucose, 28 mM Hepes, pH 7.4, including the voltage sensitive dye). The measurement was completed after 7 minutes.

Statistics

The data were evaluated by using the ActivityBase XLfit software (IDBS) for curve fitting and calculation of the half-maximal effective concentration ($EC_{50}$) and are reported as negative decadic logarithm ($pE_{50}$).

For the following examples, $pE_{50}$>6.5-7.5 has been found for: T1-15, T5-4, T6-2, T6-4.

For the following examples, $pE_{50}$>7.5-8.5 has been found for: T1-1, T1-2, T1-3, T1-4, T1-5, T1-9, T1-10, T1-11, T1-14, T2-1, T2-2, T2-3, T2-4, T3-1, T3-2, T4-1, T4-2, T5-2, T5-5, T5-6, T5-8, T6-1, T6-3.

For the following examples, $pE_{50}$>8.5 has been found for: T1-6, T1-7, T2-11, T2-12, T3-1, T3-3, T3-4, T5-1, T5-3, T5-7.

In Vitro Assay 2: *D. immitis* Slo-1—Action at a Recombinant *D. immitis* Cell Line Generation of a Stable *D. immitis* Slo-1 CHO Cell Line A CHO cell line was obtained from ATCC, code ATCC CRL-9096. For transfection with plasmid DNA to express *D. immitis* Slo-1 (based on Protein sequence JQ730003, codon optimized for hamster) CHO cells were passaged to 40% confluence before adding the transfection solution to the cell culture. The transfection solution included 300 µL OptiMEM (Life Technologies, Nr.: 31985), 2 μL (=6 μg) of plasmid DNA containing the *D. immitis* Slo 1 gene and 9 μL FugeneHD (Promega, Nr.: E2311), and was added to the cells prior to incubation for 48 hours at 37° C., 5% C02. The transfection medium was exchanged for the selection medium which contains additional G418 (2 mg/ml, Invitrogen, Nr.: 10131) and the cells were seeded into 384 well plates (300 cells/well). After a few weeks, the remaining surviving cells were tested with a voltage sensitive dye (Membrane Potential Assay Kit, Molecular Devices Nr.: R8034) for K+ channel expression. Positive cell clones were purified by the limited dilution technique. For this the clone with the highest and most robust signal in the voltage sensitive dye assay was further subcloned (incubated) in 384 well plates (0.7 cells/well) in order to obtain clonal purity. This generated a final stable CHO cell line expressing the *D. immitis*_Slo-1.

Cell Culture Conditions

Cells were cultured at 37° C. and 5% $CO_2$ in MEMalpha with Gutamax I (Invitrogen, Nr.: 32571), supplemented with 10% (v/v) heat inactivated fetal bovine serum (Invitrogen, Nr.: 10500), G418 (1 mg/ml, Invitrogen, Nr.: 10131). Cells were detached using Accutase (Sigma, Nr.: A6964).

Membrane Potential Measurements

Laboratory compound testing was performed on 384-well microtiter plates (MTPs, Greiner, Nr.: 781092). 8000 cells/well were plated onto 384-well MTPs and cultured for 20 to 24 hours at 37° C. and 5% $CO_2$. After removal of the cell culture medium, the cells were washed once with tyrode (150 mM NaCl, 0.3 mM KCl, 2 mM $CaCl_2$, 1 mM $MgCl_2$, 0.8 mM $NaH_2PO_4$, 5 mM Glucose, 28 mM Hepes, pH 7.4) and then loaded with the voltage sensitive dye of the Membrane Potential Assay Kit diluted in tyrode for 1 h at room temperature.

After starting the measurement of fluorescence using a FLIPR Tetra (Molecular Devices, Exc. 510-545 nm, Emm. 565-625 nm), test compounds were added followed by the addition of KCl tyrode (final assay concentration: 70 mM KCl, 2 mM $CaCl_2$, 1 mM $MgCl_2$, 0.8 mM $NaH_2PO_4$, 5 mM Glucose, 28 mM Hepes, pH 7.4, including the voltage sensitive dye). The measurement was completed after 7 minutes.

Statistics

The data were evaluated by using the ActivityBase XLfit software (IDBS) for curve fitting and calculation of the half-maximal effective concentration ($EC_{50}$) and are reported as negative decadic logarithm ($pE_{50}$).

For the following examples, $pE_{50}$>6.5-7.5 has been found for: T1-1, T1-2, T1-3, T1-4, T1-5, T1-8, T1-9, T1-10, T1-11, T1-12, T1-13, T1-14, T2-1, T2-4, T2-5, T2-10, T2-11, T2-12, T4-1, T4-2, T5-1, T5-2, T5-4, T5-5, T5-6, T5-7, T5-8, T6-3, T6-4.

For the following examples, $pE_{50}$>7.5-8.5 has been found for: T1-6, T1-7, T2-3, T2-6, T2-7, T2-8, T2-9, T3-1, T3-3, T3-4, T3-5, T3-6, T3-7, T3-8, T3-9, T3-10, T3-11, T3-12, T3-14, T3-15, T3-16, T3-17, T3-18, T3-19, T3-20, T5-3.

In Vitro Assay 3: *Nippostrongylus brasiliensis* (NIPOBR)

Adult *Nippostrongylus brasiliensis* were washed with saline buffer containing 100 U/ml penicillin, 0.1 mg/ml streptomycin and 2.5 μg/ml amphotericin B. Test compounds were dissolved in DMSO and worms were incubated in medium in a final concentration of 10 μg/ml (10 ppm) respectively 1 μg/ml (1 ppm). An aliquot of the medium was used to determine the acetylcholine esterase activity in comparison to a negative control. The principle of measuring acetylcholine esterase as readout for anthelmintic activity was described in Rapson et al (1986) and Rapson et al (1987).

For the following examples, activity (reduction of AChE compared to negative control) was higher than 80% at 10 μg/ml: T1-2, T1-3, T1-4, T1-5, T1-7, T1-8, T1-9, T1-10, T1-11, T1-12, T1-13, T1-14, T2-2, T2-5, T2-8, T2-9, T2-10, T2-11, T2-12, T3-8, T3-9, T3-10, T3-11, T3-12, T3-14, T3-15, T3-16, T3-17, T3-18, T3-19, T3-20, T4-1, T4-2.

For the following examples, activity (reduction of AChE compared to negative control) was higher than 80% at 1 μg/ml: T1-1, T1-2, T1-3, T1-4, T1-5, T1-6, T1-7, T1-8, T1-9, T1-11, T1-12, T1-13, T1-14, T2-1, T2-3, T2-4, T2-5, T2-8, T2-9, T2-10, T2-11, T2-12, T3-1, T3-3, T3-4, T3-8, T3-9, T3-10, T3-11, T3-12, T3-14, T3-15, T3-16, T3-17, T3-18, T3-19, T3-20, T4-1, T4-2, T5-1, T5-3, T5-5, T5-7, T6-1, T6-2, T6-3.

In Vitro Assay 4: *Dirofilaria immitis* Microfilariae (DIROIM L1)

≥250 *Dirofilaria immitis* microfilariae, which were freshly purified from blood, were added to wells of a microtitre plate containing a nutrient medium and the test compound in DMSO. Compounds were tested in concentration-response assay in duplicate. Larvae exposed to DMSO and no test compounds were used as negative controls. Larvae were evaluated after 72 h of incubation with the compound. Efficacy was determined as the reduction of motility in comparison to the negative control. Based on the evaluation of a wide concentration range, concentration-response curves as well as $EC_{50}$-values were calculated.

For the following examples, the $EC_{50}$ was <0.1 ppm: T1-1, T1-2, T1-3, T1-4, T1-5, T1-6, T1-7, T1-8, T1-10, T1-11, T1-12, T1-13, T1-14, T2-1, T2-2, T2-3, T2-4, T2-5, T2-6, T2-7, T2-8, T2-9, T2-10, T2-11, T2-12, T3-1, T3-2, T3-3, T3-4, T3-5, T3-6, T3-7, T3-8, T3-9, T3-10, T3-11, T3-12, T3-14, T3-15, T3-16, T3-17, T3-18, T3-19, T3-20, T4-1, T4-2, T5-1, T5-2, T5-3, T5-4, T5-5, T5-6, T5-7, T5-8, T6-1, T6-2, T6-3.

In Vitro Assay 5: *Dirofilaria immitis* (DIROIM L4)

10 *Dirofilaria immitis* third-stage larvae, which were freshly isolated from their vector (intermediate host), were added to wells of a microtitre plate containing a nutrient medium and the test compound in DMSO. Compounds were tested in concentration-response assay in duplicate. Larvae exposed to DMSO and no test compounds were used as negative controls. Larvae were evaluated after 72 h of incubation with the compound. Within these 72 h of incubation the majority of larvae in negative control moult to fourth-stage larvae. Efficacy was determined as the reduction of motility in comparison to the negative control. Based on the evaluation of a wide concentration range, concentration-response curves as well as $EC_{50}$-values were calculated.

For the following examples, the $EC_{50}$ was <0.1 ppm: T1-1, T1-2, T1-3, T1-4, T1-5, T1-6, T1-7, T1-8, T1-9, T1-10, T1-11, T1-12, T1-13, T1-14, T2-1, T2-3, T2-4, T2-5, T2-6, T2-7, T2-8, T2-9, T2-10, T2-11, T2-12, T3-1, T3-2, T3-3, T3-4, T3-5, T3-6, T3-7, T3-8, T3-9, T3-10, T3-11, T3-12, T3-14, T3-15, T3-16, T3-17, T3-18, T3-19, T3-20, T4-1, T4-2, T5-1, T5-3, T5-5, T5-7, T6-1, T6-3.

In Vitro Assay 6: *Litomosoides sigmodontis* (LTMOSI L3)

10 *Litomosoides sigmodontis* third-stage larvae, which were freshly isolated from the pleural cavity of an infected rodent, were added to wells of a microtitre plate containing a nutrient medium and the test compound in DMSO. Compounds were tested in concentration-response assay in duplicate. Larvae exposed to DMSO and no test compounds were used as negative controls. Larvae were evaluated after 72 h of incubation with the compound. Efficacy was determined as the reduction of motility in comparison to the negative control. Based on the evaluation of a wide concentration range, concentration-response curves as well as $EC_{50}$-values were calculated.

For the following examples, the $EC_{50}$ was <0.1 ppm: T1-1, T1-4, T1-5, T1-10, T1-12, T2-5, T2-12, T3-1, T3-3, T3-15, T3-17, T3-20, T5-7.

In Vitro Assay 6: *Cooperia curticei*

Solvent: Dimethyl Sulfoxide

To produce a suitable preparation of active compound, 10 mg of active compound are dissolved in 0.5 ml solvent, and the concentrate is diluted with "Ringer's solution" to the desired concentration.

Approximately 40 nematode larvae (*Cooperia curticei*) are transferred into a test tube containing the compound solution.

After 5 days percentage of larval mortality is recorded. 100% efficacy means all larvae are killed; 0% efficacy means no larvae are killed.

In this test for example, the following compounds from the preparation examples showed good activity of 100% at an application rate of 20 ppm: T1-1, T1-2, T1-3, T1-5, T1-6, T2-1, T2-3, T3-1, T3-3, T3-4, T5-7.

In this test for example, the following compounds from the preparation examples showed good activity of 90% at an application rate of 20 ppm: T3-2, T6-1, T6-2, T6-4.

In this test for example, the following compounds from the preparation examples showed good activity of 80% at an application rate of 20 ppm: T4-1, T5-2, T5-3, T5-5, T5-6.

In this test for example, the following compounds from the preparation examples showed good activity of 100% at an application rate of 4 ppm: T1-1, T1-2, T1-3, T1-4, T1-5, T1-6, T2-1, T3-1, T3-3, T3-4, T5-7.

In this test for example, the following compounds from the preparation examples showed good activity of 90% at an application rate of 4 ppm: T3-2.

In this test for example, the following compounds from the preparation examples showed good activity of 80% at an application rate of 4 ppm: T2-3, T5-5.

In Vitro Assay 7: *Haemonchus contortus*

Solvent: Dimethyl Sulfoxide

To produce a suitable preparation of active compound, 10 mg of active compound are dissolved in 0.5 ml solvent, and the concentrate is diluted with "Ringer's solution" to the desired concentration.

Approximately 40 larvae of the red stomach worm (*Haemonchus contortus*) are transferred into a test tube containing compound solution.

After 5 days the percentage of larval mortality is recorded. 100% efficacy means all larvae are killed, 0% efficacy means no larvae are killed.

In this test for example, the following compounds from the preparation examples showed good activity of 100% at an application rate of 20 ppm: T1-1, T1-3, T1-6, T2-1, T3-1, T3-3, T3-4, T6-1.

In this test for example, the following compounds from the preparation examples showed good activity of 90% at an application rate of 20 ppm: T1-2, T2-3, T3-2, T5-7, T6-3.

In this test for example, the following compounds from the preparation examples showed good activity of 80% at an application rate of 20 ppm: T1-5, T5-2, T5-5, T6-4.

Formulation Example

Exemplary formulations consisted of the active substance in 10% Transcutol, 10% Cremophor EL and 80% isotonic saline solution. First the active substance was dissolved in Transcutol. After solution in Transcutol, Cremophor and isotonic saline solution were added. These formulations were used as service formulations in the following in vivo assay.

Exemplary formulations consisted of the active substance in 10% Transcutol, 10% Cremophor EL and 80% isotonic saline solution. First the active substance was dissolved in Transcutol. After solution in Transcutol, Cremophor and isotonic saline solution were added. These formulations were used as service formulations in the following in vivo assay.

An example for a formulation according to the present invention is the following formulation Example F1. Therein, the active substance was dissolved in Transcutol to form a stock solution A. Then 0.100 mL of this stock solution A were taken and 0.100 mL Cremophor EL and 0.800 mL isotonic saline solution were added. The resulting liquid formulation (formulation example F1) had a volume of 1 mL.

Stocksolution A:

| 4.0 mg | compound of example T5-1, |
| 0.100 mL | Transcutol. |

Formulation Example F1

| 0.100 mL | stock solution A, |
| 0.100 mL | Cremophor EL, and |
| 0.800 mL | isotonic saline solution. |

In Vivo Assay

*Haemonchus contortus/Trichostrongylus colubriformis*/Gerbil

Gerbils, experimentally infected with *Haemonchus* and/or *Trichostrongylus*, were treated once during late prepatency. Test compounds were formulated as solutions or suspensions and applied orally or intraperitoneally. For both applications the same service formulation was used. The volume of the application amounted to normally 20 ml/kg at a maximum. By way of example, a gerbil with 40 g body weight was treated with 0.200 mL of the formulation of formulation example F1. This corresponded to a treatment with 20 mg/kg body weight.

Efficacy was determined per group as reduction of worm count in stomach and small intestine, respectively, after necropsy compared to worm count in an infected and placebo-treated control group.

The following examples were tested and had an activity of ≥70% or higher at the given treatment:

| Treatment | Haemonchus contortus | Trichostrongylus colubriformis |
|---|---|---|
| ≤2.5 mg/kg intraperitoneally | T1-3, T1-5, T1-6, T2-1, T2-3, T3-3, T3-4, T5-1 | T3-3 |

The invention claimed is:

1. A compound of formula (I):

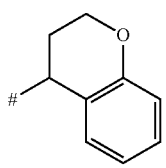

wherein:

A is

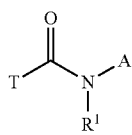

T is selected from the group consisting of $T^1$, $T^2$, $T^3$, $T^4$, $T^5$, and $T^6$;

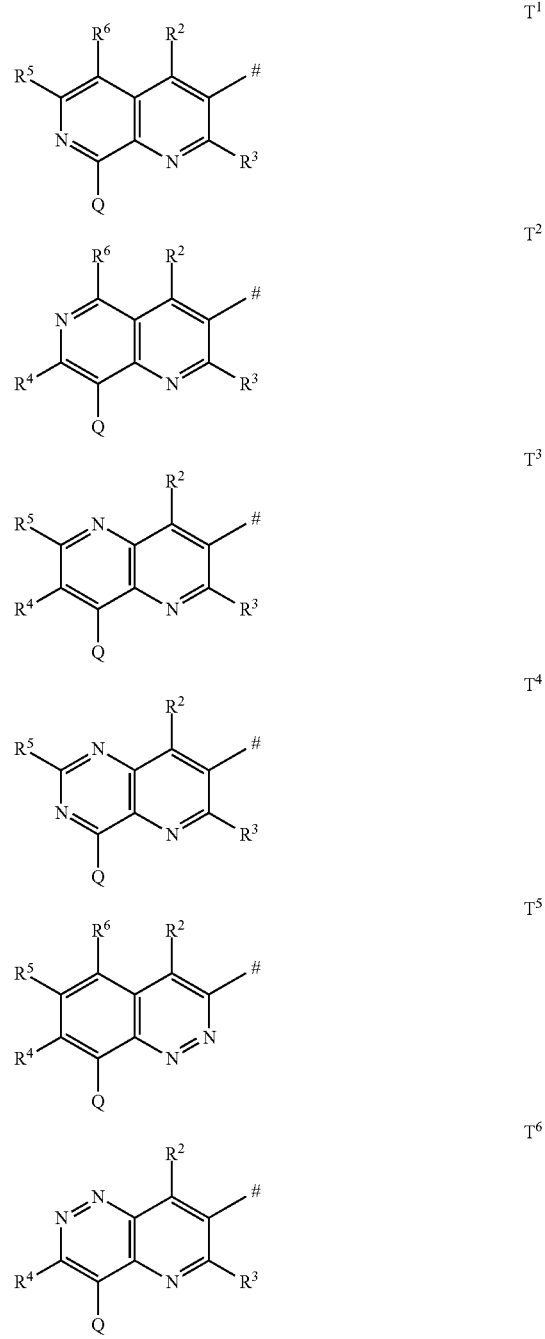

$R^1$ is selected from the group consisting of hydrogen or methyl, cyano, —CHO, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, $C_3$-$C_6$-halogenocycloalkyl having 1 to 5 halogen atoms, $C_3$-$C_4$-alkenyl, $C_3$-$C_4$-alkynyl, $C_1$-$C_4$-alkoxy-$C_1$-$C_4$-alkyl, $C_3$-$C_6$-cycloalkyl-$C_1$-$C_3$-alkyl, cyano-$C_1$-$C_4$-alkyl, —NH—$C_1$-$C_4$-alkyl, —N($C_1$-$C_4$-alkyl)$_2$, NH$_2$—$C_1$-$C_4$-alkyl-, $C_1$-$C_4$-alkyl-NH-$C_1$-$C_4$-alkyl-, ($C_1$-$C_4$-alkyl)$_2$N-$C_1$-$C_4$-alkyl-, $C_1$-$C_4$-alkyl-C(O)—, $C_1$-$C_4$-halogenoalkyl-C(O)— having 1 to 5 halogen atoms, $C_1$-$C_4$-alkoxy-C(O)—, benzyloxy-C(O)—, $C_1$-$C_4$-alkoxy-$C_1$-$C_4$-alkyl-C(O)—, —$SO_2$—$C_1$-$C_4$-alkyl, —$SO_2$—$C_1$-$C_4$-halogenoalkyl having 1 to 5 halogen atoms, phenyl-$C_1$-$C_4$-alkyl, optionally substituted by 1, 2, 3, 4, or 5 substituents independently selected from the group consisting of halogen, —OH, —$NO_2$, cyano, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S-$C_1$-$C_4$-halogenoalkyl having 1 to 5 halogen atoms, —S(O)—$C_1$-$C_4$-halogenoalkyl having 1 to 5 halogen atoms, and —$SO_2$—$C_1$-$C_4$-halogenoalkyl having 1 to 5 halogen atoms, and heterocyclyl-$C_1$-$C_4$-alkyl, wherein the heterocyclyl substituent is selected from the group consisting of 4- to 10-membered heterocycloalkyl, 5-membered heteroaryl, and 6-membered heteroaryl, each of which is optionally substituted by 1, 2, or 3 substituents independently selected from the group consisting of halogen, —OH, —$NO_2$, cyano, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, and —$SO_2$—$C_1$-$C_4$-halogenoalkyl having 1 to 5 halogen atoms;

$R^2$ is selected from the group consisting of
hydrogen, halogen, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, —$NR^{12}R^{13}$, —$OR^{14}$, —$SR^{15}$, —$S(O)R^{15}$, —$SO_2R^{15}$, $C_1$-$C_6$-alkyl, $C_3$-$C_6$-cycloalkyl, $C_2$-$C_4$-alkenyl, $C_3$-$C_6$-cycloalkenyl, $C_2$-$C_4$-alkynyl, phenyl-$C_1$-$C_4$-alkyl, each of which is optionally substituted by 1, 2, 3, 4, or 5 substituents independently selected from the group consisting of halogen, —OH, —$NO_2$, cyano, $C_1$-$C_4$-alkyl-C(O)—, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, and —$SO_2$—$C_1$-$C_4$-halogenoalkyl having 1 to 5 halogen atoms, heterocyclyl-$C_1$-$C_4$-alkyl, wherein the heterocyclyl substituent is selected from the group consisting of 4- to 10-membered heterocycloalkyl, 5-membered heteroaryl, and 6-membered heteroaryl, each of which is optionally substituted by 1, 2, or 3 substituents independently selected from the group consisting of halogen, —OH, —$NO_2$, cyano, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, and —$SO_2$—$C_1$-$C_4$-halogenoalkyl having 1 to 5 halogen atoms, phenyl which is optionally substituted by 1, 2, or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, and —$SO_2$—$C_1$-$C_4$-halogenoalkyl having 1 to 5 halogen atoms, and a monocyclic or a bicyclic heterocycle selected from the group consisting of 4- to 10-membered heterocycloalkyl, heterospirocycloalkyl, 5-membered heteroaryl, and 6-membered heteroaryl, each of which is optionally substituted by 1, 2, 3, or 4 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-alkyl-C(O)—, $C_1$-$C_4$-halogenoalkyl having 1 to 5 halogen atoms, $C_1$-$C_4$-alkoxy, hydroxy-$C_1$-$C_4$-alkyl, $C_1$-$C_4$-alkoxy-$C_1$-$C_4$-alkyl-, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, —$SO_2$—$C_1$-$C_4$-halogenoalkyl having 1 to 5 halogen atoms, and 4- to 10-membered heterocycloalkyl;

$R^3$ is selected from the group consisting of hydrogen, halogen, and $C_1$-$C_4$-alkyl;

$R^4$ is selected from the group consisting of hydrogen, halogen, —OH, cyano, $C_1$-$C_4$-alkyl, $C_3$-$C_6$-cycloalkyl, $C_1$-$C_4$-halogenoalkyl having 1 to 5 halogen atoms, $C_1$-$C_4$-alkoxy-$C_1$-$C_4$-alkyl, $C_1$-$C_4$-alkoxy, $C_1$-$C_4$-alkyl-C(O)—, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, and —$SO_2$—$C_1$-$C_4$-alkyl;

$R^5$ is selected from the group consisting of hydrogen, halogen, —OH, cyano, $C_1$-$C_4$-alkyl, $C_3$-$C_6$-cycloalkyl, $C_1$-$C_4$-halogenoalkyl having 1 to 5 halogen atoms, $C_1$-$C_4$-alkoxy-$C_1$-$C_4$-alkyl, $C_1$-$C_4$-alkoxy, $C_1$-$C_4$-alkyl-C(O)—, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, and —$SO_2$—$C_1$-$C_4$-alkyl;

$R^6$ is selected from the group consisting of hydrogen, halogen, —OH, cyano, $C_1$-$C_4$-alkyl, $C_3$-$C_6$-cycloalkyl, $C_1$-$C_4$-halogenoalkyl having 1 to 5 halogen atoms, $C_1$-$C_4$-alkoxy-$C_1$-$C_4$-alkyl, $C_1$-$C_4$-alkoxy, $C_1$-$C_4$-alkyl-C(O)—, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, and —$SO_2$—$C_1$-$C_4$-alkyl;

$R^{12}$ and $R^{13}$ are independently selected from the group consisting of
hydrogen, —OH, —$NH_2$, —NH($C_1$-$C_4$-alkyl), —N($C_1$-$C_4$-alkyl)$_2$, —NH(—C(O)—$C_1$-$C_4$-alkyl), —N($C_1$-$C_4$-alkyl)(—C(O)—$C_1$-$C_4$-alkyl), $C_1$-$C_4$-alkoxy, $C_1$-$C_4$-alkoxy-C(O)—, $C_1$-$C_4$-alkyl, $C_3$-$C_6$-cycloalkyl, phenyl-$C_1$-$C_4$-alkyl, each of which is optionally substituted by 1, 2, or 3 substituents independently selected from the group consisting of halogen, —OH, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, —NH—C(O)—$C_1$-$C_4$-alkyl, —N($C_1$-$C_4$-alkyl)(—C(O)—$C_1$-$C_4$-alkyl), $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, —$SO_2$—$C_1$-$C_4$-halogenoalkyl having 1 to 5 halogen atoms, and ($C_1$-$C_4$-alkoxy)$_2$P(=O)—, heterocyclyl-$C_1$-$C_4$-alkyl, wherein the heterocyclyl substituent is selected from the group consisting of 4- to 10-membered heterocycloalkyl, 5-membered heteroaryl, and 6-membered heteroaryl, each of which is optionally substituted by 1, 2, or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S-$C_1$-$C_4$-halogenoalkyl having 1 to 5 halogen atoms, —S(O)—$C_1$-$C_4$-halogenoalkyl having 1 to 5 halogen atoms, and —$SO_2$—$C_1$-$C_4$-halogenoalkyl having 1 to 5 halogen atoms, phenyl, benzo-$C_5$-$C_6$-cycloalkyl, each of which is optionally substituted by 1, 2, or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, and —$SO_2$—$C_1$-$C_4$-halogenoalkyl having 1 to 5 halogen atoms, and a monocyclic or a bicyclic heterocycle selected from the group of 4- to 10-membered heterocycloalkyl, 5-membered heteroaryl, and 6-membered heteroaryl, each of which is optionally substituted by 1, 2, or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S-$C_1$-$C_4$-alkyl, —S(O)—$C_1$-$C_4$-alkyl, —$SO_2$—$C_1$-$C_4$-alkyl, —S-$C_1$-$C_4$-halogenoalkyl having 1 to 5 halogen atoms, —S(O)—$C_1$-$C_4$-halogenoalkyl having 1 to 5 halogen atoms, and —$SO_2$—$C_1$-$C_4$-halogenoalkyl having 1 to 5 halogen atoms;

$R^{14}$ is selected from the group consisting of —$NH_2$, —NH($C_1$-$C_4$-alkyl), —N($C_1$-$C_4$-alkyl)$_2$, $C_1$-$C_4$-alkyl, $C_3$-$C_6$-cycloalkyl, phenyl-$C_1$-$C_4$-alkyl, each of which is optionally substituted by 1, 2, or 3 substituents independently selected from the group consisting of halogen, —OH, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, and —$SO_2$—$C_1$-$C_4$-halogenoalkyl having 1 to 5 halogen atoms, heterocyclyl-$C_1$-$C_4$-alkyl, wherein the heterocyclyl substituent is selected from the group consisting of 4- to 10-membered heterocycloalkyl, 5-membered heteroaryl, and 6-membered heteroaryl, each of which is optionally substituted by 1, 2, or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, and —$SO_2$—$C_1$-$C_4$-halogenoalkyl having 1 to 5 halogen atoms, phenyl, which is optionally substituted by 1, 2, or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, and —$SO_2$—$C_1$-$C_4$-halogenoalkyl having 1 to 5 halogen atoms, and a monocyclic or a bicyclic heterocycle selected from the group consisting of 4- to 10-membered heterocycloalkyl, 5-membered heteroaryl, and 6-membered heteroaryl, each of which is optionally substituted by 1, 2, or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, and —$SO_2$—$C_1$-$C_4$-halogenoalkyl having 1 to 5 halogen atoms;

$R^{15}$ is selected from the group consisting of $C_1$-$C_4$-alkyl, $C_3$-$C_6$-cycloalkyl, phenyl-$C_1$-$C_4$-alkyl, each of which is optionally substituted by 1, 2, or 3 substituents independently selected from the group consisting of halogen, —OH, cyano, —COOH, $C_1$-$C_4$-alkoxy-C(O)—, —C(O)—$NH_2$, —C(O)—

NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —NH$_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —SO$_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, and —SO$_2$—$C_1$-$C_4$-halogenoalkyl having 1 to 5 halogen atoms, heterocyclyl-$C_1$-$C_4$-alkyl, wherein the heterocyclyl substituent is selected from the group consisting of 4- to 10-membered heterocycloalkyl, 5-membered heteroaryl, and 6-membered heteroaryl, each of which is optionally substituted by 1, 2, or 3 substituents independently selected from the group consisting of halogen, cyano, nitro, —OH, oxo, thiono, —COOH, $C_1$-$C_4$-alkoxy-C(O)—, —C(O)—NH$_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —NH$_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —SO$_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, and —SO$_2$—$C_1$-$C_4$-halogenoalkyl having 1 to 5 halogen atoms, phenyl, which is optionally substituted by 1, 2, or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —NH$_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —SO$_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, and —SO$_2$—$C_1$-$C_4$-halogenoalkyl having 1 to 5 halogen atoms, and a monocyclic or a bicyclic heterocycle selected from the group consisting of 4- to 10-membered heterocycloalkyl, 5-membered heteroaryl, and 6-membered heteroaryl, each of which is optionally substituted by 1, 2, or 3 substituents independently selected from the group consisting of halogen, cyano, nitro, —OH, oxo, thiono, —COOH, $C_1$-$C_4$-alkoxy-C(O)—, —C(O)—NH$_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —NH$_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —SO$_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, and —SO$_2$—$C_1$-$C_4$-halogenoalkyl having 1 to 5 halogen atoms;

Q is selected from the group consisting of 6- or 10-membered aryl, and 5- to 10-membered heteroaryl, each of which is optionally substituted by 1, 2, 3, 4, or 5 substituents selected from the group consisting of halogen, SF$_5$, cyano, —CHO, nitro, oxo, $C_1$-$C_4$-alkyl, $C_1$-$C_4$-hydroxyalkyl, $C_1$-$C_4$-halogenoalkyl having 1 to 5 halogen atoms, hydroxy, $C_1$-$C_4$-alkoxy, $C_3$-$C_6$-cycloalkyl-$C_1$-$C_4$-alkoxy, cyano-$C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, —NH—SO$_2$—($C_1$-$C_4$-alkyl), —N(SO$_2$-[$C_1$-$C_4$-alkyl]) ($C_1$-$C_4$-alkyl), ($C_1$-$C_4$-alkoxyimino)-$C_1$-$C_4$-alkyl, 4- to 6-membered heterocyclyl, which is optionally substituted with 1 or 2 substituents selected from the group consisting of fluorine, chlorine, bromine, methyl, and cyano, —CH$_2$—O—($C_1$-$C_4$-alkyl), —CH$_2$—NH($C_1$-$C_4$-alkyl), —CH$_2$—N($C_1$-$C_4$-alkyl)$_2$, methyl substituted with a 4- to 6-membered heterocyclyl which itself is optionally substituted with 1 or 2 substituents selected from the group consisting of fluorine, chlorine, bromine, methyl, and cyano, —CH$_2$—S—($C_1$-$C_4$-alkyl), —CH$_2$—S(O)—($C_1$-$C_4$-alkyl), —CH$_2$—SO$_2$—($C_1$-$C_4$-alkyl), —S—($C_1$-$C_4$-alkyl), —S(O)—($C_1$-$C_4$-alkyl), —SO$_2$—($C_1$-$C_4$-alkyl), —S—($C_1$-$C_4$-halogenoalkyl) having 1 to 5 halogen atoms, —S(O)—($C_1$-$C_4$-halogenoalkyl) having 1 to 5 halogen atoms, —SO$_2$—($C_1$-$C_4$-halogenoalkyl) having 1 to 5 halogen atoms, —CONH($C_1$-$C_4$-alkyl), —CONH($C_3$-$C_6$-cycloalkyl), —NHCO($C_1$-$C_4$-alkyl), —NHCO($C_3$-$C_6$-cycloalkyl), and —NHCO($C_1$-$C_4$-halogenoalkyl) having 1 to 5 halogen atoms;

or a stereoisomer, a tautomer, or a salt thereof, or a mixture of any of the foregoing.

2. The compound according to claim 1, wherein, $R^1$ is selected from the group consisting of hydrogen, cyano, -CHO, -OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, phenyl-$C_1$-$C_4$-alkyl, optionally substituted by 1, 2, 3, 4, or 5 substituents independently selected from the group consisting of halogen, -OH, -NO$_2$, cyano, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, -NH$_2$, -NH($C_1$-$C_4$-alkyl), -N($C_1$-$C_4$-alkyl)$_2$, -S-$C_1$-$C_4$-alkyl, -S(O)-$C_1$-$C_4$-alkyl, -SO$_2$-$C_1$-$C_4$-alkyl, -S-$C_1$-$C_4$-halogenoalkyl having 1 to 5 halogen atoms, -S(O)-$C_1$-$C_4$-halogenoalkyl having 1 to 5 halogen atoms, and -SO$_2$-$C_1$-$C_4$-halogenoalkyl having 1 to 5 halogen atoms, and heterocyclyl-$C_1$-$C_4$-alkyl, wherein the heterocyclyl substituent is selected from the group consisting of 4- to 10-membered heterocycloalkyl, 5-membered heteroaryl, and 6-membered heteroaryl, each of which is optionally substituted by 1, 2, or 3 substituents independently selected from the group consisting of halogen, -OH, -NO$_2$, cyano, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, -NH$_2$, -NH($C_1$-$C_4$-alkyl), -N($C_1$-$C_4$-alkyl)$_2$, -S-$C_1$-$C_4$-alkyl, -S(O)-$C_1$-$C_4$-alkyl, -SO$_2$-$C_1$-$C_4$-alkyl, -S-$C_1$-$C_4$-halogenoalkyl having 1 to 5 halogen atoms, —S(O)-$C_1$-$C_4$-halogenoalkyl having 1 to 5 halogen atoms, and -SO$_2$-$C_1$-$C_4$-halogenoalkyl having 1 to 5 halogen atoms;

$R^2$ is selected from the group consisting of hydrogen, halogen, cyano, -COOH, $C_1$-$C_4$-alkoxy-C(O)-, -C(O)-NH$_2$, -C(O)-NH $C_1$-$C_4$-alkyl), -C(O)-N($C_1$-$C_4$-alkyl)$_2$, —NR$^{12}$R$^{13}$, —OR$^{14}$, —SR$^{15}$, -S(O)R$^{15}$, -SO$_2$R$^{15}$, $C_1$-$C_6$-alkyl, $C_3$-$C_6$-cycloalkyl, $C_2$-$C_4$-alkenyl, $C_3$-$C_6$-cycloalkenyl, $C_2$-$C_4$-alkynyl, phenyl-$C_1$-$C_4$-alkyl, each of which is optionally substituted by 1, 2, 3, 4, or 5 substituents independently selected from the group consisting of halogen, -OH, -NO$_2$, cyano, $C_1$-$C_4$-alkyl-C(O)-, $C_1$-$C_4$-alkoxy-C(O)-, -C(O)-$NH_2$, -C(O)-NH($C_1$-$C_4$-alkyl), -C(O)-N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, -$NH_2$, -NH($C_1$-$C_4$-alkyl), -N($C_1$-$C_4$-alkyl)$_2$, —S-$C_1$-$C_4$-alkyl, —S(O)-$C_1$-$C_4$-alkyl, -$SO_2$-$C_1$-$C_4$-alkyl, -S-$C_1$-$C_4$-halogenoalkyl having 1 to 5 halogen atoms, -S(O)-$C_1$-$C_4$-halogenoalkyl having 1 to 5 halogen atoms, and —$SO_2$-$C_1$-$C_4$-halogenoalkyl having 1 to 5 halogen atoms, heterocyclyl-$C_1$-$C_4$-alkyl, wherein the heterocyclyl substituent is selected from the group consisting of 4- to 10-membered heterocycloalkyl, 5-membered heteroaryl, and 6-membered heteroaryl, each of which is optionally substituted by 1, 2, or 3 substituents independently selected from the group consisting of halogen, -OH, -$NO_2$, cyano, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, -$NH_2$, -NH($C_1$-$C_4$-alkyl), -N($C_1$-$C_4$-alkyl)$_2$, -S-$C_1$-$C_4$-alkyl, -S(O)-$C_1$-$C_4$-alkyl, -$SO_2$-$C_1$-$C_4$-alkyl, -S-$C_1$-$C_4$-halogenoalkyl having 1 to 5 halogen atoms, -S(O)-$C_1$-$C_4$-halogenoalkyl having 1 to 5 halogen atoms, and -$SO_2$-$C_1$-$C_4$-halogenoalkyl having 1 to 5 halogen atoms, phenyl which is optionally substituted by 1, 2, or 3 substituents independently selected from the group consisting of halogen, cyano, nitro, -OH, $C_1$-$C_4$-alkyl, $C_1$-C4-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, -$NH_2$, -NH($C_1$-$C_4$-alkyl), -N($C_1$-$C_4$-alkyl)$_2$, -S-$C_1$-$C_4$-alkyl, -S(O)-$C_1$-$C_4$-alkyl, -$SO_2$-$C_1$-$C_4$-alkyl, -S-$C_1$-C4-halogenoalkyl having 1 to 5 halogen atoms, -S(O)-$C_1$-$C_4$-halogenoalkyl having 1 to 5 halogen atoms, and -$SO_2$-$C_1$-$C_4$-halogenoalkyl having 1 to 5 halogen atoms, and a monocyclic or a bicyclic heterocycle selected from the group consisting of 4- to 10-membered heterocycloalkyl, heterospirocycloalkyl, 5-membered heteroaryl, and 6-membered heteroaryl, each of which is optionally substituted by 1, 2, 3, or 4 substituents independently selected from the group consisting of halogen, cyano, nitro, -OH, oxo, thiono, -COOH, $C_1$-$C_4$-alkoxy-C(O)-, -C(O)-$NH_2$, -C(O)-NH($C_1$-$C_4$-alkyl), -C(O)-N($C_1$-$C_4$-alkyl)$_2$, $C_1$-$C_4$-alkyl, $C_1$-$C_4$-alkyl-C(O)-, $C_1$-$C_4$-halogenoalkyl having 1 to 5 halogen atoms, $C_1$-$C_4$-alkoxy, hydroxy-$C_1$-$C_4$-alkyl, $C_1$-$C_4$-alkoxy-$C_1$-$C_4$-alkyl, -S-$C_1$-$C_4$-halogenoalkoxy having 1 to 5 halogen atoms, C3-C6-cycloalkyl, -NH2, -NH(C1-C4-alkyl), -N($C_1$-$C_4$-alkyl)$_2$, -S-$C_1$-$C_4$-alkyl, -S(O)-$C_1$-$C_4$-alkyl, -S(O)-$C_1$-$C_4$-alkyl, -S-$C_1$-$C_4$-halogenoalkyl having 1 to 5 halogen atoms, -S(O)-$C_1$-$C_4$-halogenoalkyl having 1 to 5 halogen atoms,-$SO_2$-$C_1$-$C_4$-halogenoalkyl having 1 to 5 halogen atoms, and 4- to 10-membered heterocycloalkyl;

$R^3$ is selected from the group consisting of hydrogen, halogen, and $C_1$-$C_4$-alkyl;

$R^4$ is selected from the group consisting of hydrogen, halogen, cyano, $C_1$-$C_4$-alkyl, $C_1$-$C_4$-halogenoalkyl having 1 to 5 halogen atoms, and $C_1$-$C_4$-alkoxy;

$R^5$ is selected from the group consisting of hydrogen, halogen, cyano, $C_1$-$C_4$-alkyl, $C_1$-$C_4$-halogenoalkyl having 1 to 5 halogen atoms, and $C_1$-$C_4$-alkoxy;

$R^6$ is selected from the group consisting of hydrogen, halogen, cyano, $C_1$-$C_4$-alkyl, $C_1$-$C_4$-halogenoalkyl having 1 to 5 halogen atoms, and $C_1$-$C_4$-alkoxy;

$R^{12}$ and $R^{13}$ are independently selected from the group consisting of hydrogen, -NH(-C(O)-$C_1$-$C_4$-alkyl), $C_1$-$C_4$-alkoxy, $C_1$-$C_4$-alkyl, C3-C6-cycloalkyl, phenyl-$C_1$-$C_4$-alkyl, each of which is optionally substituted by 1, 2, or 3 substituents independently selected from the group consisting of halogen, -OH, cyano, -COOH, $C_1$-$C_4$-alkoxy-C(O)-, -C(O)-$NH_2$, -C(O)-NH($C_1$-$C_4$-alkyl), -C(O)-N($C_1$-$C_4$-alkyl)$_2$, -NH-C(O)-$C_1$-$C_4$-alkyl, -N($C_1$-$C_4$-alkyl)-C(O)-$C_1$-$C_4$-alkyl), $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, -$NH_2$, -NH($C_1$-$C_4$-alkyl), -N($C_1$-$C_4$-alkyl)$_2$, -S-$C_1$-$C_4$-alkyl, -S(O)-$C_1$-$C_4$-alkyl, -$SO_2$-$C_1$-$C_4$-alkyl, —S-$C_1$-$C_4$-halogenoalkyl having 1 to 5 halogen atoms, —S(O)-$C_1$-$C_4$-halogenoalkyl having 1 to 5 halogen atoms, —$SO_2$-$C_1$-$C_4$-halogenoalkyl having 1 to 5 halogen atoms, and ($C_1$-$C_4$-alkoxy)$_2$P(=O)-, heterocyclyl-$C_1$-$C_4$-alkyl, wherein the heterocyclyl substituent is selected from the group consisting of 4- to 10-membered heterocycloalkyl, 5-membered heteroaryl, and 6-membered heteroaryl, each of which is optionally substituted by 1, 2, or 3 substituents independently selected from the group consisting of halogen, cyano, nitro, -OH, oxo, thiono, -COOH, $C_1$-$C_4$-alkoxy-C(O)-, -C(O)-$NH_2$, -C(O)-NH($C_1$-$C_4$-alkyl), -C(O)-N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, -$NH_2$, -NH($C_1$-$C_4$-alkyl), -N($C_1$-$C_4$-alkyl)$_2$, -S-$C_1$1-$C_4$-alkyl, -S(O)-$C_1$-$C_4$-alkyl, -$SO_2$-$C_1$-$C_4$-alkyl, —S-$C_1$-$C_4$-halogenoalkyl having 1 to 5 halogen atoms, —S(O)-$C_1$-$C_4$-halogenoalkyl having 1 to 5 halogen atoms, and -$SO_2$-$C_1$-$C_4$-halogenoalkyl having 1 to 5 halogen atoms, phenyl, benzo-$C_5$-$C_6$-cycloalkyl, each of which is optionally substituted by 1, 2, or 3 substituents independently selected from the group consisting of halogen, cyano, $C_1$-$C_4$-alkyl, $C_1$-$C_4$-halogenoalkyl having 1 to 5 halogen atoms, $C_1$-$C_4$-alkoxy, and $C_1$-$C_4$-halogenoalkoxy having 1 to 5 halogen atoms, $C_3$-$C_6$-cycloalkyl, -$NH_2$, -NH($C_1$-$C_4$-alkyl), -N($C_1$-$C_4$-alkyl)$_2$, -S-$C_1$-$C_4$-alkyl, -S(O)-$C_1$-$C_4$-alkyl, -$SO_2$-$C_1$-$C_4$-alkyl, -S-$C_1$-$C_4$-halogenoalkyl having 1 to 5 halogen atoms, -S(O)-$C_1$-$C_4$-halogenoalkyl having 1 to 5 halogen atoms, and -$SO_2$-$C_1$-$C_4$-halogenoalkyl having 1 to 5 halogen atoms, and a monocyclic or a bicyclic heterocycle selected from the group of 4- to 10-membered heterocycloalkyl, 5-membered heteroaryl, and 6-membered heteroaryl, each of which is optionally substituted by 1, 2, or 3 substituents independently selected from the group consisting of halogen, cyano, nitro -OH, oxo, thiono, -COOH, $C_1$-$C_4$-alkoxy-C(O)-, -C(O)-$NH_2$, -C(O)-NH($C_1$-$C_4$-alkyl), -C(O)-N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, -$NH_2$, -NH($C_1$-$C_4$-alkyl), -N($C_1$-$C_4$-alkyl)$_2$, -S-$C_1$1-$C_4$-alkyl, -S(O)-$C_1$-$C_4$-alkyl, -$SO_2$-$C_1$-$C_4$-alkyl, —S-$C_1$-$C_4$-halogenoalkyl having 1 to 5 halogen atoms, —S(O)-$C_1$-$C_4$-halogenoalkyl having 1 to 5 halogen atoms, and -$SO_2$-$C_1$-$C_4$-halogenoalkyl having 1 to 5 halogen atoms;

R14 is selected from the group consisting of -$NH_2$, -NH($C_1$-$C_4$-alkyl), -N($C_1$-$C_4$-alkyl)$_2$, $C_1$-$C_4$-alkyl, $C_3$-$C_6$-cycloalkyl, phenyl-$C_1$-$C_4$-alkyl, each of which is optionally substituted by 1, 2, or 3 substituents independently selected from the group consisting of halogen, -OH, cyano, -COOH, $C_1$-$C_4$-alkoxy-C(O)-, -C(O)-$NH_2$, -C(O)-NH($C_1$-$C_4$-alkyl), -C(O)-N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having $_1$ to $_5$ halogen atoms, $C_3$-$C_6$-cycloalkyl, -$NH_2$, -NH($C_1$-$C_4$-alkyl), -N($C_1$-$C_4$-alkyl)$_2$, -S-$C_1$-$C_4$-alkyl, -S(O)-$C_1$-$C_4$-alkyl, -$SO$-$C_1$-$C_4$-alkyl, -S-$C_1$-$C_4$-halogenoalkyl having 1 to 5 halogen atoms, -S(O)-$C_1$-$C_4$-halogenoalkyl having 1 to 5 halogen atoms, and -$SO_2$-$C_1$-$C_4$-halogenoalkyl having 1 to 5 halogen atoms, heterocyclyl-$C_1$-$C_4$-alkyl, wherein the heterocyclyl substituent is selected from the group consisting of 4- to 10-membered heterocycloalkyl, 5-membered heteroaryl, and 6-membered heteroaryl, each of which is optionally substituted by 1, 2, or 3 substituents independently selected from the group consisting of halogen, cyano, nitro, -OH, oxo, thiono, -COOH, $C_1$-$C_4$-alkoxy-C(O)-, -C(O)-$NH_2$, -C(O)-NH($C_1$-$C_4$-alkyl), -C(O)-N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, -$NH_2$, -NH($C_1$-$C_4$-alkyl), -N($C_1$-$C_4$-alkyl)$_2$, -S-$C_1$-$C_4$-alkyl, -S(O)-$C_1$-$C_4$-alkyl, -$SO_2$-$C_1$-$C_4$-alkyl, -S-$C_1$-$C_4$-halogenoalkyl having 1 to 5 halogen atoms, -S(O)-$C_1$-$C_4$-halogenoalkyl having 1 to 5 halogen atoms, and -$SO_2$-$C_1$-$C_4$-halogenoalkyl having 1 to 5 halogen atoms, phenyl, which is optionally substituted by 1, 2, or 3 substituents independently selected from the group consisting of halogen, cyano, nitro, -OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, -$NH_2$, -NH($C_1$-$C_4$-alkyl), -N($C_1$-$C_4$-alkyl)$_2$, -S-$C_1$-$C_4$-alkyl, -S(O)-$C_1$-$C_4$-alkyl, -$SO_2$-$C_1$-$C_4$-alkyl, -S-$C_1$-$C_4$-halogenoalkyl having 1 to 5 halogen atoms, -S(O)-$C_1$-$C_4$-halogenoalkyl having 1 to 5 halogen atoms, and -$SO_2$-$C_1$-$C_4$-halogenoalkyl having 1 to 5 halogen atoms, and a monocyclic or a bicyclic heterocycle selected from the group consisting of 4- to 10-membered heterocycloalkyl, 5-membered heteroaryl, and 6-membered heteroaryl, each of which is optionally substituted by 1, 2, or 3 substituents independently selected from the group consisting of halogen, cyano, nitro, -OH, oxo, thiono, -COOH, $C_1$-$C_4$-alkoxy-C(O) -, -C(O)-$NH_2$, -C(O)-NH($C_1$-$C_4$-alkyl), -C(O)-N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, -$NH_2$, -NH($C_1$-$C_4$-alkyl), -N($C_1$-$C_4$-alkyl)$_2$, -S-$C_1$-$C_4$-alkyl, -S(O)-$C_1$-$C_4$-alkyl, -$SO_2$-$C_1$-$C_4$-alkyl, -S-$C_1$-$C_4$-halogenoalkyl having 1 to 5 halogen atoms, -S(O)-$C_1$-$C_4$-halogenoalkyl having 1 to 5 halogen atoms, and -$SO_2$-$C_1$-$C_4$-halogenoalkyl having 1 to 5 halogen atoms;

$R^{15}$ is selected from the group consisting of $C_1$-$C_4$-alkyl, $C_3$-$C_6$-cycloalkyl, phenyl-$C_1$-$C_4$-alkyl, each of which is optionally substituted by 1, 2, or 3 substituents independently selected from the group consisting of halogen, -OH, cyano, COOH, $C_1$-$C_4$-alkoxy-C(O)-, -C(O)-$NH_2$, -C(O)-NH($C_1$-$C_4$-alkyl), -C(O)-N($C_1$-$C_4$-alkyl, $C_1$-$C_4$-halogenoalkyl having 1 to 5 halogen atoms, $C_1$-$C_4$-alkoxy, $C_1$-$C_4$- halogenoalkoxy having 1 to 5 halogen atoms;

heterocyclyl-$C_1$-$C_4$-alkyl, wherein the heterocyclyl substituent is selected from the group consisting of 4- to 10-membered heterocycloalkyl, 5-membered heteroaryl, and 6-membered heteroaryl, each of which is optionally substituted by 1, 2, or 3 substituents independently selected from the group consisting of halogen, cyano, nitro, -OH, oxo, thiono, -COOH, $C_1$-$C_4$-alkoxy-C(O)-, -C(O)-$NH_2$, -C(O)-NH($C_1$-$C_4$-alkyl), -C(O)-N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, -$NH_2$, -NH($C_1$-$C_4$-alkyl), -N($C_1$-$C_4$-alkyl)$_2$, -S-$C_1$-$C_4$-alkyl, -S(O)-$C_1$-$C_4$-alkyl, -$SO_2$-$C_1$-$C_4$-alkyl, -S-$C_1$-$C_4$-halogenoalkyl having 1 to 5 halogen atoms, -S(O)-$C_1$-$C_4$-halogenoalkyl having 1 to 5 halogen atoms, and -$SO_2$-$C_1$-$C_4$-halogenoalkyl having 1 to 5 halogen atoms, phenyl, which is optionally substituted by 1, 2, or 3 substituents independently selected from the group consisting of halogen, cyano, nitro, -OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, -$NH_2$, -NH($C_1$-$C_4$-alkyl), -N($C_1$-$C_4$-alkyl)$_2$, -S-$C_1$-$C_4$-alkyl, -S(O)-$C_1$-$C_4$-alkyl, -$SO_2$-$C_1$-$C_4$-alkyl, —S-$C_1$-$C_4$-halogenoalkyl having 1 to 5 halogen atoms, —S(O)-$C_1$-$C_4$-halogenoalkyl having 1 to 5 halogen atoms, and —$SO_2$-$C_1$-$C_4$-halogenoalkyl having 1 to 5 halogen atoms;

Q is a substituted phenyl ring of the formula (Q1)

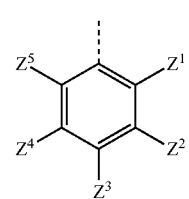

(Q1)

wherein:
- $Z^1$, $Z^2$, $Z^3$, $Z^4$, and $Z^5$ are independently selected from the group consisting of hydrogen, halogen, $SF_5$, cyano, -CHO, nitro, $C_1$-$C_4$-alkyl, $C_1$-$C_4$-halogenoalkyl having 1 to 5 halogen atoms, hydroxy, $C_1$-$C_4$-alkoxy, $C_3$-$C_6$-cycloalkyl-$C_1$-$C_4$-alkoxy, cyano-$C_1$-$C_4$-alkoxy, $C_1$-$C_4$-halogenoalkoxy having 1 to 5 halogen atoms, -NH($C_1$-$C_4$-alkyl), -N($C_1$-$C_4$-alkyl)$_2$, -NH-$SO_2$-($C_1$-$C_4$-alkyl), -N($SO_2$-[$C_1$-$C_4$-alkyl])($C_1$-$C_4$-alkyl), ($C_1$-$C_4$-alkoxyimino)-$C_1$-$C_4$-alkyl, 4- to 6-membered heterocyclyl, which is optionally substituted with 1 or 2 substituents selected from the group consisting of fluorine, chlorine, bromine, methyl, and cyano, -$CH_2$-O-($C_1$-$C_4$-alkyl), -$CH_2$-NH($C_1$-$C_4$-alkyl), -$CH_2$-N($C_1$-$C_4$-alkyl)$_2$, methyl substituted with a 4- to 6-membered heterocyclyl which itself is optionally substituted with 1 or 2 substituents selected from the group consisting of fluorine, chlorine, bromine, methyl, and cyano, -$CH_2$-S-($C_1$-$C_4$-alkyl), -$CH_2$-S(O)-($C_1$-$C_4$-alkyl), -$CH_2$-$SO_2$-($C_1$-$C_4$-alkyl), -S-($C_1$-$C_4$-alkyl), -S(O)-($C_1$-$C_4$-alkyl), -$SO_2$-($C_1$-$C_4$-alkyl), -S-($C_1$-$C_4$-halogenoalkyl) having 1 to 5 halogen atoms, -S(O)-($C_1$-$C_4$-halogenoalkyl) having 1 to 5 halogen atoms, -$SO_2$-($C_1$-$C_4$-halogenoalkyl) having 1 to 5 halogen atoms, -CONH($C_1$-$C_4$-alkyl), -CONH($C_3$-$C_6$-cycloalkyl), -NHCO($C_1$-$C_4$-alkyl), -NHCO($C_3$-$C_6$-cycloalkyl), and -NHCO($C_1$-$C_4$-halogenoalkyl) having 1 to 5 halogen atoms; or
- $Z^1$ and $Z^2$ form, together with the carbon atoms that they are connected to, a 5- or 6-membered saturated or partially saturated heterocyclic ring, a 5-membered heteroaryl, or a 6-membered heteroaryl, each of which may be optionally substituted with one or two subsituents selected from the group consisting of methyl, fluorine, and oxo; and
- $Z^3$, $Z^4$, and $Z^5$ are independently selected from the group consisting of hydrogen, halogen, $SF_5$, cyano, CHO, nitro, $C_1$-$C_4$-alkyl, $C_1$-$C_4$-halogenoalkyl having 1 to 5 halogen atoms, hydroxy, $C_1$-$C_4$-alkoxy, $C_3$-$C_6$-cycloalkyl-$C_1$-$C_4$-alkoxy, cyano-$C_1$-$C_4$-alkoxy, $C_1$-$C_4$-alkoxy-C(O)-, $C_1$-$C_4$-halogenoalkoxy having 1 to 5 halogen atoms, -NH($C_1$-$C_4$-alkyl), -N($C_1$-$C_4$-alkyl)$_2$, -NH-$SO_2$-($C_1$-$C_4$-alkyl), -N($SO_2$-[$C_1$-$C_4$-alkyl])($C_1$-$C_4$-alkyl), ($C_1$-$C_4$-alkoxyimino)-$C_1$-$C_4$-alkyl, 4- to 6-membered heterocycloalkyl which itself is optionally substituted with 1 or 2 substituents selected from the group consisting of fluorine, methyl, and cyano, -$CH_2$-S-($C_1$-$C_4$-alkyl), -$CH_2$-NH($C_1$-$C_4$-alkyl), -$CH_2$-N($C_1$-$C_4$-alkyl)$_2$, methyl substituted with a 4-to 6-membered heterocycloalkyl which itself is optionally substituted with 1 or 2 substituents selected from the group consisting of fluorine, methyl, and cyano, -$CH_2$-S-($C_1$-$C_4$-alkyl), -$CH_2$-S(O)-($C_1$-$C_4$-alkyl), -$CH_2$-$SO_2$-($C_1$-$C_4$-alkyl), -S-($C_1$-$C_4$-alkyl), -S(O)-($C_1$-$C_4$-alkyl), -S-($C_1$-$C_4$-alkyl), -S-($C_1$-$C_4$-halogenoalkyl) having 1 to 5 halogen atoms, -S(O)-($C_1$-$C_4$-halogenoalkyl) having 1 to 5 halogen atoms, -$SO_2$-($C_1$-$C_4$-halogenoalkyl) having 1 to 5 halogen atoms, -CONH($C_1$-$C_4$-alkyl), -CONH($C_3$-$C_6$-cycloalkyl), -NHCO($C_1$-$C_4$-alkyl), -NHCO($C_3$-$C_6$-cycloalkyl), and -NHCO($C_1$-$C_4$-halogenoalkyl) having 1 to 5 halogen atoms; or
- $Z^2$ and $Z^3$ form, together with the carbon atoms that they are connected to, a 5- or 6-membered saturated or partially saturated heterocyclic ring, a 5-membered heteroaryl, or a 6-membered heteroaryl, each of which may be optionally substituted with one or two subsituents selected from the group consisting of methyl, fluorine, and oxo; and
- $Z^1$, $Z^4$, and $Z^5$ are independently selected from the group consisting of hydrogen, halogen, $SF_5$, cyano, CHO, nitro, $C_1$-$C_4$-alkyl, $C_1$-$C_4$-halogenoalkyl having 1 to 5 halogen atoms, hydroxy, $C_1$-$C_4$-alkoxy, $C_3$-$C_6$-cycloalkyl-$C_1$-$C_4$-alkoxy, cyano-$C_1$-$C_4$-alkoxy, $C_1$-$C_4$-halogenoalkoxy having 1 to 5 halogen atoms, -NH($C_1$-$C_4$-alkyl), -N($C_1$-$C_4$-alkyl)$_2$, -NH-$SO_2$-($C_1$-$C_4$-alkyl), -N($SO_2$-[$C_1$-$C_4$-alkyl])($C_1$-$C_4$-alkyl), ($C_1$C4-alkoxyimino)-$C_1$-$C_4$-alkyl, 4- to 6-membered heterocycloalkyl which is optionally substituted with 1 or 2 substituents selected from the group consisting of fluorine, methyl, and cyano, -$CH_2$-O-($C_1$-$C_4$-alkyl), -$CH_2$-NH($C_1$-$C_4$-alkyl), -$CH_2$-N($C_1$-$C_4$-alkyl)$_2$, methyl substituted with a 4- to 6-membered heterocycloalkyl which itself is optionally substituted with 1 or 2 substituents selected from the group consisting of fluorine, methyl, and cyano, -$CH_2$-S-($C_1$-$C_4$-alkyl), -$CH_2$-S(O)-($C_1$-$C_4$-alkyl), -$CH_2$-$SO_2$-($C_1$-$C_4$-alkyl), -S-($C_1$-$C_4$-alkyl), -S(O)-($C_1$-$C_4$-alkyl), -$SO_2$-($C_1$-$C_4$-alkyl), -S-($C_1$-$C_4$-halogenoalkyl) having 1 to 5 halogen atoms, -S(O)-($C_1$-$C_4$-halogenoalkyl) having 1 to 5 halogen atoms, -$SO_2$-($C_1$-$C_4$-halogenoalkyl) having 1 to 5 halogen atoms, -CONH($C_1$-$C_4$-alkyl), -CONH($C_3$-$C_6$-cycloalkyl), -NHCO($C_1$-$C_4$-alkyl), -NHCO($C_3$-$C_6$-cycloalkyl), and -NHCO($C_1$-$C_4$-halogenoalkyl) having 1 to 5 halogen atoms; or
- Q is a pyridine ring of the formula (Q2)

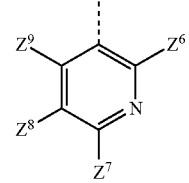

(Q2)

wherein:
- $Z^6$, $Z^7$, $Z^8$, and $Z^9$ are independently selected from the group consisting of hydrogen, halogen, cyano, C1-C4-alkyl, C1-C4-halogenoalkyl having 1 to 5 halogen atoms, $C_1$-$C_4$-alkoxy, $C_1$-$C_4$-halogenoalkoxy having 1 to 5 halogen atoms, -NH($C_1$-$C_4$-alkyl), and -N($C_1$-$C_4$-alkyl)$_2$; or
- Q is a pyrimidine ring of the formula (Q3)

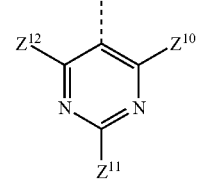

(Q3)

wherein:
- $Z^{10}$, $Z^{11}$, and $Z^{12}$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, -NH($C_1$-$C_4$-alkyl), and -N($C_1$-$C_4$-alkyl)2; or Q is a pyridine ring of the formula (Q4)

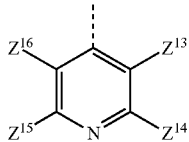

(Q4)

wherein:

$Z^{13}$, $Z^{14}$, $Z^{15}$, and $Z^{16}$ are independently selected from the group consisting of hydrogen halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_1$-$C_4$-hydroxyalkyl, $NH_2$, -NH($C_1$-$C_4$-alkyl), -N($C_1$-$C_4$-alkyl)$_2$, -NH-CO-$C_1$-$C_4$-alkyl, and monocyclic heterocycles selected from the group consisting of 4- to 7-membered heterocycloalkyl, and 5-membered heteroaryls having at least one nitrogen atom via which the heteroaryl ring is connected to the pyridine ring, each of which is optionally substituted with 1, 2, or 3 substituents independently selected from the group consisting of halogen, cyano, nitro, -OH, oxo, thiono, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, -$NH_2$, -NH($C_1$-$C_4$-alkyl), -N($C_1$-$C_4$-alkyl)$_2$, -S-$C_1$-$C_4$-alkyl, -S(O)-$C_1$-$C_4$-alkyl, -$SO_2$-$C_1$-$C_4$-alkyl, -S-($C_1$-$C_4$-halogenoalkyl) having 1 to 5 halogen atoms, -S(O)-($C_1$-$C_4$-halogenoalkyl) having 1 to 5 halogen atoms, and -$SO_2$-($C_1$-$C_4$-halogenoalkyl) having 1 to 5 halogen atoms; or Q is a pyridine ring of the formula (Q5)

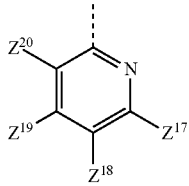

(Q5)

wherein:

$Z^{17}$, $Z^{18}$, $Z^{19}$, and $Z^{20}$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, -NH($C_1$-$C_4$-alkyl), and -N($C_1$-$C_4$-alkyl)$_2$; or Q is a 5-membered aromatic heterocycle of the formula (Q6)

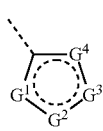

(Q6)

wherein:

$G^1$- $G^4$ are independently selected from the group consisting of N, O, S, C-$Z^{21}$, and N-$Z^{22}$, wherein not more than one of $G^1$ — $G^4$ is O, not more than one of $G^1$ — $G^4$ is S, not more than one of $G^1$ — $G^4$ is N-$Z^{22}$; and wherein each $Z^{21}$ is independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, and $C_1$-$C_4$-halogenoalkoxy having 1 to 5 halogen atoms; and each $Z^{22}$ is independently selected from the group consisting of hydrogen, $C_1$-$C_4$-alkyl, $C_1$-$C_4$-halogenoalkyl having 1 to 5 halogen atoms, $C_1$-$C_4$-alkyl-$C_3$-$C_6$-cycloalkyl, and $C_1$-$C_4$-alkoxy-$C_1$-$C_4$-alkyl; or Q is a 5-membered aromatic heterocycle of the formula (Q7)

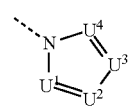

(Q7)

wherein:

$U^1$-$U^4$ are independently selected from the group consisting of N and C-$Z^{23}$, wherein not more than three of $U^1$—$U^4$ are N; and wherein each $Z^{23}$ is independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, and $C_1$-$C_4$-halogenoalkoxy having 1 to 5 halogen atoms;

or a stereoisomer, a tautomer, or a salt thereof, or a mixture of any of the foregoing.

3. The compound according to claim 1 wherein $R^1$ is selected from the group consisting of hydrogen, $C_1$-$C_4$-alkyl, $C_3$-$C_6$-cycloalkyl, $C_3$-$C_4$-alkenyl, $C_3$-$C_4$-alkynyl, $C_1$-$C_4$-alkoxy-$C_1$-$C_4$-alkyl, $C_3$-$C_6$-cycloalkyl-$C_1$-$C_3$-alkyl, and cyano-$C_1$-$C_4$-alkyl;

$R^2$ is selected from the group consisting of hydrogen, halogen, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, —$NR^{12}R^{13}$, —$OR^{14}$, —$SR^{15}$, —S(O)$R^{15}$, —$SO_2R^{15}$$C_1$-$C_4$-alkyl, $C_3$-$C_6$-cycloalkyl, $C_2$-$C_4$-alkenyl, $C_3$-$C_6$-cycloalkenyl, $C_2$-$C_4$-alkynyl, phenyl-$C_1$-$C_4$-alkyl, each of which is optionally substituted by 1, 2, 3, 4, or 5 substituents independently selected from the group consisting of halogen, -OH, cyano, $C_1$-$C_4$-alkoxy-C(O)-, -C(O)-$NH_2$, -C(O)-NH($C_1$-$C_4$-alkyl), -C(O)-N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, -$NH_2$, -NH($C_1$-$C_4$-alkyl), -N($C_1$-$C_4$-alkyl)$_2$, -S(O)-$C_1$-$C_4$-alkyl, -S(O)-$C_1$-$C_4$-alkyl, -$SO_2$-$C_1$-$C_4$-alkyl, —S(O)-$C_1$-$C_4$-halogenoalkyl having 1 to 5 halogen atoms, —S(O)-$C_1$-$C_4$-halogenoalkyl having 1 to 5 halogen atoms, and —$SO_2$-$C_1$-$C_4$-halogenoalkyl having 1 to 5 halogen atoms, and a monocyclic or a bicyclic heterocycle selected from the group consisting of 4- to 10-membered heterocycloalkyl, heterospirocycloalkyl, 5-membered heteroaryl, and 6-membered heteroaryl, each of which is optionally substituted by 1, 2, 3, or 4 substituents independently selected from the group consisting of halogen, cyano, -OH, oxo, -COOH, $C_1$-$C_4$-alkoxy-C(O)-, -C(O)-$NH_2$, -C(O)-NH($C_1$-$C_4$-alkyl), -C(O)-

$N(C_1-C_4\text{-alkyl})_2$, $C_1-C_4$-alkyl, $C_1-C_4$-alkyl-C(O)-, $C_1-C_4$-halogenoalkyl having 1 to 5 halogen atoms, $C_1-C_4$-alkoxy, hydroxy-$C_1-C_4$-alkyl, $C_1-C_4$-alkoxy-$C_1-C_4$-alkyl-, $C_1-C_4$-halogenoalkoxy having 1 to 5 halogen atoms, $C_3-C_6$-cycloalkyl, $-NH_2$, $-NH(C_1-C_4\text{-alkyl})$, $-N(C_1-C_4\text{-alkyl})_2$, and 4- to 10-membered heterocycloalkyl;

$R^3$ is selected from the group consisting of hydrogen, halogen, and $C_1-C_4$-alkyl;

$R^4$ is selected from the group consisting of hydrogen, halogen, cyano, $C_1-C_4$-alkyl, $C_1-C_4$-halogenoalkyl having 1 to 5 halogen atoms, and $C_1-C_4$-alkoxy;

$R^5$ is selected from the group consisting of hydrogen, halogen, cyano, $C_1-C_4$-alkyl, $C_1-C_4$-halogenoalkyl having 1 to 5 halogen atoms, and $C_1-C_4$-alkoxy;

$R^6$ is selected from the group consisting of hydrogen, halogen, cyano, $C_1-C_4$-alkyl, $C_1-C_4$-halogenoalkyl having 1 to 5 halogen atoms, and $C_1-C_4$-alkoxy;

$R^{12}$ and $R^{13}$ are independently selected from the group consisting of hydrogen, $-NH(-C(O)-C_1-C_4\text{-alkyl})$, $C_1-C_4$-alkoxy, $C_1-C_4$-alkyl, C3-C6-cycloalkyl, phenyl-$C_1-C_4$-alkyl, each of which is optionally substituted by 1, 2, or 3 substituents independently selected from the group consisting of halogen, -OH, cyano, -COOH, $C_1-C_4$-alkoxy-C(O)-, $-C(O)-NH_2$, $-C(O)-NH(C_1-C_4\text{-alkyl})$, $-C(O)-N(C_1-C_4\text{-alkyl})_2$, $-NH-C(O)-C_1-C_4$-alkyl, $-N(C_1-C_4\text{-alkyl})-C(O)-C_1-C_4\text{-alkyl})$, $C_1-C_4$-alkyl, $C_1-C_4$-halogenoalkyl having 1 to 5 halogen atoms, $C_1-C_4$-alkoxy, $C_1-C_4$-halogenoalkoxy having 1 to 5 halogen atoms, $C_3-C_6$-cycloalkyl, $-NH_2$, $-NH(C_1-C_4\text{-alkyl})$, $-N(C_1-C_4\text{-alkyl})_2$, $-S-C_1-C_4$-alkyl, $-S(O)-C_1-C_4$-alkyl, $-SO_2-C_1-C_4$-alkyl, $-S-C_1-C_4$-halogenoalkyl having 1 to 5 halogen atoms, $-S(O)-C_1-C_4$-halogenoalkyl having 1 to 5 halogen atoms, $-SO_2-C_1-C_4$-halogenoalkyl having 1 to 5 halogen atoms, and $(C_1-C_4\text{-alkoxy})_2P(=O)-$, heterocyclyl-$C_1-C_4$-alkyl, wherein the heterocyclyl substituent is selected from the group consisting of 4- to 10-membered heterocycloalkyl, 5-membered heteroaryl, and 6-membered heteroaryl, each of which is optionally substituted by 1, 2, or 3 substituents independently selected from the group consisting of halogen, cyano, nitro, -OH, oxo, $C_1-C_4$-halogenoalkoxy having 1 to 5 halogen atoms, phenyl, benzo-$C_5-C_6$-cycloalkyl, each of which is optionally substituted by 1, 2, or 3 substituents independently selected from the group consisting of halogen, cyano, $C_1-C_4$-alkyl, $C_1-C_4$-halogenoalkyl having 1 to 5 halogen atoms, $C_1-C_4$-alkoxy, and $C_1-C_4$-halogenoalkoxy having 1 to 5 halogen atoms, and a monocyclic or a bicyclic heterocycle selected from the group of 4- to 10-membered heterocycloalkyl, 5-membered heteroaryl, and 6-membered heteroaryl, each of which is optionally substituted by 1, 2, or 3 substituents independently selected from the group consisting of halogen, cyano, -OH, oxo, $C_1-C_4$-alkyl, $C_1-C_4$-halogenoaalkyl having 1 to 5 halogen atoms, $C_1-C_4$-halogenoalkoxy having 1 to 5 halogen atoms;

$R^{14}$ is selected from the group consisting of $C_1-C_4$-alkyl, $C_3-C_6$-cycloalkyl, phenyl-$C_1-C_4$-alkyl, each of which is optionally substituted by 1, 2, or 3 substituents independently selected from the group consisting of halogen, -OH, cyano, $C_1-C_4$-alkyl, $C_1-C_4$-halogenoalkoxy having 1 to 5 halogen atoms, $C_1-C_4$-halogenoalkoxy having 1 to 5 halogen atoms, and $C_3-C_6$-cycloalkyl, and heterocyclyl-$C_1-C_4$-alkyl, wherein the heterocyclyl substituent is selected from the group consisting of 4- to 10-membered heterocycloalkyl, 5-membered heteroaryl, and 6-membered heteroaryl, each of which is optionally substituted by 1, 2, or 3 substituents independently selected from the group consisting of halogen, cyano, nitro, -OH, oxo, $C_1-C_4$-alkyl, $C_1-C_4$-halogenoalkyl having 1 to 5 halogen atoms, $C_1-C_4$-alkoxy, and $C_1-C_4$- halogenoalkoxy having 1 to 5 halogen atoms;

$R^{15}$ is selected from the group consisting of $C_1-C_4$-alkyl, phenyl-$C_1-C_4$-alkyl, each of which is optionally substituted by 1, 2, or 3 substituents independently selected from the group consisting of halogen, -OH, cyano, $C_1-C_4$-alkyl, $C_1-C_4$-halogenoalkyl having 1 to 5 halogen atoms, $C_1-C_4$-alkoxy, and $C_1-C_4$-halogenoalkoxy having 1 to 5 halogen atoms, and heterocyclyl-$C_1-C_4$-alkyl, wherein the heterocyclyl substituent is selected from the group consisting of 4- to 10-membered heterocycloalkyl, 5-membered heteroaryl, and 6-membered heteroaryl, each of which is optionally substituted by 1, 2, or 3 substituents independently selected from the group consisting of halogen, cyano, $C_1-C_4$-alkyl, $C_1-C_4$-halogenoalkyl having 1 to 5 halogen atoms, $C_1-C_4$-alkoxy, and $C_1-C_4$-halogenoalkoxy having 1 to 5 halogen atoms;

Q is a substituted phenyl ring of the formula (Q1)

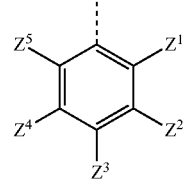

(Q1)

wherein:

$Z^1$, $Z^2$, $Z^3$, $Z^4$, and $Z^5$ are independently selected from the group consisting of hydrogen, halogen, cyano, $C_1-C_4$-alkyl, $C_1-C_4$-halogenoalkyl having 1 to 5 halogen atoms, hydroxy, $C_1-C_4$-alkoxy, $C_1-C_4$-halogenoalkoxy having 1 to 5 halogen atoms, $-NH(C_1-C_4\text{-alkyl})$, $-N(C_1-C_4\text{-alkyl})_2$, 4- to 6-membered heterocyclyl, which is optionally substituted with 1 or 2 substituents selected from the group consisting of fluorine, chlorine, bromine, methyl, and cyano, $-S-(C_1-C4\text{-alkyl})$, $-S(O)-(C_1-C_4\text{-alkyl})$, and $-SO_2-(C_1-C_4\text{-alkyl})$; or $Z^1$ and $Z^2$ form, together with the carbon atoms that they are connected to, a 5- or 6-membered heterocycloalkyl, a 5-membered heteroaryl, or a 6-membered heteroaryl, each of which may be optionally substituted with one or two subsitutents selected from the group consisting of methyl, fluorine, and oxo; and $Z^3$, $Z^4$, and $Z^5$ are independently selected from the group consisting of hydrogen, halogen, cyano, $C_1-C_4$-alkyl, $C_1-C_4$-halogenoalkyl having 1 to 5 halogen atoms, $C_1-C_4$-alkoxy, $C_1-C_4$-alkoxy-C(O)-, and $C_1-C_4$-halogenoalkoxy having 1 to 5 halogen atoms; or Z² and Z³ form, together with the carbon atoms that they are connected to, a 5- or 6-membered saturated or partially saturated heterocyclic ring, a 5-membered heteroaryl, or a 6-membered heteroaryl, each of which may be optionally substituted with one or two subsitutents selected from the group consisting of methyl, fluorine, and oxo; and Z¹, Z⁴, and Z⁵ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, and $C_1$-$C_4$-halogenoalkoxy having 1 to 5 halogen atoms;

or a stereoisomer, a tautomer, or a salt thereof, or a mixture of any of the foregoing.

4. The compound according to claim 1, wherein

R is selected from the group consisting of hydrogen, halogen, $C_1$-$C_4$-alkyl, and $C_1$-$C_4$-alkoxy;

$R^1$ is hydrogen or $C_1$-$C_4$-alkyl;

$R^2$ is selected from the group consisting of hydrogen, halogen, —$NR^{12}R^{13}$, —$OR^{14}$ –$SR^{15}$, —$S(O)R^{15}$, —$SO_2R^{15}$, $C_1$-$C_4$-alkyl, $C_3$-$C_6$-cycloalkyl, $C_2$-$C_4$-alkenyl, $C_3$-$C_6$-cycloalkenyl, each of which is optionally substituted by 1, 2, 3, 4, or 5 substituents independently selected from the group consisting of halogen, cyano, $C_1$-$C_4$-alkoxy-C(O)-, and -C(O)-$NH_2$, and a monocyclic or a bicyclic heterocycle selected from the group consisting of 4- to 10-membered heterocycloalkyl, heterospirocycloalkyl, 5-membered heteroaryl, and 6-membered heteroaryl, each of which is optionally substituted by 1, 2, 3, or 4 substituents independently selected from the group consisting of halogen, -OH, oxo, -COOH, $C_1$-$C_4$-alkoxy-C(O)-, -C(O)-$NH_2$, $C_1$-$C_4$-alkyl, $C_1$-$C_4$-alkyl-C(O)-, $C_1$-$C_4$-halogenoalkyl having 1 to 5 halogen atoms, hydroxy-$C_1$-$C_4$-alkyl-, $C_1$-$C_4$-alkoxy-$C_1$-$C_4$-alkyl-, -$NH_2$, -N($C_1$-$C_4$-alkyl)$_2$, and 4- to 10-membered heterocycloalkyl;

$R^3$ is selected from the group consisting of hydrogen, halogen, and $C_1$-$C_4$-alkyl;

$R^4$ is selected from the group consisting of hydrogen, halogen, cyano, $C_1$-$C_4$-halogenoalkyl having 1 to 5 halogen atoms, and $C_1$-$C_4$-alkoxy;

$R^5$ is selected from the group consisting of hydrogen, halogen, cyano, $C_1$-$C_4$-alkyl, $C_1$-$C_4$-halogenoalkyl having 1 to 5 halogen atoms, and $C_1$-$C_4$-alkoxy;

$R^6$ is selected from the group consisting of hydrogen, halogen, cyano, $C_1$-$C_4$-alkyl, $C_1$-$C_4$-halogenoalkyl having 1 to 5 halogen atoms, and $C_1$-$C_4$-alkoxy;

$R^{12}$ and $R^{13}$ are independently selected from the group consisting of hydrogen, -NH(-C(O)-$C_1$-$C_4$-alkyl), $C_1$-C4-alkoxy, $C_1$-$C_4$-alkyl, $C_3$-$C_6$-cycloalkyl, phenyl-C1-C4-alkyl, each of which is optionally substituted by 1, 2, or 3 substituents independently selected from the group consisting of halogen, -OH, -COOH, $C_1$-$C_4$-alkoxy-C(O)-, -C(O)-$NH_2$, -C(O)-N($C_1$-$C_4$-alkyl)$_2$, -NH-C(O)-$C_1$-$C_4$-alkyl, $C_1$-$C_4$-alkyl, $C_1$-$C_4$-alkoxy, $C_3$-$C_6$-cycloalkyl, -$NH_2$, -N($C_1$-$C_4$-alkyl)$_2$, -S-$C_1$-$C_4$-alkyl, -S(O)-$C_1$-$C_4$-alkyl, -$SO_2$-$C_1$-$C_4$-alkyl, and ($C_1$-$C_4$-alkoxy)$_2$P(-O)-, heterocyclyl-$C_1$-$C_4$-alkyl, wherein the heterocyclyl substituent is selected from the group consisting of 4- to 10-membered heterocycloalkyl, 5-membered heteroaryl, and 6-membered heteroaryl, each of which is optionally substituted by 1, 2, or 3 substituents independently selected from the group consisting of halogen, cyano, -OH, oxo, $C_1$-$C_4$-alkyl, $C_1$-$C_4$-halogenoalkyl having 1 to 5 halogen atoms, and $C_1$-$C_4$-alkoxy, phenyl and benzo-$C_5$-$C_6$-cycloalkyl, each of which is optionally substituted by 1, 2, or 3 substituents independently selected from the group consisting of halogen, cyano, $C_1$-$C_4$-alkyl, $C_1$-$C_4$-halogenoalkyl having 1 to 5 halogen atoms, $C_1$-$C_4$-alkoxy, and $C_1$-$C_4$-halogenoalkoxy having 1 to 5 halogen atoms, and a monocyclic or a bicyclic heterocycle selected from the group of 4- to 10-membered heterocycloalkyl, 5-membered heteroaryl, and 6-membered heteroaryl each of which is optionally substituted by 1, 2, or 3 substituents independently selected from the group consisting of halogen, -OH, oxo, cyano, $C_1$-$C_4$-alkyl, $C_1$-$C_4$-halogenoalkyl having 1 to 5 halogen atoms, $C_1$-$C_4$-alkoxy, and $C_1$-$C_4$-halogenoalkoxy having 1 to 5 halogen atoms;

$R^{14}$ is selected from the group consisting of $C_1$-$C_4$-alkyl, $C_3$-$C_6$-cycloalkyl, phenyl-$C_1$-$C_4$-alkyl, each of which is optionally substituted by 1, 2, or 3 substituents independently selected from the group consisting of halogen, -OH, $C_1$-$C_4$-alkyl, $C_1$-$C_4$-alkoxy, and $C_3$-$C_6$-cycloalkyl, and 4- to 10-membered heterocycloalkyl;

$R^{15}$ is selected from the group consisting of $C_1$-$C_4$-alkyl, which is optionally substituted by 1, 2, or 3 substituents independently selected from the group consisting of -OH and -COOH, and a 6-membered heteroaryl;

Q is a substituted phenyl ring of the formula (Q1)

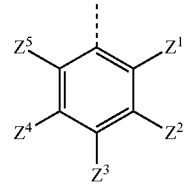

(Q1)

wherein:

$Z^1$ is selected from the group consisting of hydrogen, halogen, $C_1$-$C_4$-alkyl, and $C_1$-$C_4$-alkoxy;

$Z^2$ is selected from the group consisting of hydrogen, halogen, -OH, $C_1$-$C_4$-alkyl, $C_1$-$C_4$-alkoxy, -NH($C_1$-$C_4$-alkyl), -N($C_1$-$C_4$-alkyl)$_2$, -NH($C_3$-$C_6$-cycloalkyl), -N($C_1$-$C_4$-alkyl)($C_3$-$C_6$-cycloalkyl), $C_1$-$C_4$-halogenoalkyl having 1 to 5 halogen atoms, $C_1$-$C_4$-halogenoalkoxy having 1 to 5 halogen atoms, -S-($C_1$-$C_4$-alkyl), and a 4- to 6-membered heterocycloalkyl;

$Z^3$ is selected from the group consisting of hydrogen, halogen, $C_1$-$C_4$-alkyl, $C_1$-$C_4$-alkoxy, -NH($C_1$-$C_4$-alkyl), and -N($C_1$-$C_4$-alkyl)$_2$;

$Z^4$ is selected from the group consisting of hydrogen, halogen, -OH, $C_1$-$C_4$-alkyl, $C_1$-$C_4$-alkoxy, -NH($C_1$-$C_4$-alkyl), -N($C_1$-$C_4$-alkyl)$_2$, -NH($C_3$-$C_6$-cycloalkyl), -N($C_1$-$C_4$-alkyl)($C_3$-$C_6$-cycloalkyl), $C_1$-$C_4$-halogenoalkyl having 1 to 5 halogen atoms, $C_1$-$C_4$-halogenoalkoxy having 1 to 5 halogen atoms, -S-($C_1$-$C_4$-alkyl), and a 4- to 6-membered heterocycloalkyl; and $Z^5$ is selected from the group consisting of hydrogen, halogen, $C_1$-$C_4$-alkyl, and $C_1$-$C_4$-alkoxy;

or a stereoisomer, a tautomer, or a salt thereof, or a mixture of any of the foregoing.

5. The compound according to claim 1, wherein $R^1$ is hydrogen or methyl;

$R^2$ is selected from the group consisting of hydrogen, chlorine, fluorine, bromine, —$NR^{12}R^{13}$, —$OR^{14}$, -SR$^{15}$, -S(O)R$^{15}$, -SO$_2$R$^{15}$, methyl, ethyl, propyl, isopropyl, cyclopropyl, cyclohexyl, propenyl, cyclopentenyl, cyclohexenyl, each of which is optionally substituted by 1 or 2 substituents independently selected from the group consisting of cyano, ethoxy-C(O)-, and -C(O)-NH$_2$, and a monocyclic or a bicyclic heterocycle selected from the group consisting of azetidine, pyrrolidine, pyrazolidine, imidazolidine, 1,2,4-triazolidine, piperidine, piperazine, tetrahydropyridine, dihydro-2H-pyrane, tetrahydropyrane, 1,2-oxazolidine, 1,2-oxazine, morpholine, thiomorpholine, 3,4-dihydroisoquinoline, 2,3-dihydro-indole, 1,3-dihydro-isoindole, 3,9-dioxa-7-azabicyclo [3.3.1]nonane, 6-oxa-3-azabicyclo [3.1.1]heptane, 8-oxa-3-azabicyclo[3.2.1]octane, imidazole, pyrazole, 1,2,4-triazole, 1,2,3-triazole, 4-oxa-7-azaspiro[2.5]octane, each of which is optionally substituted by 1, 2, 3, or 4 substituents independently selected from the group consisting of fluorine, chlorine, cyano, -OH, oxo, -COOH, methoxy-C(O)-, ethoxy-C(O)-, tert-butoxy-C(O)-, -C(O)-NH$_2$, methyl, methyl-C(O)-, trifluoromethyl, hydroxymethyl-, methoxymethyl-, -NH$_2$, -NMe$_2$, and pyrrolidine;

R$^3$ is hydrogen, chlorine, or methyl;

R$^4$ is selected from the group consisting of hydrogen, fluorine, chlorine, cyano, methyl, methoxy, and trifluoromethyl;

R$^5$ is selected from the group consisting of hydrogen, fluorine, chlorine, and methyl;

R$^6$ is selected from the group consisting of hydrogen, fluorine, chlorine, methyl, and methoxy;

R$^{12}$ and R$^{13}$ are independently selected from the group consisting of hydrogen, -NH(-C(O)-methyl), methoxy, methyl, ethyl, propyl, isopropyl, butyl, isobutyl, cyclopropyl, cyclobutyl, benzyl, 1-phenylethyl, each of which is optionally substituted by 1, 2, or 3 substituents independently selected from the group consisting of fluorine, -OH, -COOH, methoxy-C(O)-, ethoxy-C(O)-, tert-butoxy-C(O)-, -C(O)-NH$_2$, -C(O)-NMe$_2$, -NH-C(O)-methyl, methyl, methoxy, cyclopropyl, -NH$_2$, NMe$_2$, S-methyl, S(O)-methyl, SO$_2$-methyl, and (EtO)$_2$P(=O)-, heterocyclyl-methyl, heterocyclyl-ethyl, wherein the heterocyclyl substituent is selected from the group consisting of pyrrolidine, morpholine, pyrazole, 1,2,4-oxadiazole, pyridine, each of which is optionally substituted by 1 substituent independently selected from the group consisting of fluorine, chlorine, -OH, oxo, and methyl, phenyl, and a monocyclic or a bicyclic heterocycle selected from the group of oxetane, thietane, pyrrolidine, morpholine, tetrahydropyrane, pyridine, and pyrazole, each of which is optionally substituted by 1 or 2 substituents independently selected from the group consisting of fluorine, chlorine, -OH, oxo, and methyl;

R$^{14}$ is selected from the group consisting of methyl, ethyl, isopropyl, butyl, cyclopentyl, benzyl, each of which is optionally substituted by 1 or 2 substituents independently selected from the group consisting of fluorine, -OH, methyl, methoxy, and cyclopentyl, and a monocyclic or a bicyclic heterocycle selected from the group consisting of pyrrolidine and tetrahydropyrane;

R$^{15}$ is selected from the group consisting of methyl and ethyl, each of which is optionally substituted by 1 substituent independently selected from the group consisting of -OH and -COOH, and pyridine;

Q is a substituted phenyl ring of the formula (Q1)

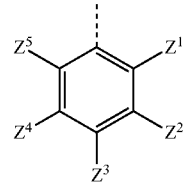

(Q1)

wherein:
Z$^1$ and Z$^5$ are independently selected from the group consisting of hydrogen, fluorine, chlorine, methyl, and methoxy;
Z$^2$ and Z$^4$ are independently selected from the group consisting of hydrogen, fluorine, chlorine, -OH, methyl, ethyl, -NHMe, -NMe$_2$, trifluoromethyl, methoxy, trifluoromethoxy, -SMe, and morpholinyl; and
Z$^3$ is independently selected from the group consisting of hydrogen, fluorine, chlorine, methyl, methoxy, and —NMe$_2$,
or a stereoisomer, a tautomer, or a salt thereof, or a mixture of any of the foregoing.

6. The compound according to claim 1, wherein,
R$^1$ is hydrogen or methyl;
R$^2$ is selected from the group consisting of hydrogen, chlorine, fluorine, bromine, -NH$_2$, -NH(CH$_3$), -N(CH$_3$)$_2$, methoxy, ethoxy, methyl, ethyl, propyl, isopropyl, cyclopropyl, and a monocyclic heterocycle selected from the group consisting of azetidine, pyrrolidine, pyrazolidine, imidazolidine, 1,2,4-triazolidine, piperazine, 1,2-oxazolidine, tetrahydropyrane, morpholine, thiomorpholine, imidazole, pyrazole, and 1,2,3-triazole, each of which is optionally substituted by 1, 2, 3, or 4 substituents independently selected from the group consisting of fluorine, -OH, oxo, -COOH, methoxy-C(O)-, ethoxy-C(O)-, tert-butoxy-C(O)-, -C(O)-NH$_2$, methyl, methyl-C(O)-, trifluoromethyl, hydroxymethyl-, methoxymethyl-, -NH$_2$, -NMe$_2$, and pyrrolidine;
R$^3$ is hydrogen;
R$^4$ is selected from the group consisting of hydrogen, chlorine, fluorine, methyl, methoxy, and trifluoromethyl;
R$^5$ is selected from the group consisting of hydrogen, chlorine, fluorine, and methyl;
R$^6$ is selected from the group consisting of hydrogen, fluorine, methyl, and methoxy;
Q is a substituted phenyl ring of the formula (Q1)

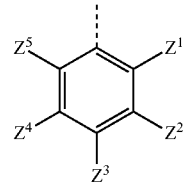

(Q1)

wherein:
Z$^1$ and Z$^5$ are independently selected from the group consisting of hydrogen, fluorine, chlorine, methyl, and methoxy;
Z$^2$ and Z$^4$ are independently selected from the group consisting of hydrogen, fluorine, chlorine, -OH, methyl, ethyl, -NHMe, -NMe$_2$, trifluoromethyl, methoxy, trifluoromethoxy, -SMe, and morpholinyl; and $Z^3$ is independently selected from the group consisting of hydrogen, fluorine, chlorine, methyl, methoxy, and —NMe$_2$;

or a stereoisomer, a tautomer, or a salt thereof, or a mixture of any of the foregoing.

7. The compound according to claim 1, wherein:

T is selected from $T^1 — T^6$ as defined in claim 1;

$R^1$ is hydrogen or methyl;

$R^2$ is selected from the group consisting of hydrogen, chlorine, fluorine, bromine, -NH(CH$_3$), -N(CH$_3$)$_2$, methoxy, ethoxy, methyl, ethyl, propyl, isopropyl, cyclopropyl, and a monocyclic heterocycle selected from the group consisting of tetrahydropyrane, morpholine, and thiomorpholine;

$R^3$ is hydrogen;

$R^4$ is selected from the group consisting of hydrogen, chlorine, fluorine, methyl, methoxy, and trifluoromethyl;

$R^5$ is selected from the group consisting of hydrogen, chlorine, fluorine, and methyl;

$R^6$ is selected from the group consisting of hydrogen, fluorine, methyl, and methoxy;

Q is selected from the group consisting of phenyl, 2,3,4-trifluorophenyl, 2,3,4-trichlorophenyl, 2,3,5-trifluorophenyl, 2,3,5-trichlorophenyl, 2,3,6-trifluorophenyl, 2,3,6-trichlorophenyl, 2,3-difluorophenyl, 2,3-dichlorophenyl, 2,4,5-trifluorophenyl, 2,4,5-trichlorophenyl, 2,4,6-trifluorophenyl, 2,4,6-trichlorophenyl, 2,6-difluorophenyl, 2,6-dichlorophenyl, 2-fluoro-3-chlorophenyl, 2-chloro-3-fluorophenyl, 2-chloro-4-fluorophenyl, 2-fluoro-4-chlorophenyl, 2-chloro-5-fluorophenyl, 2-chloro-6-fluorophenyl, 2-fluorophenyl, 2-chlorophenyl, 3,4,5-trifluorophenyl, 3,4,5-trichlorophenyl, 3,4-difluorophenyl, 3,4-dichlorophenyl, 3,5-difluoro-4-chlorophenyl, 3,5-dichloro-4-fluorophenyl, 3,5-difluorophenyl, 3,5-dichlorophenyl, 3-chloro-4-fluorophenyl, 3-chloro-5-fluorophenyl, 3-fluorophenyl, 3-chlorophenyl, 5-chloro-2,4-difluorophenyl, 5-fluoro-2,4-dichlorophenyl, and 5-chloro-2-fluorophenyl;

or a stereoisomer, a tautomer, or a salt thereof, or a mixture of any of the foregoing.

8. The compound according to claim 1, wherein T is selected from the group consisting of $T^1$, $T^2$, and $T^3$;

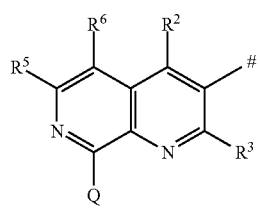

T$^1$

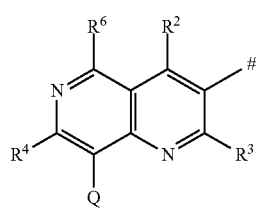

T$^2$

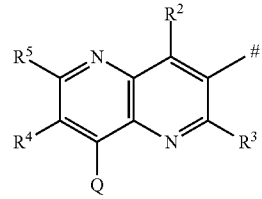

T$^3$ or a stereoisomer, a tautomer, or a salt thereof, or a mixture of any of the foregoing.

9. The compound according to claim 1, wherein $R^2$ is selected from the group consisting of $C_3$-$C_6$ cycloalkyl and azetidine, optionally substituted with fluorine.

10. The compound according to claim 2, wherein $R^2$ is selected from the group consisting of $C_3$-$C_6$ cycloalkyl and azetidine, optionally substituted with fluorine.

11. The compound according to claim 3, wherein $R^2$ is selected from the group consisting of $C_3$-$C_6$ cycloalkyl and azetidine, optionally substituted with fluorine.

12. The compound according to claim 4, wherein $R^2$ is selected from the group consisting of $C_3$-$C_6$ cycloalkyl and azetidine, optionally substituted with fluorine.

13. The compound according to claim 8, wherein $R^2$ is selected from the group consisting of $C_3$-$C_6$ cycloalkyl and azetidine, optionally substituted with fluorine.

14. A pharmaceutical composition comprising a compound of formula (I) according to claim 1, or a stereoisomer, a tautomer, or a salt thereof, or a mixture of any of the foregoing, and one or more pharmaceutically acceptable excipients.

15. A pharmaceutical composition comprising a compound of formula (I) according to claim 9, or a stereoisomer, a tautomer, or a salt thereof, or a mixture of any of the foregoing, and one or more pharmaceutically acceptable excipients.

16. A pharmaceutical composition comprising a compound of formula (I) according to claim 10, or a stereoisomer, a tautomer, or a salt thereof, or a mixture of any of the foregoing, and one or more pharmaceutically acceptable excipients.

17. A pharmaceutical composition comprising a compound of formula (I) according to claim 11, or a stereoisomer, a tautomer, or a salt thereof, or a mixture of any of the foregoing, and one or more pharmaceutically acceptable excipients.

18. A pharmaceutical composition comprising a compound of formula (I) according to claim 12, or a stereoisomer, a tautomer, or a salt thereof, or a mixture of any of the foregoing, and one or more pharmaceutically acceptable excipients.

19. A pharmaceutical composition comprising a compound of formula (I) according to claim 13, or a stereoisomer, a tautomer, or a salt thereof, or a mixture of any of the foregoing, and one or more pharmaceutically acceptable excipients.

20. A method of preparing a compound of formula (I) according to claim 1, said method comprising the step of reacting an intermediate compound of formula 1N-T1, 1N-T2, 1N-T3, 1N-T4, 1N-T5, or 1N-T6:

1N-T1
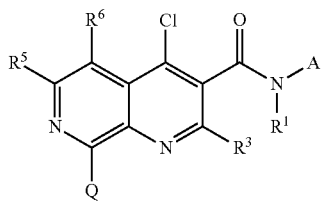

1N-T2
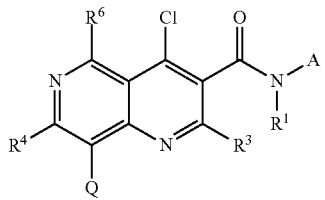

1N-T3
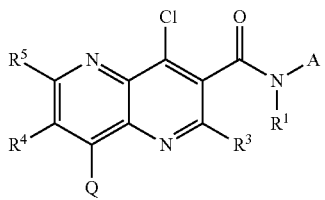

1N-T4
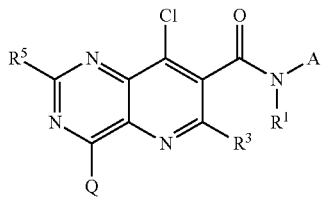

1N-T5
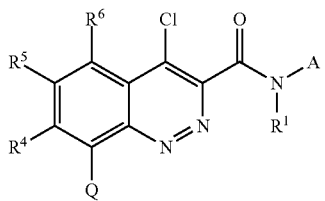

1N-T6
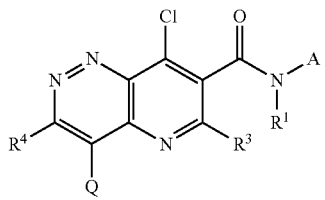

wherein A, $R^1$, $R^3$, $R^4$, $R^5$, $R^6$, and Q are as defined for the compound of formula (I) according to claim 1;
with a compound of formula 1F:

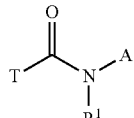

1F, wherein $R^2$ is $NR^{12}R^{13}$, $OR^{14}$, or $SR^{15}$, each as defined for the compound of formula (I) according to claim 1;

thereby giving a compound of formula (I):

(I)

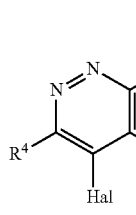

wherein T, A, $R^1$, $R^2$, $R^3$, $R^4$, $R^5$, $R^6$, and Q are as defined for the compound of formula (I) according to claim 1;
or the step of reacting an intermediate compound of formula 1M-T1, 1M-T2, 1M-T3, 1M-T4, 1M-T5, or 1M-T6:

1M-T1
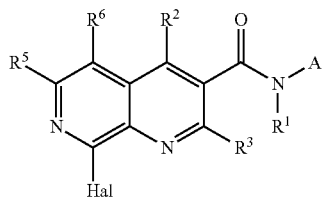

1M-T2
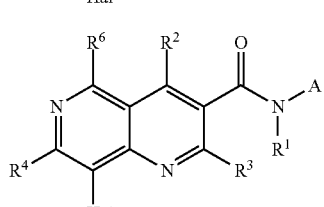

1M-T3
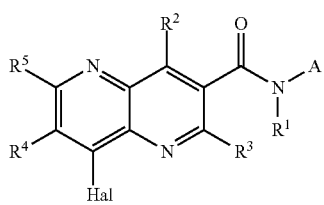

1M-T4
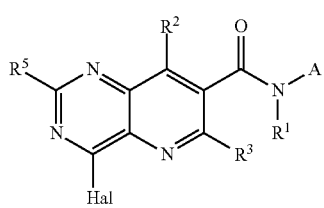

1M-T5
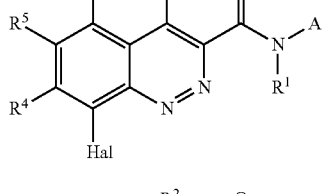

1M-T6 wherein A, $R^1$, $R^2$, $R^3$, $R^4$, $R^5$ and $R^6$ are as defined for the compound of formula (I) according to claim 1, and wherein Hal is chlorine, bromine or iodine;

with a compound of formula 1H:

   1H, wherein Q is as defined for the compound of formula (I) according to claim 1, and each R may be individually H or Me or both R are pinacolate;

thereby giving a compound of formula (I):

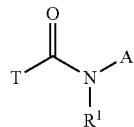   (I)

wherein T, A, $R^1$, $R^2$, $R^3$, $R^4$, $R^5$, $R^6$, and Q are as defined for the compound of formula (I) according to claim 1;

or the step of reacting an intermediate compound of formula 1W-T1, 1W-T2, 1W-T3, 1W-T4, 1W-T5, or 1W-T6:

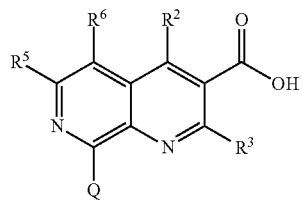   1W-T1

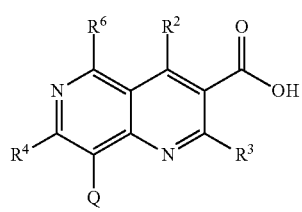   1W-T2

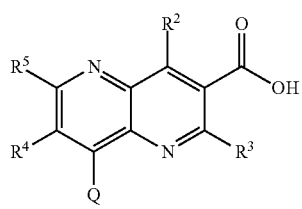   1W-T3

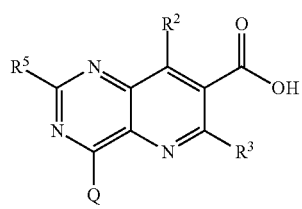   1W-T4

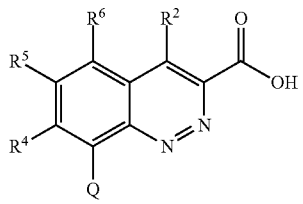   1W-T5

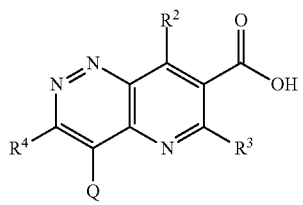   1W-T6 wherein Q, $R^2$, $R^3$, $R^4$, $R^5$ and $R^6$ are as defined for the compound of formula (I) according to claim 1;

with a compound of formula 1V:

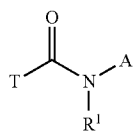   1V wherein $R^1$ and A are as defined for the compound of formula (I) according to claim 1;

thereby giving a compound of formula (I):

   (I)

wherein T, A, $R^1$, $R^2$, $R^3$, $R^4$, $R^5$, $R^6$, and Q are as defined for the compound of formula (I) according to claim 1;

or the step of reacting an intermediate compound of formula 1X-T1, 1X-T2, 1X-T3, 1X-T4, 1X-T5, or 1X-T6:

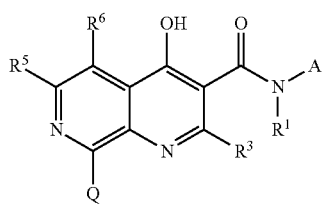   1X-T1

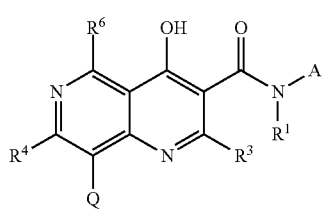   1X-T2

-continued

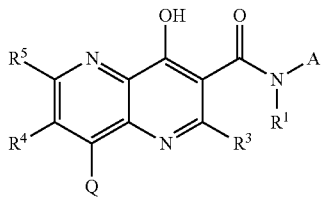
1X-T3

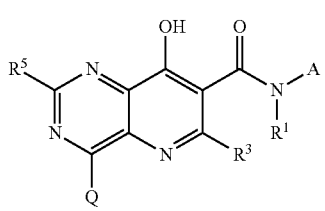
1X-T4

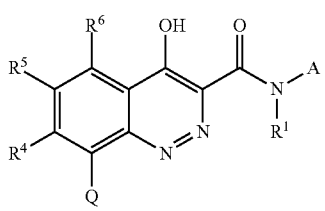
1X-T5

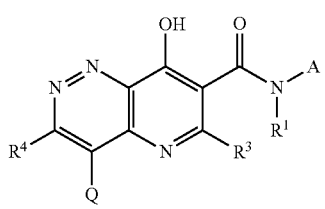
1X-T6 wherein Q, A, $R^1$, $R^3$, $R^4$, $R^5$ and $R^6$ are as defined for the compound of formula (I) according to claim 1;
with a compound of formula 1Y:

$R^2H$  1Y wherein $R^2$ is $C^1$-$C^4$-alkoxy which is optionally substituted as defined for the compound of formula (I) according to claim 1;
thereby giving a compound of formula (I):

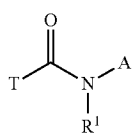
(I)

wherein T, A, $R^1$, $R^3$, $R^4$, $R^5$, $R^6$, and Q are as defined for the compound of formula (I) according to claim 1 and $R^2$ is $C^1$-$C^4$-alkoxy which is optionally substituted as defined for the compound of formula (I) according to claim 1;
or the step of reacting an intermediate compound of formula 1N-T1, 1N-T2, 1N-T3, 1N-T4, 1N-T5, or 1N-T6:

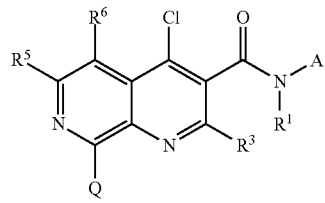
1N-T1

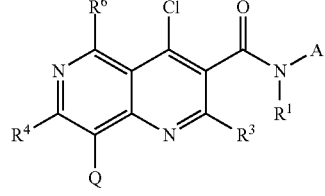
1N-T2

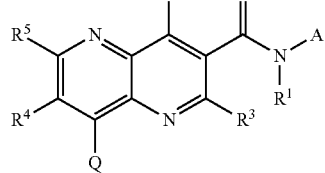
1N-T3

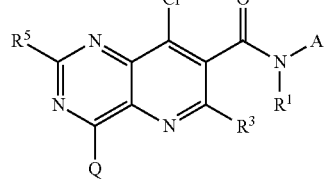
1N-T4

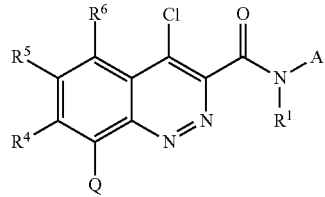
1N-T5

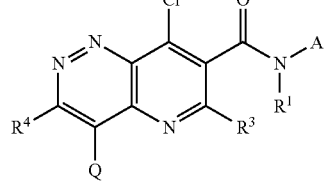
1N-T6 wherein A, $R^1$, $R^3$, $R^4$, $R^5$, $R^6$, and Q are as defined for the compound of formula (I) according to claim 1;
with a compound of formula 2A :

$R^2$Met-X,  2A wherein $R^2$ is $C_1$-$C_4$-alkyl, $C_3$-$C_6$-cycloalkyl, $C_2$-$C_4$-alkenyl, $C_3$-$C_6$-cycloalkenyl, $C_2$-$C_4$-alkynyl, phenyl-$C_1$-$C_4$-alkyl, heterocyclyl-$C_1$-$C_4$-alkyl, phenyl or a monocyclic or bicyclic heterocycle, each of which as defined for the compound of formula (I) according to claim 1, Met is magnesium or zinc, and X is chlorine, bromine or iodine;

thereby giving a compound of formula (I):

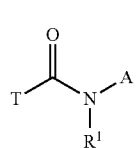
(I)

wherein T, A, $R^1$, $R^3$, $R^4$, $R^5$, $R^6$, and Q are as defined for the compound of formula (I) according to claim 1 and $R^2$ is $C_1$-$C_4$-alkyl, $C_3$-$C_6$-cycloalkyl, $C_2$-$C_4$-alkenyl, $C_3$-$C_6$-cycloalkenyl, $C_2$-$C_4$-alkynyl or phenyl-$C_1$-$C_4$-alkyl, each of which is optionally substituted as defined for the compound of formula (I) according to claim 1.

* * * * *

UNITED STATES PATENT AND TRADEMARK OFFICE
CERTIFICATE OF CORRECTION

| | | |
|---|---|---|
| PATENT NO. | : 11,485,733 B2 | Page 1 of 2 |
| APPLICATION NO. | : 16/624117 | |
| DATED | : November 1, 2022 | |
| INVENTOR(S) | : Nils Griebenow et al. | |

It is certified that error appears in the above-identified patent and that said Letters Patent is hereby corrected as shown below:

In the Claims

Column 206, Line 31, following text should be added after halogenalkoxy having 1 to 5 halogen atoms, --C3-C6-cycloalkyl, C3-C6-halogenocycloalkyl having 1 to 5 halogen atoms, C3-C4-alkenyl, C3-C4-alkynyl, C1-C4-alkoxy-C1-C4-alkyl, C3-C6-cycloalkyl-C1-C3-alkyl, cyano-C1-C4-alkyl, -NH-C1-C4-alkyl, -N(C1-C4-alkyl)2, NH2-C1-C4-alkyl-, C1-C4-alkyl-NH-C1-C4-alkyl-,(C1-C4-alkyl)2N-C1-C4-alkyl-, C1-C4-alkyl-C(O)-, C1-C4-halogenoalkyl-C(O)- having 1 to 5 halogen atoms, C1-C4-alkoxy-C(O)-, benzyloxy-C(O)-, C1-C4-alkoxy-C1-C4-alkyl-C(O)-, -SO2-C1-C4-alkyl,-SO2-C1-C4-halogenoalkyl having 1 to 5 halogen atoms,--; Line 60, add --(-- between -C(O)-NH and C1-C4-alkyl), -C(O)-N Column 207, Line 51, delete "-S-C1-C4-halogeno-" and replace with -- -C1-C4-halogeno- --; Line 54, delete the second occurrence of "-S(O)-C1-C4-alkyl" and replace with -- -SO2-C1-C4-alkyl--

Column 208, Line 5, add -- -OH, NH2, -NH(C1-C4-alkyl)2, -N(C1-C4-alkyl),-- between hydrogen, and -NH(-C(O)-C1-C4-alkyl), Column 209, Line 14, replace "-SO-C1-C4-alkyl" with -- -SO2-C1-C4-alkyl--

Column 210, Line 4, add --)2, C1-C4-alkyl-- between -C(O)-N(C1-C4-alkyl and, C1-C4-halogenoalkyl having; Line 6, delete ";" after enoalkoxy having 1 to 5 halogen atoms, and add --C3-C6-cycloalkyl, -NH2, -NH(C1-C4-alkyl), -N(C1-C4-alkyl)2, -S-C1-C4-alkyl, -S(O)-C1-C4-alkyl, -SO2-C1-C4-alkyl, -S-C1-C4-halogenoalkyl having 1 to 5 halogen atoms, -S(O)-C1-C4-halogenoalkyl having 1 to 5 halogen atoms and -SO2-C1-C4-halogenoalkyl having 1 to 5 halogen atoms,--

Column 211, Line 49, delete "-CH2-S-(C1-C4-alkyl)" and replace with -- -CH2-O-(C1-C4-alkyl)--; Line 56, at the end of the line delete "-S-" and replace with -- -SO2- --

Column 214, Line 54, delete "-S(O)-C1-C4-alkyl" and replace with -- -S-C1-C4-alkyl--; Line 55, delete "-S(O)-C1-" and replace with -- -S-C1- --

Signed and Sealed this
Eighth Day of April, 2025

Coke Morgan Stewart
*Acting Director of the United States Patent and Trademark Office*

CERTIFICATE OF CORRECTION (continued)

Column 215, Line 27, add --(-- between -N(C1-C4-alkyl)-C(O)- and C1-C4-alkyl),; Line 43, delete "nitro," and add --C1-C4-alkyl, C1-C4-halogenoalkyl having 1 to 5 halogen atoms C1-C4-alkoxy and-- between oxo, and C1-C4-; Line 58, replace the word "halogenoaalkyl" with --halogenoalkyl-- and add --C1-C4-alkoxy, and-- after atoms,; Line 65, replace the word "halogenoalkoxy" with --halogenoalkyl-- and add --C1-C4-alkoxy,-- after atoms, Column 216, Line 7, delete "nitro,"

Column 217, Line 40, add --C1-C4-alkyl-- between cyano, and C1-C4-halogenoalkyl; Line 58, delete "P(-O)-" and replace with --P(=O)- --